(12) United States Patent
Miao et al.

(10) Patent No.: US 11,459,304 B2
(45) Date of Patent: Oct. 4, 2022

(54) IONIZABLE LIPIDOIDS AND THEIR USES

(71) Applicant: Massachusetts Institute of Technology, Cambridge, MA (US)

(72) Inventors: Lei Miao, San Jose, CA (US); Linxian Li, Malden, MA (US); Daniel Griffith Anderson, Framingham, MA (US); Yuxuan Huang, Cambridge (GB)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/556,470

(22) Filed: Aug. 30, 2019

(65) Prior Publication Data

US 2020/0109121 A1    Apr. 9, 2020

Related U.S. Application Data

(60) Provisional application No. 62/725,445, filed on Aug. 31, 2018.

(51) Int. Cl.
| | |
|---|---|
| *C07D 233/40* | (2006.01) |
| *C07C 251/08* | (2006.01) |
| *A61K 39/39* | (2006.01) |
| *C07D 403/06* | (2006.01) |
| *C07C 237/06* | (2006.01) |
| *A61K 39/00* | (2006.01) |

(52) U.S. Cl.
CPC ............ *C07D 233/40* (2013.01); *A61K 39/39* (2013.01); *C07C 237/06* (2013.01); *C07C 251/08* (2013.01); *C07D 403/06* (2013.01); *A61K 2039/53* (2013.01); *A61K 2039/55555* (2013.01)

(58) Field of Classification Search
None
See application file for complete search history.

(56) References Cited

FOREIGN PATENT DOCUMENTS

| WO | WO 2016/201377 A1 | 12/2016 |
|---|---|---|
| WO | WO 2017/109494 A1 | 6/2017 |

OTHER PUBLICATIONS

Chemical Abstract Registry No. 1629605-04-4, indexed in the Registry File on STN CAS Online Oct. 21, 2014.*
Chen et al., In situ cancer vaccination using lipidoid nanoparticles. Science Advances, 2021, 7, p. 1-13.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
International Search Report and Written Opinion for Application No. PCT/US2019/049050 dated Jan. 14, 2020.
Miao et al., Delivery of mRNA vaccines with heterocyclic lipids increases anti-tumor efficacy by STING-mediated immune cell activation. Nat Biotechnol. Oct. 2019;37(10):1174-1185. doi: 10.1038/s41587-019-0247-3. Epub Sep. 30, 2019.
Pardi et al., mRNA vaccines—a new era in vaccinology. Nat Rev Drug Discov. Apr. 2018;17(4):261-279. doi:10.1038/nrd.2017.243. Epub Jan. 12, 2018.

* cited by examiner

*Primary Examiner* — Po-Chih Chen
(74) *Attorney, Agent, or Firm* — Wolf, Greenfield & Sacks, P.C.

(57) ABSTRACT

Provided herein are lipidoid compounds of Formulae (I) and (II), and pharmaceutically acceptable salts, co-crystals, tautomers, stereoisomers, solvates, hydrates, polymorphs, isotopically labeled derivatives, prodrugs, and compositions thereof. Also provided are methods and kits involving the inventive lipidoid compounds, compositions, or formulations for treating and/or preventing diseases (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject, methods for synthesizing the compounds described herein, and compounds described herein synthesized by the synthetic methods described herein. The compounds are effective carriers for the delivery of an agent such as a polynucleotide (e.g., RNA) to a cell.

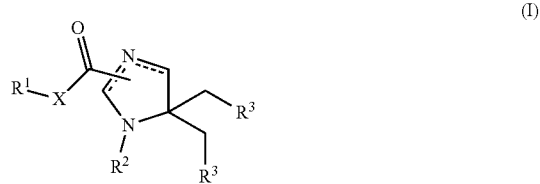

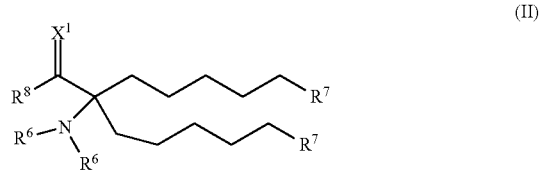

22 Claims, 79 Drawing Sheets

A18 head

$K_D$: 51.33 μM

A25 head

$K_D$: 756.34 μM

A2-Iso5-2DC18

A12-Iso5-2DC18

| Tukey's multiple comparisons test | Delivery Efficiency | | Encapsulation Efficiency | | Size | |
|---|---|---|---|---|---|---|
| | Significance | P Value | Significance | P Value | Significance | P Value |
| A2-iso5-4DC18 vs. A2-iso5-2DC18 | No | 0.0511 | No | 0.6098 | No | 0.934 |
| A2-iso5-4DC18 vs. A12-iso5-4DC18 | No | 0.2024 | No | 0.998 | No | 0.5256 |
| A2-iso5-4DC18 vs. A12-iso5-2DC18 | No | 0.2749 | No | 0.4911 | No | 0.2391 |
| A2-iso5-2DC18 vs. A12-iso5-4DC18 | No | 0.8656 | No | 0.7103 | No | 0.8394 |
| A2-iso5-2DC18 vs. A12-iso5-2DC18 | No | 0.7682 | No | 0.9967 | No | 0.4844 |
| A12-iso5-4DC18 vs. A12-iso5-2DC18 | No | 0.9972 | No | 0.5901 | No | 0.9082 |

Figure 11C

| PDB Code | # | Binding Energy (kcal/mol) | $K_D$ (µM) |
|---|---|---|---|
| 4EF4 | A2 | -5.42 | 106.18 |
| | A12 | -4.75 | 329.81 |
| | A18 | -5.85 | 51.33 |
| | A25 | -4.26 | 756.34 |
| 4KSY | A2 | -6.28 | 24.98 |
| | A12 | -5.92 | 46.14 |
| | A18 | -6.43 | 19.26 |
| | A25 | -5.00 | 217.81 |
| 4QXP | A2 | -5.33 | 124.78 |
| | A12 | -4.94 | 238.7 |
| | A18 | -6.66 | 13.2 |
| | A25 | -4.91 | 253.67 |

Figure 22E

| LNP | Structure | pKa | D(nm) | PDI | Zeta (mV) | EE(%) |
|---|---|---|---|---|---|---|
| U4 | 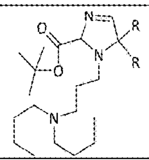 | 6.28 | 107.4±0.8 | 0.181 | -6.00 | 59.8 |
| U5 | 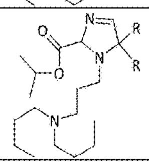 | 6.56 | 121.6±6.1 | 0.086 | -4.58 | 27.6 |
| U6 | 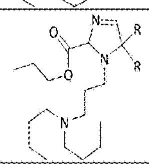 | 6.71 | 119.4±1.3 | 0.105 | -4.06 | 49.4 |
| U7 | 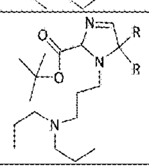 | 7.17 | 105.7±0.8 | 0.056 | -8.69 | 62.1 |
| U10 | 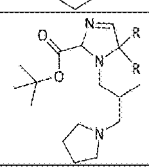 | 7.48 | 165.2±1.0 | 0.152 | 9.7 | 85.6 |
| U11 | 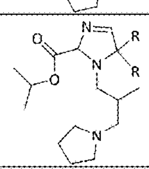 | 7.34 | 103.4± 0.2 | 0.171 | 9.5 | 94.1 |
| MC3 | 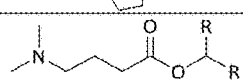 | 6.29 | 92.5±8.6 | 0.127 | 1.47 | 84.2 |
| R= | | | | | | |

IONIZABLE LIPIDOIDS AND THEIR USES

RELATED APPLICATIONS

This application claims priority under 35 U.S.C. § 119(e) to U.S. Provisional Application No. 62/725,445, filed Aug. 31, 2018, the content of which is incorporated herein by reference in its entirety.

GOVERNMENT SUPPORT

This invention was made with Government support under Grant No. W32P4Q-13-1-0011 awarded by the Defense Advanced Research Projects Agency (DARPA). The Government has certain rights in the invention.

BACKGROUND OF THE INVENTION

Therapeutic mRNA has broad potential as a vaccine. Optimal efficacy requires both intracellular delivery, to allow antigen translation, and appropriate immune activation. mRNA vaccines are a promising class of therapeutics for cancer prevention and treatment. In contrast to DNA vaccines, mRNA vaccination results in transient expression of encoded proteins, and so avoids complications associated with insertional mutagenesis.[1] mRNA vaccines can be specifically designed to encode a wide variety of peptide and protein structures, allowing expression of the entire antigen. With a larger number of epitopes presented by Class I and Class II Major Histocompatibility Complex (MHC), mRNA vaccines can potentially induce a stronger cellular and humoral response than stimulation with peptide antigen vaccines.[2]

A number of clinical trials have explored mRNA vaccination over the past decade, however, successful clinical translation has been limited by two major challenges: 1) insufficient intracellular protein expression due to catalytic hydrolysis of mRNA, and 2) inadequate antigen loading and maturation of antigen-presenting cells (APC). To improve mRNA delivery and in vivo protein expression, a number of liposomes and polymeric micelle-based formulations are in development, including nanoparticle delivery vehicles made from lipid-like materials.[3, 4]

In contrast, the design of therapeutics which can carefully balance antigen specific immune cell maturation and activation, while preventing systemic activation of the immune system, remains challenging. There is a growing body of evidence to suggest that adjuvant effects associated with targeted stimulation of Type I Interferons (IFNs) may support advantageous adaptive immune responses.[1, 5, 6] A number of pathways which can activate IFN secretion have been identified, including Toll-Like Receptors (TLRs), Rig-1 Like Receptors (RLRs), and the Stimulation of Interferon Gene (STING) pathway.[7] Activation of these pathways has been reported to correlate with reduced disease progression and better clinical outcomes in human cancer patients,[8, 9, 10] and a number of strategies have been developed to specifically target them.[11] RNA nanoparticles encoding TLR target proteins [12, 13] and cancer vaccine adjuvants derived from *Salmonella Minnesota* lipid-like TLR agonists have both been used to activate the TLR pathway.[14]

Despite this, many TLR agonists are unsuitable adjuvants for mRNA delivery. Exogenous mRNA can intrinsically bind to TLRs, which can stimulate beneficial IFN secretion. However, indiscriminate activation of the immune system, can upregulate protein kinase R, which can ultimately inhibit antigen expression and result in a limited antigen-specific immune response.[1] Fine-tuning TLR activation and IFN responses in systems with both mRNA (an intrinsic TLR agonist) and TLR agonists (which act as adjuvants) remains challenging. mRNAs incorporating chemically modified nucleotides or optimized codon sequences have therefore been developed and are reported to reduce mRNA-associated immunogencity.[6]

In an alternative approach, type I IFN secretion can be modulated by co-administering adjuvants (including aluminum salts and TriMix mRNA[15]) that target other immune cell activation pathways, or by altering mRNA delivery kinetics via optimized vaccine administration.[16, 17] Recently, the STING signaling pathway has emerged as a Toll-like receptor (TLR)-independent mediator of host innate immune response.[18] Additionally, small molecule or polymeric STING agonists have been reported to induce relatively low levels of local and systemic inflammation when used as adjuvants, as compared to TLR agonists.[11, 19, 20, 21] A number of small molecule STING agonists are currently in clinical trials[9, 22]; however, their success has been limited due to the challenges of cytosolic delivery of these molecules[23, 24] (CITE).

Meanwhile, non-viral vectors such as lipidoids have been used as RNA delivery vehicles for decades. These lipidoid particles consist of lipid-like amphipathic molecules, often containing a hydrophilic amine head group and a hydrophobic carbon tail. Upon exposure to aqueous environments, these lipidoids can form a lipid-bilayer around therapeutic cargos (e.g., siRNA, mRNA) with an aqueous core. These formulated lipidoids can subsequently be used to deliver their therapeutic cargo into cells. However, the current obstacle that limits the use of lipidoids is low efficiency of identifying safe and efficient ionizable lipidoids (e.g., cationic lipidoids). The traditional method of generating lipidoids is tedious and time consuming.

Thus, given the targetability, adaptability, and biocompatability of lipidoids for delivering agents including mRNA, it is important to develop lipidoid compounds for delivering mRNA therapeutics in vivo to treat various diseases (e.g., proliferative diseases, infectious diseases) and activate the immune system. It is important to develop a fast and efficient method to quickly generate a large number of lipidoids to achieve safe and efficient delivery of agents (e.g., mRNA).

SUMMARY OF THE INVENTION

Provided herein is the development of a combinatorial library of ionizable lipid-like materials that facilitate both mRNA delivery in vivo and optimized immune cell activation. Using a three-dimensional multi-component reaction system, the vaccine potential of over 1000 new lipidoid formulations was synthesized and evaluated. Optimized formulations induce a robust immune response and were able to inhibit tumor growth and prolong survival in both melanoma and human papillomavirus E7 in vivo tumor models. Interestingly, exemplary lipidoids share a common structure; an unsaturated lipid tail, a dihydroimidazole linker, and cyclic amine head groups. Furthermore, the well-performing formulations induced antigen presenting cell maturation via the intracellular Stimulator of Interferon Genes (STING) pathway, rather than through Toll-like receptors (TLRs) typically activated with mRNA and lipid adjuvants. Small molecule STING agonists are promising adjuvants in cancer vaccination; however, they have previously been difficult to target due to the challenge of intracellular delivery. It is believed that the STING-activating lipidoid formulations developed here may provide a generalized approach for mRNA vaccine systems.

Presented herein is the first systematic study of lipidoid compounds described herein, which can simultaneously aid mRNA vaccine delivery and can be easily internalized to provide targeted adjuvant stimulation via the STING pathway. These lipidoids are based on a new lipid library, synthesized using a one-step Three Component Reaction (3-CR).[25] This strategy increases the diversity of synthesized lipid structures and facilitates identification of structure-function relationships. Using this approach, the head group has been identified as a key component; changing the chemical structure of the lipidoid head group allows tuning of the immunostimulatory effect of these lipids. It is further shown that lipidoids with cyclic amino head groups activate the MyD88-independent STING pathway. This is the first known evidence of lipidoid adjuvant-assisted mRNA vaccination, using lipid nanoparticles designed to efficiently deliver mRNA and simultaneously activate the immune system through an mRNA independent STING pathway. These lipidoids can be used to deliver mRNA in vivo and provide robust anti-tumor T-cell responses that significantly inhibit tumor growth The therapeutic efficacy and ease of fabrication with these materials provides an attractive platform for the development of mRNA therapeutics.

The disclosure provides new ionizable lipidoid compounds (e.g., cationic lipidoids), compositions, kits, methods for the treatment of various diseases (e.g., genetic diseases, proliferative diseases, hematological diseases, neurological diseases, painful condition, psychiatric disorder, metabolic disorder, long-term medical condition, inflammatory diseases, autoinflammatory diseases, liver diseases, lung diseases, spleen diseases, familial amyloid neuropathy, cardiovascular diseases, viral infection, infectious diseases, fibrotic condition, or autoimmune diseases), methods of synthesizing the ionizable lipidoid compounds described herein, and methods of using the compounds for delivering agents (e.g., RNA (e.g., mRNA)) to cells for the treatment of these various diseases by causing the expression of a specific gene (e.g., activating the STING pathway) in the cell.

In one aspect, the present disclosure provides compounds of Formula (I):

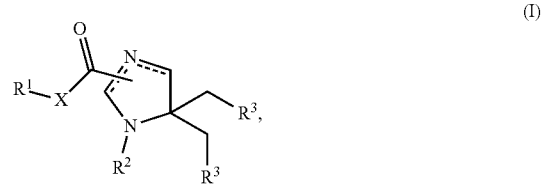

and pharmaceutically acceptable salts, co-crystals, tautomers, stereoisomers, solvates, hydrates, polymorphs, and isotopically labeled derivatives thereof, wherein $R^1$, $R^2$, $R^3$, $R^4$, and X are as defined herein.

In certain embodiments, Formula (I) is of Formula (I-A):

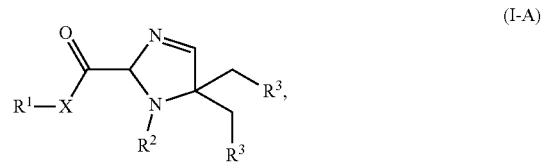

and pharmaceutically acceptable salts, co-crystals, tautomers, stereoisomers, solvates, hydrates, polymorphs, and isotopically labeled derivatives thereof, wherein $R^1$, $R^2$, $R^3$, and X are as defined herein.

In certain embodiments, Formula (I) is of Formula (I-B):

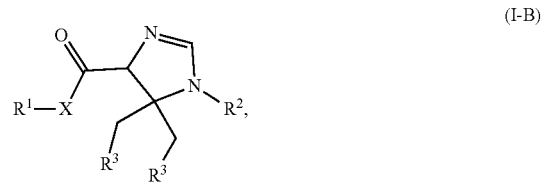

and pharmaceutically acceptable salts, co-crystals, tautomers, stereoisomers, solvates, hydrates, polymorphs, and isotopically labeled derivatives thereof, wherein $R^1$, $R^2$, $R^3$, and X are as defined herein.

Exemplary compounds of Formula (I) include, but are not limited to:

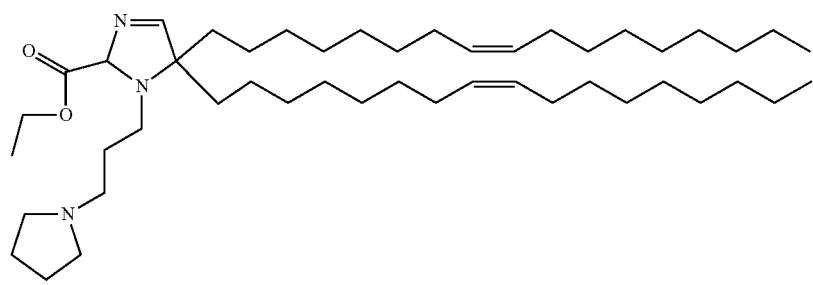

-continued

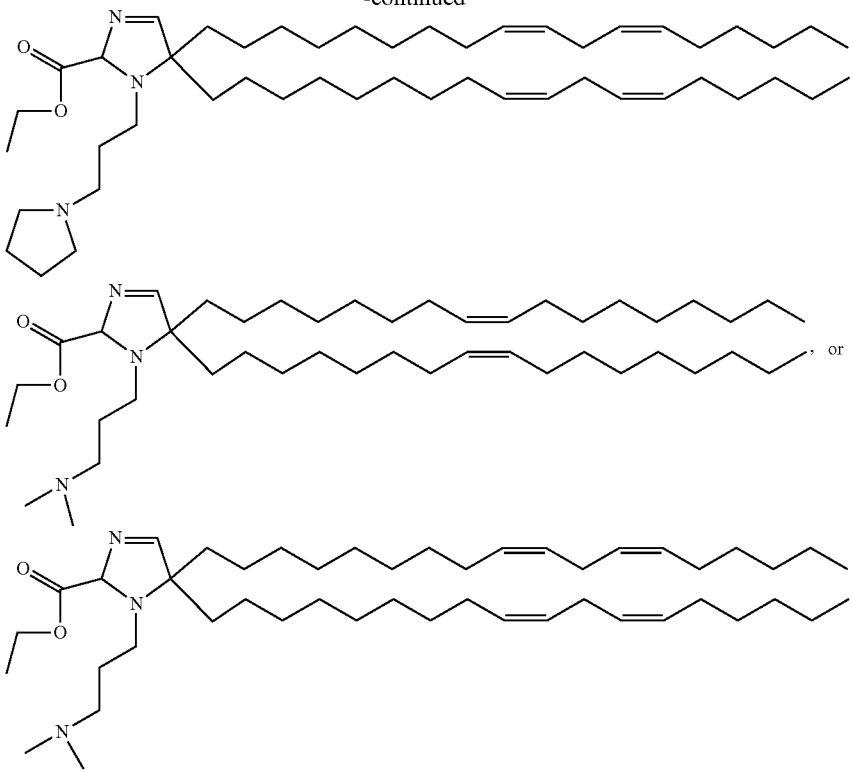

and pharmaceutically acceptable salts, co-crystals, tautomers, stereoisomers, solvates, hydrates, polymorphs, and isotopically labeled derivatives.

In another aspect, the present disclosure provides compounds of Formula (II):

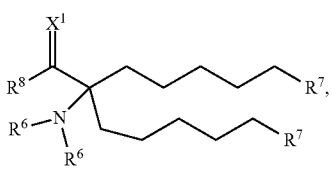

(II)

and pharmaceutically acceptable salts, co-crystals, tautomers, stereoisomers, solvates, hydrates, polymorphs, and isotopically labeled derivatives, wherein $R^6$, $R^7$, $R^8$, and $X^1$ are as defined herein.

Exemplary compounds of Formula (II) include acyclic compounds that are the products of the three-component synthesis disclosed in FIG. 1B using the amine, isocyanide, and alkyl ketone components disclosed in FIGS. 1C and 1D. Exemplary compounds of Formula (II) also include acyclic compounds that are the products of the three-component synthesis disclosed in FIG. 1B using the amine, isocyanide, and alkyl ketone components disclosed above in Table A. Exemplary compounds of Formula (II) include the above-described acyclic products of the three-component synthesis, and pharmaceutically acceptable salts, co-crystals, tautomers, stereoisomers, solvates, hydrates, polymorphs, and isotopically labeled derivatives thereof.

In another aspect, described herein are compositions (e.g., pharmaceutical compositions) including a compound described herein, and optionally an agent (e.g., a small organic molecule, inorganic molecule, nucleic acid, protein, peptide, or polynucleotide (e.g., RNA)). In certain embodiments, the composition is in the form of a particle (e.g., a nanoparticle or a microparticle). In certain embodiments, a composition described herein includes a therapeutically or prophylactically effective amount of a compound described herein. The compositions may be useful in delivering an agent (e.g., a polynucleotide (e.g., RNA)) to a cell and/or causing the expression of a specific gene (e.g., activating the STING pathway and/or activating an innate immune response) in the cell (e.g., by contacting the cell with compositions described herein), in treating a disease (e.g., a genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof, or in preventing a disease in a subject in need thereof. In certain embodiments, the compound is administered or used in treating and/or preventing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof.

In still another aspect, described herein are kits including a container with a compound or composition described herein. A kit described herein may include a single dose or multiple doses of the compound or composition. The described kits may be useful in treating and/or preventing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof, and/or in delivering an agent (e.g., a polynucleotide (e.g., RNA)) to a cell and/or causing the expression of a specific gene (e.g., activating the STING pathway and/or activating an innate immune response) in the cell (e.g., by contacting the cell with compositions described herein). In certain embodiments, a kit described herein further includes instructions for using the compound or composition included in the kit.

In certain embodiments, the compositions are useful in delivering an agent (e.g., a polynucleotide (e.g., RNA)) to a cell and/or causing the expression of a specific gene (e.g., activating the STING pathway and/or activating an innate immune response) in the cell (e.g., by contacting the cell with compositions described herein). In certain embodiments, the compositions activate the intracellular Stimulator of Interferon Genes (STING) pathway. In certain embodiments, the compositions induce antigen presenting cell maturation via the intracellular STING pathway. In certain embodiments, the compositions are adjuvants in cancer vaccination. In certain embodiments, the compositions are adjuvants in mRNA vaccine systems. In certain embodiments, the compositions are used to deliver mRNA agents as part of vaccine systems with a range of antigens including tumor-associated antigens, personalized multi-epitope antigens, and bacterial and viral proteins. In certain embodiments, the compositions activate an innate immune response in the subject. Another aspect of the present disclosure relates to methods of treating a disease in a subject in need thereof, the methods comprising administering to the subject a therapeutically effective amount of a compound or composition described herein. In another aspect, the present disclosure provides methods of preventing a disease in a subject in need thereof, the methods comprise administering to the subject a prophylactically effective amount of a compound or composition described herein.

In yet another aspect, the present disclosure provides methods for making compounds of Formula (I), e.g., compounds of Formula (I-A) and (I-B). In yet another aspect, the present disclosure provides compounds of Formula (I), e.g., compounds of Formula (I-A) and (I-B), synthesized by methods described herein.

In yet another aspect, the present disclosure provides compounds and compositions described herein for use in a method of the disclosure (e.g., a method of delivering an agent (e.g., a polynucleotide (e.g., RNA)) to a cell, or a method of treating and/or preventing a disease (e.g., proliferative disease, infectious disease, autoimmune disease)).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, Tables of Resolving Agents and Optical Resolutions p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array)

having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^c$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON (R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O) N(R$^{ff}$)$_2$, —NR$^{ff}$C(=O)R$^{ee}$, —NR$^{ff}$CO$_2$R$^{ee}$, —NR$^{ff}$C(=O)N (R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R)$_2$, —NR$^{ff}$C (=NR)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi (R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP (=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion; each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2$+X$^-$, —NH$_2$(C$_{1-6}$ alkyl)+X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, F$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4$—, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety of the formula: —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$ alkynyl, C$_{3-10}$carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1- methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)$ $(OR^{cc})_2$, and —$P(=O)(N(R^{bb})\ 2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —$OC(=O)SR^{aa}$a, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})$ $N(R^{bb})_2$, —$OS(=O)R^{aa}$, —$OSO_2R^{aa}$, —$OP(R^{cc})_2$, —$OP$ $(R^{cc})_3$, —$OP(=O)_2R^{aa}$, —$OP(=O)(R^{aa})_2$, —$OP(=O)$ $(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

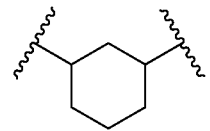 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

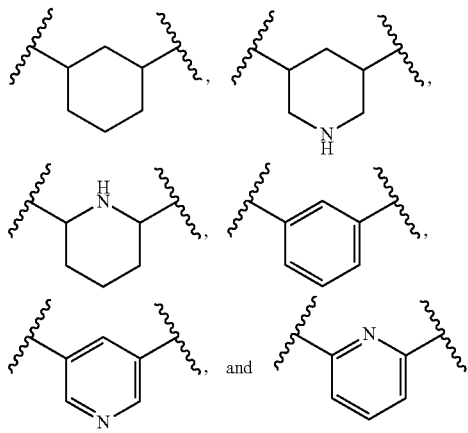

are all examples of a hydrocarbon chain. In contrast, in certain embodiments,

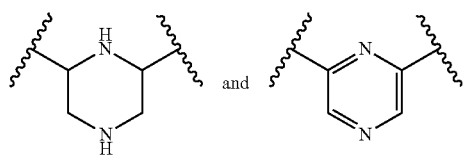 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

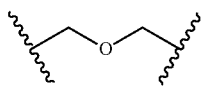 [SMILES: *COC*]

is a $C_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

The term "solvate" refers to forms of the compound, or a salt thereof that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

As used herein the term "inhibit" or "inhibition" in the context of disease treatment (e.g., tumor growth), refers to a reduction in the level of tumor growth. In some embodiments, the term refers to a reduction of the level of tumor growth to a level that is statistically significantly lower than an initial level, which may, for example, be a baseline level of tumor growth. In some embodiments, the term refers to a reduction of the level of tumor growth to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of tumor growth.

When a compound, pharmaceutical composition, method, use, or kit is referred to as "selectively," "specifically," or "competitively" targeting a disease in a target (e.g., cell (e.g., cancer cell)), the compound, pharmaceutical composition, method, use, or kit inhibits the target, to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than binding or inhibiting a different target (e.g., different cell).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection; samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a biological sample.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for for treating a disease.

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for preventing and/or treating a disease (e.g., a proliferative disease (e.g., cancer)).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic *porphyria*, hepatic *porphyria* (e.g., acute intermittent *porphyria*, *porphyria* cutanea *tarda*), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders*—Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, *cannabis* dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

An "effective amount" of a compound or composition described herein refers to an amount sufficient to elicit the desired biological response. An effective amount of a polymer or composition described herein may vary depending on such factors as the desired biological endpoint, the pharmacokinetics of the composition, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a composition or pharmaceutical composition described herein in a single dose. In certain embodiments, an effective amount is the combined amounts of a composition or pharmaceutical composition described herein in multiple doses.

A "therapeutically effective amount" of a compound or composition described herein is an amount sufficient to provide a therapeutic benefit in the treatment of a condition or to delay or minimize one or more symptoms associated with the condition. A therapeutically effective amount of a compound or composition means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound or composition described herein is an amount sufficient to prevent a condition, or one or more symptoms associated with the condition or prevent its recurrence. A prophylactically effective amount of a compound or composition means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "nucleic acid" or "nucleic acid sequence", "nucleic acid molecule", "nucleic acid fragment" or "polynucleotide" are used interchangeably. A polynucleotide molecule is a biopolymer composed of nucleotide monomers covalently bonded in a chain. DNA (deoxyribonucleic acid) and RNA (ribonucleic acid) are examples of polynucleotides with distinct biological function. DNA consists of two chains of polynucleotides, with each chain in the form of a helical spiral. RNA is more often found in nature as a single-strand folded onto itself. Exemplary types of RNA include double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA).

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "RNA interference" or "RNAi" refers to a biological process in which RNA molecules inhibit gene expression or translation, by neutralizing targets mRNA molecules. Since the discovery of RNAi and its regulatory potentials, it has become evident that RNAi has immense potential in suppression of desired genes. RNAi is now known as precise, efficient, stable, and better than antisense technology for gene suppression. Two types of small ribonucleic acids molecules are central to RNA interference: miRNA and siRNA. These small RNAs can bind to mRNA molecules and either increase or decrease their activity (e.g., preventing an mRNA from being translated into a protein). The RNAi pathway is found in many eukaryotes, including animals, and is initiated by the enzyme Dicer, which cleaves long dsRNA molecules into short double-stranded fragments of ~20 nucleotide siRNAs. Each siRNA is unwound into two single-stranded RNAs (ssRNAs), the passenger strand and the guide strand. The passenger strand is degraded and the guide strand is incorporated into the RNA-induced silencing complex (RISC). The most well-studied outcome is post-transcriptional gene silencing, which occurs when the guide strand pairs with a complementary sequence in a mRNA molecule and induces cleavage by Argonaute 2 (Ago2), the catalytic component of the RISC complex. In some organisms, this process spreads systematically, despite the initially limited molar concentrations of siRNA.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The disclosure is not intended to be limited in any manner by the above exemplary listing of substituents. Additional terms may be defined in other sections of this disclosure.

BRIEF DESCRIPTION OF THE DRAWINGS

FIG. 1A shows a schematic to illustrate the advantages of using a three-dimensional combinatorial synthesis library compared to a traditional two-dimensional combinatorial library. FIG. 1B shows the isocyanide-mediated one-pot reaction. FIG. 1C shows structures of representative amines used in the synthesis library. FIG. 1D shows structures of representative isocyanides used in the synthesis library. FIG. 1E shows structures of representative ketones used in the synthesis library.

FIG. 2A: HeLa cells were treated with mLuc-loaded LNPs. The relative luciferase expression/cell viability after incubating with mLuc LNPs overnight at 0.1 mg Fluc mRNA/well (96 well plate) is shown in a heat map. Analysis of lipid tail (FIG. 2B), isocyanides (FIG. 2C) and amines (FIG. 2D) structures on transfection efficiency, quantified for the 232 well-performing lipidoids highlighted from FIG. 7. In FIG. 2B, FIG. 2C, and FIG. 2D, the y-axis represents the number of lipids that has outstanding mRNA delivery efficiency (luciferase expression to over 10,000-units). FIGS. 2E to 2G: 48 lipidoids with 2DC18 tails, Iso 4,5,6,9 were screened in BMDCs and BMDMs. Four exemplary lipidoids are highlighted. The relative luciferase expression was calculated by setting the median expression level lipidoids as Log 0 in each cell line (n=3 for HeLa cells, n=4 for BMDMs and BMDCs). FIGS. 2H to 2J show the schematic and results of the in vivo batch analysis, where (FIG. 2H) batch 1 analysis determined the optimal ketone structure (2.5 mg/kg mLuc, 120 LNP mixtures per mice); (FIG. 2I) batch 2 analysis identified the optimal isocyanide structure (0.75 mg/kg, 12 LNP mixtures per mice), and finally (FIG. 2J) batch 3 identified exemplary individual lipidoids (0.5 mg/kg mLuc/mice). All the in vivo studies presented here were dosed through s.c. injection (n=2, initial screening).

FIG. 3A: A schematic of the structure of exemplary lipidoids.

FIG. 4A shows a schematic of the structure for the second lipidoid library, where R is one of four linear amines or one of five heterocyclic amines. FIGS. 4B to 4D show ELISpot analysis of IFN-γ-spot-forming cells among splenocytes after ex vivo re-stimulation with SIINFEKLpeptide on day 10 in different NP groups (15 μg mOVA/mice, n=6 biologically independent mice/group for cyclic and linear LNPs, n=3 biologically independent mice/group for control groups). FIGS. 4E to 4G show CTL analysis of vaccinated mice (n=3 biologically independent mice/group). FIGS. 4H and 4I show FACS analysis of IFN-γ expression in CD4⁺ T cells and CD8+ T cells at indicated time points (data were subtracted by PBS treatment at Day 0). Results demonstrate long-lived CD8+ T cell response (n=3 biologically independent mice/group). FIG. 4J shows OVA-specific production of IgG in response to mOVA vaccination in various LNPs (n=6 biologically independent mice/group). Data are presented as mean±S.D.

FIG. 5A shows a schematic illustrating the process of APC activation and antigen presentation. FACS analysis of surface markers indicative of BMDC (FIGS. 5B and 5C) and APCs (FIGS. 5D and 5E) maturation, cells isolated from local LNs following treatment with cyclic LNPs (n=4 biologically independent mice/group, 15 μg mOVA/mice). FIGS. 5F to 5G show mRNA Expression levels of interferon-stimulated genes (CXCL10) at local LNs at 1,3,5 days after vaccination, quantified using quantitative polymer chain reaction (qPCR) (n=6 biologically independent mice/group). FIG. 5H shows IRF activation after incubating with LNPs (0.1 μg mOVA per well) for 24 h in different CDS reporter cells (wild type, RIG-I, MDA5, MYD88 or STING knockout) (n=4 biologically independent experiments/group). FIG. 5I shows CXCL10 protein levels measured by Bioplex ELISA in BMDCs (wild type, Stinggt/gt and Ifnαβr−/−) treated with representative cyclic and linear mOVA LNPs (1 μg mOVA RNA per well in a 12-well plate, n=4 biologically independent mice/group). FIG. 5J shows the percent of CD86+ CD11c dendritic cells in BMDCs (wild type, Stinggt/gt and Ifnαβr−/−) treated with representative cyclic and linear mOVA LNPs, measured by flow cytometry (1 μg mOVA RNA per well in a 12-well plate, n=4 biologically independent mice/group). FIG. 5K shows ELISpot Assay quantifications in different knockout mouse groups (15 μg mOVA/mice, n=4 biologically independent mice/group). FIG. 5L shows Molecular docking of A25 and A18 with hSTING. $K_D$ values are calculated from the simulation. Data are presented as mean±S.D. Statistical significance was calculated by One-way ANOVA and Dunnett's multiple comparisons test compared to untreated blank group: ** P<0.0001, *P<0.001, **P<0.01, *P<0.05. ns, not significant.

FIGS. 6A to 6F: tumor inhibition and survival curves of three different types of tumor B16F10-OVA (n=7 biologically independent mice/group per test), B16F10 (n=6 biologically independent mice/group per test), and TC-1 (n=7 biologically independent mice/group per test) treated with different therapeutic mRNA vaccines alone, or together with anti-PD-1 antibody. PBS and A18 mOVA LNPs in all three models were repeated twice (n=5 biologically independent mice/group in the second repeat, individual mice data presented in FIG. S20) with similar results. Arrows indicate the dosing schedule; 15 μg mRNA was dosed once or multiple times. Data are presented as mean±s.e.m. Two-way ANOVA combined with Tukey's multiple comparisons test was used to analyze the difference between different treatment groups. Unless stated otherwise, statistical analysis compared treatment groups and PBS controls. Survival curves were compared using Log-rank (Mantel-Cox) test. In 6B and 6E, the statistical data on the chart compares A18 Trp2 mRNA and A18 E7 mRNA+anti-PD-1 separately. * P<0.05,  P<0.01, * P<0.001, **** P<0.0001. FIGS. 6G to 6I show representative immunofluorescence staining of CD8/IFNγ killer T cells within tumor regions of untreated or vaccine-treated mice. CD8 staining is shown as green, IFNγ is shown as red, counter stain with DAPI and then merge together is shown on the left (n=5 biologically independent mice/group).

FIG. 9A: IVIS images of i.m. delivered Fluc mRNA LNPs. FIG. 9B: IVIS images of s.c. delivered Fluc mRNA LNPs. Quantifications of the images are shown in FIG. 9C. Exemplary lipidoids are listed in FIG. 9D.

FIG. 10A shows the effect of a single parameter on the in vivo delivery efficacy. FIG. 10B shows a plot depicting the model predicted value versus the actual value obtained.

FIGS. 11A-C show characterization of exemplary lipidoids derived from the first library. FIG. 11A: IVIS images of i.m. injected LNPs (5 h after injection). FIG. 11B: Characterization of delivery efficiency (n=5 biologically independent mice/group), mRNA expression kinetics (n=3 independent experiments/group), encapsulation efficiency (n=4 independent experiments/group) and particle size of the top performing lipids (n=3 independent experiments/group). There are no statistical differences among different LNPs for all these physicochemical characterizations (One-way ANOVA and Tukey's multiple comparisons test) Figure C: Tukey's multiple comparisons test. Data are presented as mean±S.D.

FIGS. 17A and 17B: IVIS images of Fluc expression in Injection Site and LNs. FIG. 17C: Quantification of mRNA delivery efficiency of the new LNPs in local injection sites (n=2 biologically independent mice/group, initial screening), draining LNs (n=2 biologically independent mice/group, initial screening), BMDCs (n=4 independent tests/group) and BMDMs (n=4 independent tests/group). Representative data from three independent experiments are presented as mean±S.D.

FIG. 21A: Histogram of mOVA loaded LNP treated BMDCs. FIG. 21B: quantification of maturation of different treatment groups. FIG. 21C: Gating of CD11c+ dendritic cells. FIG. 21D: Double staining of CD86 and MHCII (n=5).

FIGS. 22A-22E show STING protein binding assay. FIG. 22A: Schematic demonstrates the protein/lipid binding assay. FIG. 22B: LC-MS quantification of lipid bind to STING proteins. FIG. 22C shows co-localization of Rhod-LNPs with ER tracker and STING protein 3 h after incubation. FIGS. 22D and 22E show molecular docking of the head group of A2, A12, A17 and A25 with STING CTD (PDB:4EF4, 4KSY, 4QXP, respectively). Experiments were repeated twice with similar results.

Data suggest that all LNPs distributed to liver and spleen, and the clearance of U7 LNPs was faster than U4 LNPs. Data are means±SD; n=3.

Figure 36A:
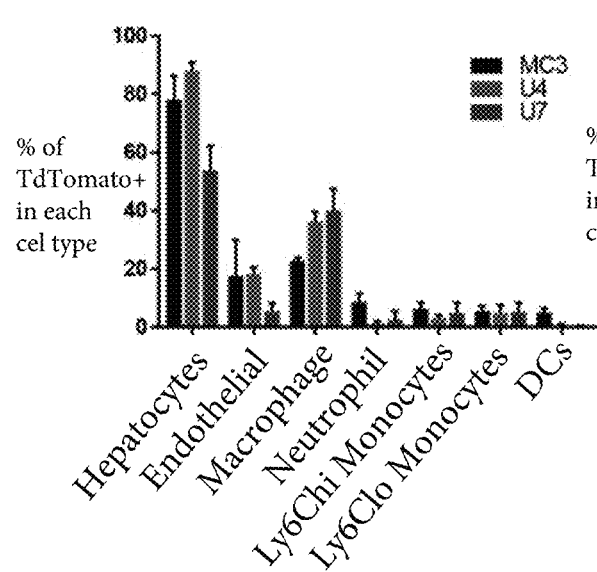
Figure 36B:
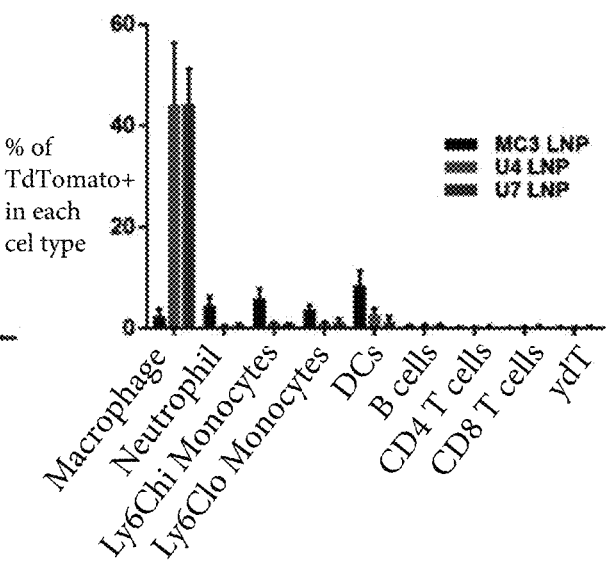

FIGS. 36A-36B show expression of mRNA delivered by LNPs in different cell types. Cre-recombinase mRNA was encapsulated into LNPs and injected into LoxP-tdTomato mice (0.75 mg/kg). Two days after injection, tdTomato expression was quantified using flow cytometry (n=4). (A) and (B) Quantifications % of tdTomato+ in each cell types (Mean±S.E.M)

DETAILED DESCRIPTION OF CERTAIN EMBODIMENTS OF THE INVENTION

Before the disclosed systems, compounds, compositions, methods, reagents, uses, and kits are described in more detail, it should be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

Provided herein are new ionizable lipidoid compounds (e.g., cationic lipidoids), compositions, kits, methods for the treatment of various diseases (e.g., genetic diseases, proliferative diseases, hematological diseases, neurological diseases, painful condition, psychiatric disorder, metabolic disorder, long-term medical condition, inflammatory diseases, autoinflammatory diseases, liver diseases, lung diseases, spleen diseases, familial amyloid neuropathy, cardiovascular diseases, viral infection, infectious diseases, fibrotic condition, or autoimmune diseases). Also provided are methods of synthesizing compounds described herein. Additionally provided are methods of using the compounds for delivering agents (e.g., RNA (e.g., mRNA)) to cells for the treatment of various diseases (e.g., genetic diseases, proliferative diseases, hematological diseases, neurological diseases, painful condition, psychiatric disorder, metabolic disorder, long-term medical condition, inflammatory diseases, autoinflammatory diseases, liver diseases, lung diseases, spleen diseases, familial amyloid neuropathy, cardiovascular diseases, viral infection, infectious diseases, fibrotic condition, or autoimmune diseases) by causing the expression of a specific gene (e.g., activating the STING pathway) in the cell.

In one aspect, disclosed are compounds of Formula (I):

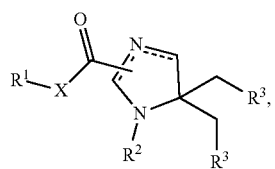

(I)

or a pharmaceutically acceptable salt, co-crystal, tautomer, stereoisomer, solvate, hydrate, polymorph, or isotopically enriched derivative thereof, wherein:

⸗ is a single or double bond, as valency allows;

X is N, O, or S;

$R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group; and each instance of $R^3$ is independently optionally substituted alkyl, optionally substituted alkenyl, or optionally substituted alkynyl; or wherein two instances of $R^3$ are taken together with their intervening atoms to form a ring.

In certain embodiments, Formula (I) is of Formula (I-A):

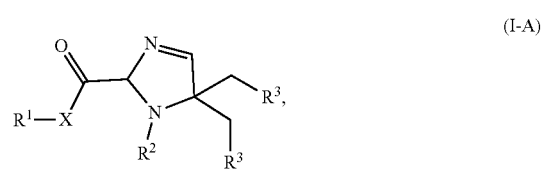

(I-A)

or a pharmaceutically acceptable salt, co-crystal, tautomer, stereoisomer, solvate, hydrate, polymorph, or isotopically enriched derivative thereof.

In certain embodiments, Formula (I) is of Formula (I-B):

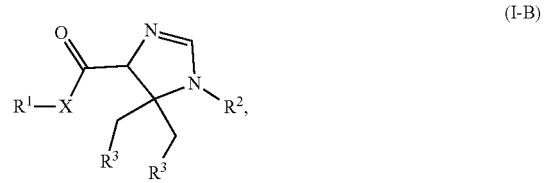

(I-B)

or a pharmaceutically acceptable salt, co-crystal, tautomer, stereoisomer, solvate, hydrate, polymorph, or isotopically enriched derivative thereof.

Formula (I) includes substituent X. In certain embodiments, X is N. In certain embodiments, X is O. In certain embodiments, X is S.

Formula (I) includes substituent $R^1$. In certain embodiments, $R^1$ is hydrogen. In certain embodiments, $R^1$ is optionally substituted acyl (e.g., —C(=O)Me). In certain embodiments, $R^1$ is optionally substituted alkyl. In certain embodiments, $R^1$ is optionally substituted $C_{1-6}$alkyl. In certain embodiments, $R^1$ is optionally substituted methyl. In certain embodiments, $R^1$ is unsubstituted methyl, unsubstituted ethyl, or unsubstituted isopropyl. In certain embodiments, $R^1$ is unsubstituted n-butyl or unsubstituted n-pentyl. In certain embodiments, $R^1$ is unsubstituted methyl. In certain embodiments, $R^1$ is substituted methyl. In certain embodiments, $R^1$ is unsubstituted methyl, unsubstituted ethyl, unsubstituted n-propyl, unsubstituted isopropyl, unsubstituted n-butyl, unsubstituted t-butyl, or unsubstituted n-pentyl. In certain embodiments, $R^1$ is unsubstituted ethyl. In certain embodiments, $R^1$ is optionally substituted ethyl. In certain embodiments, $R^1$ is unsubstituted ethyl. In certain embodiments, $R^1$ is unsubstituted ethyl. In certain embodiments, $R^1$ is unsubstituted n-propyl. In certain embodiments, $R^1$ is unsubstituted isopropyl. In certain embodiments, $R^1$ is unsubstituted n-butyl. In certain embodiments, $R^1$ is unsubstituted t-butyl. In certain embodiments, $R^1$ is unsubstituted n-pentyl. In certain embodiments, $R^1$ is of the formula: —(CH$_2$)$_n$SO$_2$R$^{1A}$, wherein n is 1, 2, 3, 4, 5, or 6; and $R^{1A}$ is optionally substituted aryl. In certain embodiments, $R^{1A}$ is optionally substituted phenyl. In certain embodiments, $R^1$ is of the formula:

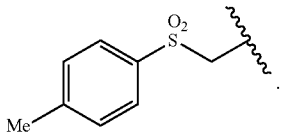

In certain embodiments, $R^1$ is optionally substituted alkenyl (e.g., substituted or unsubstituted $C_{2-6}$ alkenyl). In certain embodiments, $R^1$ is optionally substituted alkynyl (e.g., substituted or unsubstituted $C_{2-6}$ alkynyl). In certain embodiments, $R^1$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^1$ is optionally substituted cyclohexyl. In certain embodiments, $R^1$ is unsubstituted cyclohexyl. In certain embodiments, $R^1$ is

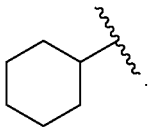 [SMILES: *C1CCCCC1]

In certain embodiments, $R^1$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^1$ is optionally substituted aryl (e.g., substituted or unsubstituted, 6- to 10-membered aryl). In certain embodiments, $R^1$ is benzyl. In certain embodiments, $R^1$ is substituted or unsubstituted phenyl. In certain embodiments, $R^1$ is unsubstituted phenyl. In certain embodiments, $R^1$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, X is O and $R^1$ is optionally substituted alkyl. In certain embodiments, X is O and $R^1$ is optionally substituted $C_{1-6}$ alkyl. In certain embodiments, X is S and $R^1$ is optionally substituted alkyl. In certain embodiments, X is S and $R^1$ is optionally substituted $C_{1-6}$ alkyl.

Formula (I) includes substituent $R^2$. In certain embodiments, $R^2$ is optionally substituted alkyl (e.g., substituted or unsubstituted $C_{1-6}$ alkyl). In certain embodiments, $R^2$ is optionally substituted $C_{1-6}$ alkyl. In certain embodiments, $R^2$ is of the formula: $-(CH_2)_nN(R^{D1a})_2$, wherein each instance of $R^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or optionally two instances of $R^{D1a}$ are taken together with their intervening atoms to form a substituted or unsubstituted heterocyclic or substituted or unsubstituted heteroaryl ring; and n is 1, 2, 3, 4, 5, or 6. In certain embodiments, $R^2$ is of the formula: $-(CH_2)_nN(R^{D1a})_2$, wherein each instance of $R^{D1a}$ is independently selected from the group consisting of hydrogen and optionally substituted alkyl; and n is 1, 2, 3, 4, 5, or 6. In certain embodiments, n is 1. In certain embodiments, n is 2. In certain embodiments, n is 3. In certain embodiments, n is 4. In certain embodiments, n is 5. In certain embodiments, n is 6. In certain embodiments, at least one instance of $R^{D1a}$ is hydrogen. In certain embodiments, at least one instance of $R^{D1a}$ is optionally substituted acyl (e.g., $-C(=O)Me$). In certain embodiments, at least one $R^{D1a}$ is substituted or unsubstituted alkyl (e.g., substituted or unsubstituted $C_{1-6}$ alkyl). In certain embodiments, at least one $R^{D1a}$ is optionally substituted $C_{1-6}$ alkyl. In certain embodiments, at least one instance of $R^{D1a}$ is optionally substituted methyl. In certain embodiments, at least one instance of $R^{D1a}$ is optionally substituted ethyl. In certain embodiments, at least one instance of $R^{D1a}$ is optionally substituted methyl or optionally substituted ethyl. In certain embodiments, at least one instance of $R^{D1a}$ is substituted or unsubstituted propyl. In certain embodiments, at least one instance of $R^{D1a}$ is substituted or unsubstituted alkenyl (e.g., substituted or unsubstituted $C_{2-6}$ alkenyl). In certain embodiments, at least one instance of $R^{D1a}$ is substituted or unsubstituted alkynyl (e.g., substituted or unsubstituted $C_{2-6}$ alkynyl). In certain embodiments, at least one instance of $R^{D1a}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{D1a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D1a}$ is substituted or unsubstituted aryl (e.g., substituted or unsubstituted, 6- to 10-membered aryl). In certain embodiments, at least one instance of $R^{D1a}$ is benzyl. In certain embodiments, at least one instance of $R^{D1a}$ is substituted or unsubstituted phenyl. In certain embodiments, at least one instance of $R^{D1a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{D1a}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{D1a}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two instances of $R^{D1a}$ are taken together with their intervening atoms to form a substituted or unsubstituted heterocyclic ring. In certain embodiments, two instances of $R^{D1a}$ are taken together with their intervening atoms to form a substituted or unsubstituted pyrrolidine ring. In certain embodiments, two instances of $R^{D1a}$ are taken together with their intervening atoms to form a substituted or unsubstituted imidazoline ring, a substituted or unsubstituted pyrazoline ring, substituted or unsubstituted piperidine ring, substituted or unsubstituted piperazine ring. In certain embodiments, $R^2$ is of the formula: —$(CH_2)_n$(substituted or unsubstituted, 5- to 10-membered monocyclic or bicyclic heterocyclic ring, wherein one or two atoms in the heterocyclic ring are independently nitrogen, oxygen, or sulfur), wherein n is 1, 2, 3, 4, 5, or 6. In certain embodiments, $R^2$ is of the formula: —$(CH_2)_n$(substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^2$ is —$(CH_2)_3$(unsubstituted pyrrolidine). In certain embodiments, $R^2$ is of the formula: —$(CH_2)_3NMe_2$, —$(CH_2)_2NMe_2$, —$(CH_2)_2N(Et)_2$, —$(CH_2)_3NH(Et)$, —$(CH_2)_3$(unsubstituted pyrrolidine). In certain embodiments, $R^2$ is of the formula: —$(CH_2)_2N(Et)_2$, —$(CH_2)_3$(unsubstituted pyrrolidine), —$(CH_2)_3NH(Et)$, —$(CH_2)_2NH(Me)$, —$(CH_2)_2NMe_2$, —$(CH_2)_3NMe_2$, or —$(CH_2)_2NMe(Et)$.

In certain embodiments, $R^2$ is of the formula: —$(CH_2)_nOR^{D1}$, wherein $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom; and n is 1, 2, 3, 4, 5, or 6. In certain embodiments, n is 1. In certain embodiments, n is 2. In certain embodiments, n is 3. In certain embodiments, n is 4. In certain embodiments, n is 5. In certain embodiments, n is 6. In certain embodiments, $R^{D1}$ is hydrogen. In certain embodiments, $R^{D1}$ is optionally substituted acyl (e.g., —C(=O)Me). In certain embodiments, $R^{D1}$ is substituted or unsubstituted alkyl (e.g., substituted or unsubstituted $C_{1-6}$ alkyl). In certain embodiments, $R^{D1}$ is optionally substituted $C_{1-6}$ alkyl. In certain embodiments, $R^{D1}$ is optionally substituted methyl. In certain embodiments, $R^{D1}$ is optionally substituted ethyl. In certain embodiments, $R^{D1}$ is optionally substituted methyl or optionally substituted ethyl. In certain embodiments, $R^{D1}$ is substituted or unsubstituted propyl. In certain embodiments, $R^{D1}$ is substituted or unsubstituted alkenyl (e.g., substituted or unsubstituted $C_{2-6}$ alkenyl). In certain embodiments, $R^{D1}$ is substituted or unsubstituted alkynyl (e.g., substituted or unsubstituted $C_{2-6}$ alkynyl). In certain embodiments, $R^{D1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{D1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D1}$ is substituted or unsubstituted aryl (e.g., substituted or unsubstituted, 6- to 10-membered aryl). In certain embodiments, $R^{D1}$ is benzyl. In certain embodiments, $R^{D1}$ is substituted or unsubstituted phenyl. In certain embodiments, $R^{D1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{D1}$ is an oxygen protecting group when attached to an oxygen atom (e.g., methyl, methoxylmethyl (MOM), trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS)). In certain embodiments, $R^2$ is of the formula: —$(CH_2)_2OH$. In certain embodiments, $R^2$ is of the formula: —$(CH_2)_nOR^{D1}$, wherein $R^{D1}$ is independently selected from hydrogen and optionally substituted alkyl; and n is 1, 2, 3, 4, 5, or 6. In certain embodiments, $R^2$ is of the formula: —$(CH_2)_nOR^{D1}$, wherein $R^{D1}$ is independently selected from hydrogen and optionally substituted $C_{1-6}$ alkyl; and n is 1, 2, 3, 4, 5, or 6.

In certain embodiments, $R^2$ is substituted or unsubstituted methyl. In certain embodiments, $R^2$ is substituted or unsubstituted ethyl. In certain embodiments, $R^2$ is unsubstituted ethyl. In certain embodiments, $R^2$ is substituted or unsubstituted propyl. In certain embodiments, $R^2$ is unsubstituted n-propyl. In certain embodiments, $R^2$ is unsubstituted methyl or isopropyl. In certain embodiments, $R^2$ is optionally substituted alkenyl (e.g., substituted or unsubstituted $C_{2-6}$ alkenyl). In certain embodiments, $R^2$ is optionally substituted alkynyl (e.g., substituted or unsubstituted $C_{2-6}$ alkynyl). In certain embodiments, $R^2$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^2$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^2$ is optionally substituted aryl (e.g., substituted or unsubstituted, 6- to 10-membered aryl). In certain embodiments, $R^2$ is benzyl. In certain embodiments, $R^2$ is substituted or unsubstituted phenyl. In certain embodiments, $R^2$ is unsubstituted phenyl. In certain embodiments, $R^2$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^2$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (I) includes two instances of substituent $R^3$. In certain embodiments, both instances of $R^3$ are the same. In certain embodiments, each instance of $R^3$ is different. In certain embodiments, at least one instance of $R^3$ is optionally substituted alkyl (e.g., substituted or unsubstituted $C_{1-30}$ alkyl). In certain embodiments, at least one instance of $R^3$ is optionally substituted $C_{4-30}$ alkyl. In certain embodiments, at least one instance of $R^3$ is optionally substituted $C_{4-24}$ alkyl. In certain embodiments, both instances of $R^3$ are each optionally substituted $C_{4-24}$ alkyl. In certain embodiments, at least one instance of $R^3$ is optionally substituted $C_{4-12}$ alkyl.

In certain embodiments, at least one instance of $R^3$ is unsubstituted $C_{4-12}$ alkyl. In certain embodiments, at least one instance of $R^3$ is optionally substituted $C_{12-24}$ alkyl. In certain embodiments, at least one instance of $R^3$ is optionally substituted $C_{12-20}$ alkyl. In certain embodiments, at least one instance of $R^3$ is optionally substituted $C_{10-24}$ alkyl. In certain embodiments, at least one instance of $R^3$ is unsubstituted $C_{12-24}$ alkyl. In certain embodiments, at least one instance of $R^3$ is unsubstituted n-butyl, unsubstituted n-pentyl, unsubstituted n-hexyl, unsubstituted n-heptyl, unsubstituted n-octyl, or unsubstituted n-nonyl.

In certain embodiments, at least one instance of $R^3$ is optionally substituted alkenyl (e.g., substituted or unsubstituted $C_{2-6}$ alkenyl). In certain embodiments, at least one instance of $R^3$ is optionally substituted alkenyl. In certain embodiments, at least one instance of $R^3$ is optionally substituted $C_{12-24}$ alkenyl. In certain embodiments, at least one instance of $R^3$ is optionally substituted $C_{12-20}$ alkenyl. In certain embodiments, at least one instance of $R^3$ is optionally substituted $C_{14-20}$ alkenyl. In certain embodiments, at least one instance of $R^3$ is of the formula:

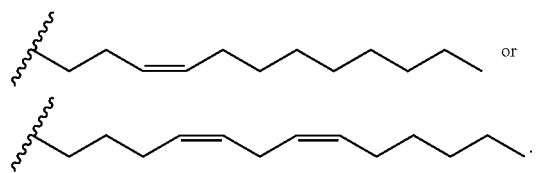

or

In certain embodiments, at least one instance of $R^3$ is of the formula:

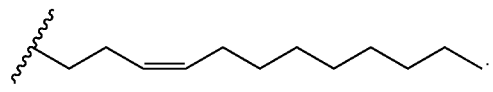 [SMILES: *CC/C=C\CCCCCCCC]

In certain embodiments, both instances of $R^3$ are of the formula:

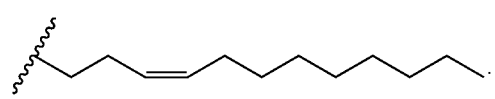 [SMILES: *CC/C=C\CCCCCCCC]

In certain embodiments, at least one instance of $R^3$ is of the formula:

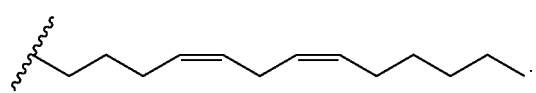

In certain embodiments, both instances of $R^3$ are of the formula:

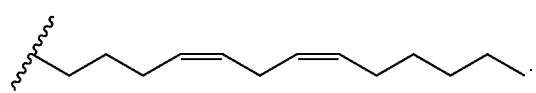 [SMILES: *CCC/C=C\C/C=C\CCCCC]

In certain embodiments, at least one instance of $R^3$ is optionally substituted alkynyl (e.g., substituted or unsubstituted $C_{2-6}$ alkynyl). In certain embodiments, two instances of $R^3$ are taken together with their intervening atoms to form a ring. In certain embodiments, two instances of $R^3$ are taken together with their intervening atoms to form a substituted or unsubstituted carbocyclyl ring. In certain embodiments, two instances of $R^3$ are taken together with their intervening atoms to form a substituted or unsubstituted $C_{6-30}$ carbocyclyl ring. In certain embodiments, two instances of $R^3$ are taken together with their intervening atoms to form a substituted or unsubstituted $C_{12-30}$ carbocyclyl ring. In certain embodiments, two instances of $R^3$ are taken together with their intervening atoms to form a substituted or unsubstituted $C_{12-24}$ carbocyclyl ring. In certain embodiments, two instances of $R^3$ are taken together with their intervening atoms to form a substituted or unsubstituted $C_{12-15}$ carbocyclyl ring. In certain embodiments, two instances of $R^3$ are taken together with their intervening atoms to form a substituted or unsubstituted $C_{10}$ carbocyclyl ring, substituted or unsubstituted $C_{11}$ carbocyclyl ring, substituted or unsubstituted $C_{12}$ carbocyclyl ring, substituted or unsubstituted $C_{13}$ carbocyclyl ring, substituted or unsubstituted $C_{14}$ carbocyclyl ring, substituted or unsubstituted $C_{15}$ carbocyclyl ring, substituted or unsubstituted $C_{16}$ carbocyclyl ring, substituted or unsubstituted $C_{17}$ carbocyclyl ring, substituted or unsubstituted $C_{18}$ carbocyclyl ring, substituted or unsubstituted $C_{19}$ carbocyclyl ring, or substituted or unsubstituted $C_{20}$ carbocyclyl ring. In certain embodiments, two instances of $R^3$ are taken together with their intervening atoms to form a ring of formula:

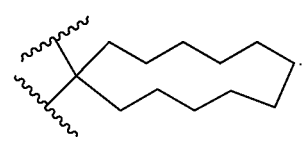 [SMILES: *C1(*)CCCCCCCCCCC1]

In certain embodiments, two instances of $R^3$ are taken together with their intervening atoms to form a ring of formula:

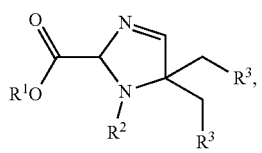

In certain embodiments, the compound of Formula (I) is of the formula:

or a pharmaceutically acceptable salt, co-crystal, tautomer, stereoisomer, solvate, hydrate, polymorph, or isotopically enriched derivative thereof.

In certain embodiments, Formula (I) is of the formula:

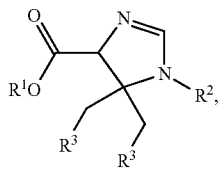

or a pharmaceutically acceptable salt, co-crystal, tautomer, stereoisomer, solvate, hydrate, polymorph, or isotopically enriched derivative thereof.

In certain embodiments, the compound of Formula (I) is of the formula:

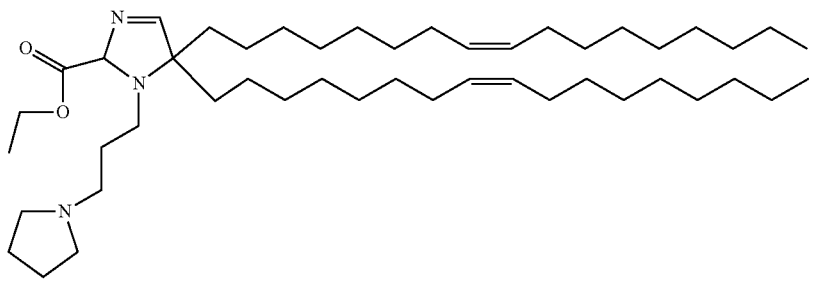

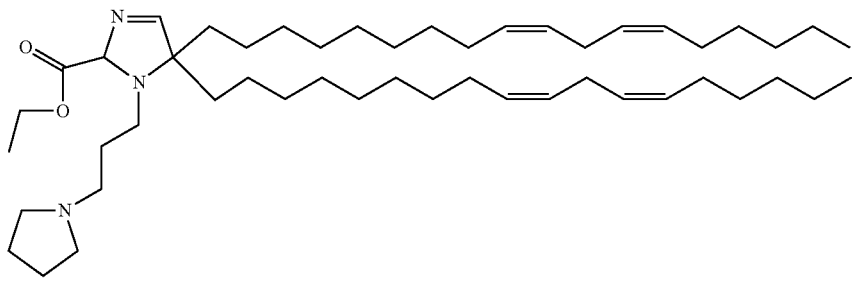

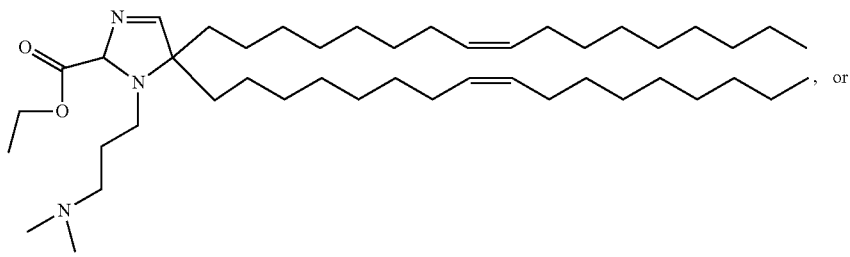

, or

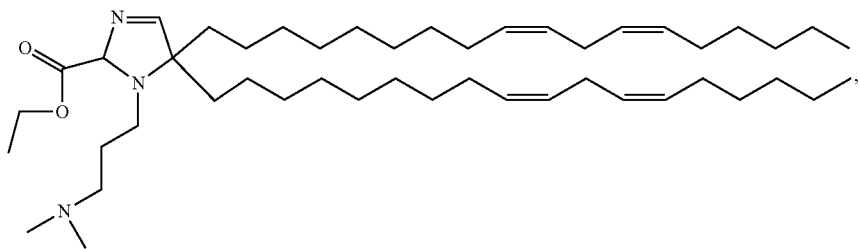

or a pharmaceutically acceptable salt, co-crystal, tautomer, stereoisomer, solvate, hydrate, polymorph, or isotopically enriched derivative thereof.

Figure 33:
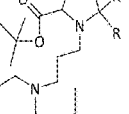
FIG. 33 shows characterization data for representative LNPs.
Figure 33:
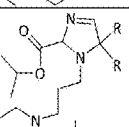
Figure 33:
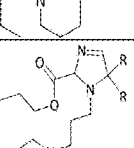
Figure 33:
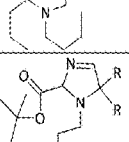
Figure 33:
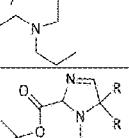
Figure 33:
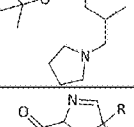
Figure 33:
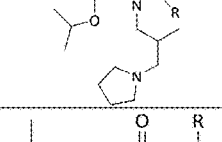
Figure 34A:
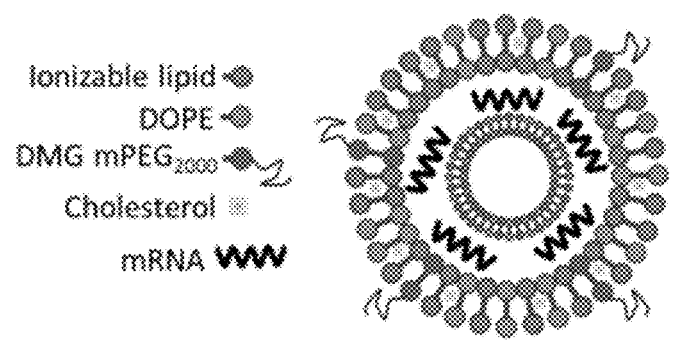
FIGS. 34A-34E show In vitro and in vivo screening of lipidoids for mRNA delivery. (A) Schematic representation of LNPs. (B) HeLa cells were treated with mLuc-loaded LNPs. The relative luciferase expression/cell viability after incubating with mLuc LNPs overnight at 0.1 mg FLuc mRNA/well is presented in a heat map (n=3). Particularly well-performing LNPs (high transfection efficiency, low toxicity) are highlighted in rectangle boxes. (C) Exemplary lipidoids screened from HeLa cell lines were purified and formulated to encapsulate mRNA encoding hEPO. The mEPO LNPs were intravenously injected into C57BL/6 mice. Six hour after injection, serum was collected from the treated mice. The amount of EPO protein that synthesized and secreted into serum was analyzed and compared using hEPO ELISA kit. Data are presented as mean±SD; n=4; the high-performance candidates lipidoids are highlighted in red. (D) Representative Cryo-TEM images of U4 nanoparticles. (E) Chemical structure of U4, U7, U5 and U10.
Figure 34B:
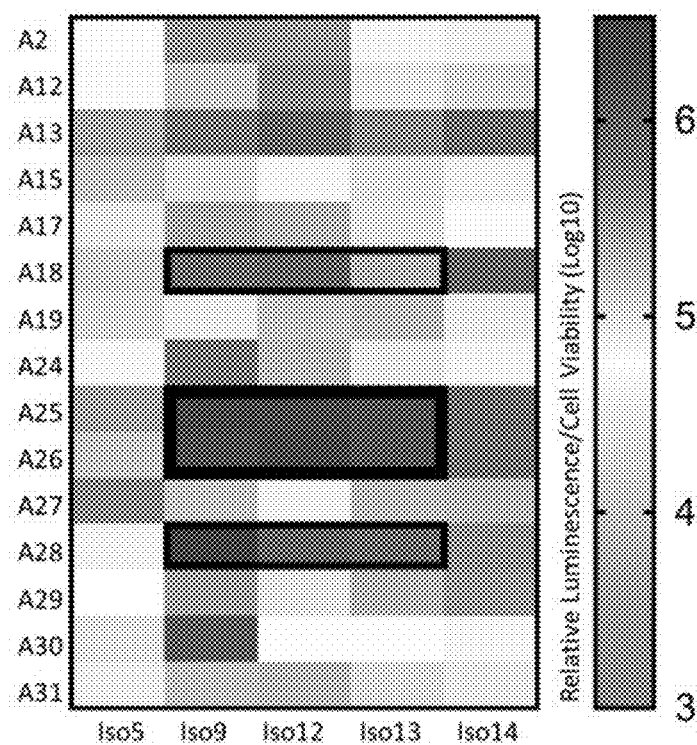
Figure 34C:
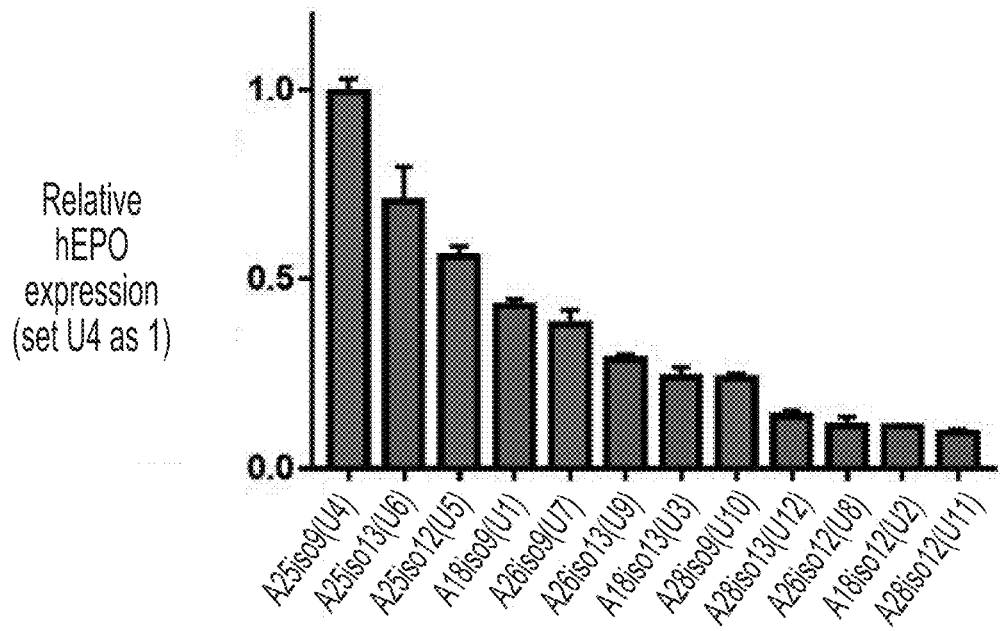
Figure 34D:
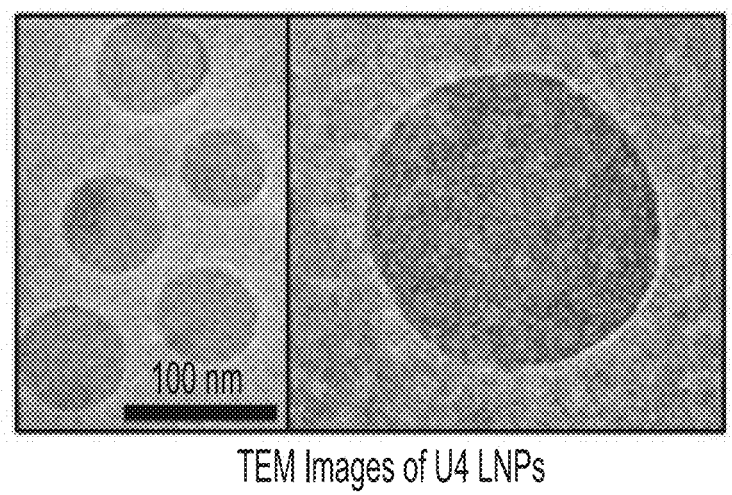
Figure 34E:
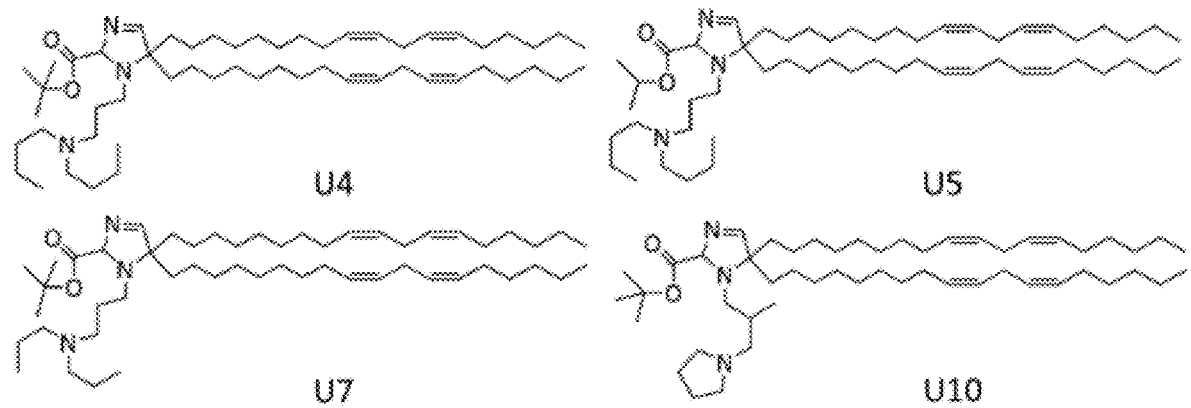
Figure 35A:
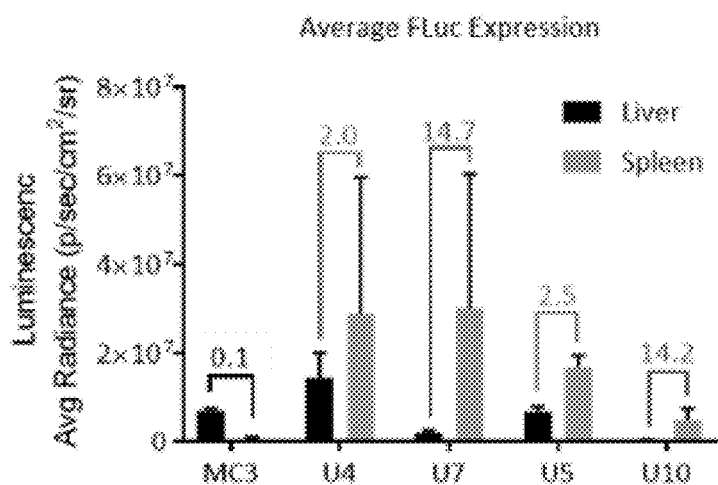
FIGS. 35A-35E show In vivo expression and bio-distribution of LNP candidates. Candidate LNPs were formulated to encapsulate hEPO mRNA and injected intravenously into C57BL/6 mice at different dosages (0.75, 1.5 and 2.25 mg/kg, respectively). Expression of hEPO was evaluated 6 h after injection by using ELISA. (A) Time-dependent expression of mEPO LNPs. Same LNPs were dosed at 1.5 mg/kg. hEPO expression was quantified at different time points. (B) Candidate LNPs were formulated to encapsulate luciferase mRNA and injected intravenously into C57BL/6 mice. Expression of luciferase was evaluated 6 h after injection using IVIS imaging, and quantifications were shown in (C). Major expression of mRNA was found in liver and spleen. U4 and U5 have higher or similar mRNA expression as compared to the control MC3, whereas U7 and U10 were mainly expressed in spleen. Data are means±SD; n=4. (D) Distribution of LNPs were determined by encapsulating Cy-5 labeled mRNA. At predetermined time points (1 and 4 h) post injection, major organs were collected and imaged using IVIS, the quantifications are shown on (E).
Figure 35B:
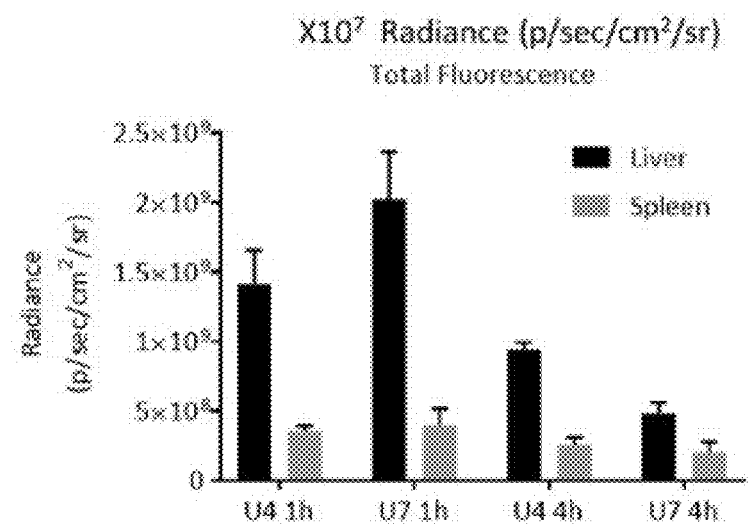
Figure 35C:
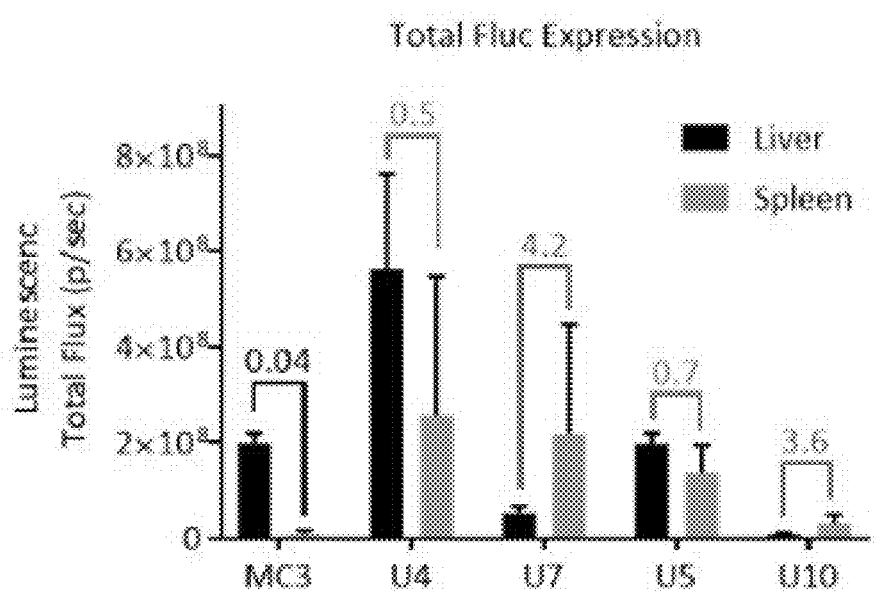
Figure 35D:
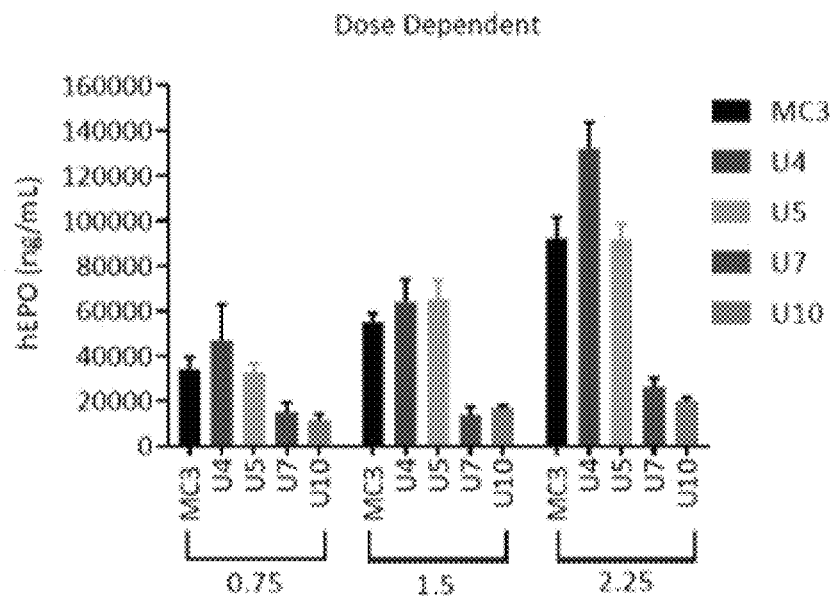
Figure 35E:
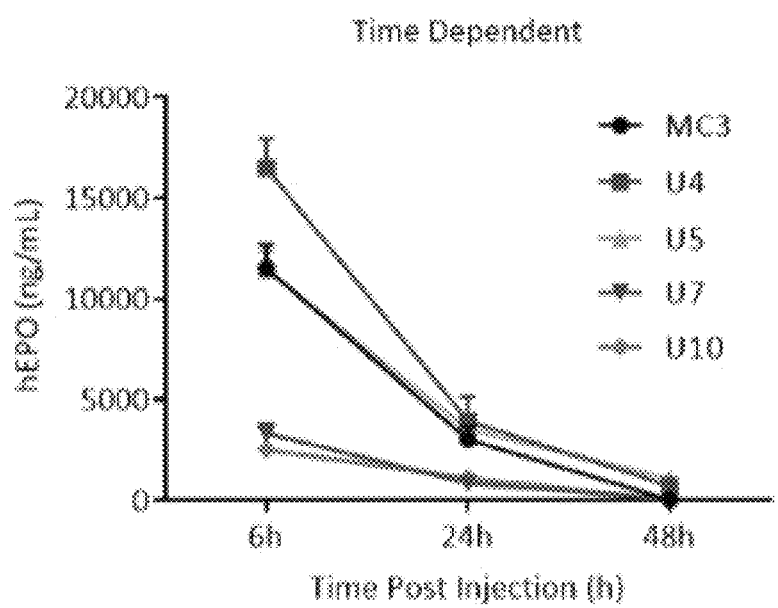

In certain embodiments, the compound of Formula (I) is of a formula selected from FIG. 33.

In certain embodiments, the compound of Formula (I) is a compound provided in any one of the Examples below. In certain embodiments, the compound of Formula (I) is a compound provided in Example 1 below. In certain embodiments, the compound of Formula (I) is a compound provided in Example 2 below. In certain embodiments, the compound of Formula (I) is a cyclic compound that is a product of the three-component synthesis disclosed in FIG. 1B using the amine, isocyanide, and alkyl ketone components disclosed in FIG. 1C. In certain embodiments, the compound of Formula (I) is a cyclic compound that is a product of the three-component synthesis disclosed in FIG. 1B using the amine, isocyanide, and alkyl ketone components disclosed below in Table A or Table B.

TABLE A

Amine, Isocyanide, and Alkyl Ketone Components for Lipidoid Synthesis

Amines

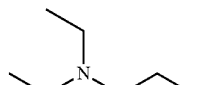 A1

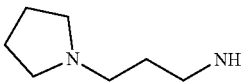 A2

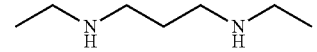 A3

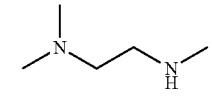 A4

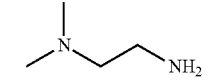 A5

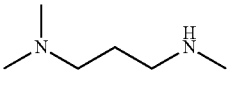 A6

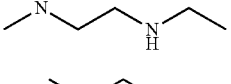 A7

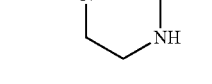 A8

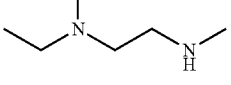 A9

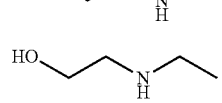 A10

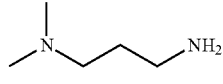 A11

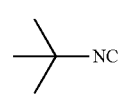 A12

Isocyanides

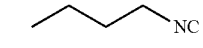 Iso1

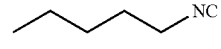 Iso2

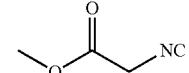 Iso3

TABLE A-continued

Amine, Isocyanide, and Alkyl Ketone Components for Lipidoid Synthesis

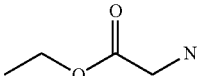 Iso4

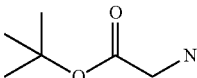 Iso5

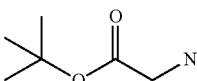 Iso6

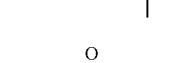 Iso7

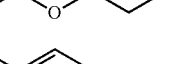 Iso8

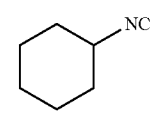 Iso9

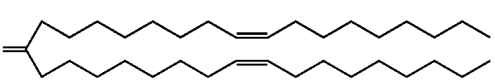 Iso10

Alkyl Ketones

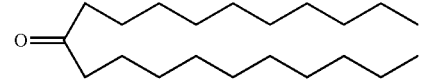 [SMILES: CCCCCCCCCCC(=O)CCCCCCCCCC] 2DC18

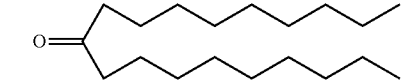 [SMILES: CCCCCCCCCC(=O)CCCCCCCCC] C11

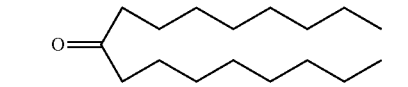 [SMILES: CCCCCCCCC(=O)CCCCCCCC] C10

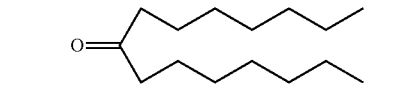 [SMILES: CCCCCCCC(=O)CCCCCCC] C9

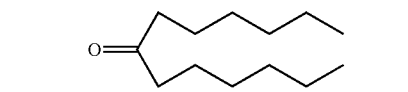 C8

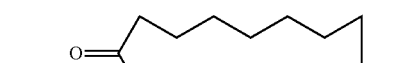 C7

CC7

TABLE A-continued

Amine, Isocyanide, and Alkyl Ketone Components for Lipidoid Synthesis

TABLE B

Amine, Isocyanide, and Alkyl Ketone Components for Lipidoid Synthesis

TABLE B-continued

Amine, Isocyanide, and Alkyl Ketone Components for Lipidoid Synthesis

In another aspect, disclosed are compounds of Formula (II):

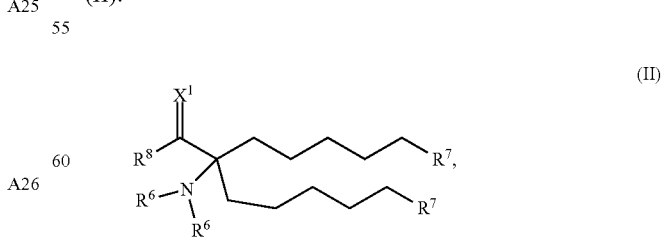

(II)

or a pharmaceutically acceptable salt, co-crystal, tautomer, stereoisomer, solvate, hydrate, polymorph, or isotopically enriched derivative thereof, wherein:

$X^1$ is =$NR^5$ or =O;

$R^5$ is hydrogen, optionally substituted alkyl, optionally substituted alkenyl, optionally substituted alkynyl, optionally substituted heteroalkyl, optionally substituted carbocyclyl, optionally substituted heterocyclyl, optionally substituted aryl, or optionally substituted heteroaryl, or a nitrogen protecting group;

each instance of $R^6$ is independently hydrogen, optionally substituted alkyl, optionally substituted alkenyl, optionally substituted alkynyl, optionally substituted heteroalkyl, optionally substituted carbocyclyl, optionally substituted heterocyclyl, optionally substituted aryl, or optionally substituted heteroaryl; or two instances of $R^6$ are taken together with their intervening atoms to form a substituted or unsubstituted heterocyclic or substituted or unsubstituted heteroaryl ring; and each instance of $R^7$ is independently hydrogen, optionally substituted alkyl, optionally substituted alkenyl, optionally substituted alkynyl, optionally substituted heteroalkyl, optionally substituted carbocyclyl, optionally substituted heterocyclyl, optionally substituted aryl, optionally substituted heteroaryl, or nitrogen protecting group; or wherein two instances of $R^7$ are taken together with their intervening atoms to form a ring; and $R^8$ is hydrogen, —$OR^5$, or —$NH(R^5)$.

In certain embodiments, Formula (II) is of Formula (II-A):

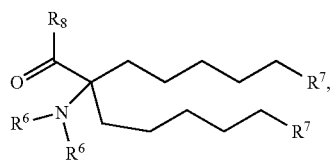

(II-A)

or a pharmaceutically acceptable salt, co-crystal, tautomer, stereoisomer, solvate, hydrate, polymorph, or isotopically enriched derivative thereof.

In certain embodiments, Formula (II) is of Formula (II-B):

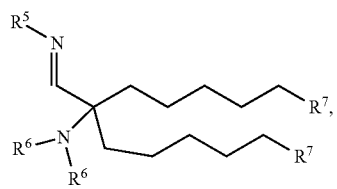

(II-B)

or a pharmaceutically acceptable salt, co-crystal, tautomer, stereoisomer, solvate, hydrate, polymorph, or isotopically enriched derivative thereof.

Formula (II) includes substituent $X^1$. In certain embodiments, $X^1$ is =O. In certain embodiments, $X^1$ is =$NR^5$. In certain embodiments, $R^5$ is hydrogen. In certain embodiments, $R^5$ is substituted or unsubstituted alkyl (e.g., substituted or unsubstituted $C_{1-6}$ alkyl). In certain embodiments, $R^5$ is optionally substituted $C_{1-6}$alkyl. In certain embodiments, $R^5$ is substituted or unsubstituted methyl. In certain embodiments, $R^5$ is optionally substituted ethyl. In certain embodiments, $R^5$ is unsubstituted ethyl. In certain embodiments, $R^5$ is unsubstituted ethyl. In certain embodiments, $R^5$ is unsubstituted n-propyl. In certain embodiments, $R^5$ is unsubstituted isopropyl. In certain embodiments, $R^5$ is unsubstituted n-butyl. In certain embodiments, $R^5$ is unsubstituted t-butyl. In certain embodiments, $R^5$ is unsubstituted n-pentyl. In certain embodiments, $R^5$ is of the formula: —$(CH_2)_nCOOR^{14}$, wherein n is 1, 2, 3, 4, 5, or 6; and $R^{14}$ is optionally substituted $C_{1-6}$ alkyl. In certain embodiments, $R^5$ is of the formula: —(CH)MeCOOR$^{14}$, wherein n is 1, 2, 3, 4, 5, or 6; and $R^{14}$ is optionally substituted $C_{1-6}$ alkyl. In certain embodiments, n is 1. In certain embodiments, n is 2. In certain embodiments, n is 3. In certain embodiments, n is 4. In certain embodiments, n is 5. In certain embodiments, n is 6. In certain embodiments, $R^5$ is of the formula:

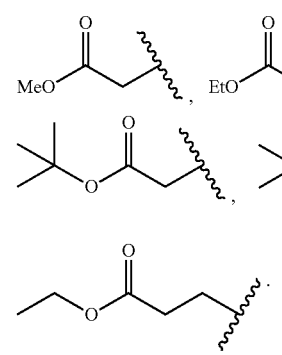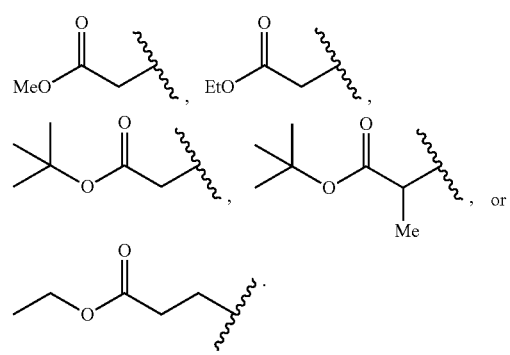

In certain embodiments, $R^5$ is of the formula: —$(CH_2)_nSO_2R^{14}$, wherein n is 1, 2, 3, 4, 5, or 6; and $R^{14}$ is optionally substituted aryl. In certain embodiments, $R^{14}$ is optionally substituted phenyl. In certain embodiments, $R^5$ is of the formula:

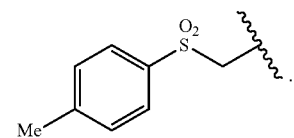

In certain embodiments, $R^5$ is of the formula: unsubstituted methyl, unsubstituted ethyl, unsubstituted isopropyl, unsubstituted n-butyl, unsubstituted n-pentyl,

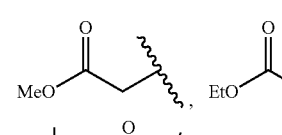

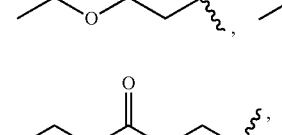

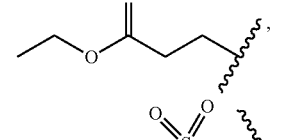

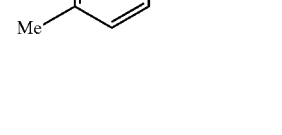

-continued

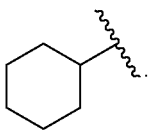

In certain embodiments, $R^5$ is unsubstituted methyl. In certain embodiments, $R^5$ is substituted or unsubstituted ethyl. In certain embodiments, $R^5$ is substituted or unsubstituted propyl. In certain embodiments, $R^5$ is substituted or unsubstituted isopropyl. In certain embodiments, $R^5$ is unsubstituted isopropyl. In certain embodiments, $R^5$ is substituted or unsubstituted n-butyl. In certain embodiments, $R^5$ is unsubstituted n-butyl. In certain embodiments, $R^5$ is substituted or unsubstituted n-pentyl. In certain embodiments, $R^5$ is unsubstituted n-pentyl. In certain embodiments, $R^5$ is optionally substituted alkenyl (e.g., substituted or unsubstituted $C_{2-6}$ alkenyl). In certain embodiments, $R^5$ is optionally substituted alkynyl (e.g., substituted or unsubstituted $C_{2-6}$ alkynyl). In certain embodiments, $R^5$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^5$ is optionally substituted cyclohexyl. In certain embodiments, $R^5$ is

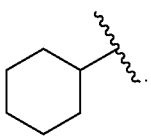

,

In certain embodiments, $R^5$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^5$ is optionally substituted aryl (e.g., substituted or unsubstituted, 6- to 10-membered aryl). In certain embodiments, $R^5$ is benzyl. In certain embodiments, $R^5$ is substituted or unsubstituted phenyl. In certain embodiments, $R^5$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^5$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (II) includes two instances of substituent $R^6$. In certain embodiments, both instances of $R^6$ are the same. In certain embodiments, each instance of $R^6$ is different. In certain embodiments, at least one instance of $R^6$ is hydrogen. In certain embodiments, at least one instance of $R^6$ is optionally substituted alkyl. In certain embodiments, at least one instance of $R^6$ is optionally substituted $C_{1-6}$alkyl. In certain embodiments, at least one instance of $R^6$ is optionally substituted methyl. In certain embodiments, at least one instance of $R^6$ is of the formula: $-(CH_2)_nN(R^{D1a})_2$, wherein each instance of $R^{D1a}$ is independently selected from the group consisting of hydrogen, optionally substituted alkyl, optionally substituted alkenyl, optionally substituted alkynyl, optionally substituted heteroalkyl, optionally substituted carbocyclyl, optionally substituted heterocyclyl, optionally substituted aryl, optionally substituted heteroaryl, and a nitrogen protecting group; or optionally two instances of $R^{D1a}$ are taken together with their intervening atoms to form a substituted or unsubstituted heterocyclic or substituted or unsubstituted heteroaryl ring; and n is 1, 2, 3, 4, 5, or 6. The definition of $R^{D1a}$ is the same as discussed above with reference to substituent $R^2$. In certain embodiments, at least one instance of $R^6$ is of the formula: $-(CH_2)_nN(R^{D1a})_2$, wherein each instance of $R^{D1a}$ is independently selected from the group consisting of hydrogen and optionally substituted alkyl; and n is 1, 2, 3, 4, 5, or 6. In certain embodiments, at least one instance of $R^6$ is of the formula: $-(CH_2)_n$(substituted or unsubstituted, 5- to 10-membered monocyclic or bicyclic heterocyclic ring, wherein one or two atoms in the heterocyclic ring are independently nitrogen, oxygen, or sulfur); wherein n is 1, 2, 3, 4, 5, or 6. In certain embodiments, at least one instance of $R^6$ is of the formula: $-(CH_2)_n$(substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^6$ is of the formula: $-(CH_2)_3NMe_2$, $-(CH_2)_2NMe_2$, $-(CH_2)_2N(Et)_2$, $-(CH_2)_3NH(Et)$, or $-(CH_2)_3$(unsubstituted pyrrolidine). In certain embodiments, at least one instance of $R^6$ is of the formula: $-(CH_2)_2N(Et)_2$, $-(CH_2)_3$(unsubstituted pyrrolidine), $-(CH_2)_3NH(Et)$, $-(CH_2)_2NH(Me)$, $-(CH_2)_2NMe_2$, $-(CH_2)_3NMe_2$, or $-(CH_2)_2NMe(Et)$. In certain embodiments, at least one instance of $R^6$ is of the formula: $-(CH_2)_nOR^{D1}$, wherein $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom; and n is 1, 2, 3, 4, 5, or 6. In certain embodiments, n is 1. In certain embodiments, n is 2. In certain embodiments, n is 3. In certain embodiments, n is 4. In certain embodiments, n is 5. In certain embodiments, n is 6. The definition of $R^{D1}$ is the same as discussed above with reference to substituent $R^2$. In certain embodiments, at least one instance of $R^6$ is of the formula: $-(CH_2)_nOR^{D1}$, wherein $R^{D1}$ is independently selected from hydrogen and optionally substituted alkyl; and n is 1, 2, 3, 4, 5, or 6. In certain embodiments, $R^2$ is of the formula: $-(CH_2)_nOR^{D1}$, wherein $R^{D1}$ is independently selected from hydrogen and optionally substituted $C_{1-6}$ alkyl; and n is 1, 2, 3, 4, 5, or 6. In certain embodiments, at least one instance of $R^6$ is of the formula: $-(CH_2)_2OH$. In certain embodiments, at least one instance of $R^6$ is unsubstituted methyl, unsubstituted ethyl, or unsubstituted isopropyl. In certain embodiments, at least one instance of $R^6$ is unsubstituted n-butyl or unsubstituted n-pentyl. In certain embodiments, $R^6$ is unsubstituted methyl. In certain embodiments, at least one instance of $R^6$ is substituted methyl. In certain embodiments, at least one instance of $R^6$ is optionally substituted alkenyl (e.g., substituted or unsubstituted $C_{2-6}$ alkenyl). In certain embodiments, at least one instance of $R^6$ is optionally substituted alkynyl (e.g., substituted or unsubstituted $C_{2-6}$ alkynyl). In certain embodiments, at least one instance of $R^6$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^6$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^6$ is optionally substituted aryl (e.g., substituted or unsubstituted, 6- to 10-membered aryl). In certain embodiments, at least one instance of $R^6$ is benzyl. In certain embodiments, at least one instance of $R^6$ is substituted or unsubstituted phenyl. In certain embodiments, at least one instance of $R^6$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two instances of $R^6$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (II) includes two instances of substituent $R^7$. In certain embodiments, both instances of $R^7$ are the same. In certain embodiments, each instance of $R^7$ is different. In certain embodiments, at least one instance of $R^7$ is hydrogen. In certain embodiments, at least one instance of $R^7$ is optionally substituted alkyl. In certain embodiments, at least one instance of $R^7$ is optionally substituted $C_{1-6}$ alkyl. In certain embodiments, at least one instance of $R^7$ is optionally substituted $C_{1-10}$ alkyl. In certain embodiments, at least one instance of $R^7$ is unsubstituted $C_{1-10}$ alkyl. In certain embodiments, at least one instance of $R^7$ is methyl, ethyl, n-propyl, n-butyl, or n-pentyl. In certain embodiments, at least one instance of $R^7$ is unsubstituted $C_{4-12}$ alkyl. In certain embodiments, at least one instance of $R^7$ is unsubstituted $C_{12-20}$ alkyl. In certain embodiments, at least one instance of $R^7$ is unsubstituted $C_{10-20}$ alkyl. In certain embodiments, at least one instance of $R^7$ is optionally substituted $C_{4-24}$ alkyl. In certain embodiments, at least one instance of $R^7$ is optionally substituted $C_{4-20}$ alkyl. In certain embodiments, wherein both instances of $R^7$ are each optionally substituted $C_{4-20}$ alkyl.

In certain embodiments, at least one instance of $R^7$ is optionally substituted alkenyl. In certain embodiments, at least one instance of $R^7$ is optionally substituted $C_{6-20}$ alkenyl. In certain embodiments, at least one instance of $R^7$ is optionally substituted $C_{10-20}$ alkenyl. In certain embodiments, at least one instance of $R^7$ is optionally substituted $C_{10-15}$ alkenyl. In certain embodiments, at least one instance of $R^7$ is optionally substituted $C_{10}$ alkenyl, optionally substituted $C_{11}$ alkenyl, optionally substituted $C_{12}$ alkenyl, optionally substituted $C_{13}$ alkenyl, optionally substituted $C_{14}$ alkenyl, optionally substituted $C_{15}$ alkenyl, or optionally substituted $C_{16}$ alkenyl. In certain embodiments, at least one instance of $R^7$ is unsubstituted $C_{12}$ alkenyl or unsubstituted $C_{13}$ alkenyl. In certain embodiments, at least one instance of $R^7$ is unsubstituted $C_{12}$ alkenyl. In certain embodiments, at least one instance of $R^7$ is unsubstituted $C_{13}$ alkenyl. In certain embodiments, at least one instance of $R^7$ is optionally substituted $C_{12-24}$ alkenyl. In certain embodiments, at least one instance of $R^7$ is of the formula:

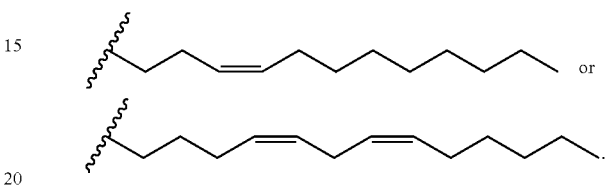

In certain embodiments, at least one instance of $R^7$ is of the formula:

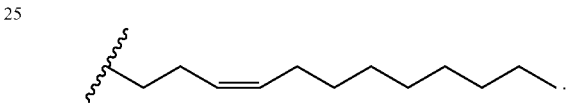

In certain embodiments, at least one instance of $R^7$ is of the formula:

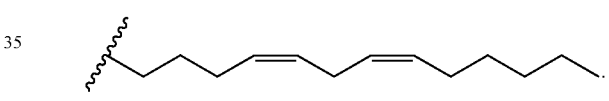

In certain embodiments, both instances of $R^7$ are of the formula:

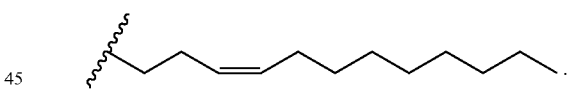

In certain embodiments, both instances of $R^7$ are of the formula:

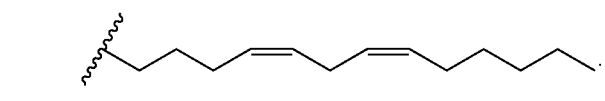

In certain embodiments, at least one instance of $R^7$ is optionally substituted alkynyl (e.g., substituted or unsubstituted $C_{2-6}$ alkynyl). In certain embodiments, at least one instance of $R^7$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^7$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^7$ is optionally substituted aryl (e.g., substituted or unsubstituted, 6- to 10-membered, aryl). In certain embodiments, at least one instance of $R^7$ is benzyl. In certain embodiments, at least one instance of $R^7$ is substituted or unsubstituted phenyl. In certain embodiments, at least one instance of $R^7$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two instances of $R^7$ are taken together with their intervening atoms to form a substituted or unsubstituted ring. In certain embodiments, two instances of $R^7$ are taken together with their intervening atoms to form a substituted or unsubstituted carbocyclic ring.

Formula (II-A) includes substituent $R^8$. In certain embodiments, $R^8$ is hydrogen. In certain embodiments, $R^8$ is —$OR^5$. Substituent $R^5$ is defined above. In certain embodiments, $R^8$ is —$OR^5$, wherein $R^5$ is optionally substituted alkyl. In certain embodiments, $R^8$ is —$OR^5$, wherein $R^5$ is optionally substituted $C_{1-10}$ alkyl. In certain embodiments, $R^8$ is —$NH(R^5)$. In certain embodiments, $R^8$ is —$NH(R^5)$, wherein $R^5$ is optionally substituted alkyl. In certain embodiments, $R^8$ is —$NH(R^5)$, wherein $R^5$ is optionally substituted $C_{1-10}$ alkyl. In certain embodiments, $R^8$ is —$NH(R^5)$, wherein $R^5$ is optionally substituted carbocyclyl. In certain embodiments, $R^5$ is of the formula: —$(CH_2)_nCOOR^{14}$, wherein n is 1, 2, 3, 4, 5, or 6; and $R^{14}$ is optionally substituted $C_{1-6}$alkyl. In certain embodiments, $R^5$ is of the formula: —$(CH)MeCOOR^{14}$, wherein n is 1, 2, 3, 4, 5, or 6; and $R^{14}$ is optionally substituted $C_{1-6}$alkyl. In certain embodiments, n is 1. In certain embodiments, n is 2. In certain embodiments, n is 3. In certain embodiments, n is 4. In certain embodiments, n is 5. In certain embodiments, n is 6. In certain embodiments, $R^5$ is of the formula:

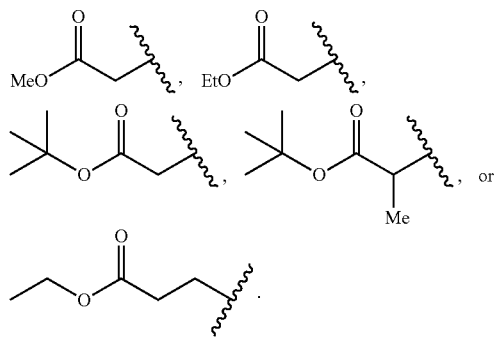

In certain embodiments, $R^5$ is of the formula: —$(CH_2)_nSO_2R^{14}$, wherein n is 1, 2, 3, 4, 5, or 6; and $R^{14}$ is optionally substituted aryl. In certain embodiments, $R^{14}$ is optionally substituted phenyl. In certain embodiments, $R^5$ is of the formula:

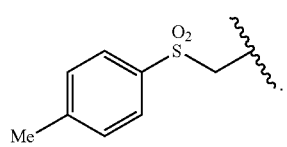 [SMILES: *CS(=O)(=O)c1ccc(C)cc1]

In certain embodiments, $R^5$ is of the formula: unsubstituted isopropyl, unsubstituted n-butyl, unsubstituted n-pentyl,

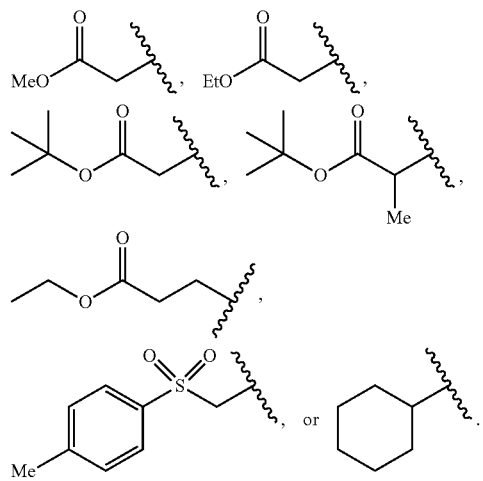

In certain embodiments, the compound of Formula (II) is of the formula:

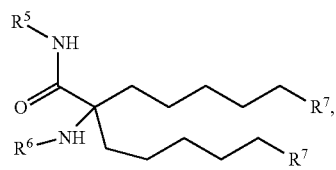

or a pharmaceutically acceptable salt, co-crystal, tautomer, stereoisomer, solvate, hydrate, polymorph, or isotopically enriched derivative thereof.

In certain embodiments, the compound of Formula (II) is of the formula:

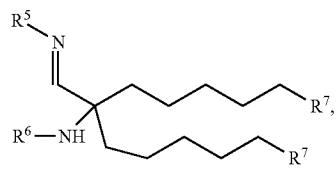

or a pharmaceutically acceptable salt, co-crystal, tautomer, stereoisomer, solvate, hydrate, polymorph, or isotopically enriched derivative thereof.

In certain embodiments, the compound of Formula (II) is a compound provided in any one of the Examples below. In certain embodiments, the compound of Formula (II) is a compound provided in Example 1 below. In certain embodiments, the compound of Formula (II) is a compound provided in Example 2 below. In certain embodiments, the compound of Formula (II) is an acyclic compound that is a product of the three-component synthesis disclosed in FIG. 1B using the amine, isocyanide, and alkyl ketone components disclosed in FIGS. 1C and 1D. In certain embodiments, the compound of Formula (II) is a acyclic compound that is a product of the three-component synthesis disclosed in FIG. 1B using the amine, isocyanide, and alkyl ketone components disclosed above in Table A.

Compositions and Kits

The present disclosure provides compositions (e.g., pharmaceutical compositions) comprising a compound described herein, and an excipient (e.g., pharmaceutically acceptable excipient). In certain embodiments, the composition is a pharmaceutical composition. In certain embodiments, the composition is a cosmetic composition. In certain embodiments, the composition is a nutraceutical composition. In certain embodiments, the composition is a composition with a non-medical application. In certain embodiments, the excipient is a pharmaceutically acceptable excipient. In certain embodiments, the composition further comprises an active ingredient (e.g., RNA, small molecule compound).

Compositions described herein can be prepared by any method known in the art. In general, such preparatory methods include bringing the compound described herein into association with one or more excipients, and may include one or more agents and then, if necessary and/or desirable, shaping, and/or packaging the product into a desired single- or multi-dose unit. In certain embodiments, the agent and the compound of the composition are not covalently attached.

In certain embodiments, the composition is in the form of a particle. In certain embodiments, the particle is a nanoparticle or a microparticle. In certain embodiments, the particle is a micelle, liposome, or lipoplex. In certain embodiments, the particle encapsulates an agent, as described herein. In certain embodiments, the particle facilitates delivery of the agent into a cell. See, e.g., Example 1. In certain embodiments, the particle facilitates delivery of the agent to a subject, e.g., a human.

Lipidoid Nanoparticle Formulations

The present disclosure provides formulations (e.g., pharmaceutical compositions) comprising an ionizable compound (e.g., a compound of Formula (I) or (II)) described herein, and helper lipids (e.g., lipids that contribute to the stability and delivery efficiency of formulations (e.g., fatty acids or cholesteryl hemisuccinate (CHEMS)), phospholipids (e.g., non-cationic phospholipids), lipids for membrane structure (e.g., sterols), and PEG-lipids. In certain embodiments, the formulation is a pharmaceutical formulation. In certain embodiments, the formulation is a nanoparticle formulation comprising lipids (a "lipid nanoparticle formulation"). In certain embodiments, the formulation is in the form of a particle (e.g., nanoparticle).

In certain embodiments, the formulations comprise an ionizable compound described herein, and one or more of the following types of lipids: helper lipids (e.g., lipids that contribute to the stability and delivery efficiency of formulations (e.g., fatty acids or cholesteryl hemisuccinate (CHEMS))), phospholipids (e.g., non-cationic phospholipids), lipids for membrane structure (e.g., sterols), and PEG-lipids. In certain embodiments, the formulations comprise an ionizable compound described herein, and two or more of the following types of lipids: helper lipids (e.g., lipids that contribute to the stability and delivery efficiency of formulations (e.g., fatty acids or cholesteryl hemisuccinate (CHEMS))), phospholipids (e.g., non-cationic phospholipids), lipids for membrane structure (e.g., sterols), and PEG-lipids. In certain embodiments, the formulations comprise an ionizable compound described herein, and three or more of the following types of lipids: helper lipids (e.g., lipids that contribute to the stability and delivery efficiency of formulations (e.g., fatty acids or cholesteryl hemisuccinate (CHEMS))), phospholipids (e.g., non-cationic phospholipids), lipids for membrane structure (e.g., sterols), and PEG-lipids.

In certain embodiments, helper lipids are lipids that contribute to the stability and delivery efficiency of formulations. In certain embodiments, the helper lipid is a fatty acid. In certain embodiments, the helper lipid is oleic acid. In certain embodiments, the helper lipid is a neutral phospholipid. In certain embodiments, the helper lipid is a phosphatidylethanolamine. In certain embodiments, the helper lipid is dioleoylphosphatidylethanolamine (DOPE). In certain embodiments, the helper lipid is 1,2-Distearoylphosphatidylethanolamine (DSPE). In certain embodiments, the helper lipid is a phosphatidylcholine. In certain embodiments, the helper lipid is 1,2-Distearoyl-sn-glycero-3-phosphocholine (DSPC). In certain embodiments, the helper lipid is 1-palmitoyl-2-oleoyl-sn-glycero-3-phosphocholine (POPC or GPCho). In certain embodiments, the helper lipid is 1,2 Dipalmitoylphosphatidylcholine (DPPC). In certain embodiments, the helper lipid is DOPE or DSPC. In certain embodiments, the helper lipid is cholesteryl hemisuccinate (CHEMS).

In certain embodiments, the phospholipid is a non-cationic phospholipid. In certain embodiments, the non-cationic phospholipid is DSPC. In certain embodiments, the lipid for membrane structure is a sterol. In certain embodiments, the lipid for membrane structure is an animal sterol. In certain embodiments, the lipid for membrane structure is cholesterol. In certain embodiments, the PEG-lipid is a lipid that comprises polyethylene glycol (PEG). In certain embodiments, the PEG-lipid is an mPEG-comprising phospholipid. In certain embodiments, the PEG-lipid is a phospholipid comprising PEG2000 (PEG with a molecular weight of 2000 g/mol).

In certain embodiments, the PEG-lipid is 1,2-dimyristoyl-sn-glycero-3-phosphoethanolamine-N-[methoxy-(polyethyleneglycol)-2000] (ammonium salt) ("C14-PEG 2000"). In certain embodiments, the PEG-lipid is 1,2-dipalmitoyl-sn-glycero-3-phosphoethanolamine-N-[methoxy(polyethylene glycol)-2000] (ammonium salt) ("16:0 PEG2000 phospholipid"). In certain embodiments, the PEG-lipid is 1,2-dioleoyl-sn-glycero-3-phosphoethanolamine-N-[methoxy (polyethylene glycol)-2000] (ammonium salt) ("18:1 PEG2000 phospholipid"). In certain embodiments, the PEG-lipid is 1,2-distearoyl-sn-glycero-3-phosphoethanolamine-N-[methoxy(polyethylene glycol)-2000] (ammonium salt) ("18:0 PEG2000 phospholipid"). In certain embodiments, the PEG-lipid is a phospholipid comprising PEG750 (PEG with a molecular weight of 750 g/mol), PEG1000 (PEG with a molecular weight of 1000 g/mol), PEG3000 (PEG with a molecular weight of 3000 g/mol), PEG3000 (PEG with a molecular weight of 3000 g/mol), or PEG5000 (PEG with a molecular weight of 5000 g/mol).

In certain embodiments, the formulations comprise a weight ratio of the lipidoid compounds described herein ("lipidoids") to the mRNA of approximately 10:1. In certain embodiments, the formulations comprise a lipidoid to mRNA weight ratio of approximately 18:1, approximately 17:1, approximately 16:1, approximately 15:1, approximately 14:1, approximately 13:1, approximately 12:1, approximately 11:1, approximately 10:1, approximately 9:1, approximately 8:1, approximately 7:1, approximately 6:1, approximately 5:1, approximately 3:1, or approximately 2:1. In certain embodiments, the formulations comprise a lipidoid to mRNA weight ratio of approximately 15:1 to approximately 5:1. In certain embodiments, the formulations comprise a lipidoid to mRNA weight ratio of approximately 15:1 to approximately 10:1. In certain embodiments, the formulations comprise a lipidoid to mRNA weight ratio of approximately 12:1 to approximately 8:1, approximately 11:1 to approximately 8:1, approximately 11:1 to approximately 9:1, approximately 10:1 to approximately 8:1, or approximately 10:1 to approximately 9:1. In certain embodiments, the formulations comprise a lipidoid to mRNA weight ratio of approximately 10:1.

In certain embodiments, the formulations comprise approximately 3-30 molar % ("mol %") of a helper lipid. In certain embodiments, the formulations comprise approximately 3-30 mol %, approximately 5-30 mol %, approximately 5-25 mol %, approximately 5-20 mol %, approximately 5-15 mol %, approximately 10-15 mol %, approximately 10-12 mol %, approximately 12-15 mol %, approximately 12-18 mol %, or approximately 12-20 mol % of a helper lipid. In certain embodiments, the formulations comprise approximately 3-30 mol % of a helper lipid. In certain embodiments, the formulations comprise approximately 10-20 mol % of DOPE. In certain embodiments, the formulations comprise 3-30 mol %, approximately 5-30 mol %, approximately 5-25 mol %, approximately 5-20 mol %, approximately 5-15 mol %, approximately 10-15 mol %, approximately 10-12 mol %, approximately 12-15 mol %, approximately 12-18 mol %, or approximately 12-20 mol % of DOPE.

In certain embodiments, the formulations comprise approximately 35-75 mol % of lipidoids described herein. In certain embodiments, the formulations comprise approximately 35-75 mol %, approximately 35-70 mol %, approximately 35-65 mol %, approximately 35-60 mol %, approximately 35-55 mol %, approximately 35-50 mol %, approximately 35-52 mol %, approximately 35-45 mol %, or approximately 35-40 mol % of lipidoids. In certain embodiments, the formulations comprise approximately 25-60 mol %, approximately 30-60 mol %, approximately 35-60 mol %, approximately 33-60 mol %, approximately 33-58 mol %, approximately 33-57 mol %, approximately 33-55 mol %, approximately 30-45 mol %, approximately 35-45 mol %, or approximately 35-50 mol % of lipidoids. In certain embodiments, the formulations comprise approximately 35-50 mol % of lipidoids. In certain embodiments, the formulations comprise approximately 30 mol %, approximately 31 mol %, approximately 32 mol %, approximately 33 mol %, approximately 34 mol %, approximately 35 mol %, approximately 36 mol %, approximately 37 mol %, approximately 38 mol %, approximately 39 mol %, approximately 40 mol %, approximately 41 mol %, approximately 42 mol %, approximately 43 mol %, approximately 44 mol %, approximately 45 mol %, approximately 46 mol %, approximately 47 mol %, approximately 48 mol %, approximately 49 mol %, or approximately 50 mol % of lipidoids.

In certain embodiments, the formulations comprise approximately 0.5-3.0 mol % of PEG-lipid. In certain embodiments, the formulations comprise approximately 0.5-3.0 mol %, approximately 0.5-2.5 mol %, 1.0-3.0 mol %, approximately 1.0-2.8 mol %, approximately 1.0-2.5 mol %, approximately 1.5-2.5 mol %, or approximately 1.5-2.0 mol % of PEG-lipid.

In certain embodiments, the formulations comprise approximately 1.0-3.0 mol %, approximately 1.2-2.8 mol %, 1.5-2.8 mol %, or approximately 1.5-2.5 mol % of PEG-lipid. In certain embodiments, the formulations comprise approximately 1.5 mol %, approximately 1.75 mol %, approximately 2.0 mol %, approximately 2.25 mol %, or approximately 2.5 mol % of PEG-lipid. In certain embodiments, the PEG-lipid is 1,2-dimyristoyl-sn-glycero-3-phosphoethanolamine-N-[methoxy-(polyethyleneglycol)-2000] (ammonium salt) ("C14-PEG 2000"), and the formulations comprise approximately 1.5 mol %, approximately 1.75 mol %, approximately 2.0 mol %, approximately 2.25 mol %, or approximately 2.5 mol % of PEG-lipid.

In certain embodiments, the PEG-lipid is 1,2-dimyristoyl-sn-glycero-3-phosphoethanolamine-N-[methoxy-(polyethyleneglycol)-2000] (ammonium salt) ("C14-PEG 2000"), and the formulations comprise approximately 1.5-2.5 mol % PEG-lipid.

In certain embodiments, the formulations comprise a lipidoid to mRNA weight ratio of approximately 10:1; approximately 10-20 mol % of helper lipid; approximately 35-50 mol % of lipidoid; approximately 1.5-2.5 mol % of PEG-lipid. In certain embodiments, the formulations comprise a lipidoid to mRNA weight ratio of approximately 10:1; approximately 10-20 mol % of helper lipid DOPE; approximately 35-50 mol % of lipidoid; or approximately 1.5-2.5 mol % of PEG-lipid C14-PEG 2000.

In certain embodiments, the formulations comprise a lipid composition weight ratio of lipidoid/helper lipid/sterol/PEG-lipid of 45/15/45/2.0. In certain embodiments, the formulations comprise a lipid composition weight ratio of lipidoid/helper lipid/sterol/PEG-lipid of 45/10/42.5/2.5, wherein the helper lipid is DOPE, the sterol is cholesterol, and the PEG-lipid is C14-PEG 2000. In certain embodiments, the formulations comprise a lipid composition weight ratio of lipidoid/helper lipid/sterol/PEG-lipid of 45/15/45/2.0; 40/15/43/2.5; 35/12/43/2.5; 35/16/37/2.5; or 35/16/37/2.5.

In certain embodiments, the formulations comprise one or more agents (e.g., a polynucleotide) described herein. In certain embodiments, the agent is RNA. In certain embodiments, the agent is mRNA. In certain embodiments, the agent is an mRNA vaccine.

Formulations described herein can be prepared by any method known in the art.

Compositions can be prepared, packaged, and/or sold in bulk, as a single unit dose, and/or as a plurality of single unit doses. A "unit dose" is a discrete amount of the composition comprising a predetermined amount of the agent. The amount of the agent is generally equal to the dosage of the agent which would be administered to a subject and/or a convenient fraction of such a dosage, such as one-half or one-third of such a dosage.

Relative amounts of the compound, excipient, agent, and/or any additional ingredients in a composition described herein will vary, depending upon the identity, size, and/or condition of the subject treated and further depending upon the route by which the composition is to be administered. The composition may comprise between 0.1% and 100% (w/w) agent. The composition may comprise no agent.

Excipients and accessory ingredients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients and accessory ingredients, such as cocoa butter, PEGylated lipids, phospholipids, suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon,

*litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In certain embodiments, the compositions further comprise an agent and are useful for delivering said agent (e.g., to a subject or cell). In certain embodiments, the compositions are pharmaceutical compositions which are useful for treating a disease in a subject in need thereof. In certain embodiments, the pharmaceutical compositions are useful for preventing a disease in a subject.

A composition as described herein may further comprise, or can be administered in combination with, one or more additional agents. In certain embodiments, the agent is a small organic molecule, inorganic molecule, nucleic acid, protein, peptide, or polynucleotide. In certain embodiments, the agent is a pharmaceutical agent (e.g., therapeutically and/or prophylactically active agent). Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, polynucleotides, lipids, hormones, vitamins, vaccines, immunological agents, and cells or other biological materials.

In certain embodiments, the agent is a polynucleotide. In certain embodiments, the polynucleotide is DNA. In certain embodiments, the polynucleotide is RNA. In certain embodiments, the polynucleotide carries out RNA interference. The RNA is selected from the group consisting of double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA). In certain embodiments, the RNA is dsRNA. In certain embodiments, the RNA is siRNA. In certain embodiments, the RNA is shRNA. In certain embodiments, the RNA is miRNA. In certain embodiments, the RNA is mRNA. In certain embodiments, the mRNA encodes proteins (e.g., peptide and protein structures, allowing expression of the entire antigen). In certain embodiments, the mRNA encodes an antigen. In certain embodiments, the mRNA encodes a Class I Major Histocompatibility Complex (MHC) antigen. In certain embodiments, the mRNA encodes a Class II MHC antigen. In certain embodiments, the mRNA encodes a Class I and II MHC antigen. In certain embodiments, the RNA is an mRNA vaccine. In certain embodiments, the RNA is antisense RNA. In certain embodiments, the RNA is dsRNA, siRNA, shRNA, miRNA, mRNA, or antisense RNA.

In certain embodiments, the agent described herein is provided in an effective amount in the composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating an autoimmune disease in a subject in need thereof. In certain embodiments, the effective amount is an amount effective for preventing an autoimmune disease in a subject in need thereof. In certain embodiments, the effective amount is an amount effective for reducing the risk of developing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof.

Compositions may be formulated into liquid dosage forms for oral and parenteral administration include pharmaceutically acceptable emulsions, microemulsions, solutions, suspensions, syrups, and elixirs. In addition to the agents, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the particles described herein are mixed with solubilizing agents, such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Dosage forms for topical and/or transdermal administration of a composition described herein may include ointments, pastes, creams, lotions, gels, powders, solutions, sprays, inhalants, and/or patches. Generally, the agent is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an agent to the body. Such dosage forms can be prepared, for example, by dissolving and/or dispensing the agent in the proper medium. Alternatively or additionally, the rate can be controlled by either providing a rate controlling membrane and/or by dispersing the agent in a polymer matrix and/or gel.

Suitable devices for use in delivering intradermal compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) agent, although the concentration of the agent can be as high as the solubility limit of the agent in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the agent and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the agent dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the agent may constitute 0.1 to 20% (w/w) of the composition. The propellant may further comprise additional ingredients such as a liquid non-ionic and/or solid anionic surfactant and/or a solid diluent (which may have a particle size of the same order as particles comprising the agent).

Compositions described herein formulated for pulmonary delivery may provide the agent in the form of droplets of a solution and/or suspension. Such formulations can be prepared, packaged, and/or sold as aqueous and/or dilute alcoholic solutions and/or suspensions, optionally sterile, comprising the agent, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the agent and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the agent, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) agent, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the agent. Such powdered, aerosolized, and/or aerosolized formulations, when dispersed, may have an average particle and/or droplet size in the range from about 0.1 to about 200 nanometers, and may further comprise one or more of the additional ingredients described herein.

A composition described herein can be prepared, packaged, and/or sold in a formulation for ophthalmic administration. Such formulations may, for example, be in the form of eye drops including, for example, a 0.1-1.0% (w/w) solution and/or suspension of the agent in an aqueous or oily liquid carrier or excipient. Such drops may further comprise buffering agents, salts, and/or one or more other of the additional ingredients described herein. Other opthalmically-administrable formulations which are useful include those which comprise the agent in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific agent employed; the specific composition employed; the age, body weight, general health, sex, and diet of the subject; the time of administration, route of administration, and rate of excretion of the specific agent employed; the duration of the treatment; drugs used in combination or coincidental with the specific agent employed; and like factors well known in the medical arts.

The compositions (e.g., LNPs) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In a particular embodiment, the LNPs disclosed herein are administered by intravenous injection, In certain embodiments, the composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

The lipidoids in the compositions can be administered in combination with additional agents that improve their activity (e.g., activity (e.g., potency and/or efficacy) in treating a disease in a subject in need thereof, in preventing a disease in a subject in need thereof, in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a composition described herein including a lipidoid compound described herein and an agent shows a synergistic effect that is absent in a composition including one of the lipidoid compound and an agent, but not both.

The composition can be administered concurrently with, prior to, or subsequent to one or more additional agents (e.g., a pharmaceutical agent), in addition to the lipidoid in the composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease). Each additional pharmaceutical agent may be administered at a dose and/or on a time schedule determined for that pharmaceutical agent. The additional pharmaceutical agents may also be administered together with each other and/or with the polymer or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or compositions (e.g., pharmaceutical compositions) can be administered in combination with an anti-cancer therapy including surgery, radiation therapy, transplantation (e.g., stem cell transplantation, bone marrow transplantation), immunotherapy, and chemotherapy.

In some embodiments, the composition is a particle (e.g., a nanoparticle). In some embodiments, the particle is substantially soluble in water (e.g., hydrophilic). In some embodiments, the particle is substantially insoluble in water (e.g., hydrophobic). In some embodiments, the particle is substantially insoluble in water and greater than about 10,000 parts water are required to dissolve 1 part compound. In one embodiment, the particle is amphiphilic. In one embodiment, the particle comprises a segment that is hydrophobic and a segment that is hydrophilic.

In some embodiments, the percentage of the particle that comprises an agent is between about 1 and about 100% (e.g., about 1%, about 2%, about 3%, about 4%, about 5%, about 10%, about 15%, about 20%, about 30%, 0%, a 40%, about 50%, about 60%, about 70%, about 80%, about 90%, or about 100%). In some embodiments, the percentage of the particle that comprises an agent is less than about 50%, e.g., less than about 40%, less than about 35%, less than about 30%, less than about 25%, less than about 20%, less than about 15%, or less than about 10%. In some embodiments, the percentage of the particles that comprise an agent is between about 5% and about 50%, about 5% and about 40%, about 5% and about 30%, about 5% and about 25%, or about 5% and about 20%. In some embodiments, the percentage of the particle that comprises an agent is between about 5% and 90%. In some embodiments, the percentage of the particles that comprise an agent is between about 5% and about 75%. In the some embodiments, the percentage of particle that comprises an agent is between about 5% and about 50%. In the some embodiments, the percentage of the particle that comprises an agent is between about 10% and about 25%.

In some embodiments, the total amount of the agent present in the particle is greater than about 5% (e.g., about 6%, about 7%, about 8%, about 9%, about 10%, about 12%, about 15%, about 20%, about 25%, about 30%, or more) of the total size or weight of the conjugate or particle. In some embodiments, the total amount of the agent present in the conjugate or particle is greater than about 10% (e.g., about 12%, about 15%, about 20%, about 25%, about 30%, or more) of the total size or weight of the conjugate or particle.

Without being bound by theory, the compounds or particles disclosed herein may improve the efficiency of an agent by one or more of increasing the localization and/or release (e.g., preferential release) of the agent to a target cell (e.g., a cancer or a fibrotic cell; a cell associated with a hypoxic environment), or increasing the half life of the agent, thus resulting in a significantly higher amount of a released agent at a target site (e.g., a tumor or liver (e.g., cirrhotic cell), and causing the expression of a specific gene in the cell (e.g., where the RNA agent activates the STING pathway and/or activates an innate immune response)). According, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a compound, conjugate or particle described herein).

Without being bound by theory, due to the localized delivery of the compositions described herein (e.g., the agent-containing particles), a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a particle at a dose that is less than the dose or amount of said agent in free form to have a desired effect (e.g., a desired therapeutic effect), e.g., the standard of care dose for the intended use of the free agent.

In another aspect, provided are kits including a first container comprising a compound or composition described herein and instructions for use. The kits may further comprise a container (e.g., a vial, ampule, bottle, syringe, and/or dispenser package, or other suitable container). In some embodiments, provided kits may optionally further include a second container comprising an excipient for dilution or suspension of a composition or polymer described herein. In some embodiments, the compositions described herein provided in the first container and the second container are combined to form one unit dosage form.

In certain embodiments, the kits are useful for delivering an agent (e.g., to a subject or cell). In certain embodiments, the kits are useful for treating a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof. In certain embodiments, the kits are useful for preventing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof. In certain embodiments, the kits are useful for reducing the risk of developing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for delivering an agent. In certain embodiments, the kits and instructions provide for treating a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof. In certain embodiments, the kits and instructions provide for preventing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof. In certain embodiments, the kits and instructions provide for reducing the risk of developing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease) in a subject in need thereof. A kit described herein may include one or more additional pharmaceutical agents described herein as a separate composition.

Methods of Synthesis

The present disclosure provides methods for making a compound of Formula (I):

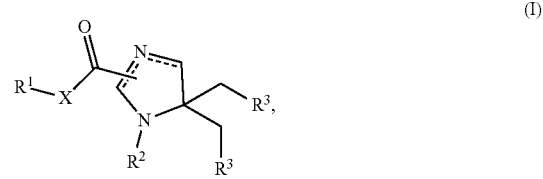

or a pharmaceutically acceptable salt thereof, the method comprising reacting:

an amine of Formula (A):

an isocyanide of Formula (B):

and a ketone of Formula (C):

under suitable conditions to form a compound of Formula (I); wherein:

$\equiv\equiv\equiv$ is a single or double bond, as valency allows;

X is N, O, or S;

$R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group; and each instance of $R^3$ is independently optionally substituted alkyl, optionally substituted alkenyl, or optionally substituted alkynyl.

The present disclosure provides a compound of Formula (I):

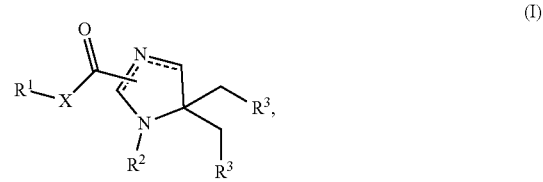

or a pharmaceutically acceptable salt thereof, synthesized by a method comprising reacting:

an amine of Formula (A):

(A);

an isocyanide of Formula (B):

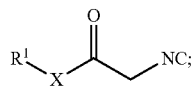

(B)

and a ketone of Formula (C):

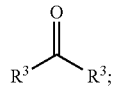

(C)

under suitable conditions to form a compound of Formula (I); wherein:

--- is a single or double bond, as valency allows;

X is N, O, or S;

$R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group; and each instance of $R^3$ is independently optionally substituted alkyl, optionally substituted alkenyl, or optionally substituted alkynyl.

In certain embodiments, the compound of Formula (I) is a compound of Formula (I-A):

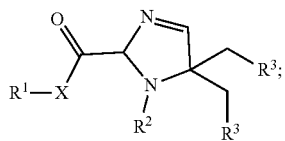

(I-A)

a compound of Formula (I-B):

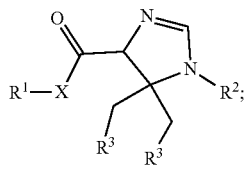

(I-B)

or a combination thereof.

In a particular embodiment, the compound of Formula (I) is a compound of Formula (I-A). In another particular embodiment, the compound of Formula (I) is a compound of Formula (I-B).

In certain embodiments of the method, X is O. In certain embodiments, $R^1$ is optionally substituted $C_{1-6}$ alkyl. In certain embodiments, $R^1$ is unsubstituted methyl, unsubstituted ethyl, or unsubstituted isopropyl. In certain embodiments, $R^2$ is optionally substituted $C_{1-6}$ alkyl.

In certain embodiments, $R^1$ is optionally substituted $C_{1-6}$ alkyl, $R^2$ is optionally substituted $C_{1-6}$ alkyl, and each $R^3$ independently is optionally substituted $C_{1-20}$ alkyl, optionally substituted $C_{2-20}$ alkenyl, or optionally substituted $C_{2-20}$ alkynyl.

Figure 1A:
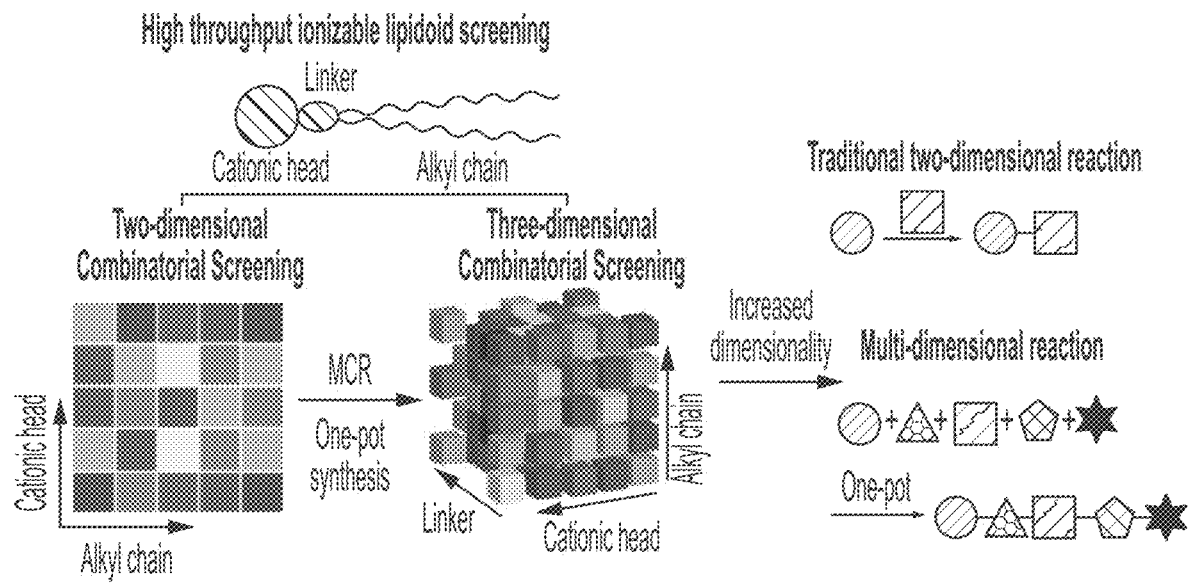
FIGS. 1A-1E show an isocyanide-mediated 3-Component Reaction (3-CR) for the high throughput synthesis of lipidoids.
Figure 1B:
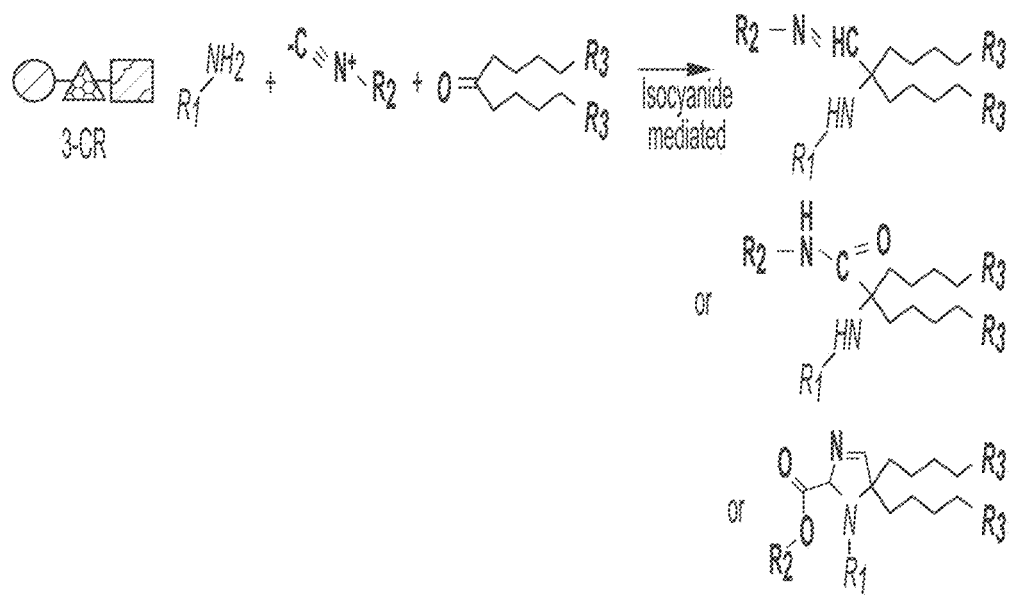
Figure 1C:
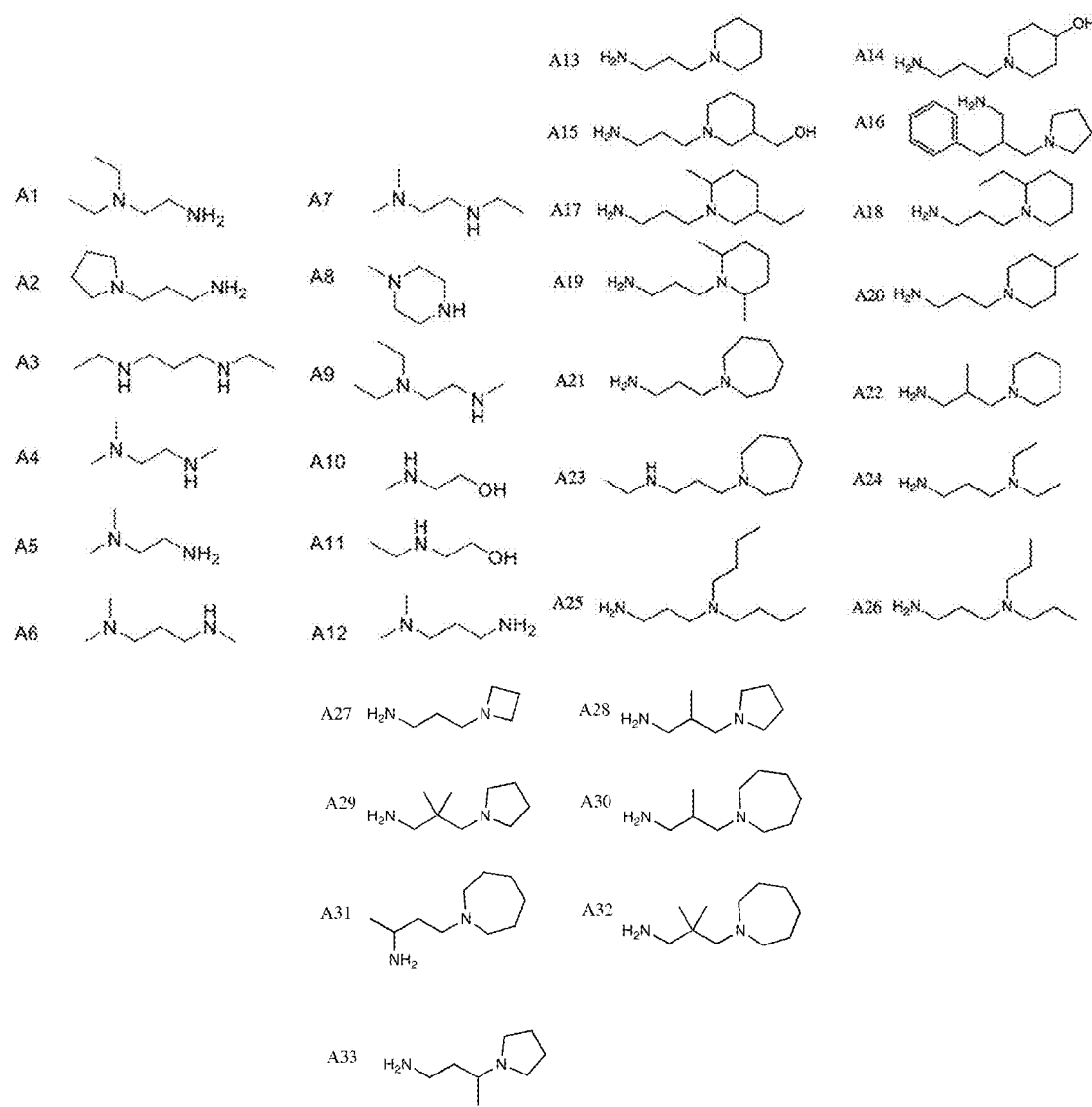

In certain embodiments, the amine of Formula (A) is selected from compounds A1, A2, A5, A12, A13-A22, and A24-A33 of FIG. 1C.

Figure 1D:
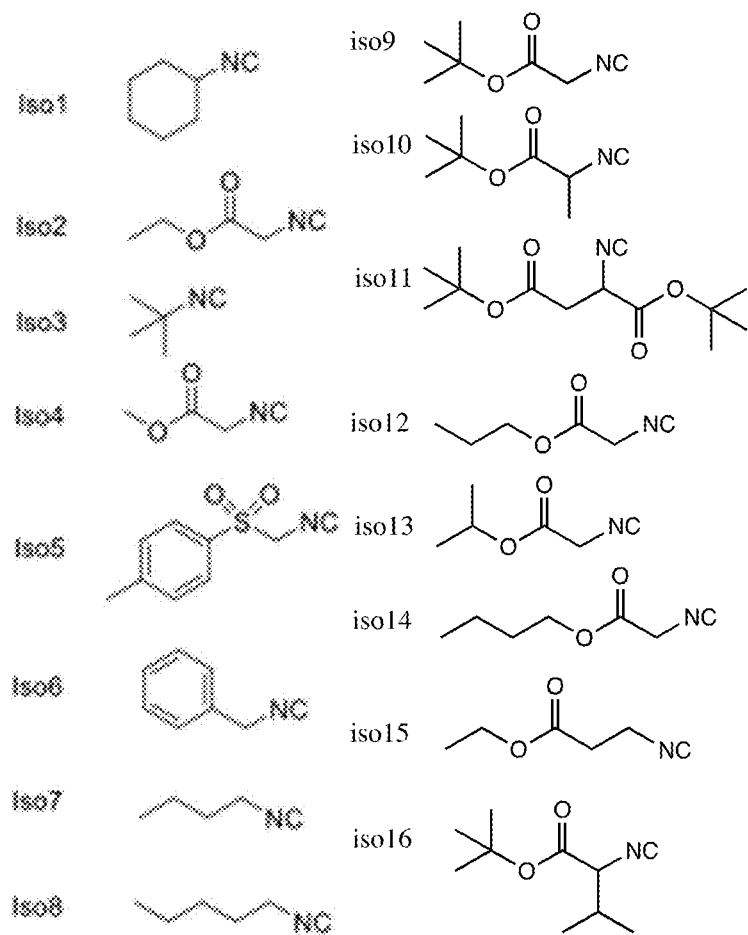

In certain embodiments, the isocyanide of Formula (B) is selected from Iso2, Iso4, Iso9, Iso12, Iso13, and Iso14 of FIG. 1D.

Figure 1E:
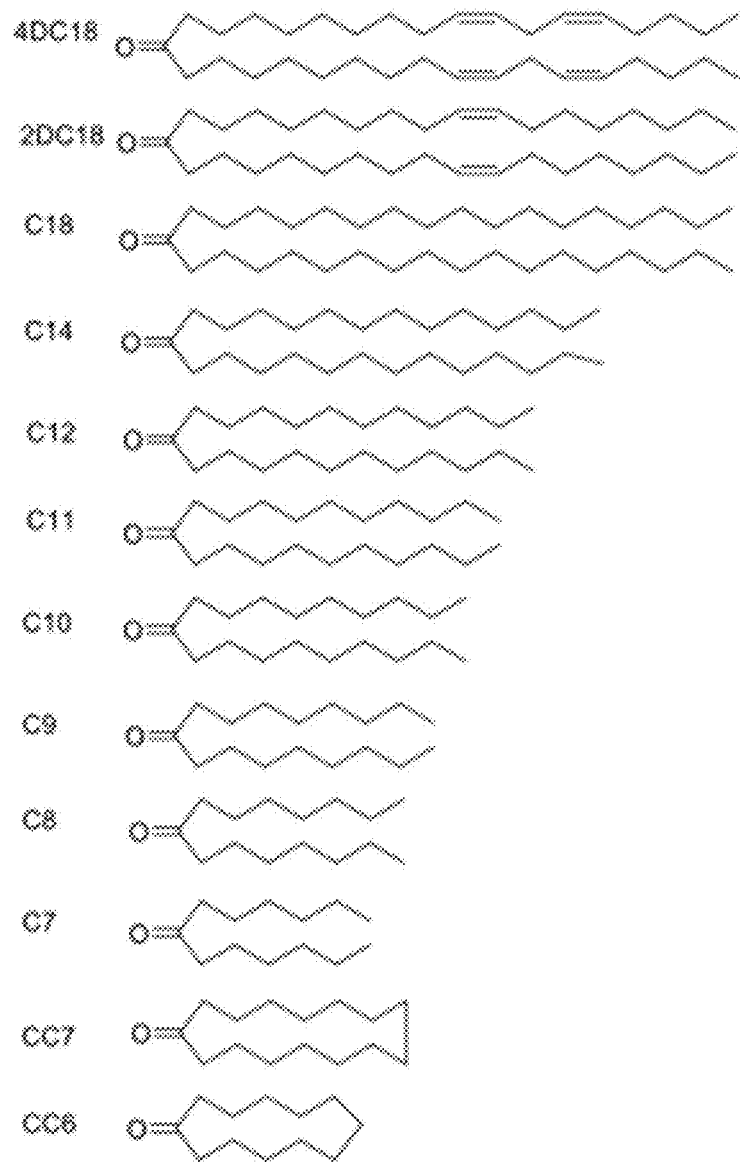

In certain embodiments, the ketone of Formula (C) is selected from FIG. 1E.

In certain embodiments of the method, the compound of Formula (I) is selected from:

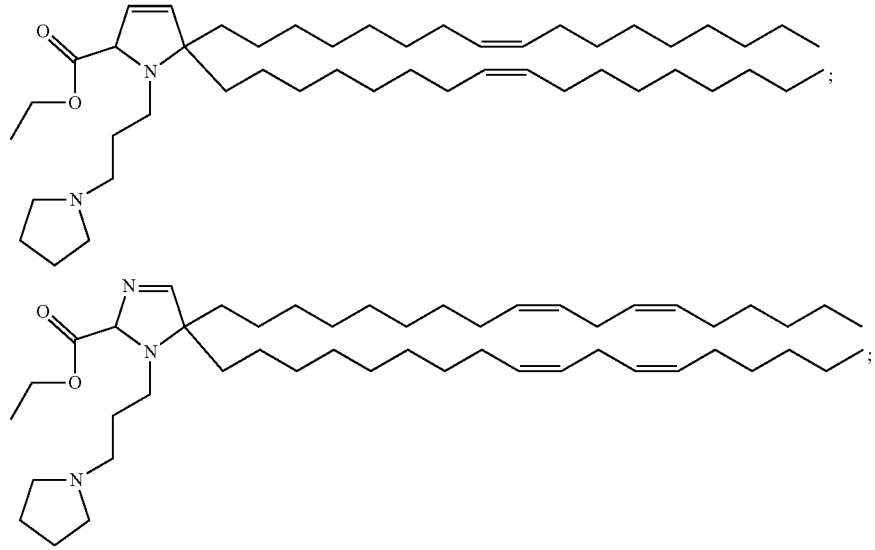

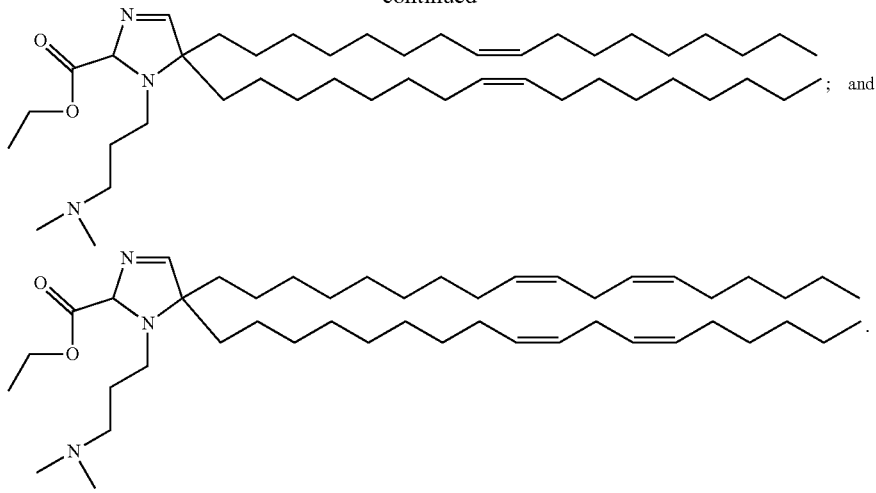

; and

.

In certain embodiments, the suitable conditions comprise a molar ratio of Formula (A):Formula (B):Formula (C) of about 1:1:1. In certain embodiments, the suitable conditions comprise a protic solvent. For example, the reaction solvent may be a protic solvent, or a mixture of protic and aprotic solvents. The protic solvent may be an alcohol, e.g., methanol, ethanol, or isopropanol. The alcohol may be anhydrous, or it may contain water. For example, the reaction solvent may include dichloromethane. In certain embodiments, the compounds of Formula (I) are synthesized by adding the components of Formula (A), Formula (B), and Formula (C) together, and heating. In certain embodiments, the compounds of Formula (I) are synthesized by adding the components of Formula (A), Formula (B), and Formula (C) together at room temperature for 8-12 hours, and stirring. In certain embodiments, the compounds of Formula (I) are synthesized by adding the components of Formula (A), Formula (B), and Formula (C) together at room temperature for 8-20 hours, and stirring.

Methods of Treatment and Uses

The present disclosure also provides methods of using the compounds described herein, or compositions (e.g., pharmaceutical compositions) or formulations thereof, for delivering an agent (e.g., a polynucleotide (e.g., RNA)). The present disclosure also provides methods of using the compounds described herein, or compositions (e.g., pharmaceutical compositions) thereof, for the treatment, prevention, or diagnosis of a disease or condition (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease).

The present disclosure also provides a compound of Formula (I), (II), or a pharmaceutically acceptable salt, co-crystal, tautomer, stereoisomer, solvate, hydrate, polymorph, isotopically enriched derivative, or prodrug, or composition thereof, for use in the treatment of diseases, such as genetic diseases, proliferative diseases, hematological diseases, neurological diseases, painful condition, psychiatric disorder, metabolic disorder, long-term medical condition, inflammatory diseases, autoinflammatory diseases, liver diseases, lung diseases, spleen diseases, familial amyloid neuropathy, cardiovascular diseases, viral infection, infectious diseases, fibrotic condition, or autoimmune diseases, in a subject in need thereof. In certain embodiments, provided herein are compositions including compounds described herein for delivering an agent. In certain embodiments, provided herein are compositions including compounds described herein for delivering an RNA agent.

In certain embodiments, the methods described herein include treating a disease, disorder, or condition from which a subject suffers, comprising administering to a subject in need thereof an effective amount of a composition described herein. In certain embodiments, the methods described herein include implanting in a subject an effective amount of the composition described herein. In certain embodiments, the methods described herein comprise treating a disease or condition in a subject in need thereof by administering to or implanting in the subject a therapeutically effective amount of a composition. In certain embodiments, the methods described herein comprise preventing a disease or condition in a subject in need thereof by administering to or implanting in the subject a prophylactically effective amount of a composition. In certain embodiments, the methods described herein comprise diagnosing a disease or condition in a subject in need thereof by administering to or implanting in the subject a diagnostically effective amount of a composition. In certain embodiments, the disease or condition is a genetic disease, proliferative disease, hematological disease, neurological disease, painful condition, psychiatric disorder, metabolic disorder, long-term medical condition, cancer (e.g. lung cancer, large bowel cancer, pancreas cancer, biliary tract cancer, or endometrial cancer), neoplasm, angiogenesis, inflammatory disease, autoinflammatory disease, liver disease, lung disease, spleen disease, familial amyloid neuropathy, cardiovascular disease, viral infection, infectious disease, fibrotic condition, or autoimmune disease. In some embodiments, the compositions are useful in treating cancer.

In some embodiments, the compositions are useful in treating lung cancer, head-and-neck cancer, esophagus cancer, stomach cancer, breast cancer, pancreas cancer, liver cancer, kidney cancer, prostate cancer, glioblastomas, metastatic melanomas, peritoneal or pleural mesotheliomas. In some embodiments, the compositions are useful in treating lung cancer. In some embodiments, the compositions are useful in treating non-small cell lung cancer. In some embodiments, the compositions are useful in treating breast cancer. In some embodiments, the compositions are useful in treating pancreas cancer. In some embodiments, the compositions are useful in treating liver cancer. In some embodiments, the compositions are useful in treating melanoma. In some embodiments, the compositions are useful in treating prostate cancer.

In some embodiments, the proliferative disease is a benign neoplasm. All types of benign neoplasms disclosed herein or known in the art are contemplated as being within the scope of the disclosure. In some embodiments, the proliferative disease is associated with angiogenesis. All types of angiogenesis disclosed herein or known in the art are contemplated as being within the scope of the disclosure. In certain embodiments, the proliferative disease is an inflammatory disease. All types of inflammatory diseases disclosed herein or known in the art are contemplated as being within the scope of the disclosure. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the disclosure. In some embodiments, the proliferative disease is an autoimmune disease. All types of autoimmune diseases disclosed herein or known in the art are contemplated as being within the scope of the disclosure.

In certain embodiments, the disease is a cardiovascular disease. In certain embodiments, the disease is atherogenesis or atherosclerosis. In certain embodiments, the disease is arterial stent occlusion, heart failure (e.g., congestive heart failure), a coronary arterial disease, myocarditis, pericarditis, a cardiac valvular disease, stenosis, restenosis, in-stent-stenosis, angina pectoris, myocardial infarction, acute coronary syndromes, coronary artery bypass grafting, a cardiopulmonary bypass procedure, endotoxemia, ischemia-reperfusion injury, cerebrovascular ischemia (stroke), renal reperfusion injury, embolism (e.g., pulmonary, renal, hepatic, gastrointestinal, or peripheral limb embolism), or myocardial ischemia.

In certain embodiments, the disease is an infectious disease. In certain embodiments, the disease is a viral infection. In certain embodiments, the disease is an infection caused by DNA virus. In certain embodiments, the disease is an infection caused by a dsDNA virus. In certain embodiments, the disease is an infection caused by an ssDNA virus. In certain embodiments, the disease is an infection caused by an RNA virus. In certain embodiments, the disease is an infection caused by a dsRNA virus. In certain embodiments, the disease is an infection caused by a (+)ssRNA virus. In certain embodiments, the disease is an infection caused by a (−)ssRNA virus. In certain embodiments, the disease is an infection caused by a reverse transcribing (RT) virus. In certain embodiments, the disease is an infection caused by an ssRNA-RT virus. In certain embodiments, the disease is an infection caused by a dsDNA-RT virus. In certain embodiments, the disease is an infection caused by human immunodeficiency virus (HIV). In certain embodiments, the disease is an infection caused by acquired immunodeficiency syndrome (AIDS). In certain embodiments, the disease is an infection caused by human papillomavirus (HPV). In certain embodiments, the disease is an infection caused by hepatitis C virus (HCV). In certain embodiments, the disease is an infection caused by a herpes virus (e.g., herpes simplex virus (HSV)). In certain embodiments, the disease is an infection caused by Ebola virus. In certain embodiments, the disease is an infection caused by severe acute respiratory syndrome (SARS). In certain embodiments, the disease is an infection caused by influenza virus. In certain embodiments, the disease is an infection caused by an influenza virus. In certain embodiments, the disease is an infection caused by an influenza A virus. In certain embodiments, the disease is human flu (e.g., human flu caused by H1N1, H2N2, H3N2, H5N1, H7N7, H1N2, H9N2, H7N2, H7N3, or H10N7 virus). In certain embodiments, the disease is bird flu (e.g., bird flu caused by H5N1 or H7N9 virus). In certain embodiments, the disease is swine influenza (e.g., swine influenza caused by H1N1, H1N2, H2N1, H3N1, H3N2, H2N3, or influenza C virus). In certain embodiments, the disease is Dengue fever, Dengue hemorrhagic fever (DHF), Dengue shock syndrome (DSS), hepatitis A, hepatitis B, hepatitis D, hepatitis E, hepatitis F, infection caused by Coxsackie A virus, infection caused by Coxsackie B virus, fulminant viral hepatitis, viral myocarditis, infection caused by parainfluenza virus, infection caused by an RS virus (RSV) (e.g., RSV bronchiolitis, RSV pneumonia, especially an infant and childhood infection caused by RSV and RSV pneumonia in the patients with cardiopulmonary disorders), infection caused by measles virus, infection caused by vesicular stomatitis virus, infection caused by human metapneumovirus (HMPV), infection caused by rabies virus, Japanese encephalitis, infection caused by Junin virus, infection caused by human cytomegalovirus, infection caused by varicellovirus, infection caused by cytomegalovirus, infection caused by muromegalovirus, infection caused by proboscivirus, infection caused by roseolovirus, infection caused by lymphocryptovirus, infection caused by macavirus, infection caused by percavirus, infection caused by rhadinovirus, infection caused by poliovirus, infection caused by Zika virus, infection caused by Marburg virus, infection caused by Lassa fever virus, Venezuelan equine encephalitis, infection caused by Rift Valley Fever virus, infection caused by Korean hemorrhagic fever virus, infection caused by Crimean-Congo hemorrhagic fever virus, encephalitis, Saint Louise encephalitis, Kyasanur Forest disease, Murray Valley encephalitis, tick-borne encephalitis, West Nile encephalitis, yellow fever, infection caused by adenovirus, infection caused by poxvirus, or a viral infection in subjects with immune disorders.

In certain embodiments, the methods described herein include contacting a cell with an effective amount of a composition thereof. In certain embodiments, the cell is in vitro. In certain embodiments, the cell is in vivo.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Heterocyclic Lipidoids for Combined mRNA Vaccine Delivery and STING-Mediated Immune Cell Activation Design and Synthesis of a Lipidoid Library An isocyanide-mediated 3 component reaction (3-CR) was designed to simultaneously couple primary or secondary amines[26], ketones[27] and isocyanides or isocyanide derivatives[28] (FIG. 1A). The structures are composed of alkyl and alkylene ketone lipid tails, isocyanide linkers and amine head groups (FIG. 1B). Using this 3-CR, a pilot library of 1080 lipidoids was synthesized (FIG. 1C) containing combinations of the following sub-structures; (i) varied alkyl chain lengths from C6 to C18, with different degrees of saturation[29]; (ii) new side chains coupled to the lipid tail via imine, amide and dihydroimadazole bonds; (iii) degradable isocyanoacetate ester bonds in selected side chains; (iv) polar head groups containing primary or secondary amines, with the distance between amines varied from two to three carbons; and (v) polar head groups containing —OH or cyclic structures.[30] The unique chemistry of isocyanides was used to couple these lipidoids in a one-pot, high-throughput reaction using polar, protic solvents (ethanol and propanol)[31]. The isocyanides chosen in this reaction scheme can function as both electrophiles and nucleophiles, and therefore offer advantages over conventional lipidoids synthesized using multi-step reactions[3, 30, 32, 33] which require toxic catalysts, solvent exchange, and protection/de-protection steps. The Examples section above provides synthesis and characterization details.[28] The one-pot synthesis was carried out overnight at room temperature, and product yields were typically over 70%. This three-dimensional combinatorial approach facilitated simple and rapid synthesis of a large and diverse library of materials, with which mRNA delivery efficiency was tested.[30] Key features of this new lipidoid nanoparticle include: (1) introduction of a side chain contains imine and ester groups in parallel with the ionizable head groups; (2) testing of different lengths of lipidoid tails and different head groups to maximize the efficiency of mRNA delivery; (3) optimization of lipidoid formulations by changing the ratios of ionizable lipidoids, helper lipids, phospholipids, cholesterol, and PEG-lipid. The results show that the new lipidoid nanoparticle-mRNA complex can achieve efficient expression with low cytotoxicity in vivo. Furthermore, this lipidoid nanoparticle can stimulate strong antigen specific immune response after s.c. injection.

Lipidoid-Mediated mRNA Delivery In Vitro and In Vivo

Figure 2A:
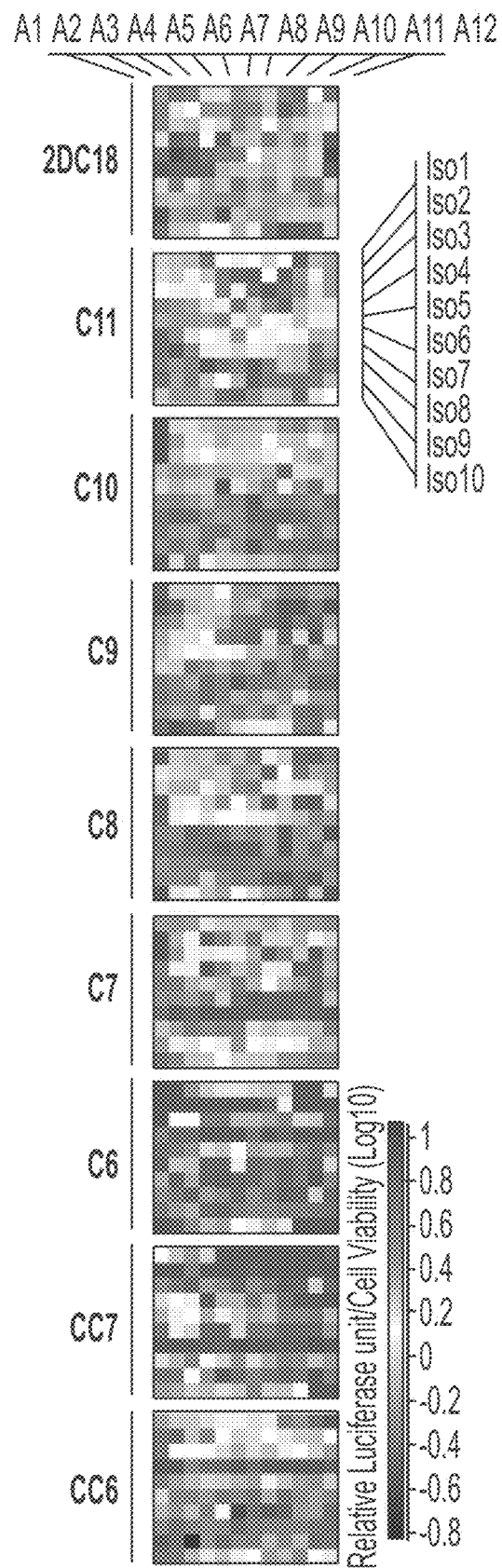
FIGS. 2A-2J show in vivo and in vitro screening of lipidoids for Fluc mRNA delivery.
Figure 2B:
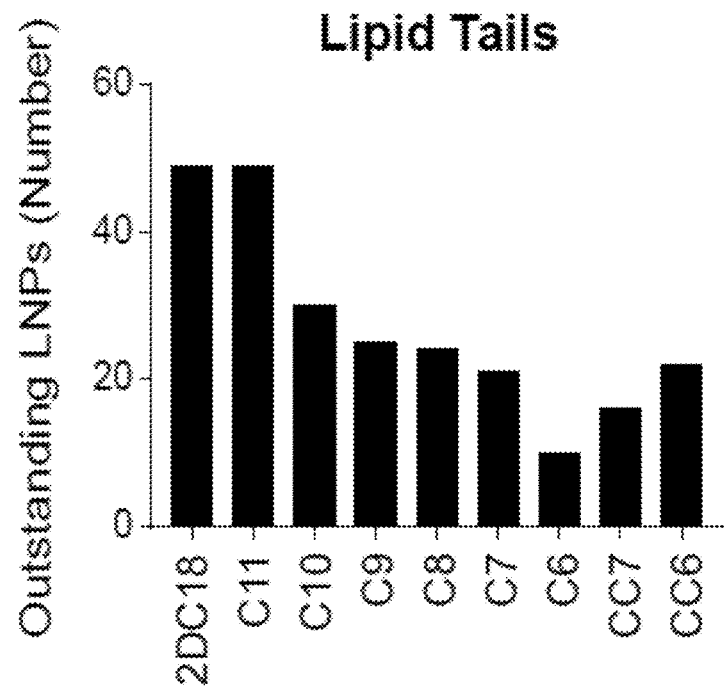
Figure 2C:
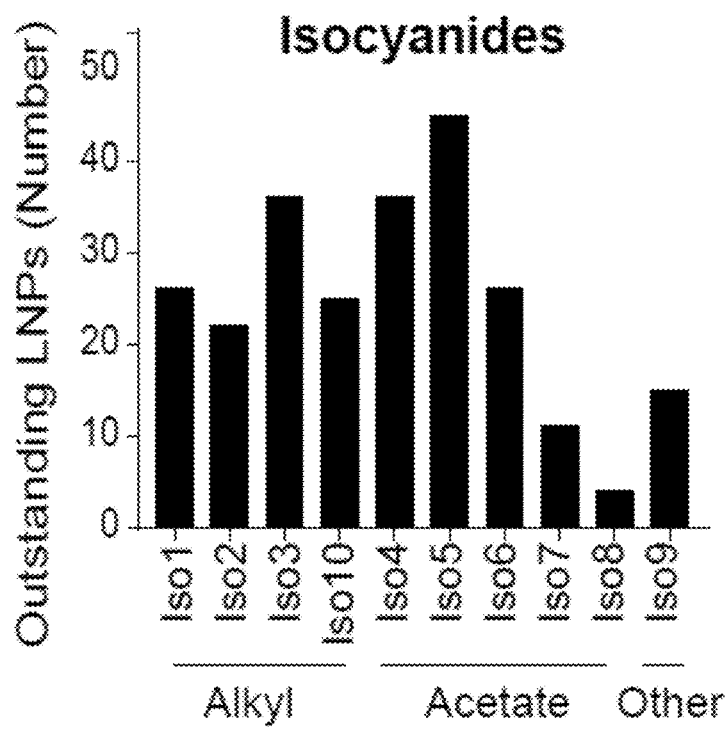
Figure 2D:
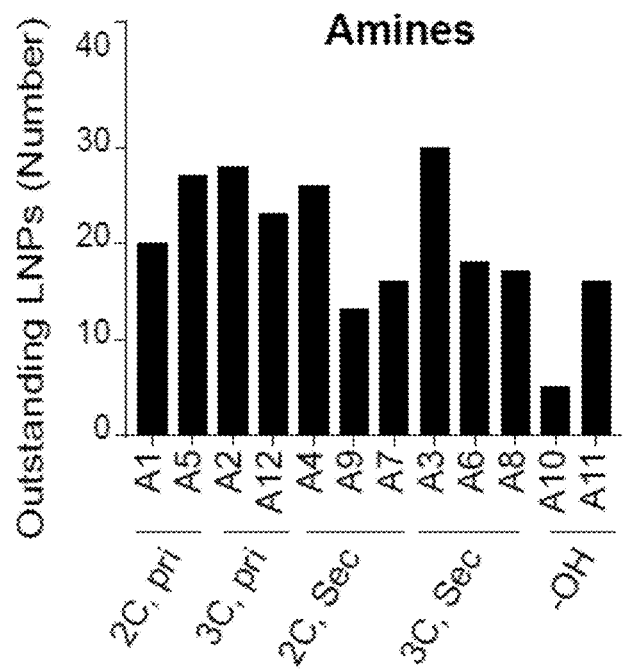
Figure 2E:
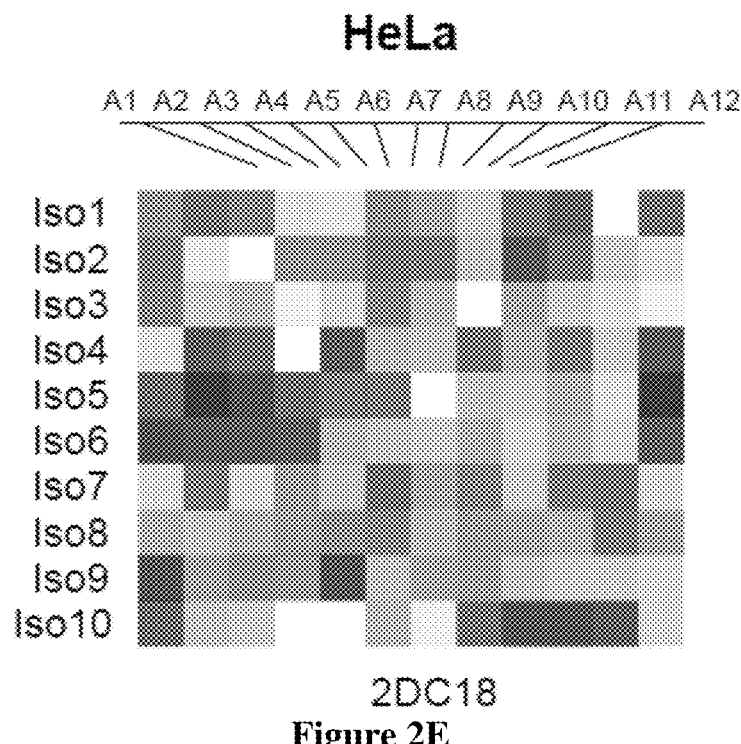
Figure 2F:
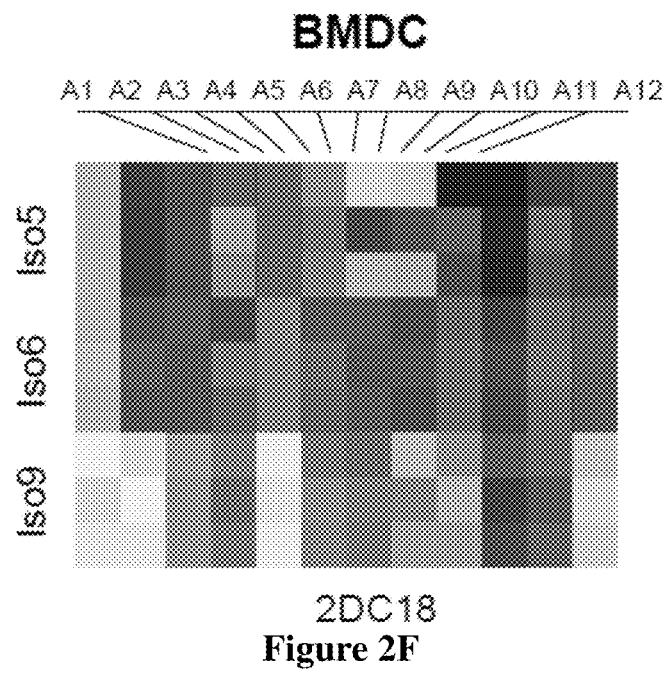
Figure 2G:
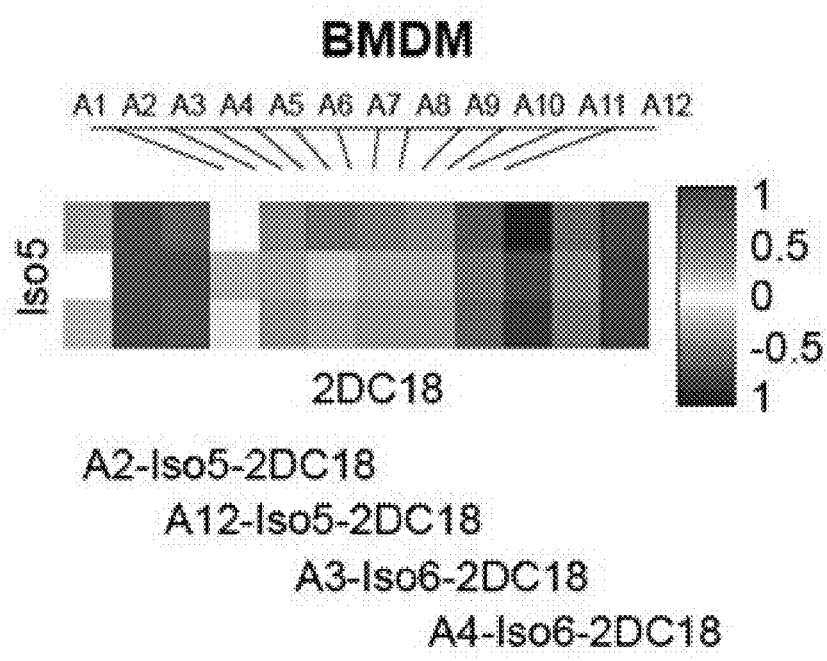
Figure 7:
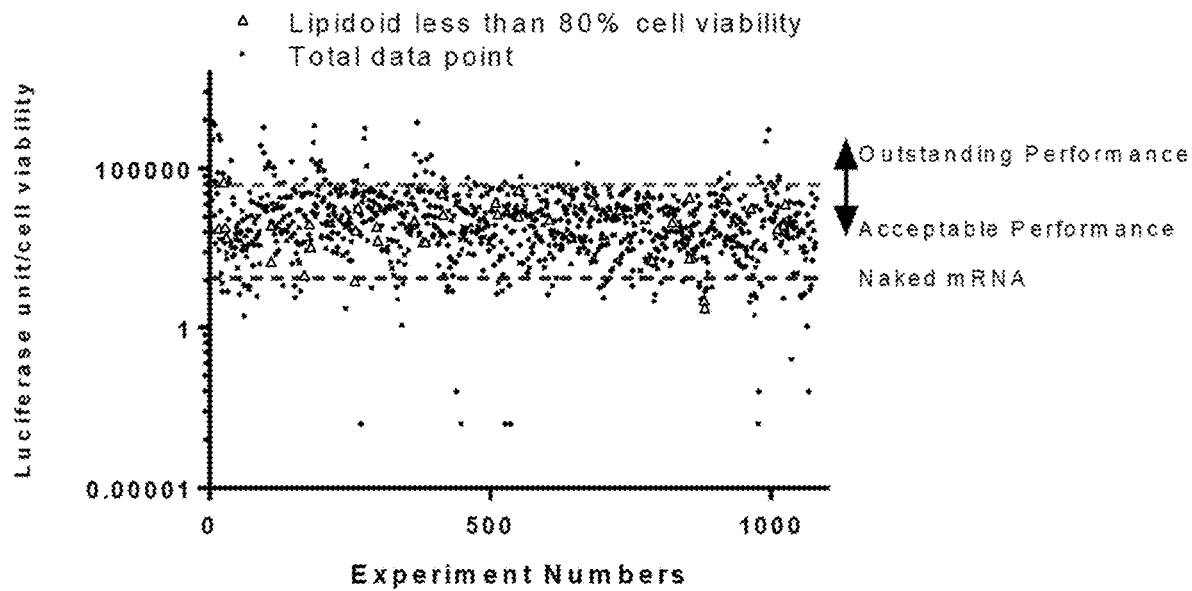
FIG. 7 shows luciferase activity/cell viability shown as scatter plots for the 1,080 LNP experiments. 969 lipidoids exhibited an mRNA transfection efficiency better than directly using the naked mRNA (above the lower dotted line). 232 lipidoids induced more than 10,000-unit luciferase expression (above the upper dotted line). Lipidoids with toxicity (<80% cell viability) are labeled as triangles, and were excluded from the analysis.

Effective mRNA vaccination requires both efficient intracellular antigen expression and subsequent immune cell activation to generate a robust immune response. The mRNA delivery efficacy of the lipidoid library was first evaluated by comparing luciferase protein expression in cell lines. Firefly luciferase mRNA (mLuc) was delivered to HeLa cells using lipioid nanoparticles (LNPs). These LNPs were composed of a lipid mixture containing one of the synthesized ionizable lipidoids, helper lipid, cholesterol, and C14-PEG (FIG. 2A).[34] Materials that caused cell viability <80% were eliminated from future studies (FIG. 7, marked as triangles). Of the 1080 lipidoid members, 969 lipidoids demonstrated improved mRNA transfection efficiency compared to naked mRNA. Of these, 232 lipidoids increased luciferase expression to over 10,000-units (FIG. 7). Analysis of these 232 lipidoids revealed that mRNA delivery and protein expression was generally enhanced in lipidoid systems containing longer alkyl chains with reduced saturation (FIG. 2B). The inclusion of an ester bond in the lipidoids appeared to enhance delivery efficiency, whereas adding an —OH group to the lipid head, in most cases, decreased delivery efficacy (FIG. 2B). Next, mLuc delivery to primary antigen presenting cells (APCs) known to be important in vaccine therapeutic efficacy was tested. A range of lipidoids containing the ketone 2DC18 were formulated into LNPs, and were used to deliver mLuc to mouse bone marrow derived dendritic cells (BMDCs) and macrophages (BMDMs). The results suggest that delivery efficiency is similar in BMDCs, BMDMs, and HeLa cells, and A2-Iso5-2DC18 and A12-Iso5-2DC18 were identified as the most potent mRNA delivery vehicles across these three cell types (FIGS. 2E to 2G).

Figure 2H:
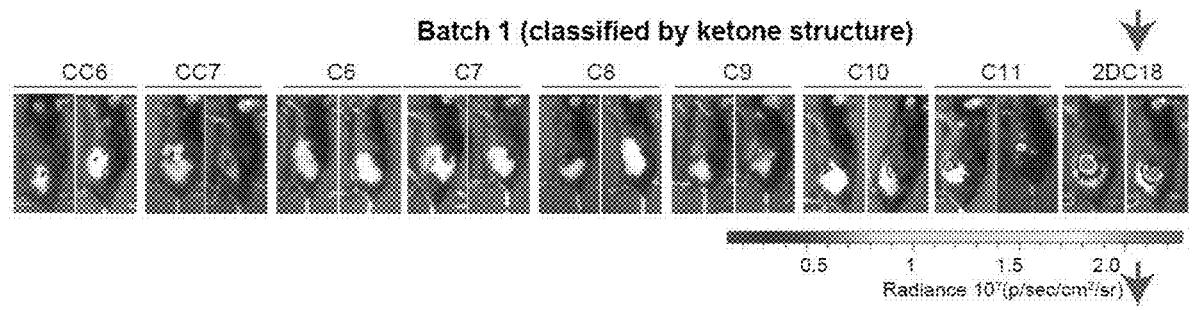
Figure 2I:
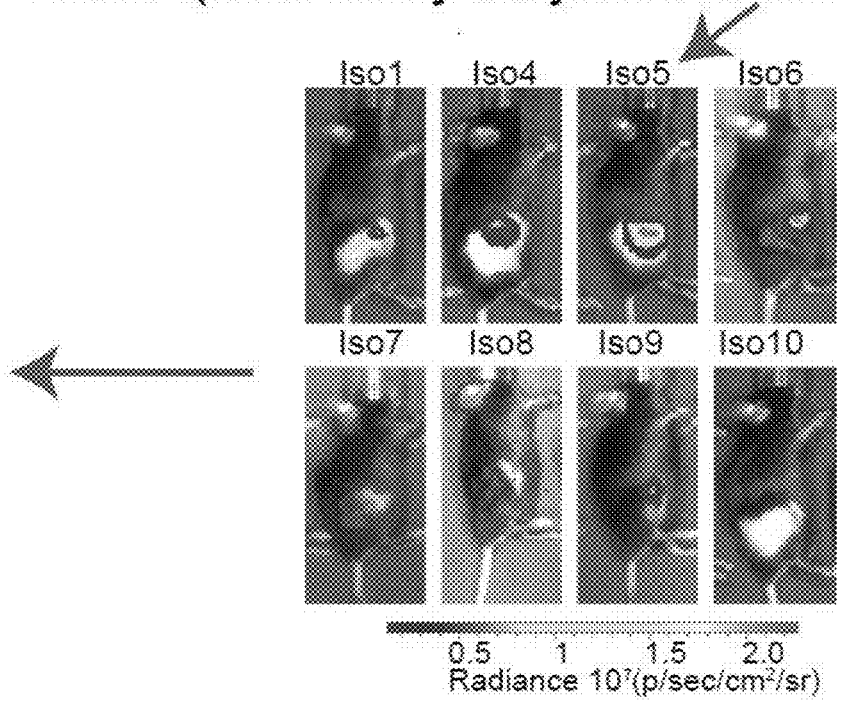
Figure 2J:
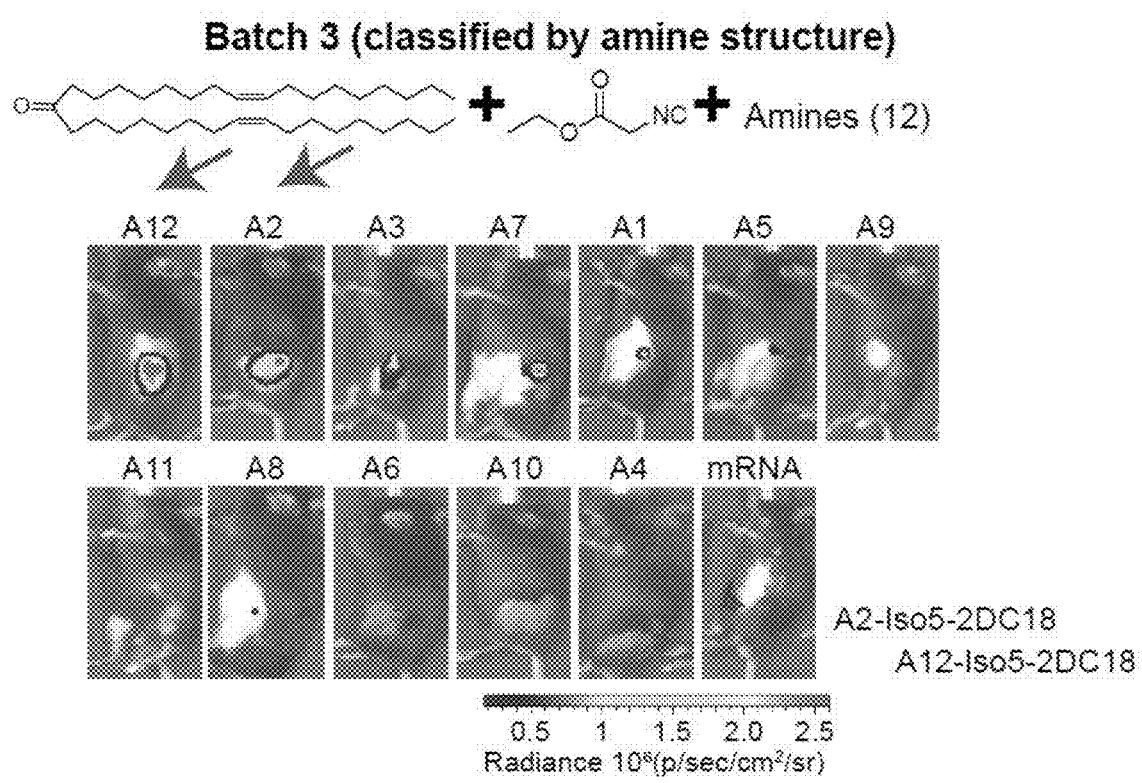
Figure 8:
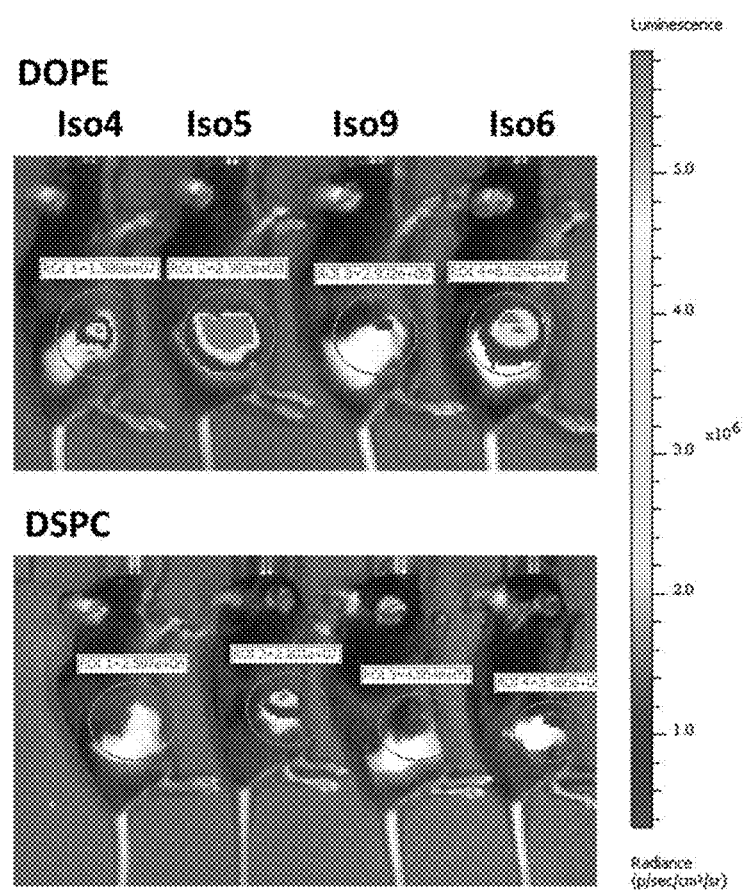
FIG. 8 shows lipidoid formulations using DOPE vs DSPC as the helper lipid. Results suggest DOPE as a helper lipid can improve the in vivo delivery efficiency of mRNA.
Figure 9A:
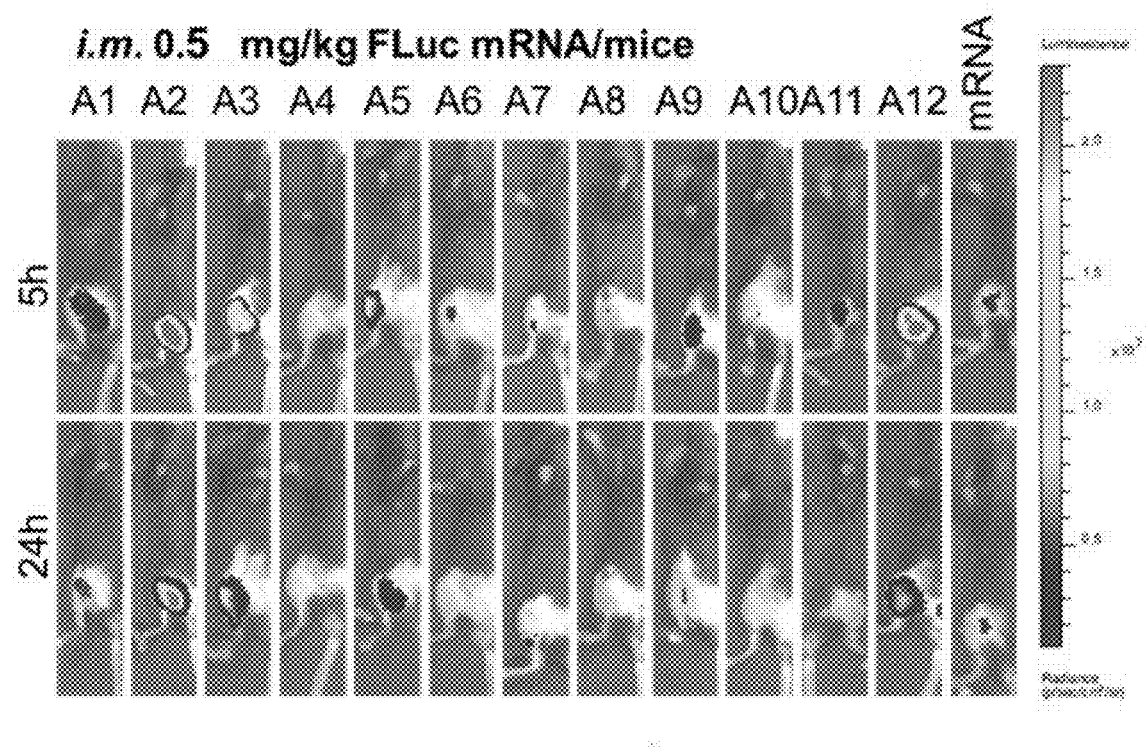
FIGS. 9A-9D show local injection (i.m. and s.c.) of lipidoid delivered Luc mRNA at two different time points (5 h and 24 h).
Figure 9B:
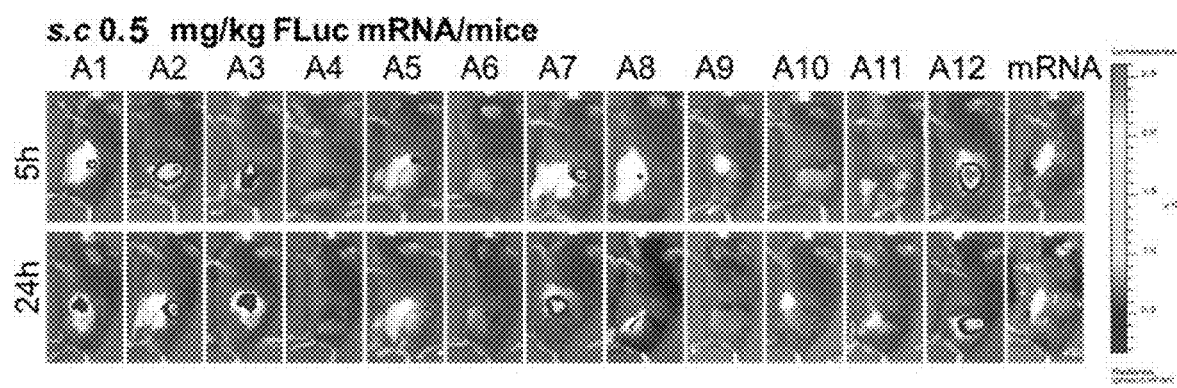
Figures 9C, 9D:
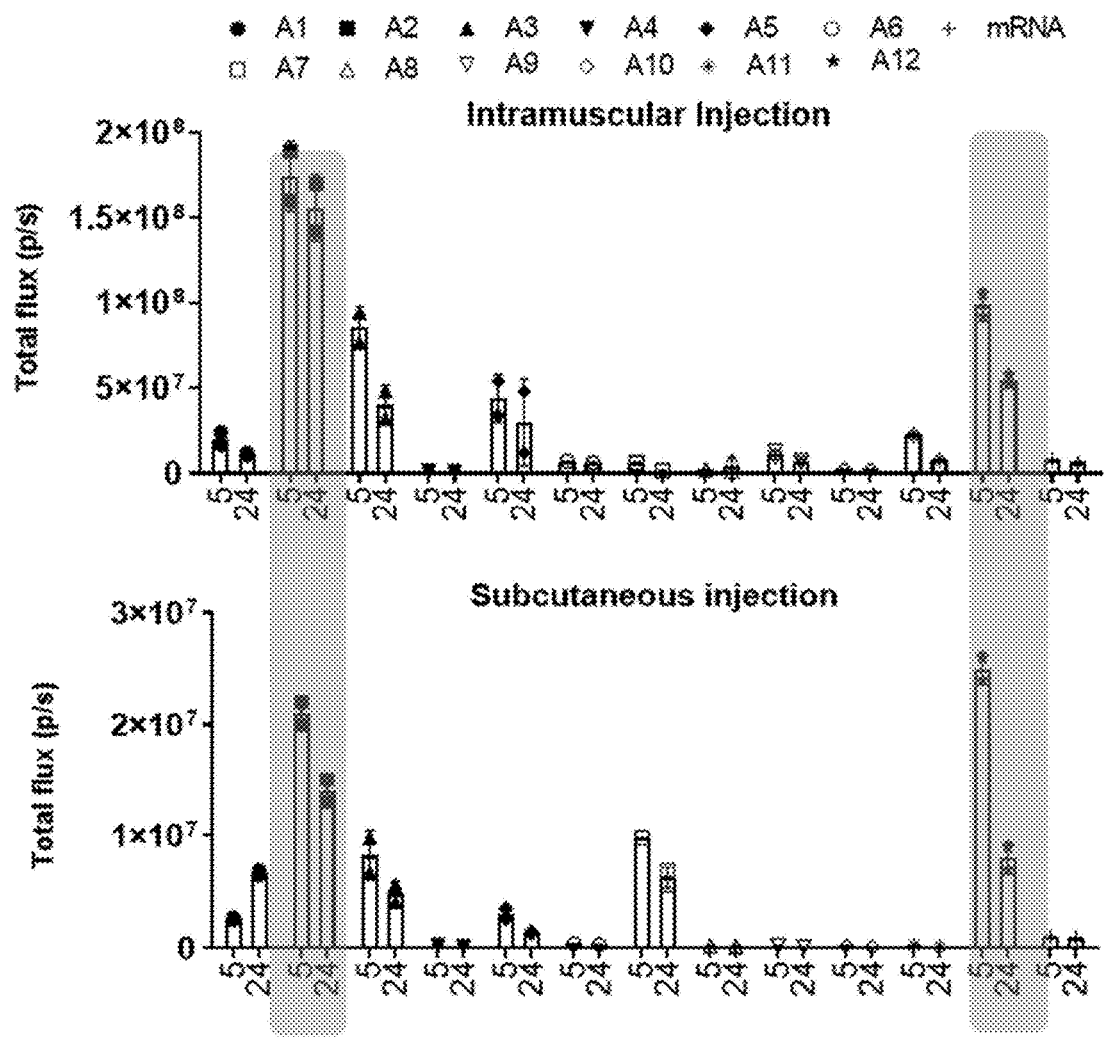
Figure 17A:
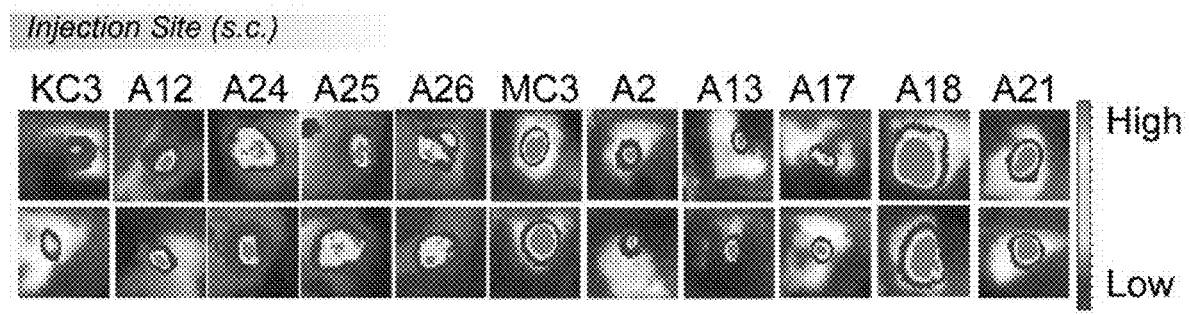
FIGS. 17A-17C show local and APCs expression of LNP-loaded mLuc RNA.
Figure 17B:
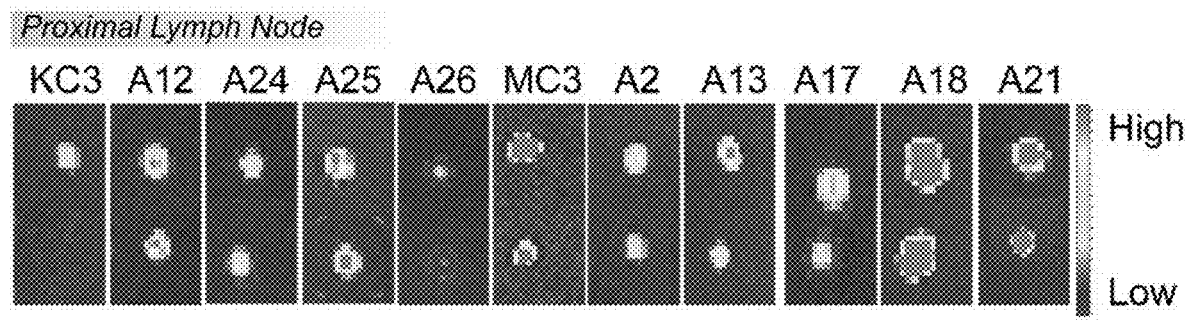
Figure 17C:
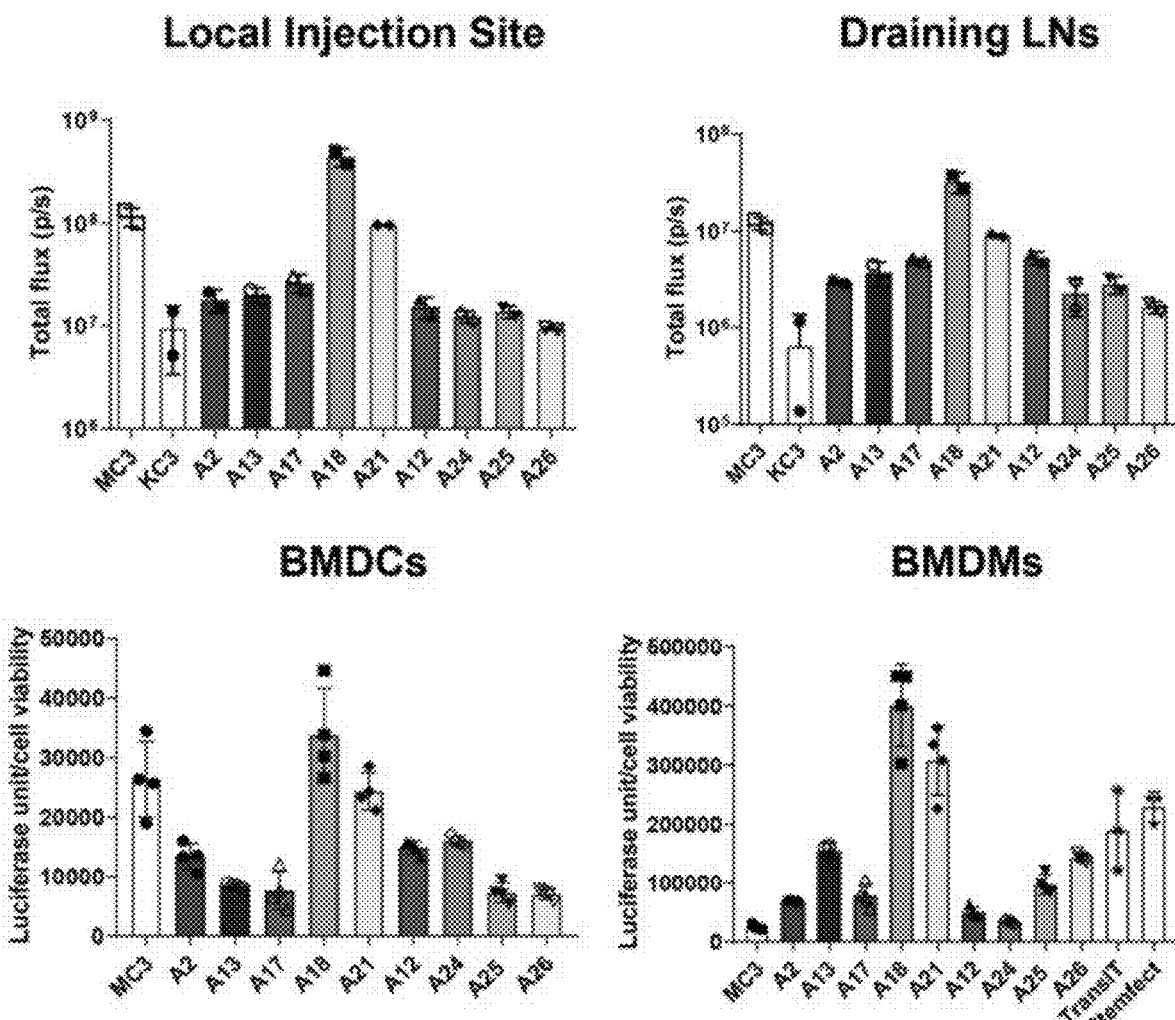

The in vivo delivery efficacy of these candidate lipidoids was next explored, using two different helper lipids, DOPE and DSPC to formulate LNPs.[35, 34] Fusogenic DOPE enhanced delivery compared to DSPC and was therefore chosen for the remainder of the LNP formulation studies (FIG. 8). LNPs from all lipidoids in the library were individually prepared, and lipidoids were classified into one of 9 groups based on their ketone structure. LNPs with the same ketone structure were mixed immediately prior to injection, and delivered using intramuscular (i.m) or subcutaneous (s.c) injection to mimic typical clinical vaccination approaches.[20, 36, 37] These 9 groups each contained a mixture of LNPs with a conserved ketone structure and various other functional groups. Consistent with our in vitro data, this screen revealed that longer, unsaturated alkyl tails increased delivery efficacy (FIG. 2H). 2DC18 ketone derivatives were identified as the most efficacious, and 2DC18 lipidoids were further categorized based on their isocyanide sub-structure (FIG. 2I). It was noted that isocyanoacetate lipidoids (butyl, ethyl or methyl) enhanced mRNA delivery compared to lipidoids synthesized using the conventional isocyanide. Lipidoids containing ethyl isocyanoacetate and 2DC18 ketones were therefore classified as optimal substructures for lipidoid mRNA delivery, and further evaluated lipidoids composed of these two sub units (FIG. 2J). Using this batch screening and analysis method significantly reduced the number of animals, time and cost required to screen all 1000 compounds in our lipidoid library, and A2-Iso5-2DC18 and A12-Iso5-2DC18 are provided as exemplary lipidoids for both s.c. and i.m. injection (FIG. 9), consistent with the in vitro cell-based studies. These lipidoids contain several structural similarities; (1) two amines in the polar head group, spaced three carbons apart; (2) no —OH group; and (3) the presence of at least one tertiary amine. Notably, the transfection efficiency of these two lipidoids is around 2-fold higher than that of LNPs formulated with commercially available Dlin-KC3-DMA (FIG. 17C).

Exemplary Lipidoids Exhibiting Different Antitumor Immunity

Figure 3A:
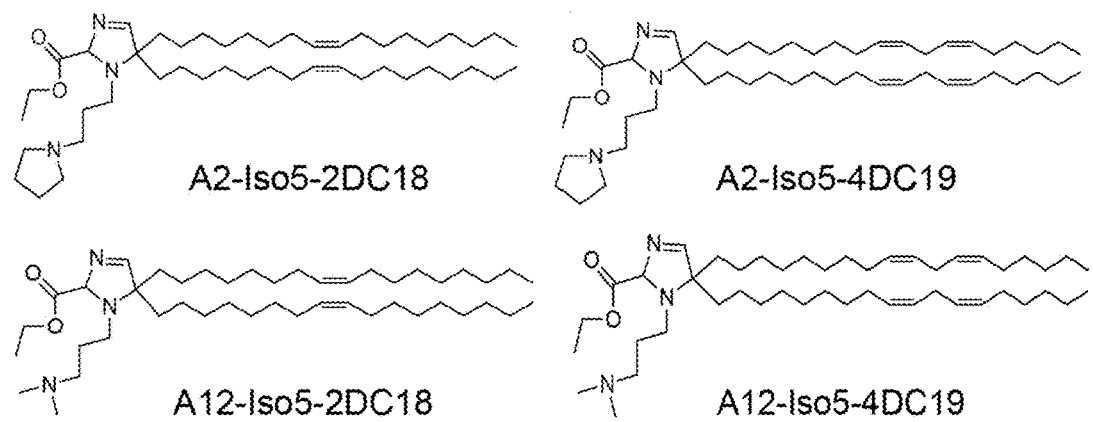
FIGS. 3A-3N show that exemplary lipidoids exhibit different antitumor immunity.
Figure 3B:
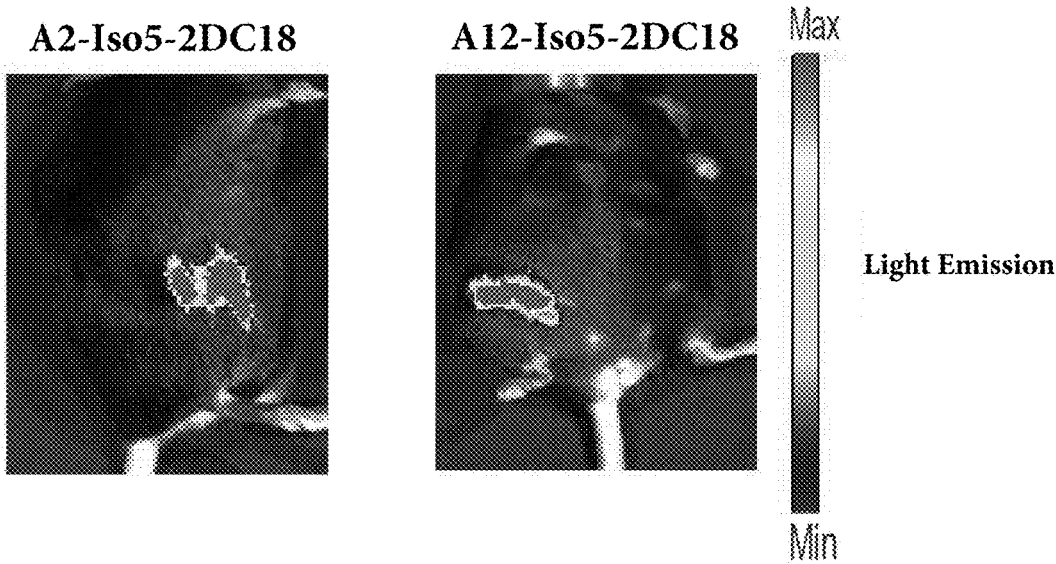
FIGS. 3B and 3D: Protein expression levels in the local injection site and the draining LNs following mLuc LNP injection. Quantification of Firefly luciferase (Fluc) protein expression in local injection site and draining LNs are shown in FIG. 3B and FIG. 3D. Female B6 mice were dosed with 0.1 mg/kg mLuc (n=4 biologically independent mice/group) and 0.5 mg/kg mLuc/mice (n=2 biologically independent mice/group) respectively. A2 and A12 LNP treatment groups were compared using unpaired two-tailed Student's t-test).
Figure 3C:
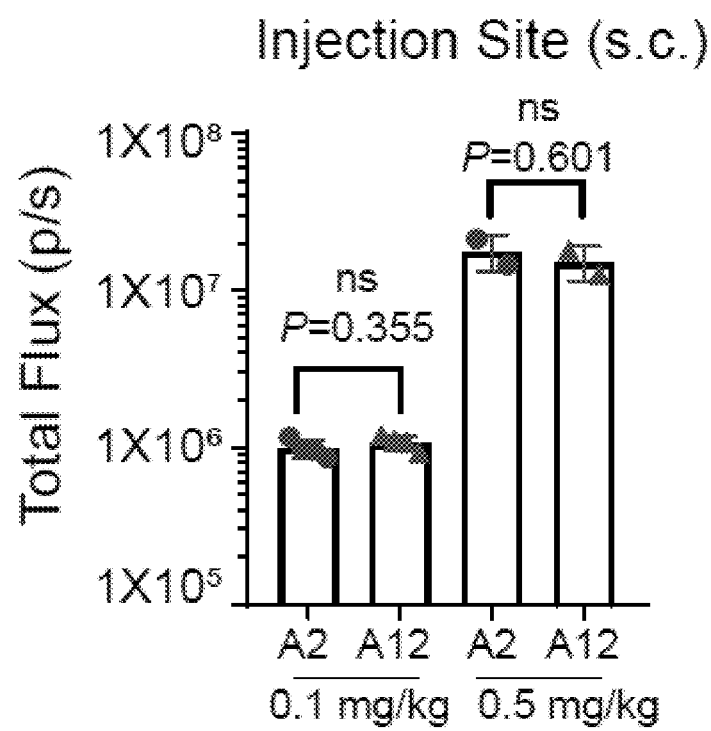
FIG. 3C and FIG. 3E: one of the representative images of Fluc expression and distribution locally and in the lymph nodes (dosed at 0.1 mg/kg mRNA).
Figure 3D:
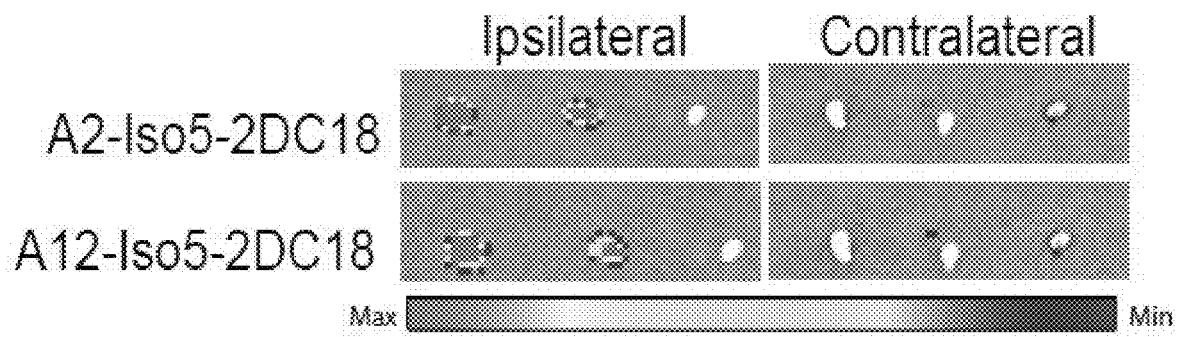
Figure 3E:
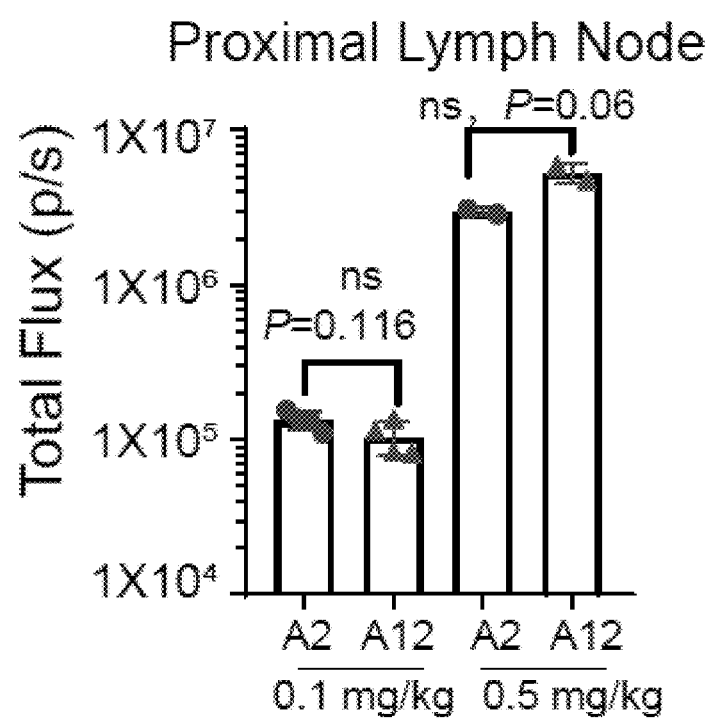

Exemplary lipidoids A2-Iso5-2DC18 and A12-Iso5-2DC18 were purified, their formulation was optimized, (Examples: Synthetic Method 2, Table 5, and FIGS. 10A and 10B[34, 38]) and their chemical structures were confirmed using NMR and mass spectrometry (Examples: Synthetic Method 1). Notably, the isocyanoacetate moiety contains a carbanion between the carbonyl and imine groups. This carbanion appears susceptible to electrophilic attack by the local secondary amine, generating a heterocyclic dihydroimidazole (FIG. 3A). The dihydroimidazole heterocycle appears to stabilize the reactive imine, and constitutes a stable and rigid linker between the polar head group and the alkyl tail. It is believed this is the first evidence of dihydroimidazole linked lipidoids suitable for mRNA delivery.

Figure 11A:
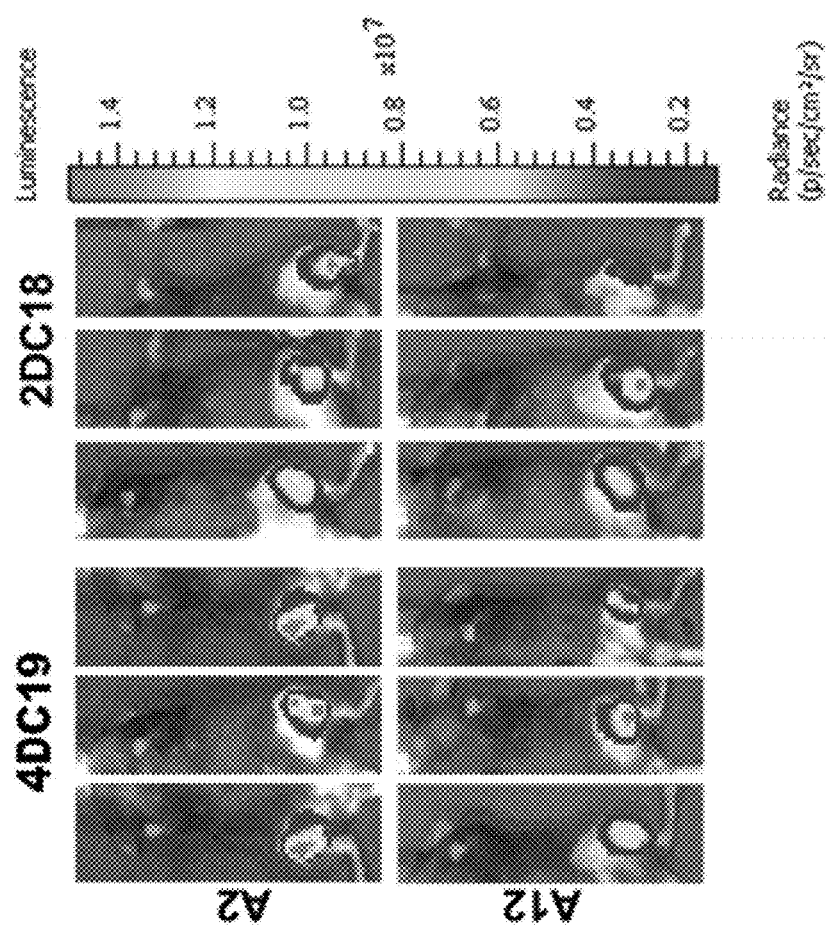
Figure 11B:
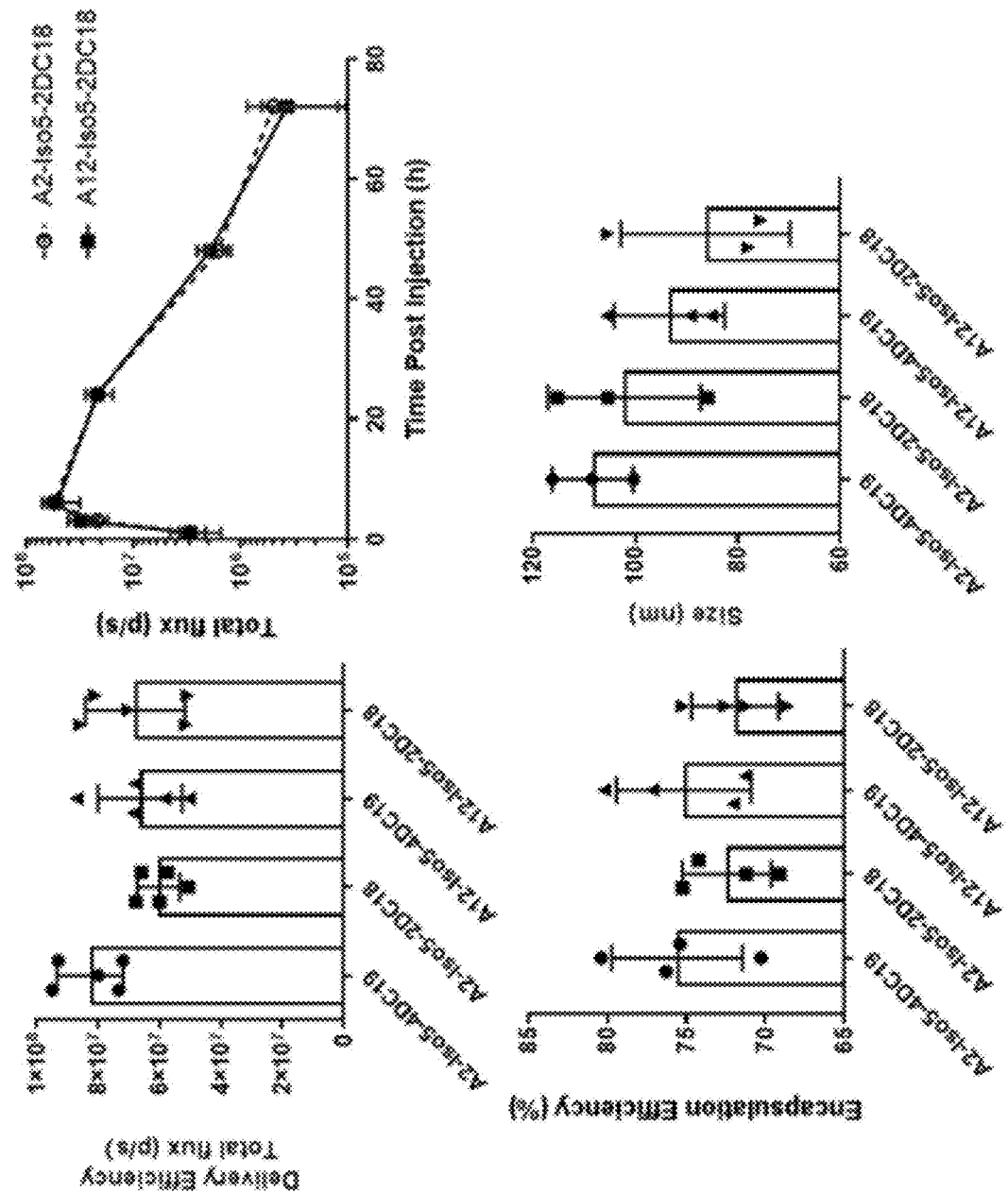

Separately, decreasing lipid tail saturation is thought to increase transfection efficiency through enhanced fusogenic $H_{II}$ phase formation.[29, 39] To determine if this approach could enhance delivery in the present system, ketones with two (2DC18) or four (4DC19) double bonds in the lipidoid tail were compared. LNPs exhibited comparable particle size, encapsulation efficiency and protein expression levels (statistically no difference) between systems with two or four double bonds in the lipidoid tail (FIG. 11).

Figure 3F:
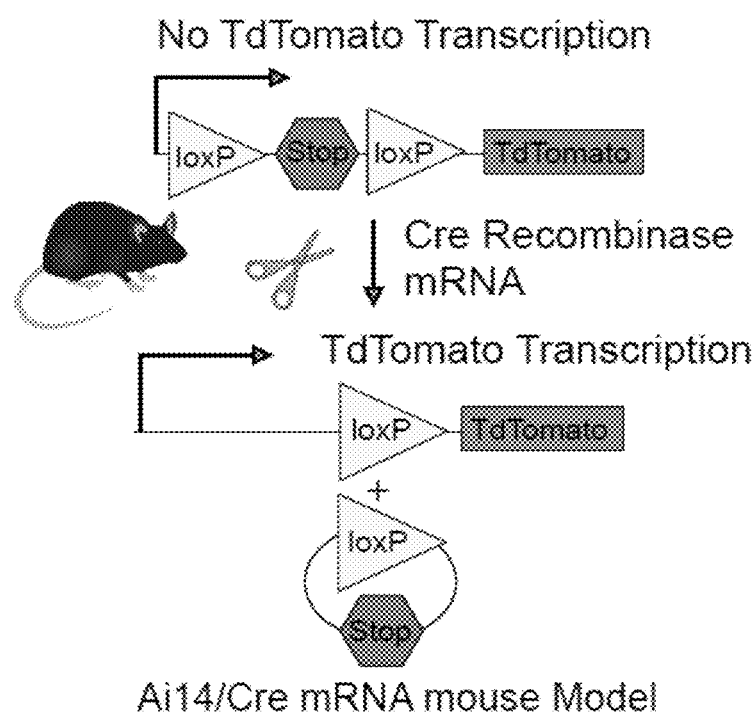
FIG. 3F: A schematic of the A14/Cre mRNA mouse model.
Figure 3G:
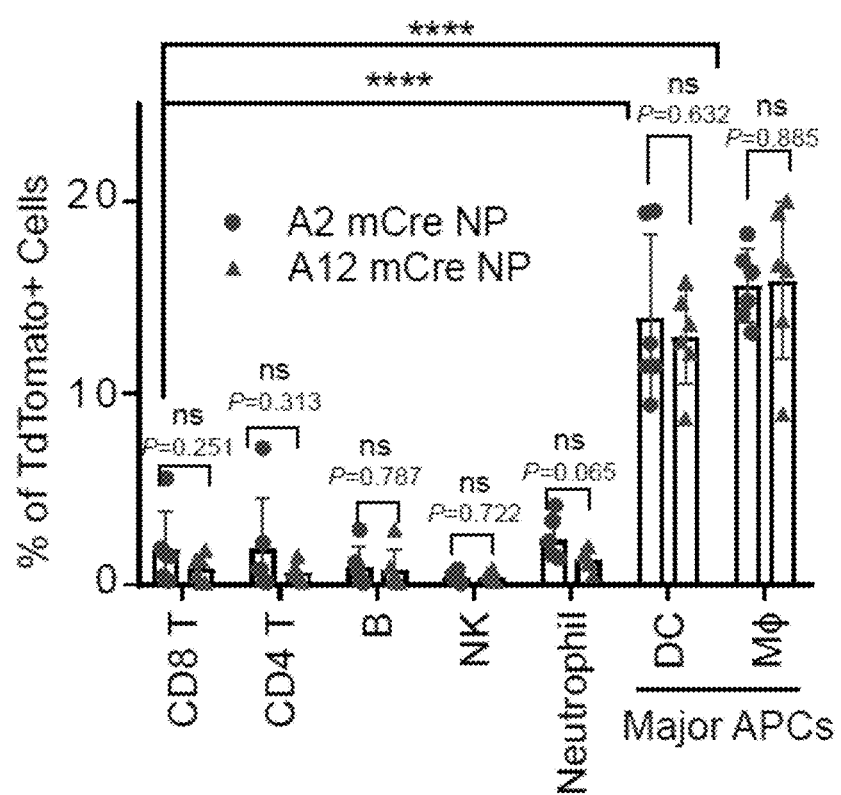
FIG. 3G: FACS quantification of tdTomato positive cells expressed in LNs 48 hours after injection of mCre LNPs (0.5 mg/kg mCre/mice). mRNA is mainly expressed in macrophages/monocytes and DCs (n=6 biologically independent mice/group, unpaired two-tailed Student's t-test).
Figure 12:
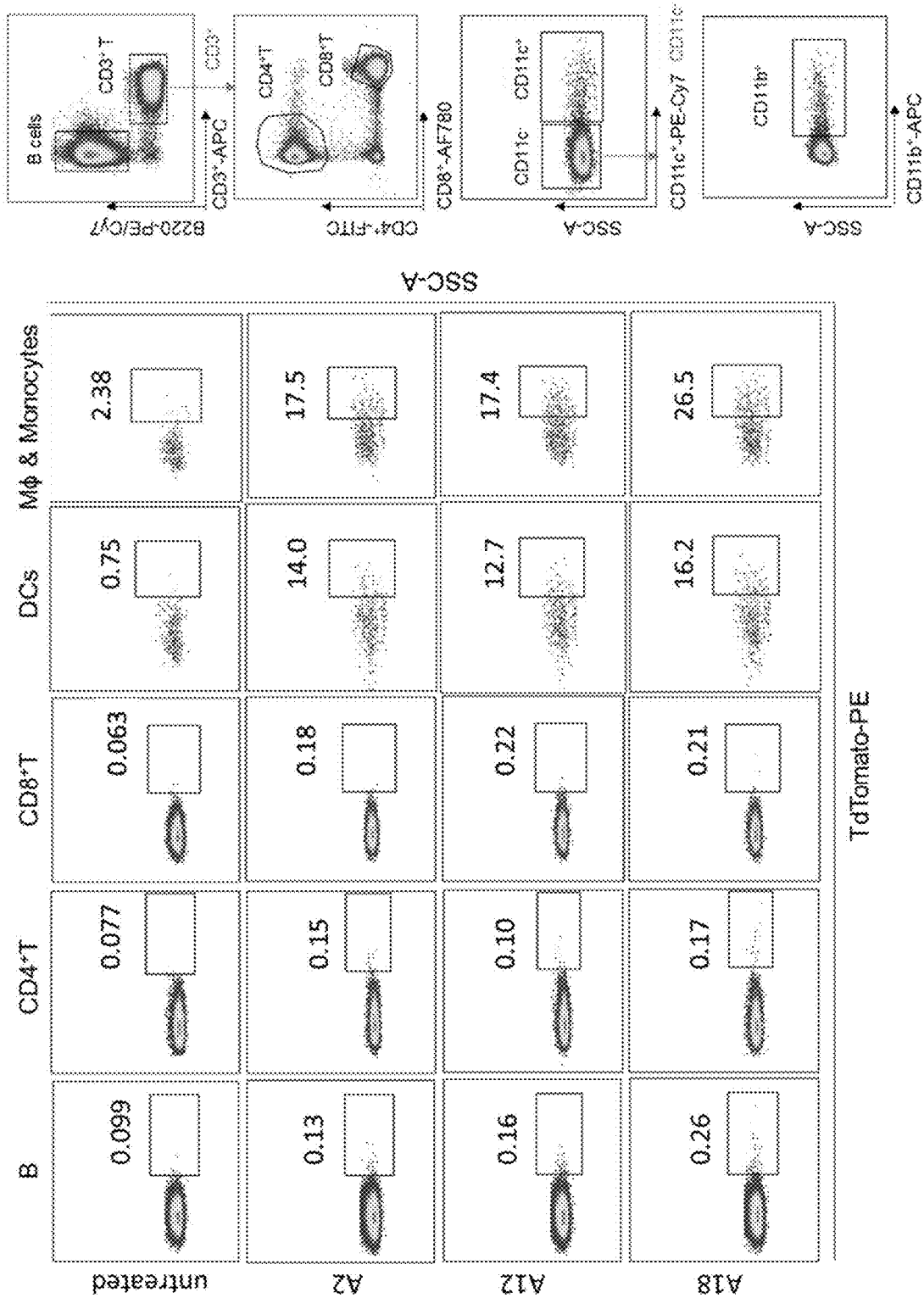
FIG. 12 shows quantification of the percentage of transfected APCs two days after the injection of LNPs containing mRNA coding for Cre-recombinase in Ai14D reporter mice, as determined by FACS Analysis. mRNA was mainly delivered and expressed in macrophages/monocytes and DCs (n=6).

Next the vaccination potential of the well-performing lipidoids (A2-Iso5-2DC18 and A12-Iso5-2DC18, referred to as A2 and A12 respectively) were tested following subcutaneous injection.[40,41] It was found that both the A2 and A12-loaded mLuc LNPs could induce protein expression in the local injection site and the draining lymph nodes (FIGS. 3B to 3E). To determine whether APCs were transfected within lymph nodes, Cre-recombinase mRNA LNPs (mCre) were delivered to the Ail4D reporter mouse model. These mice harbor a mutation in the Gt(ROSA)26Sor locus and cells co-express tdTomato upon injection of mCre (FIG. 3F). The results indicated that the A2 and A12 LNPs induced similar levels of protein expression, and were able to transfect central APCs including macrophages/monocytes and dendritic cells (FIGS. 3G and 12).

Figure 3H:
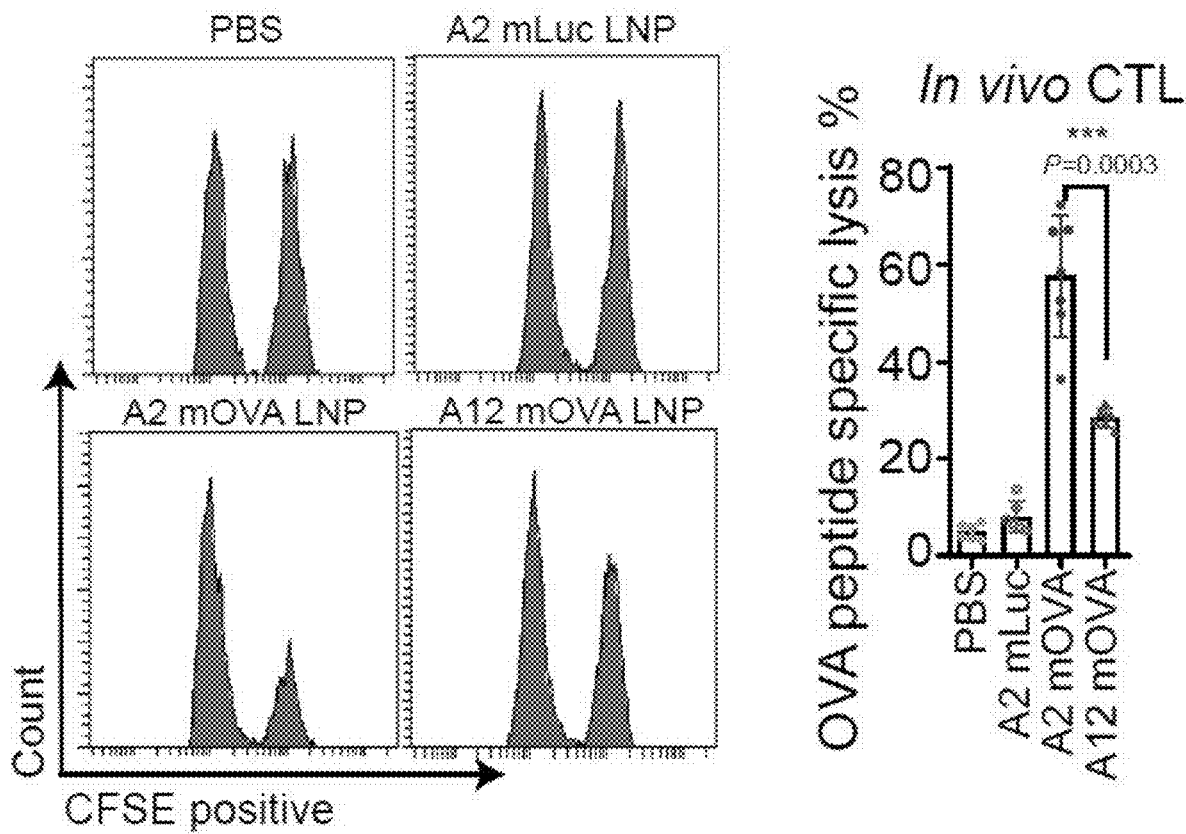
FIG. 3H: An in vivo CTL assay of mOVA-loaded LNPs was performed 5 days after second injection (15 µg mOVA/mice). Quantification is shown on right (n=6 for PBS, A2 and A12 mOVA groups and n=7 for A2 mOVA group. Biologically independent mice were used in each group, data were analyzed by one-way ANOVA and Tukey's multiple comparisons test). Tumor volume was measured following (FIG. 3I) mOVA-loaded LNP vaccination using 15 µg mRNA, administered once per week for the first two weeks (arrows) (n=6) or (FIG. 3J) in combination with anti-PD1 antibody, and overall survival plotted (FIG. 3K) (n=6 biologically independent mice/group, 2way ANOVA repeated measures and Tukey's multiple comparisons test). Mice were rechallenged on day 15 with an i.v. injection of tumor cells (2×10⁵), and lungs were evaluated 21 days later (FIG. 3L). CD8+ T cells were isolated from splenocytes (FIG. 3M) and within tumor regions (FIG. 3N) and stained with OVA tetramer before FACS analysis five days after the repeat injection (n=4). * P<0.05,  P<0.01, * P<0.001, n.s., no statistical significance.
Figure 3I:
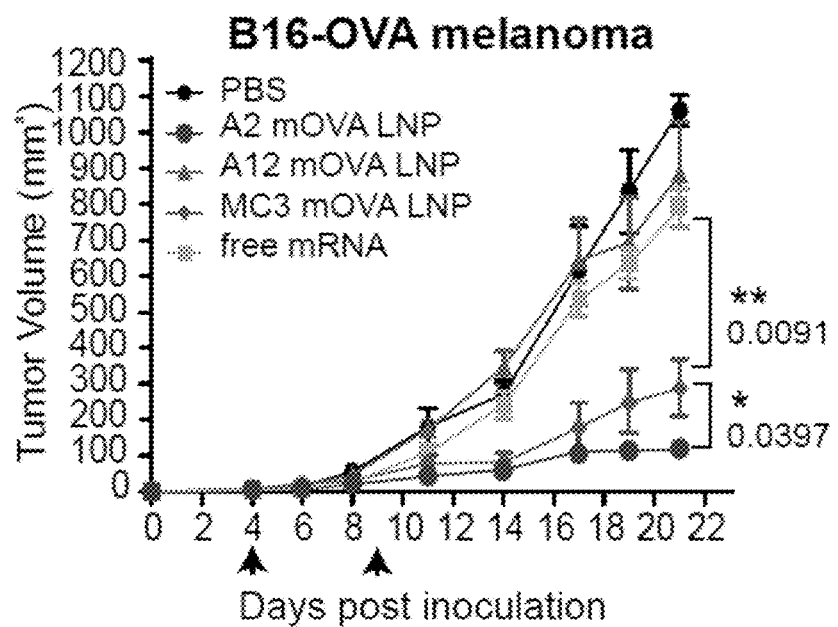
Figure 3J:
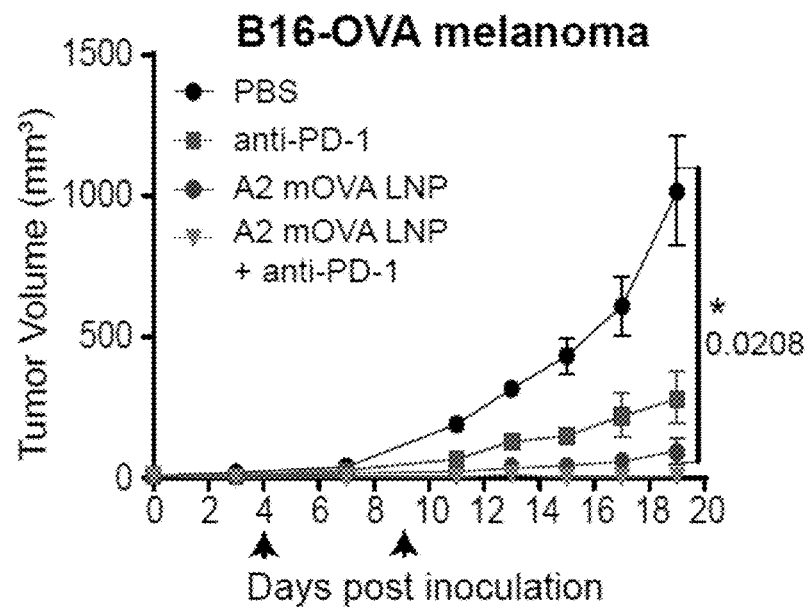
Figure 3K:
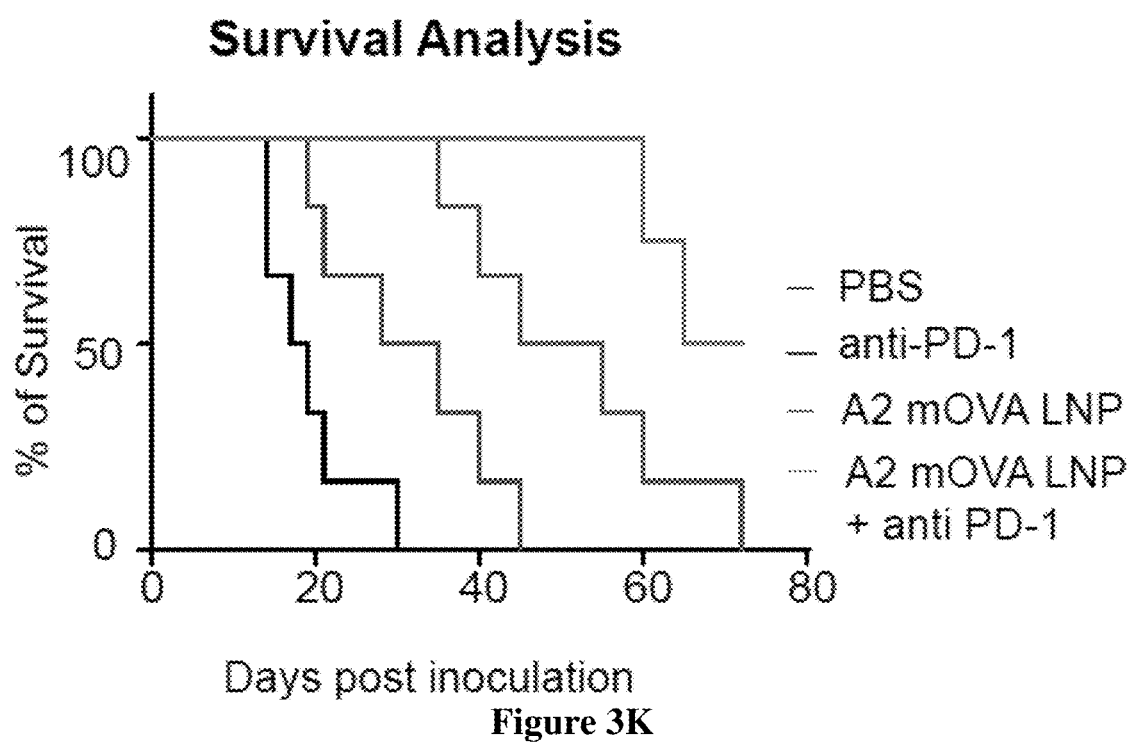
Figure 3L:
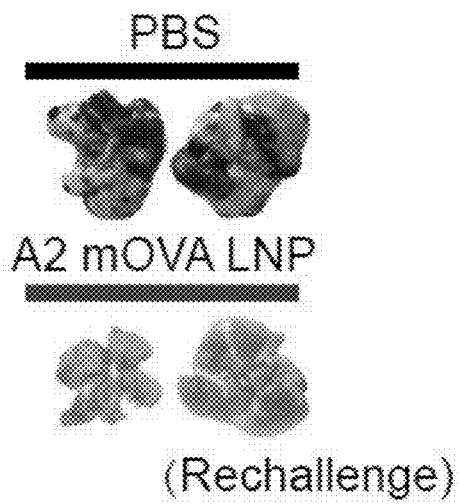
Figure 3M:
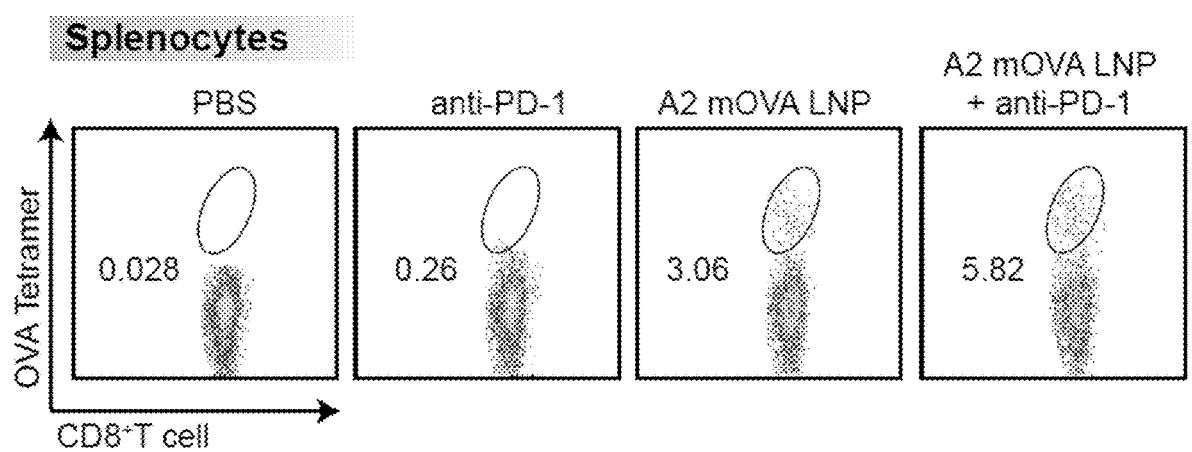
Figure 3N:
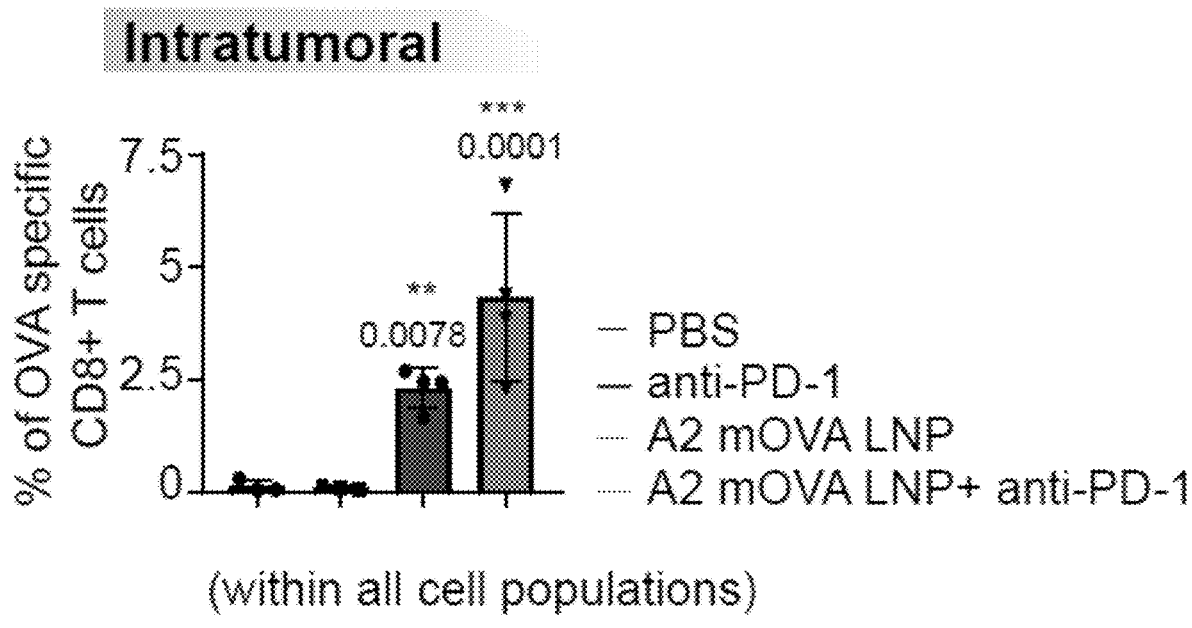
Figure 13:
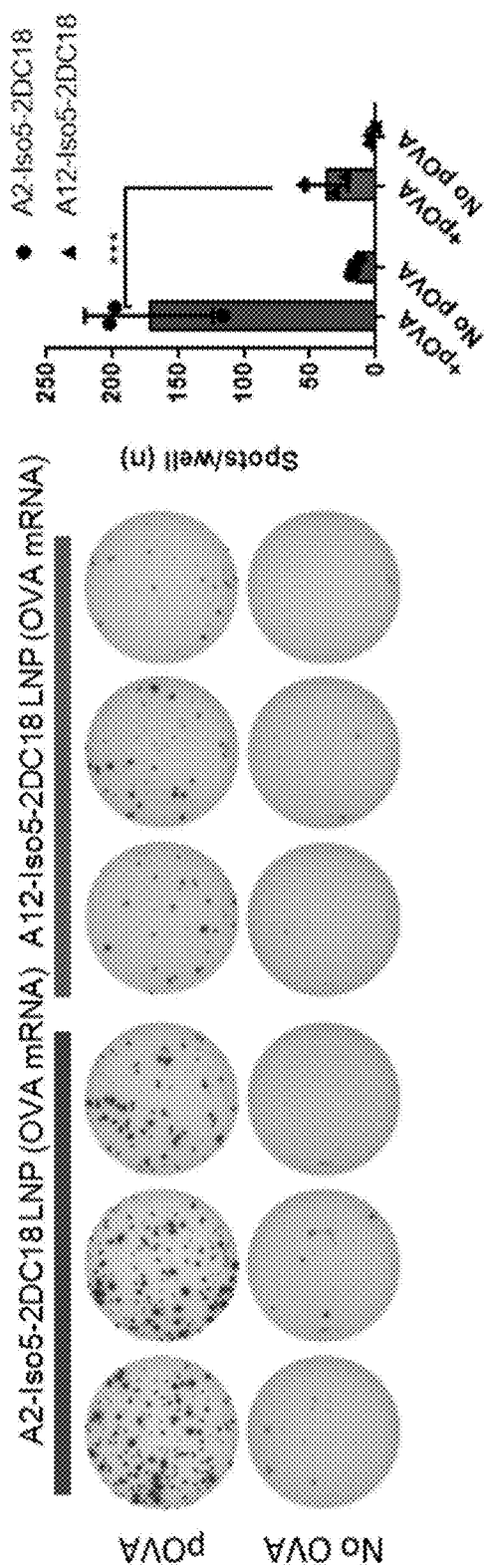
FIG. 13 shows IFN-γ ELISpot Assay of A2 and A12 LNP delivered OVA mRNA. Splenocytes were pulsed with and without OVA peptide 257-264 (pOVA). Results suggest that A2 LNPs can induce an antigen specific CD8+ T cell mediated secretion of IFN-γ (n=3 biologically independent mice/group). Data are presented as means±S.D. *** P=0.0002, Two-sided Student's T-Test.
Figure 14:
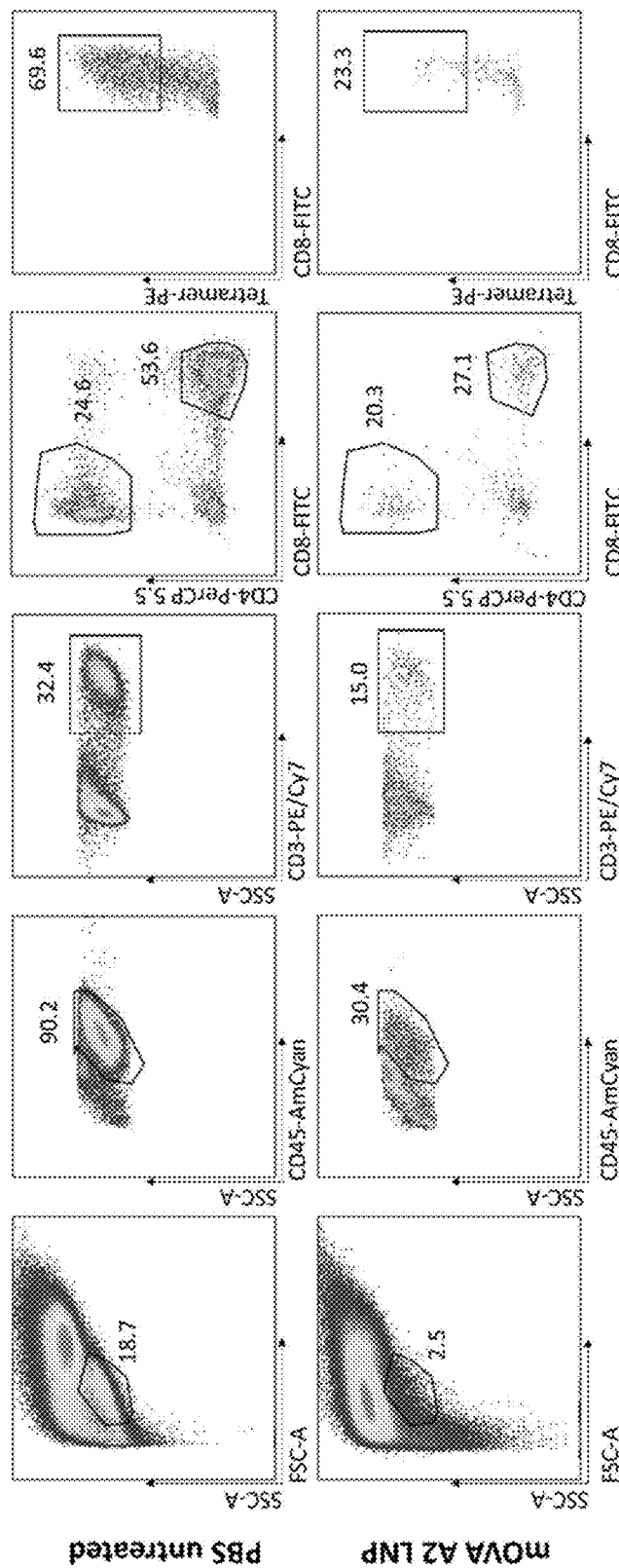
FIG. 14 shows tetramer staining of the OVA-specific CD8+ T cells within tumor regions five days after the second injection of vaccine. Vaccine treatment improved the infiltration of CD45+ leucocytes. Within the CD45+ leucocyte population, the ratio of antigen-specific T cells was dramatically increased (CD3+CD8+ Tetramer+).

The adaptive immune response and anti-tumor efficacy of the mRNA lipidoid delivery systems were then tested using the Ovalbumin (OVA) expressing B16F10 mouse melanoma model, and an OVA mRNA (mOVA) vaccine. Surprisingly, it was found that the A2 mOVA LNPs induced a significantly higher antigen-specific cytotoxic T lymphocyte response (CTL) compared to the A12 mOVA LNPs, in parallel with robust IFNγ secretion (FIGS. 3H and 13). Additionally, the A2 mOVA LNP vaccines induced robust tumor suppression with only two doses (once per 5 days) (FIG. 3I), whereas the A12 mOVA LNPs showed almost no anti-tumor efficacy in the B16F10-OVA mouse melanoma model. When the A2 mOVA LNPs were co-delivered with an anti-PD1 antibody, this combination therapy significantly retarded tumor growth and improved overall survival (FIGS. 3J and 3K). The number of systemic and tumor-infiltrating antigen-specific T cells also increased dramatically (20-30 fold) following A2 vaccination using the mOVA or mOVA/anti-PD1 combination vaccination approach (FIGS. 3M, 3N, and 14).

Finally, using a tumor re-challenge model, the durability of T-cell responses following vaccination with A2 mOVA LNPs was examined. Mice were able to efficiently eliminate B16-OVA cells following intravenous vaccination (FIG. 3L), demonstrating long-lived protection against tumor challenge. Although the A2 and A12 LNPs demonstrated similar mRNA delivery efficacy to local lymph nodes and APCs, only the A2 LNP system was able to induce robust tumor immunity.

Figure 4A:
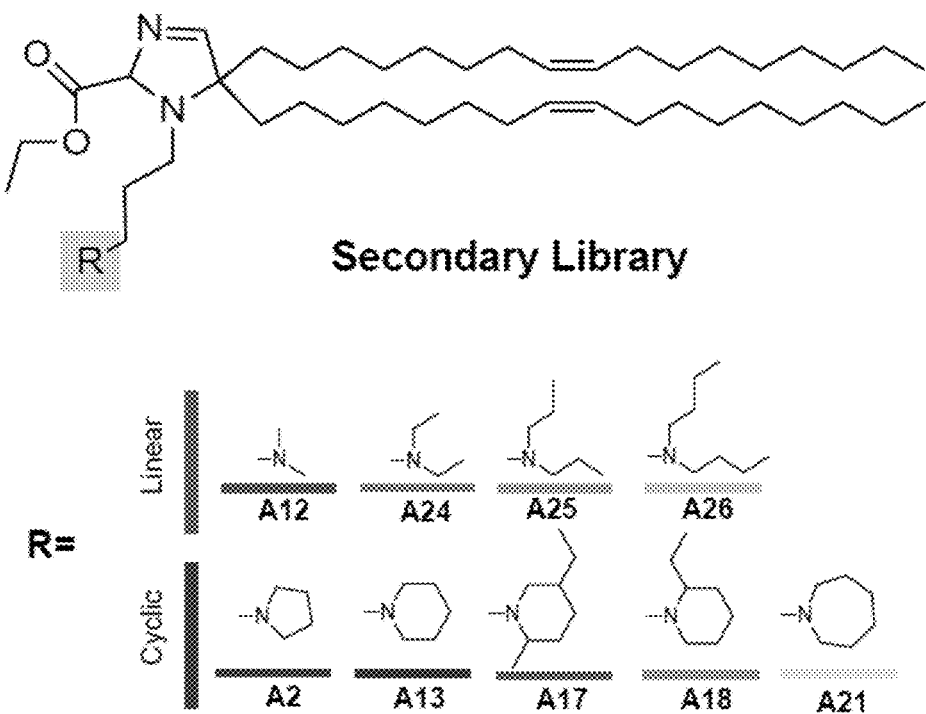
FIGS. 4A-4J. mRNA vaccines delivered by heterocyclic amine-containing lipidoids induced robust antigen-specific T cell and humoral response.
Figure 4B:
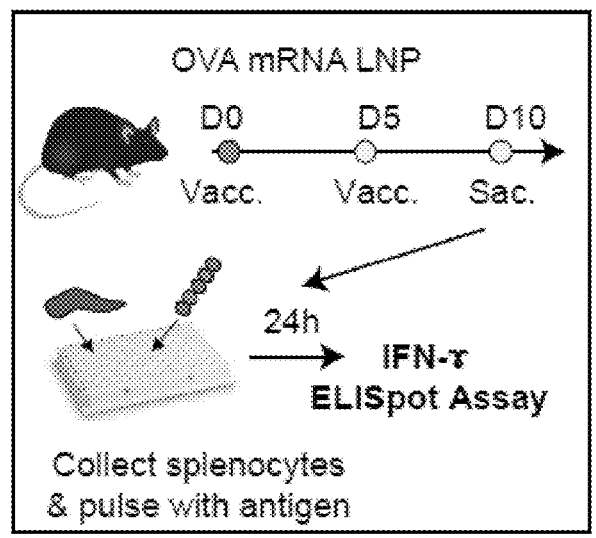

Generating a Second Lipidoid Library to Identify Immune Stimulatory Lipidoid Structures Structural analogues of well-performing lipids were explored, focusing on the heterocyclic[20] amine head groups present in A2-like lipidoids and probing their role in lipidoid-associated immunogenicity and vaccination efficacy. A second lipidoid library with conserved 2DC18 and ethyl isocyanoacetate moieties was generated, and the amine components were varied to include either linear tertiary amines or heterocyclic tertiary amines (FIG. 4A, Table 5). LNPs with similar particle size and encapsulation efficiency were formulated using these lipidoids, and compared IFNγ expression following mOVA vaccination (FIG. 4B).

Figure 4C:
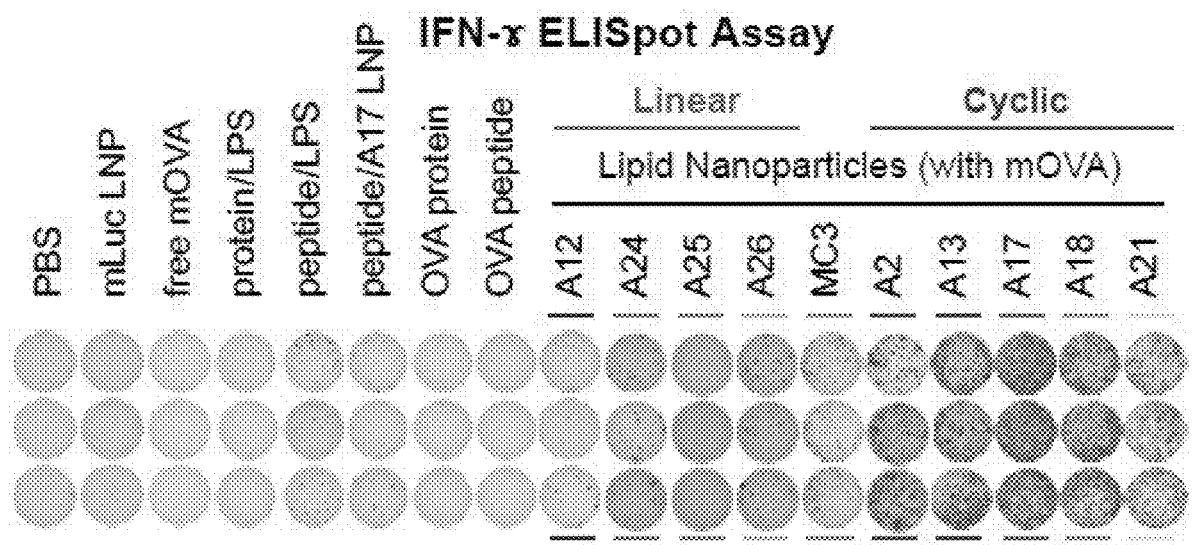
Figure 4D:
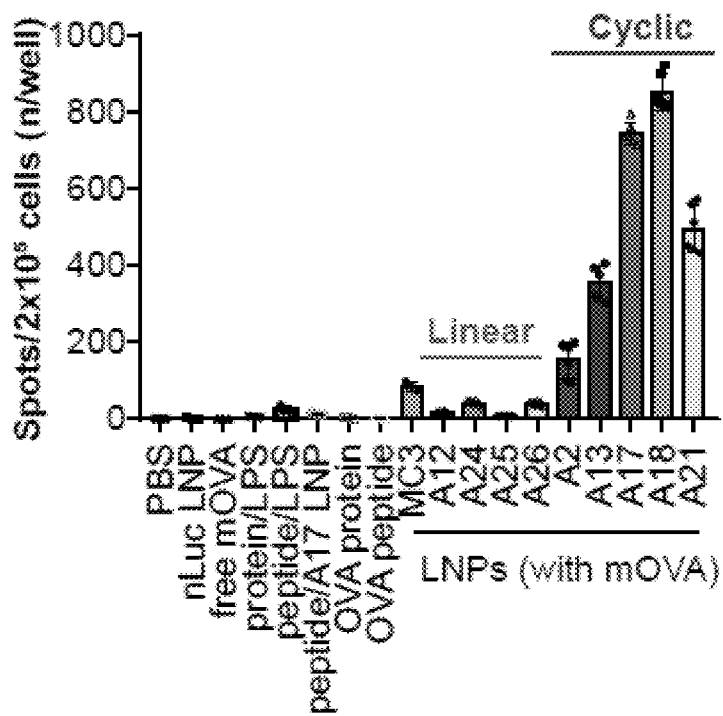
Figure 4E:
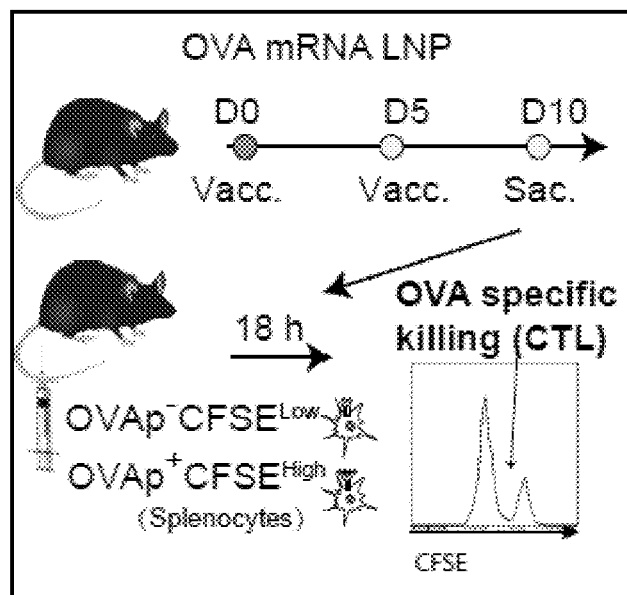
Figure 4F:
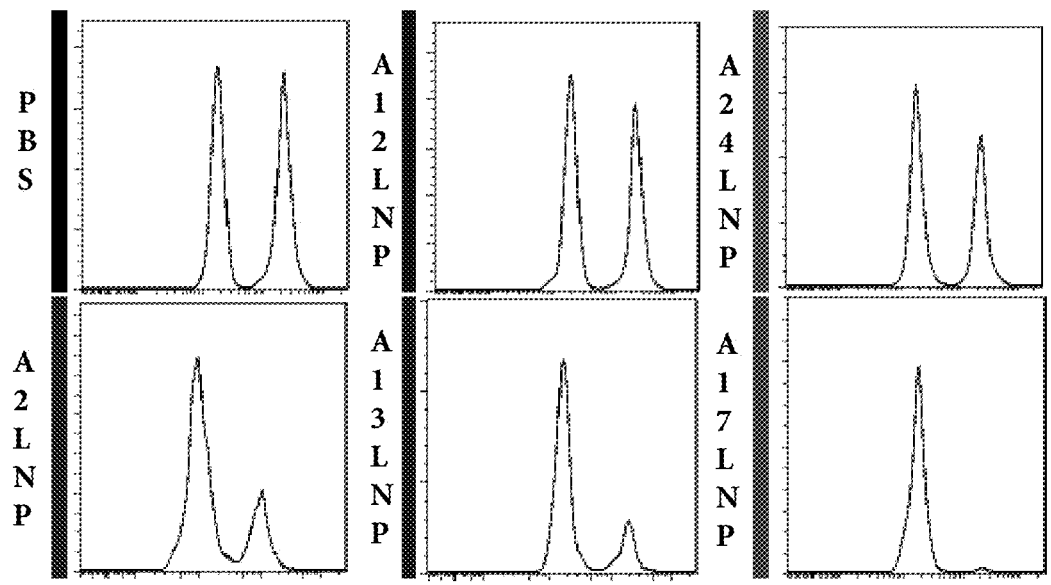
Figure 4G:
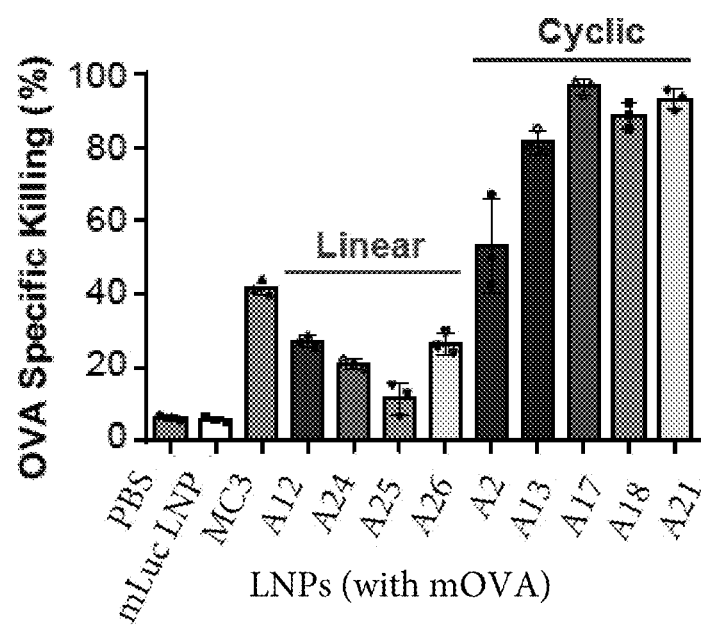
Figure 4H:
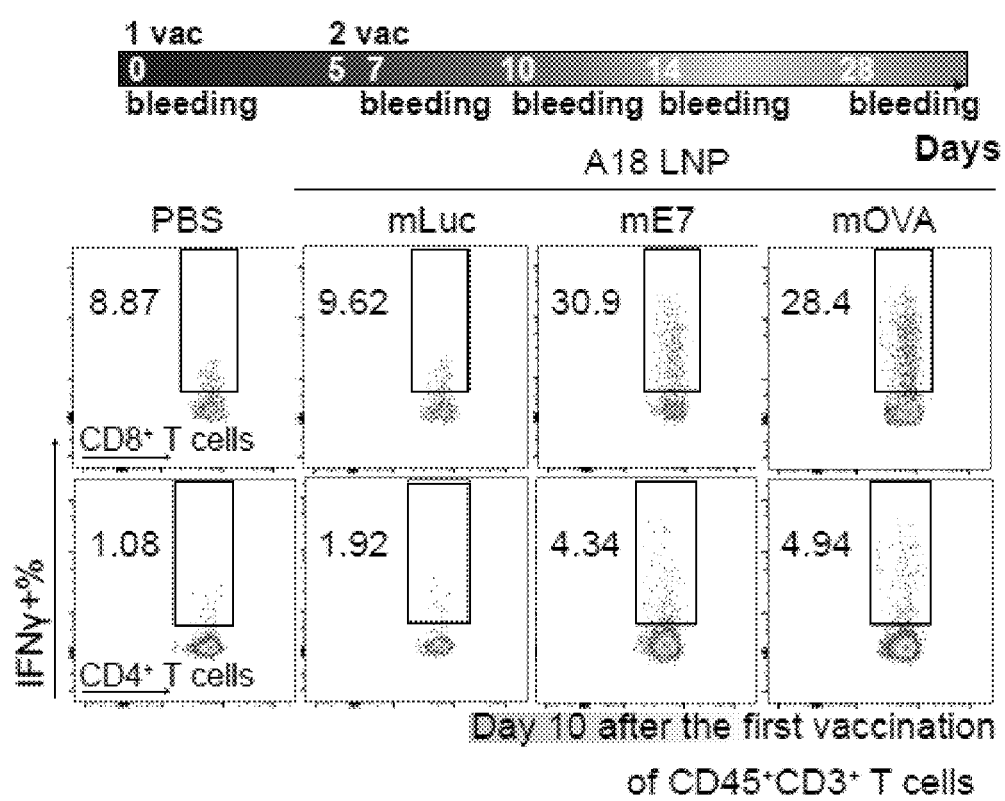
Figure 4I:
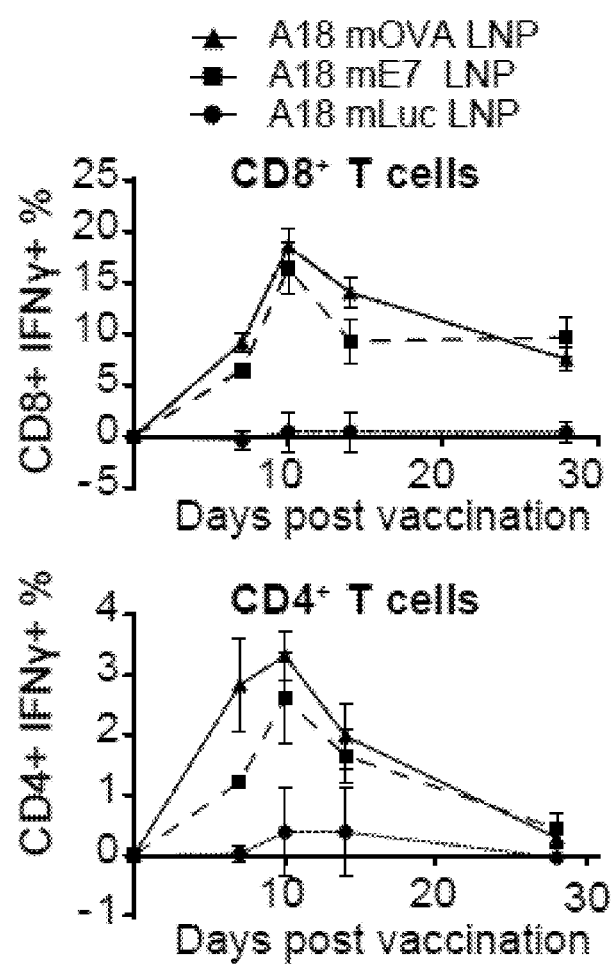
Figure 4J:
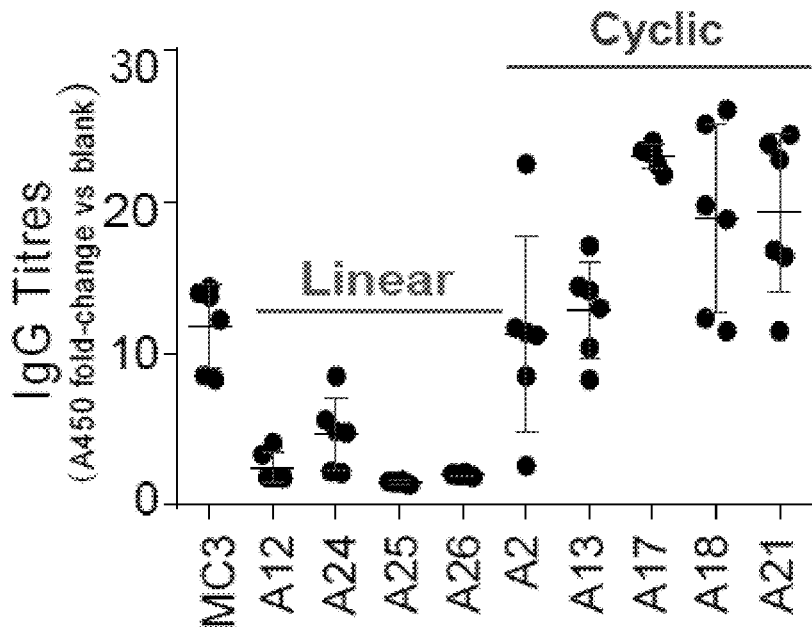
Figure 15A:
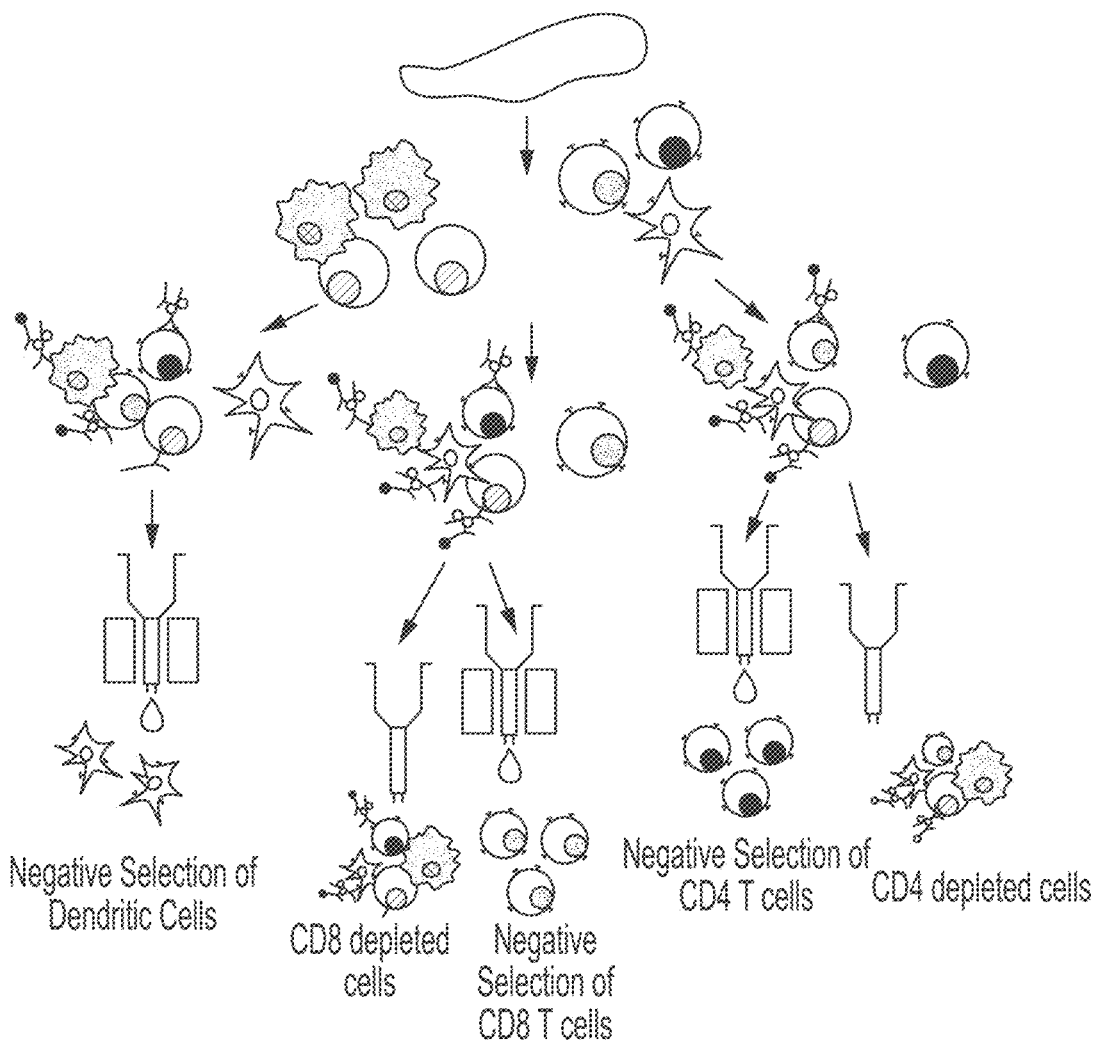
FIGS. 15A-15C show characterization of CD4+ and CD8+ T cells from mice vaccinated with A18 LNPs after in vitro stimulation of purified T cell populations with OVA-peptide pulsed autologous DCs or using peptide-pulsed CD4+ T cell- or CD8+ T cell-depleted splenocytes in an IFN-γ ELISpot read-out assay. (a) isolation process of CD4+, CD8+ T and autologous DCs. (b) confirmation of cell isolation purification. >90% purity can be achieved. (c) ELISpot assay using purified or depleted T cells with autologous DCs pulsed with OVA-peptide (n=4). Data were analyzed by One-way ANOVA. Important statistics are shown. **** P<0.0001, ns, no significant difference.
Figure 15B:
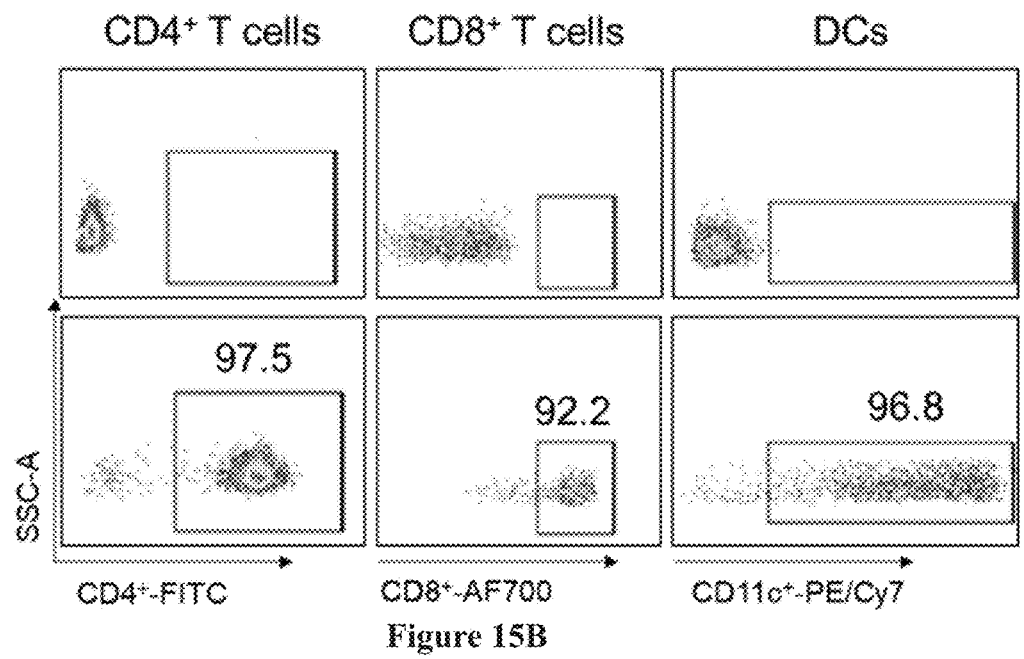
Figure 15C:
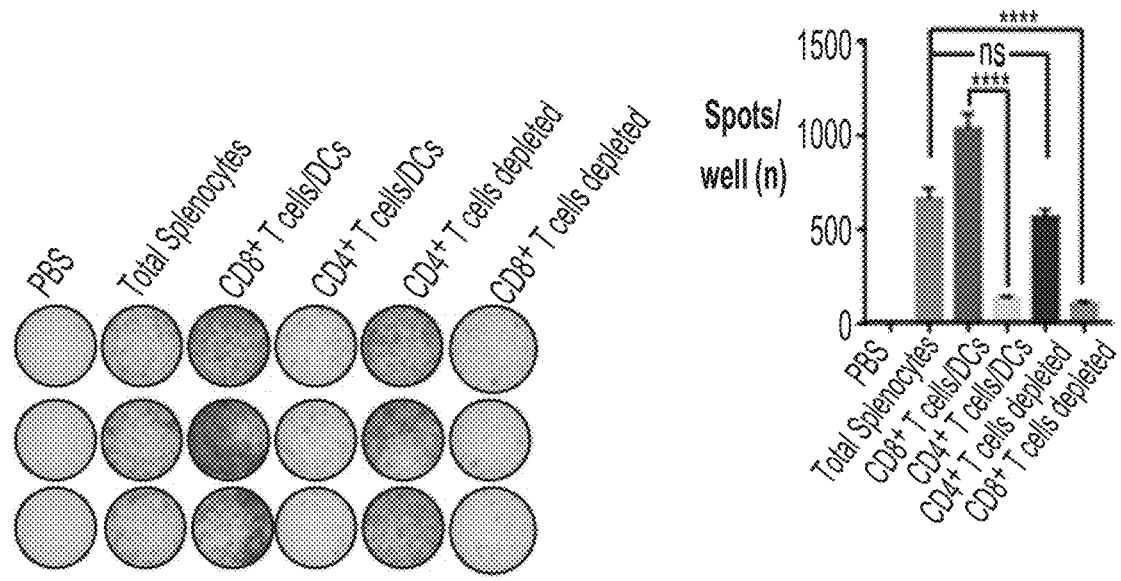
Figure 16:
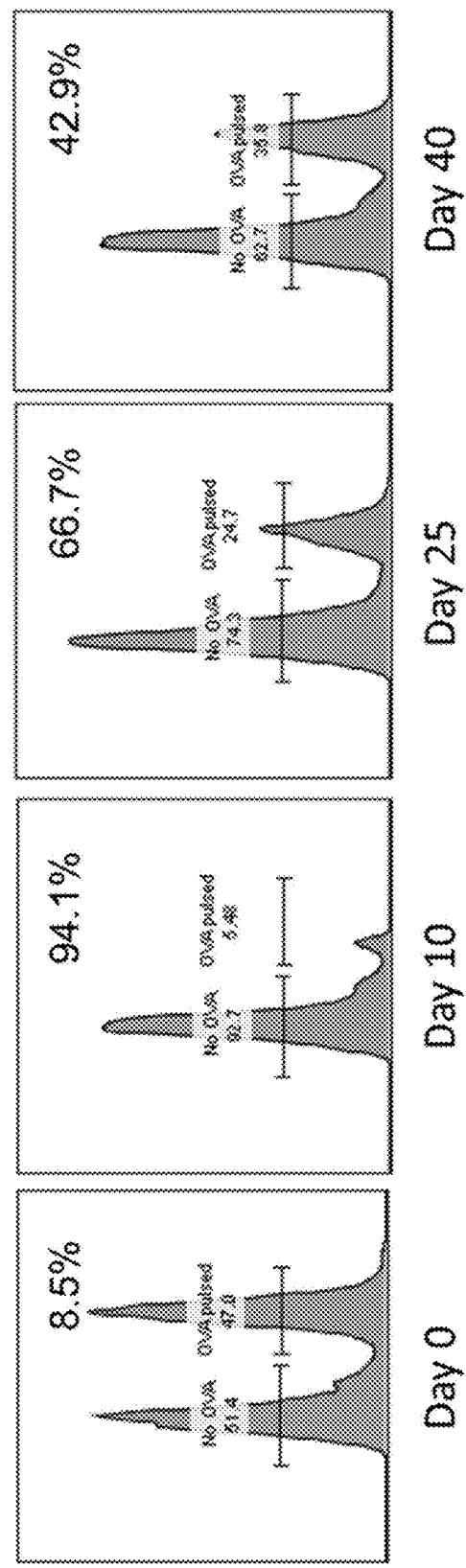
FIG. 16 shows duration of the cytotoxic T cell activation in A18 mOVA LNP vaccinated mice. Histograms show the CTL assay of mice different days after the initial vaccination. Splenocytes lysis was calculated and is shown on top of the histogram.

Lipidoids containing heterocyclic groups showed significantly increased IFN-x secretion compared to lipidoids containing linear tertiary amines (FIG. 4C). In particular, LNPs containing the lipidoid A18 increased IFN-x positive secretion in splenocytes 10.5-, 4.2- and 75.5-fold compared to MC3-based LNPs (FIG. 4C), one of the lipid materials currently FDA approved for RNA delivery, and in-house generated A2 and A12 LNPs (FIGS. 4C and 4D). In contrast, treatment with free mRNA, peptide- or recombinant OVA protein failed to induce a T cell response, and T cell responses were minimal even when these agents were combined with a known TLR-4 agonist, lipopolysaccharide (FIG. 4C). Interestingly, co-delivery of empty A18 LNPs with free OVA peptide improved this T cell response, demonstrating that the lipidoid A18 has intrinsic stimulatory effects; CD8+ T cells were identified as having a leading role in orchestrating the IFNγ secretion (FIG. 15). The OVA-specific cytotoxic lymphocyte (CTL) response associated with these LNPs was then measured. It was found that lipidoids containing cyclic head groups increased OVA-specific splenocyte death, with A17, A18 and A21 LNPs able to reduce the number of OVA peptide-pulsed splenocytes by 98% (FIG. 4F). The durability of T cell responses was examined; it was found that CD8+ T cells responses were greatest on day 10 (~20%) and that cells were able to kill up to 50% of the peptide pulsed splenocytes on day 40 (FIGS. 4G, 4H, and 16). Mice immunized with A17, A18 and A21 LNPs showed OVA-specific serum IgG antibody titers over 2.5-fold higher than mice treated with MC3 LNPs (FIG. 4I). Next, the importance of this cyclic head group on immune cell activation was examined.

Cyclic Lipidoids Activate the STING Pathway and Stimulate Adaptive Immune Cells

Using the second-generation lipidoid library (FIG. 4A), protein expression was investigated in vivo following mLuc vaccination (FIGS. 17A to 17C), and compared to in vitro protein expression (FIG. 17C). The majority of lipidoids exhibited similar protein expression levels, however it was noted that LNPs formulated with A18 or A21 (containing a piperidinyl six member and an azepanyl seven member side chain, respectively) enhanced delivery efficacy.[3] Protein expression was also observed in macrophages and monocytes,[42] as seen for the A2 and A12 LNPs tested earlier (FIG. 3G), suggesting that the A18 and A21 LNPs induce robust antigen expression in several key immune cells.

Figure 5A:
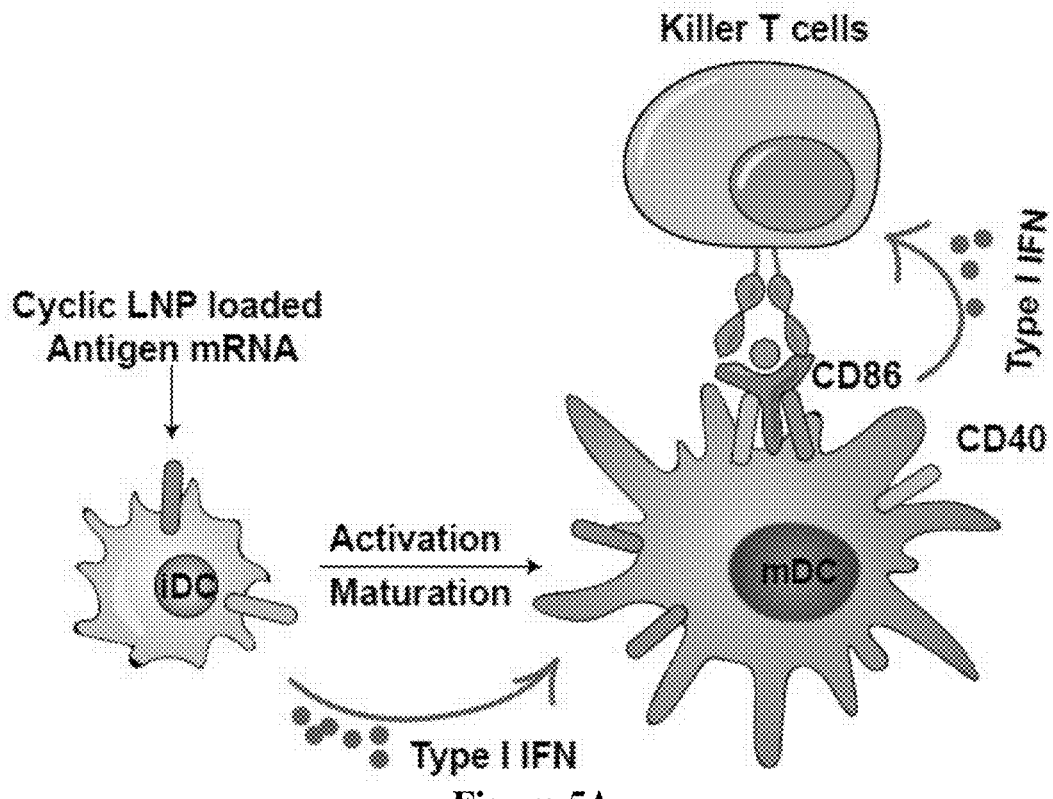
FIGS. 5A-5L show that cyclic lipidoids facilitate the maturation of APCs in local LNs through STING-dependent activation of Type I IFN.
Figure 5B:
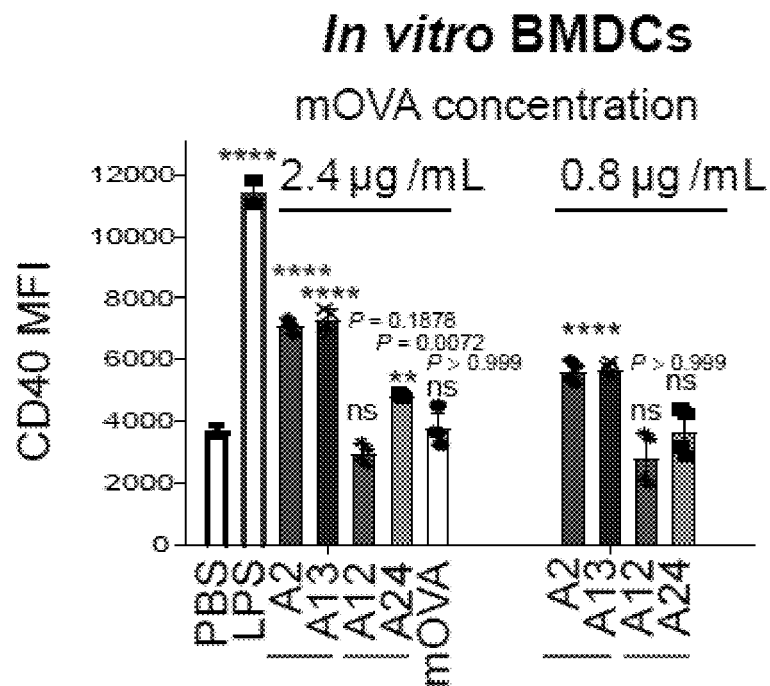
Figure 5C:
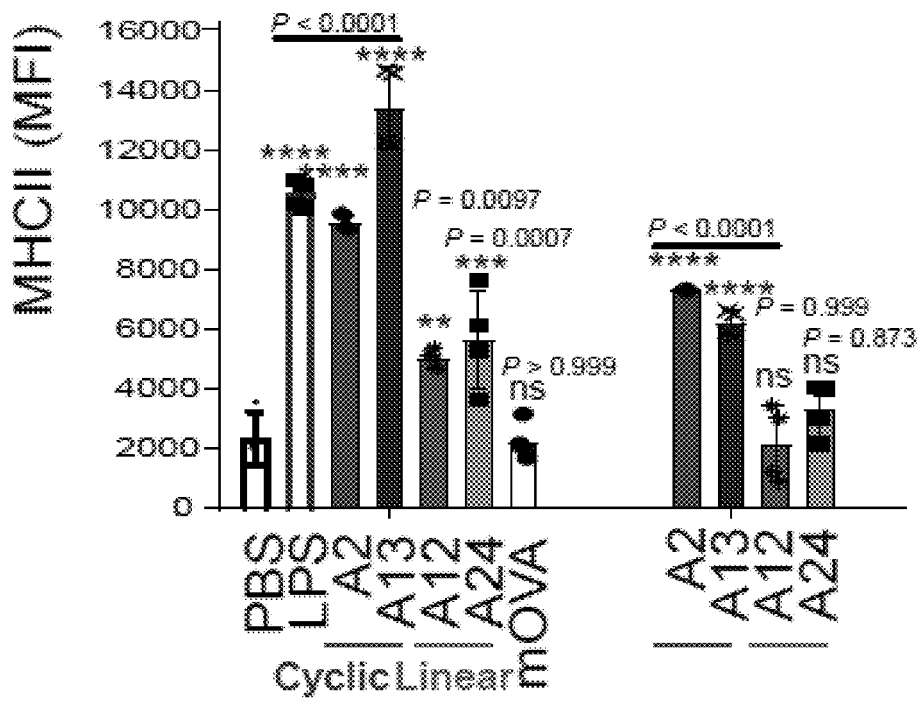
Figure 5D:
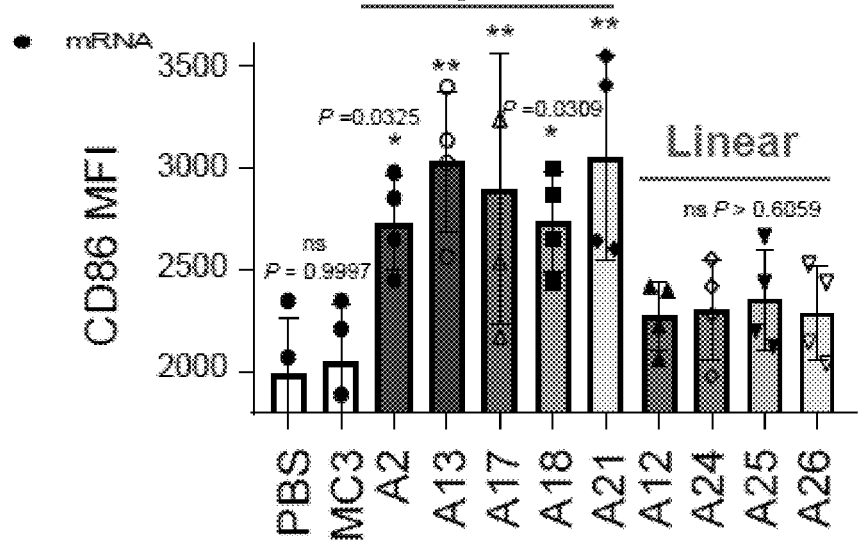
Figure 5E:
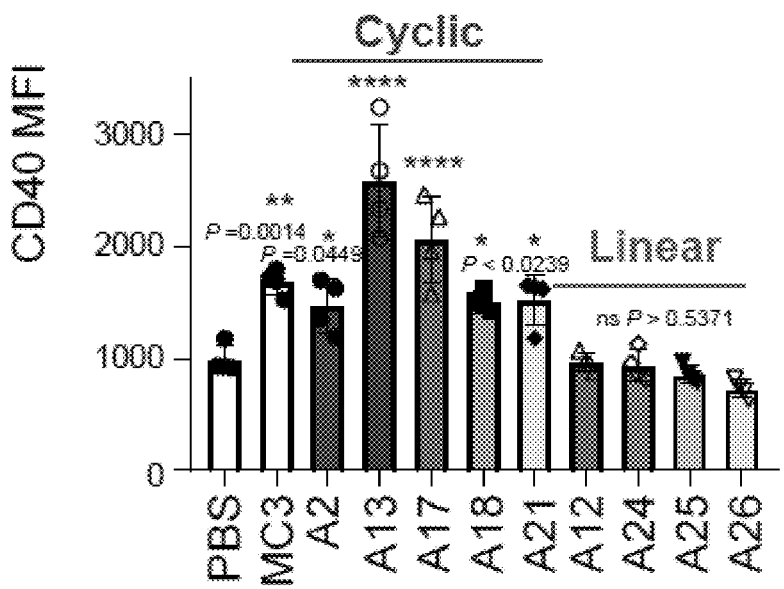
Figure 18:
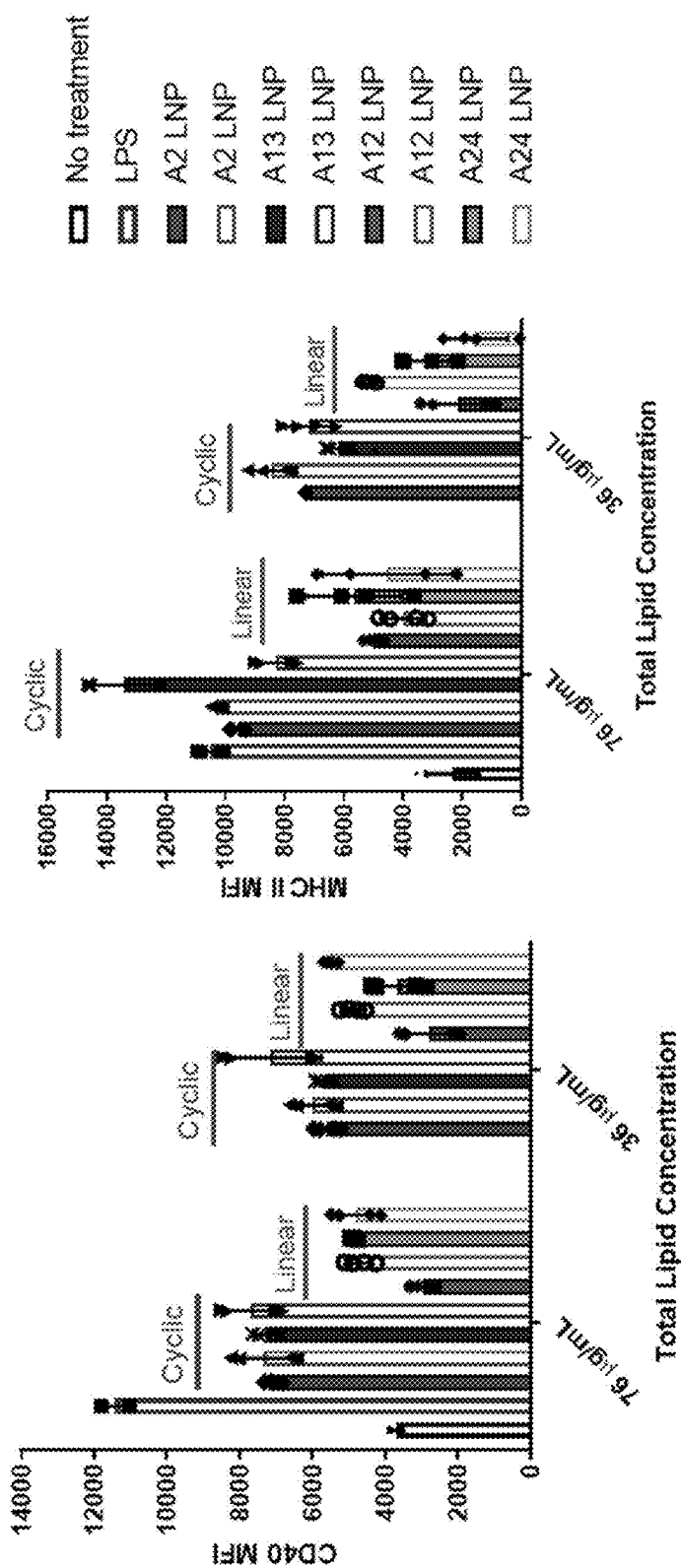
FIG. 18 shows activation and maturation of BMDCs. Immature BMDCs were treated with OVA mRNA loaded or empty LNPs at two different concentrations overnight (mRNA loaded LNPs were prepared at mRNA/lipid weight ratio: 10:1. Concentration presented here were based on the total lipid concentration). The activation markers CD40 (left) and MHCII (right) were examined by FACs (n=4 independent tests/group). Data were presented as means±S.D. LPS was used as a positive control.

To test the ability of the second-generation LNPs to directly activate APCs (FIG. 5a)[43,44], naïve BMDCs were treated for 24 hours with cyclic or linear lipidoids containing OVA mRNA. Lipidoids with comparable mRNA delivery efficiency were selected (cyclic-A2, A13; linear-A12, A24) and 5-methoxyuridine modified OVA mRNA was used to further reduce mRNA immunogenicity, ensuring the comparison of immunostimulatory effect of the lipidoid structure. It was found that mRNA encapsulated in cyclic lipidoids increased expression of dendritic cell activation markers (CD40, MHCII) 2-3 fold compared to linear lipidoids (FIGS. 5B and 5C). Interestingly, empty cyclic LNPs were also able to upregulate these activation markers (FIG. 18), clearly indicating that the activation of APCs is not only triggered by mRNA, but also by the unique structural features of this class of cyclic lipidoids. Similar trends were seen in vivo, where CD86/CD40 expression was upregulated in DCs collected from the draining LNs of mice treated with cyclic LNPs compared to mice treated with linear LNPs (FIGS. 5D and 5E).

Figure 5F:
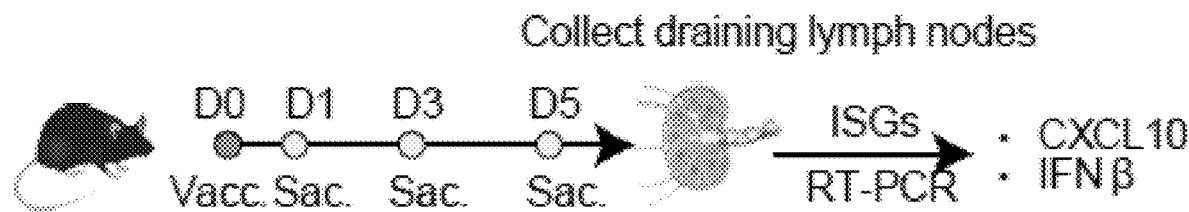
Figure 5G:
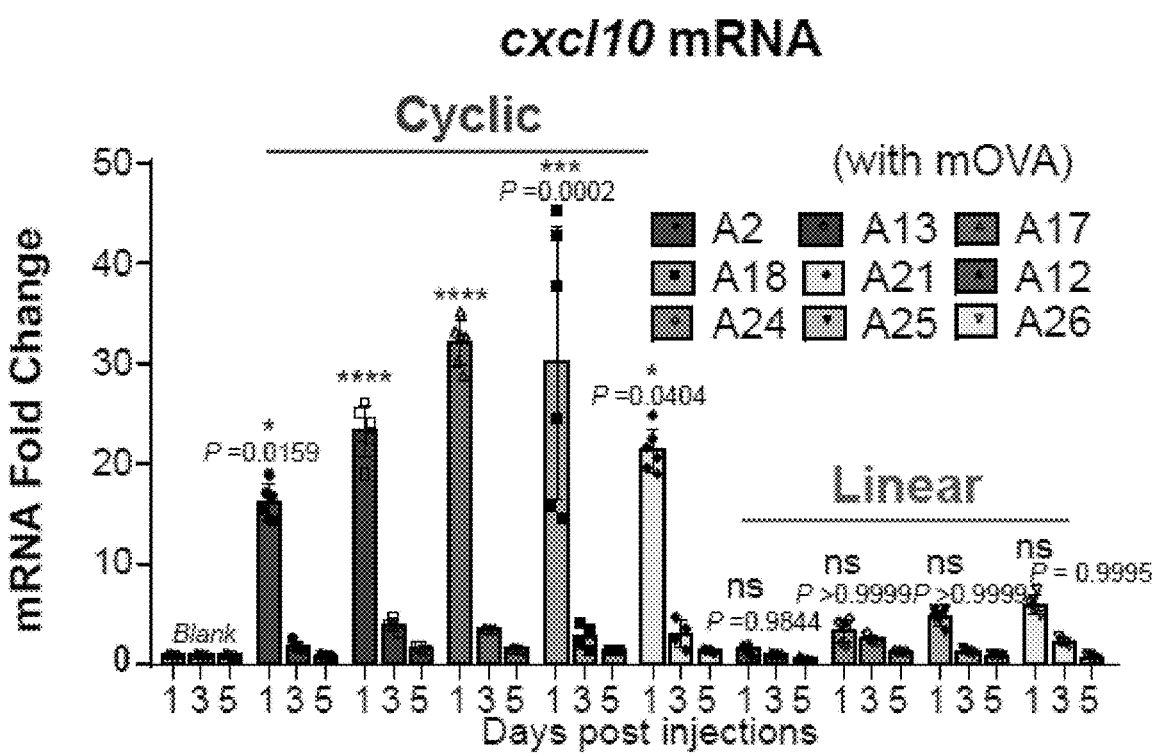
Figure 5H:
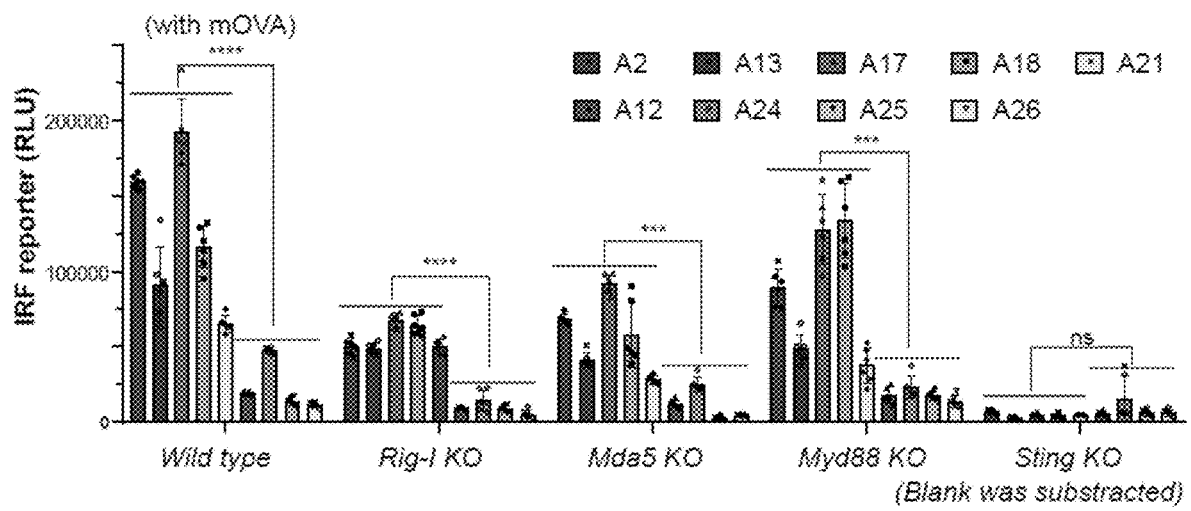
Figure 5I:
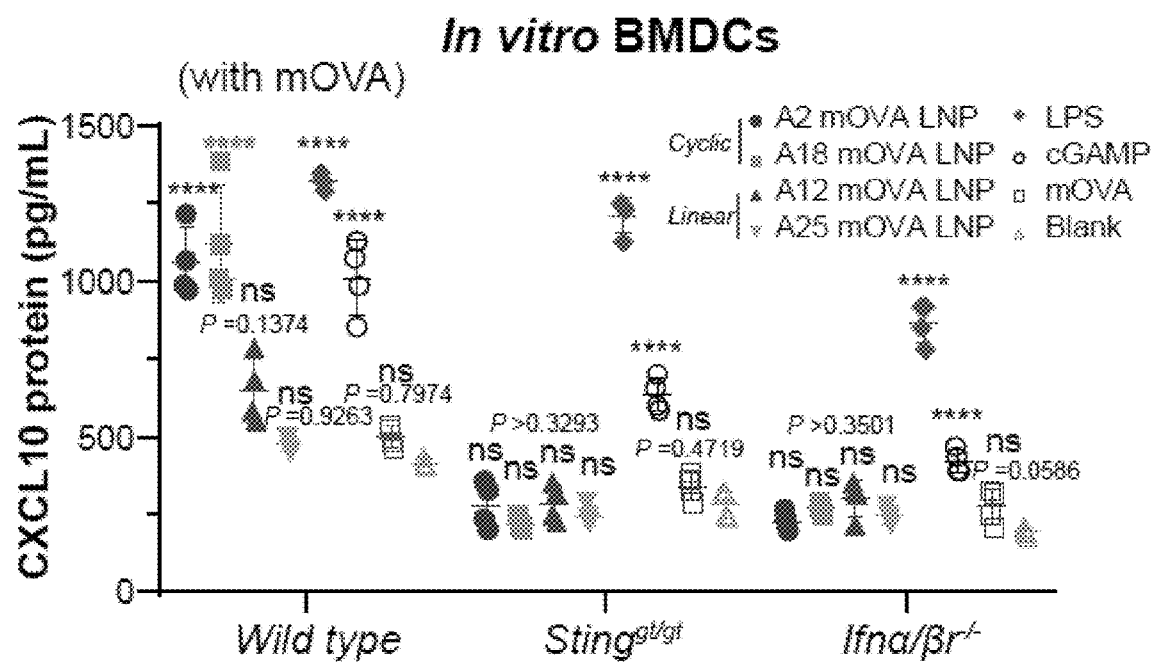
Figure 5J:
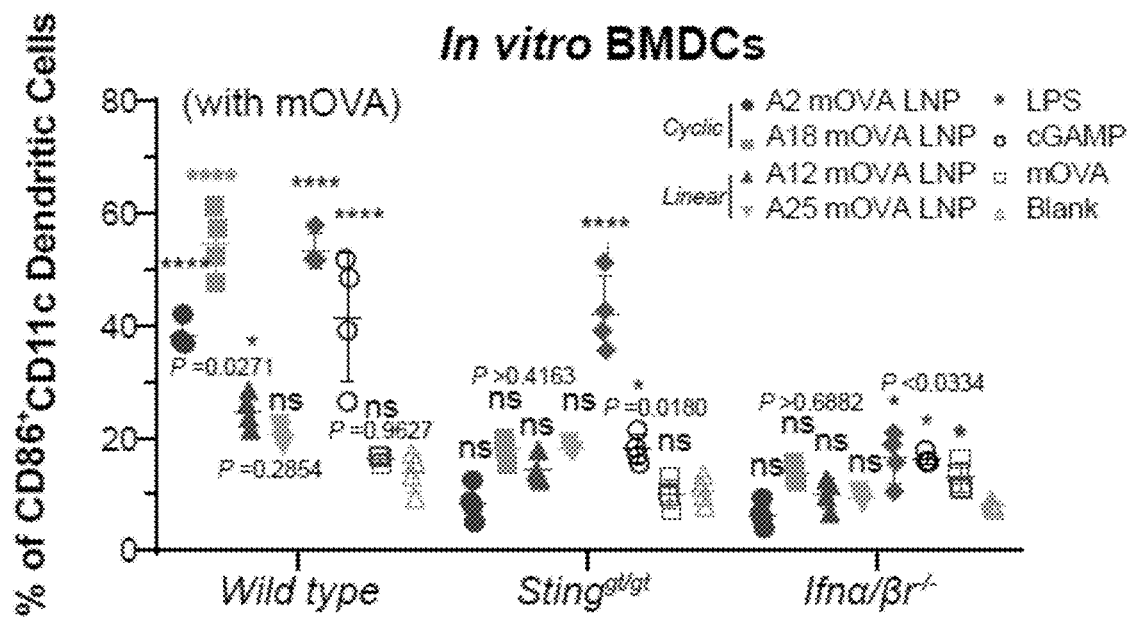
Figure 5K:
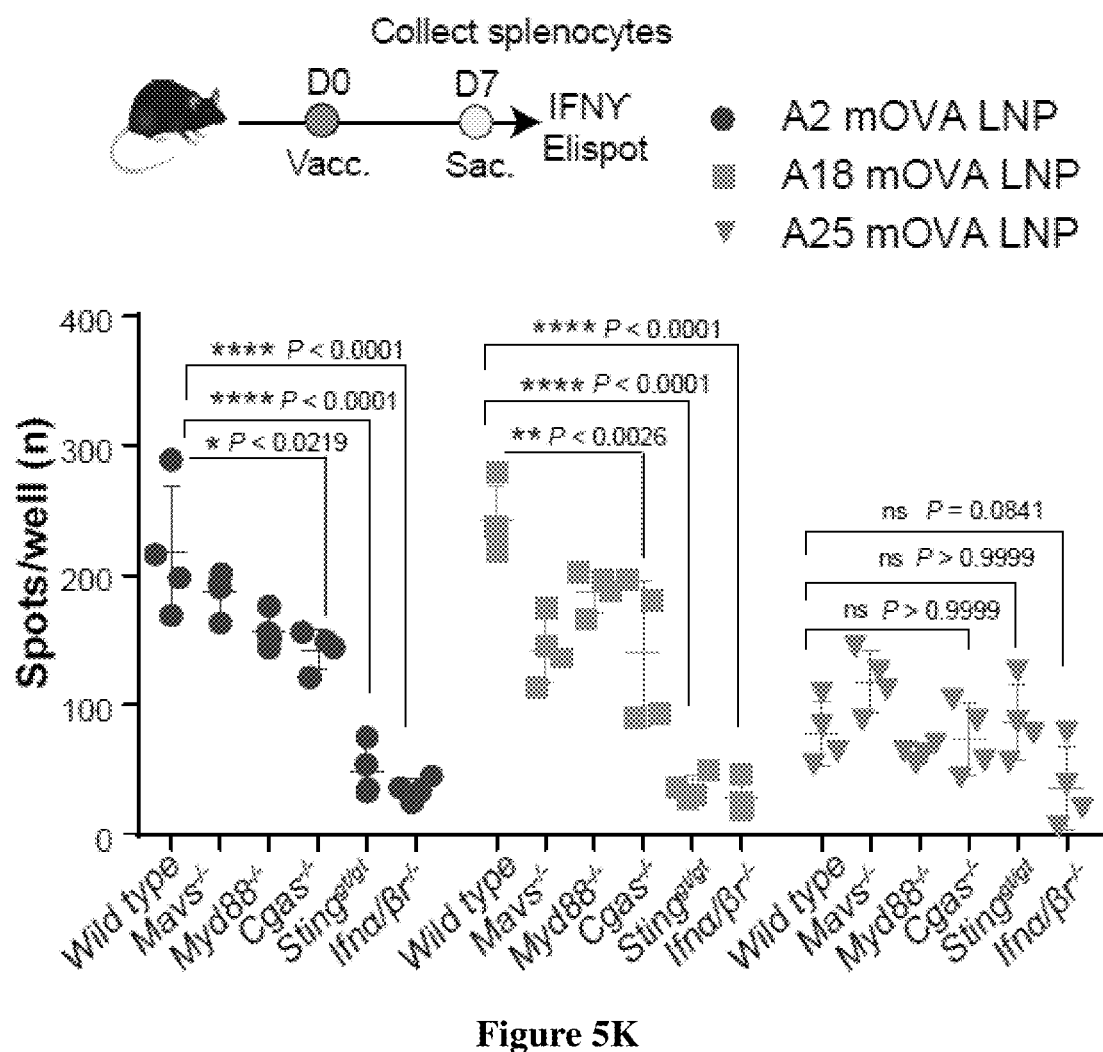
Figure 5L:
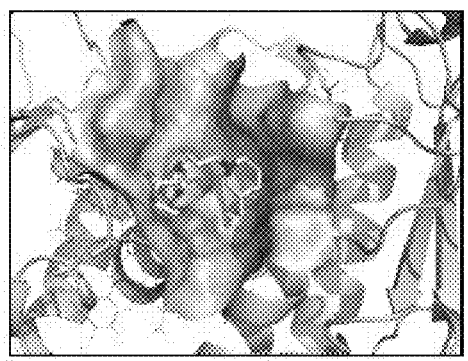
Figure 5L:
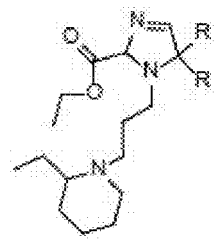
Figure 5L:
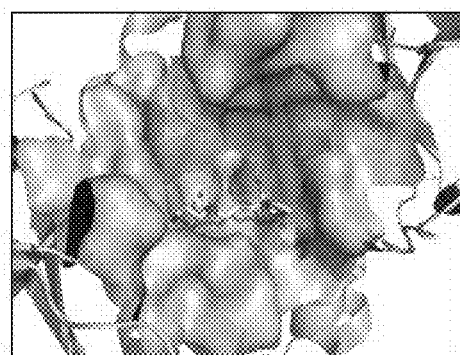
Figure 5L:
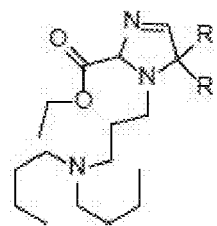
Figure 19A:
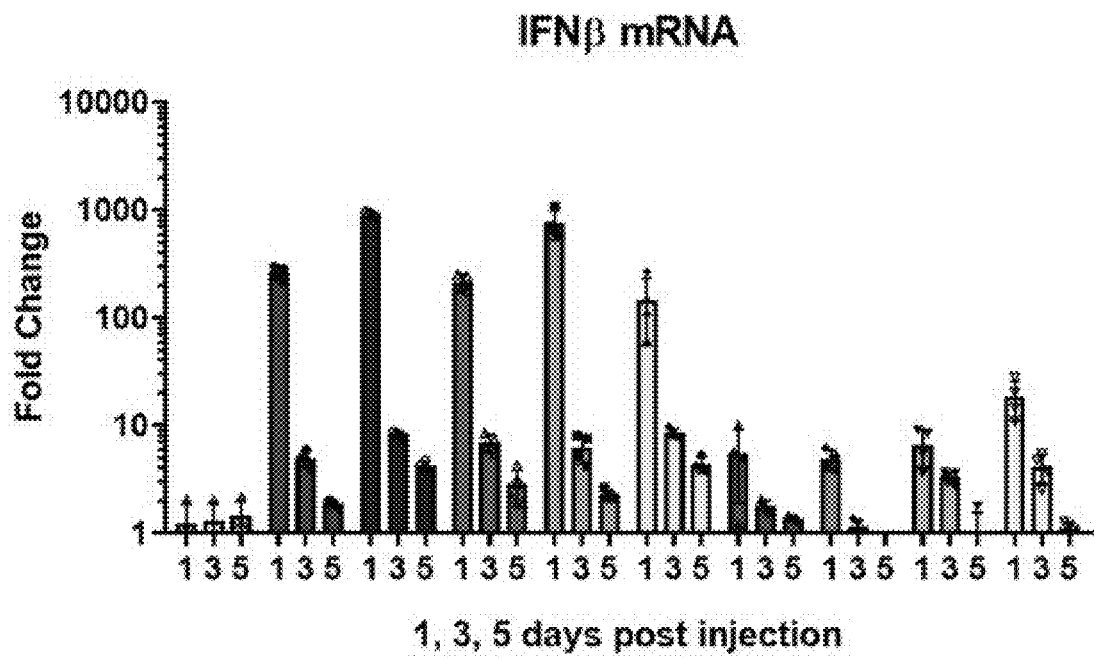
FIGS. 19A-B show mRNA expression levels of interferon-stimulated genes (a: IFNβ, b: IRF7) at local LNs at 1, 3, 5 days after vaccination. mRNA levels were quantified using quantitative polymer chain reaction (qPCR) (n=4 biologically independent mice/group). Data are presented as means±S.D.
Figure 19B:
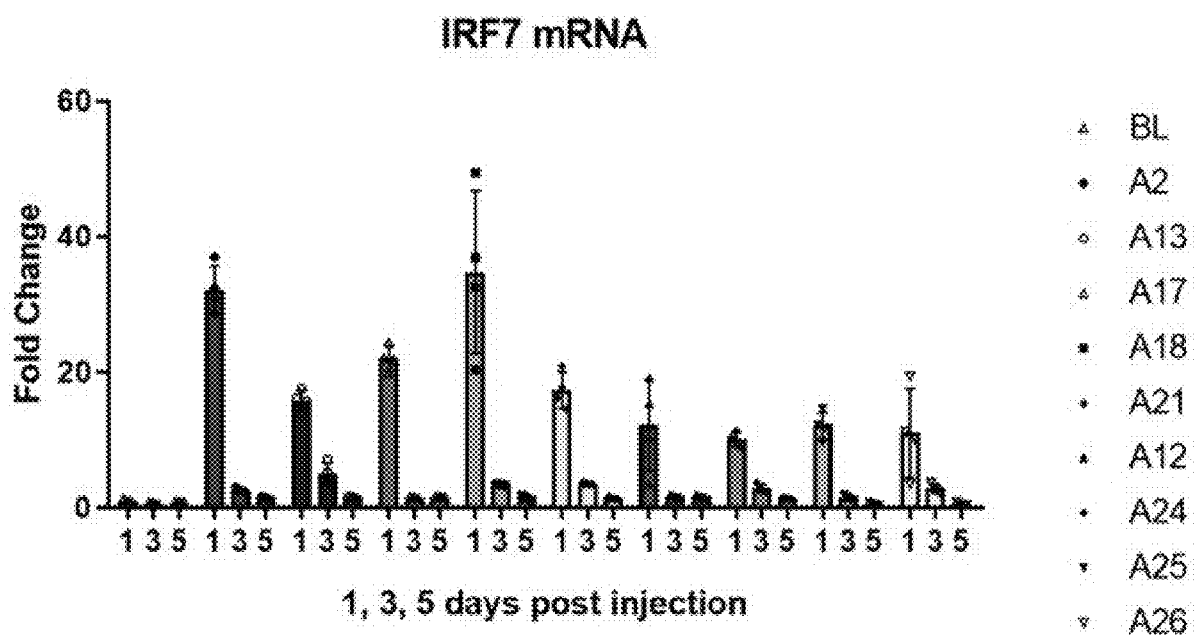
Figure 20:
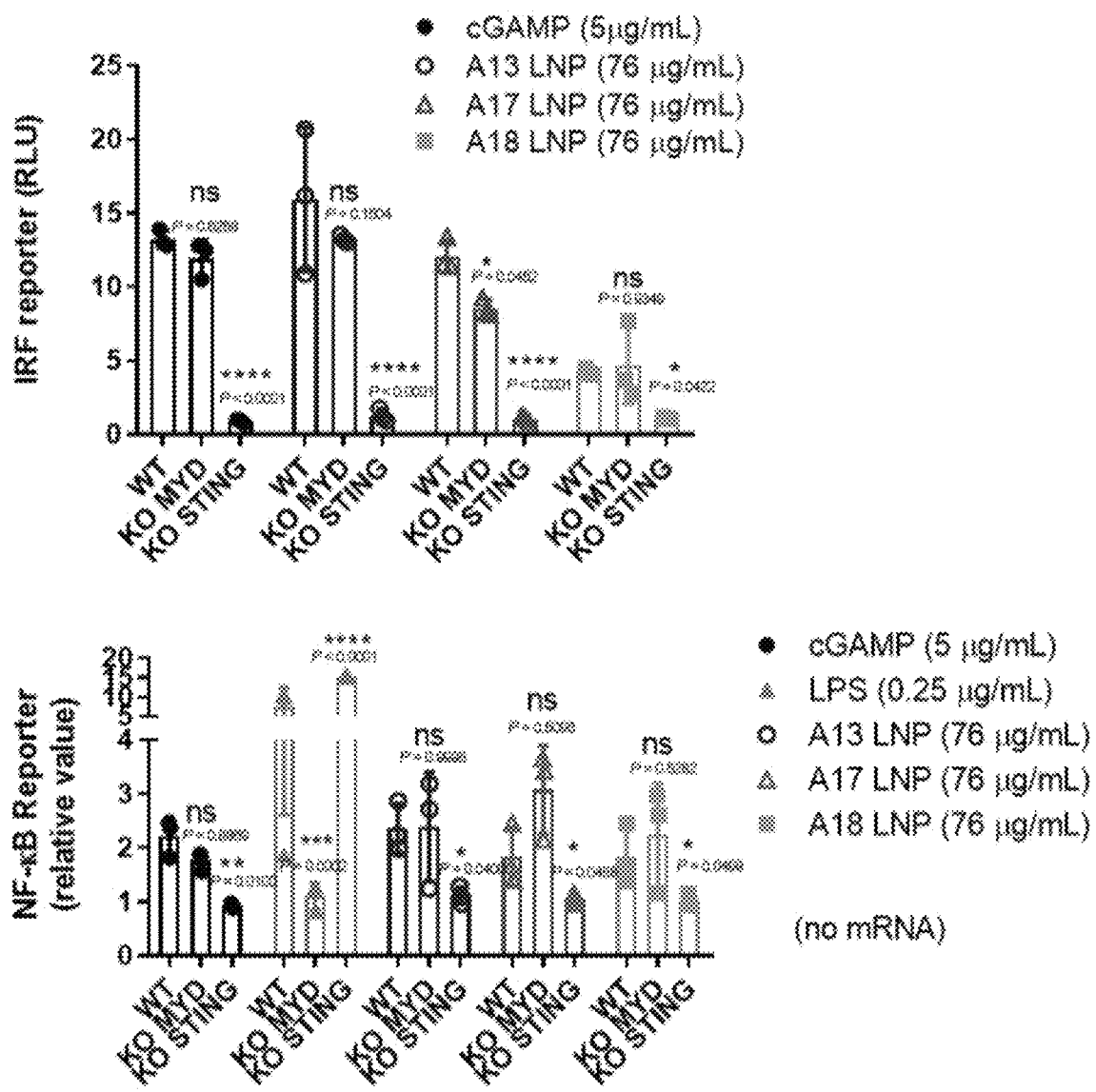
FIG. 20 shows THP-1 Dual Reporter assay after incubation with empty LNPs. (a) IRF reporter (RLU). (b) NF-κB reporter. **, P<0.0001, *, P<0.001, **, P<0.01, *, P<0.05, ns, no significant difference, Two-way ANOVA with Dunnett's multiple comparisons test compared to WT (in each treatment groups), (n=3 different wells/group). Data are presented as means±S.D.
Figure 21A:
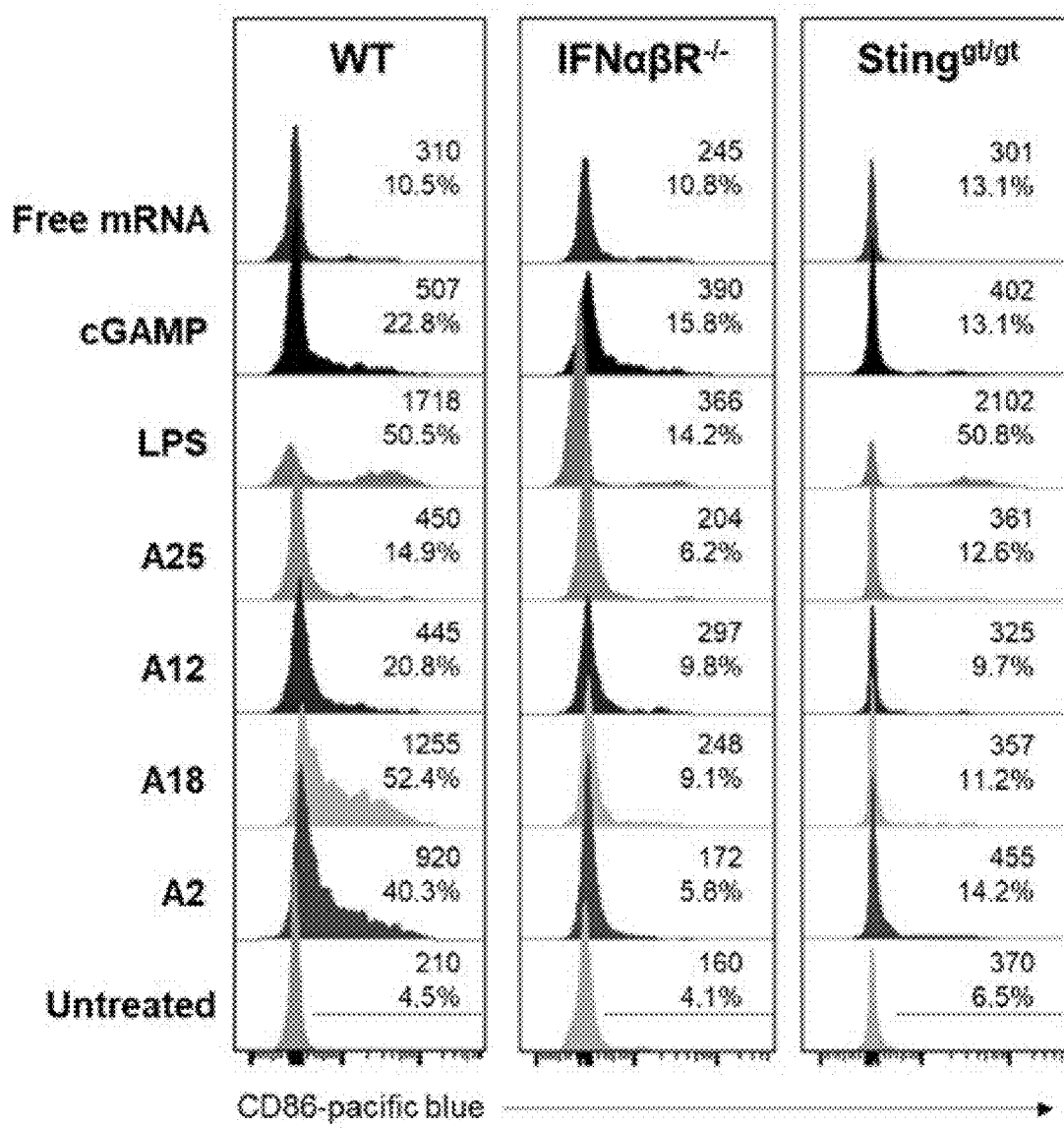
FIGS. 21A-21D show BMDCs activation and maturation in different knockout mouse models. BMDCs were isolated from IFNαβR−/− and Sting$^{gt/gt}$ mice and cultured with mOVA loaded or empty LNPs for 24 h. Activation of BMDCs was analyzed by FACs.
Figure 21B:
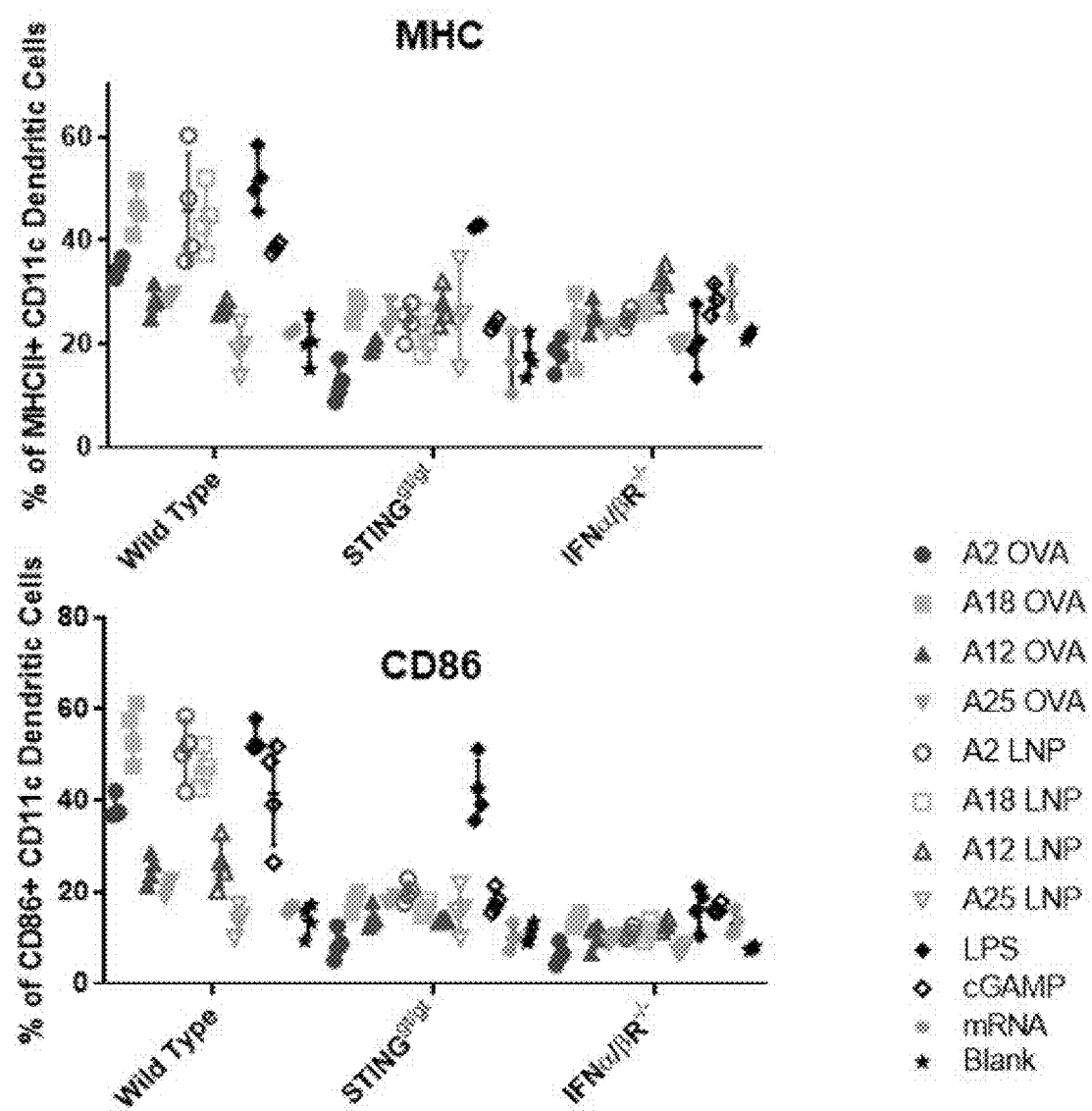
Figure 21C:
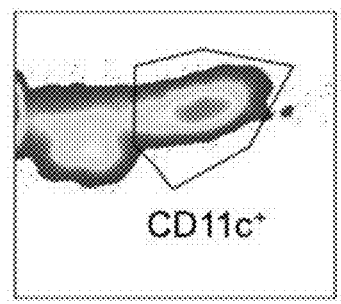
Figure 21D:
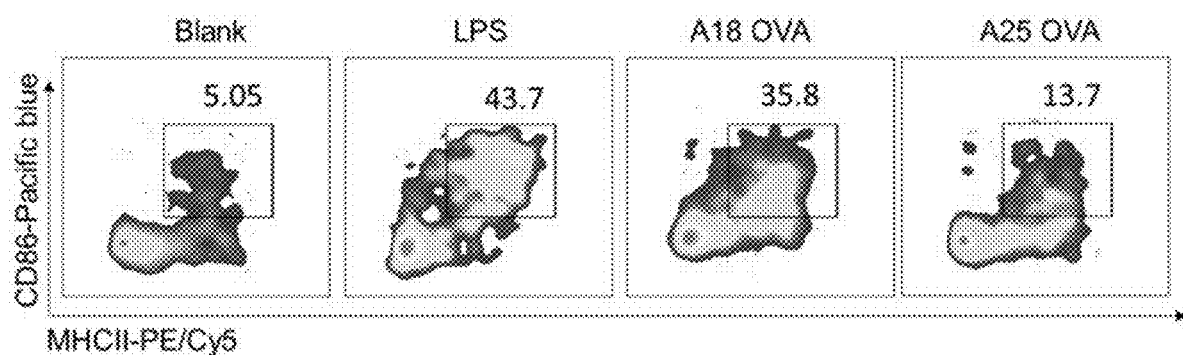

Given the importance of type I IFNs in APC activation and generation of a robust T cell response, IFN-stimulated gene (ISG) expression was examined in lymph nodes following mOVA LNP vaccination. Cyclic lipids were able to elicit up-regulation of IRF7, CXCL10, and IFNPβ 1 day post-injection, but this expression was transient and decreased to background levels over the subsequent 5 days (FIGS. 5G, 5H, and 19). mRNA delivery has been reported to activate type I IFN mediated immune responses through the TLR pathway, however there is emerging evidence that some polymeric materials may also activate innate immune responses through the STING pathway.[16,14,45,46,47,20] The potential mechanisms of Type I IFN activation in the lipidoids was therefore examined, using a MYD88 knockout (defective in most TLR signaling except TLR3) and a STING knockout THP-dual reporter cell line. Using cGAMP (STING-dependent) and LPS (TLR-dependent) controls, it was demonstrated that in wild type cells, cyclic mOVA LNPs upregulated IRF expression compared to linear mOVA LNPs (FIGS. 5I and 20). IRF expression was slightly reduced in MYD88 knockout cells treated with cyclic LNPs, however was entirely absent in STING knockout mice, demonstrating that the STING pathway (rather than the TLR pathway) governs the lipidoid-based adjuvant effect of cyclic LNPs (FIG. 5I). Furthermore, the importance of the STING pathway was validated in vivo using STING$^{gt/gt}$ and IFN receptor (IFN-$\alpha/\beta$R$^{-/-}$) knockout mouse models. Mice were vaccinated with either cyclic mOVA LNPs (A17, A18) or linear mOVA LNPs (A25) and IFN-$\gamma$ secretion was measured by an ELISpot assay. Cyclic LNPs were able to induce a strong IFN-$\gamma$ response in wild type animals, but this response was almost completely eliminated in STING and IFN receptor (IFN-$\alpha/\beta$BR$^{-/-}$) knockout mice. It is noted that BMDCs isolated from wild type animals matured when treated with cyclic LNPs (empty or containing mRNA), but this was not observed in BMDCs isolated from STING knockout or IFN receptor knockout animals (FIG. 21). In contrast, the linear LNPs (A25) were unable to elicit a strong IFN-$\gamma$ response in any of the models tested, confirming that the additional adjuvant effect is specific to cyclic LNPs, and is mediated by the STING pathway (FIGS. 5I and 5J).

Figure 22A:
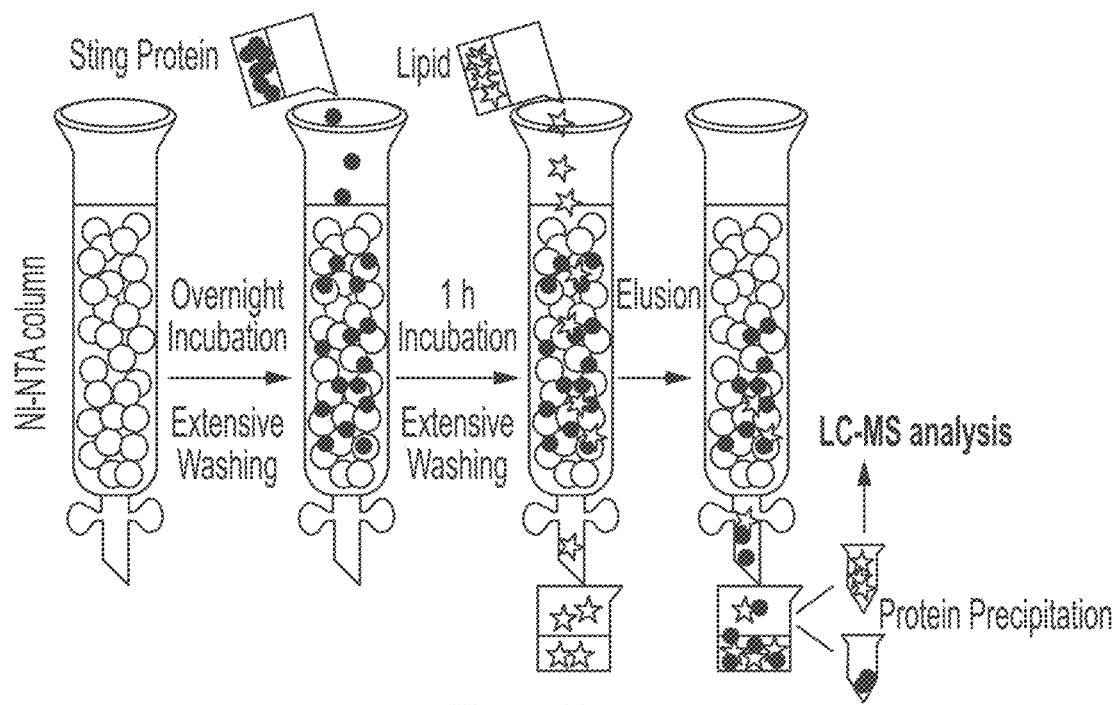
Figure 22B:
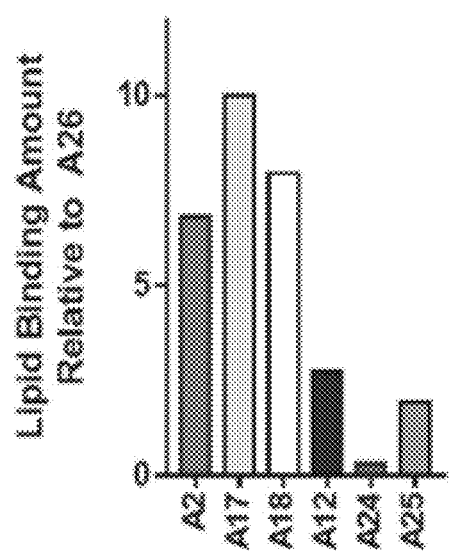
Figure 22C:
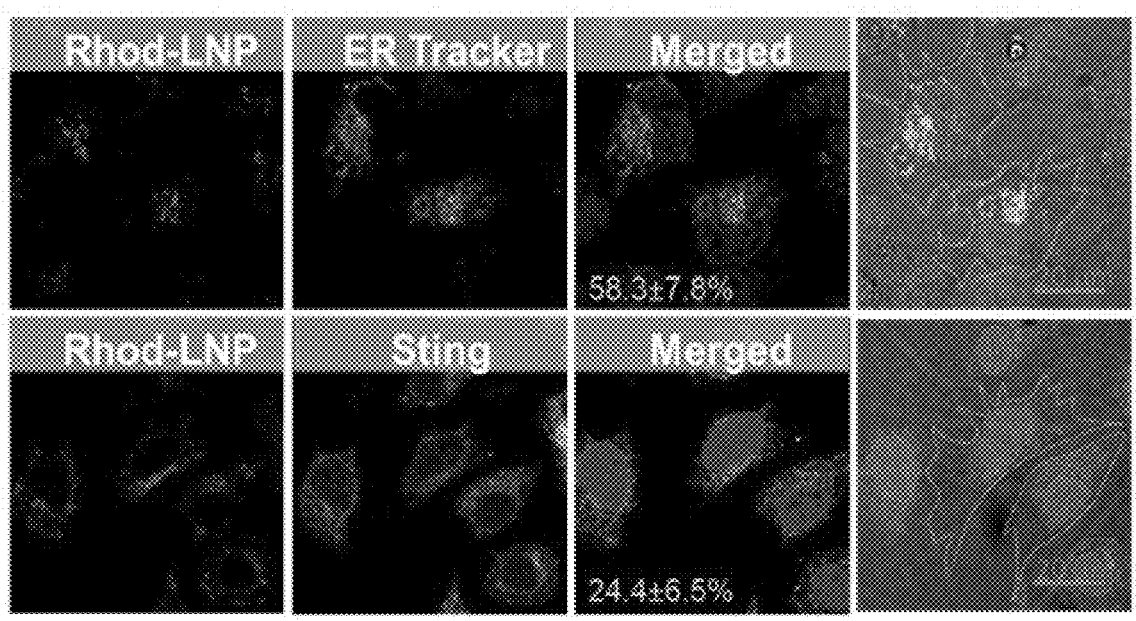
Figure 22D:
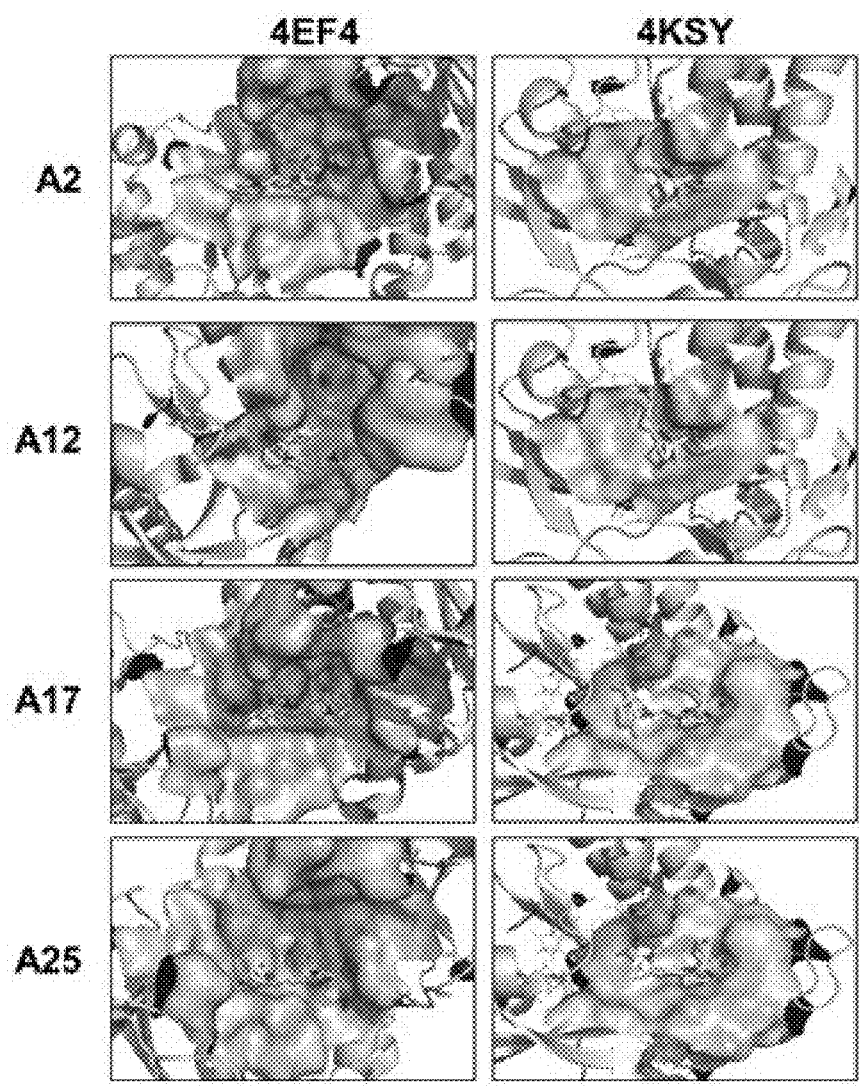

Activation of the STING pathway can occur following direct binding to STING proteins.[20] A number of tests were therefore performed to determine if the cyclic lipidoids are able to bind to STING proteins. A lipidoid pulldown assay was used to assess binding between synthetic lipidoids and a His-tagged STING C-terminal Domain (CTD). Extraction of His-tagged STING CTD after incubation with lipidoids suggested that in contrast to linear lipidoid structures, cyclic lipidoids (notably A17 and A18) associate with STING protein (FIGS. 22A and 22B). In vitro, fluorescently labelled A18 cyclic LNPs were found within the endoplasmic reticulum (ER) (58.3% of LNPs) and co-localized with ER-associated STING protein (24.4% of LNPs) (FIG. 22C). Using dynamic molecular docking, the interaction between lipidoid heads groups and STING was next explored, and the STING CTD binding pocket (typically shared by the natural ligand c[G(2',5')pA(3',5')p] (PDB:4EF4, 4KSY) and the small molecule DMXAA (PDB:4QXP)) were identified as a likely binding site (FIGS. 22D and 22E). Simulations suggested that cyclic lipidoid head groups bind with ~3-fold to ~20-fold greater affinity than their linear counterparts (cyclic A17, K$_i$: 43.33 µM; linear A25, K$_i$: 756.34 µM; cyclic A2, K$_i$: 106.18 µM; linear A12, K$_i$: 329.81, PDB:4EF4) (FIG. 22E).

Figure 6A:
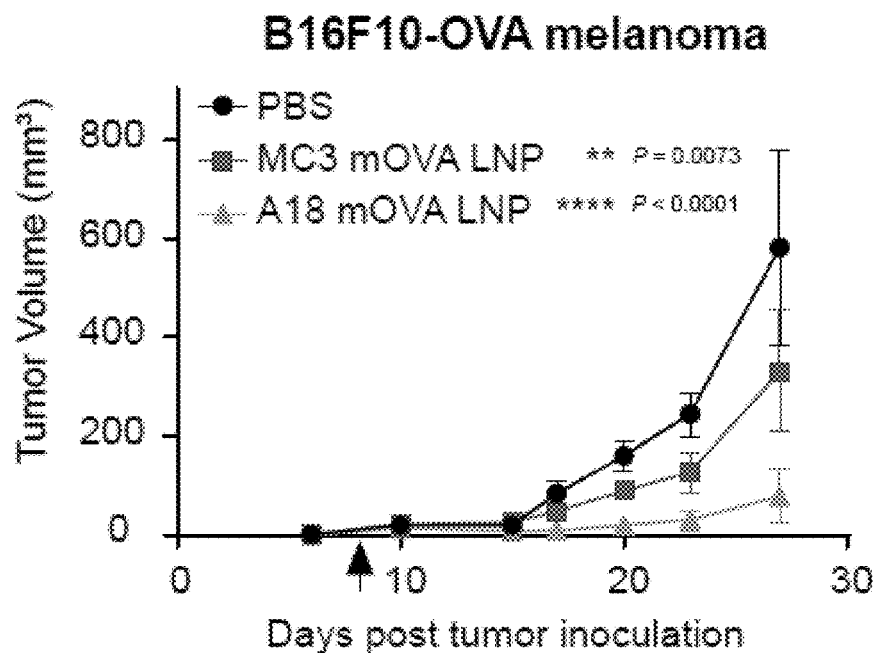
FIGS. 6A-6I show the effect of A18 mRNA antigen vaccines on tumor growth.
Figure 6B:
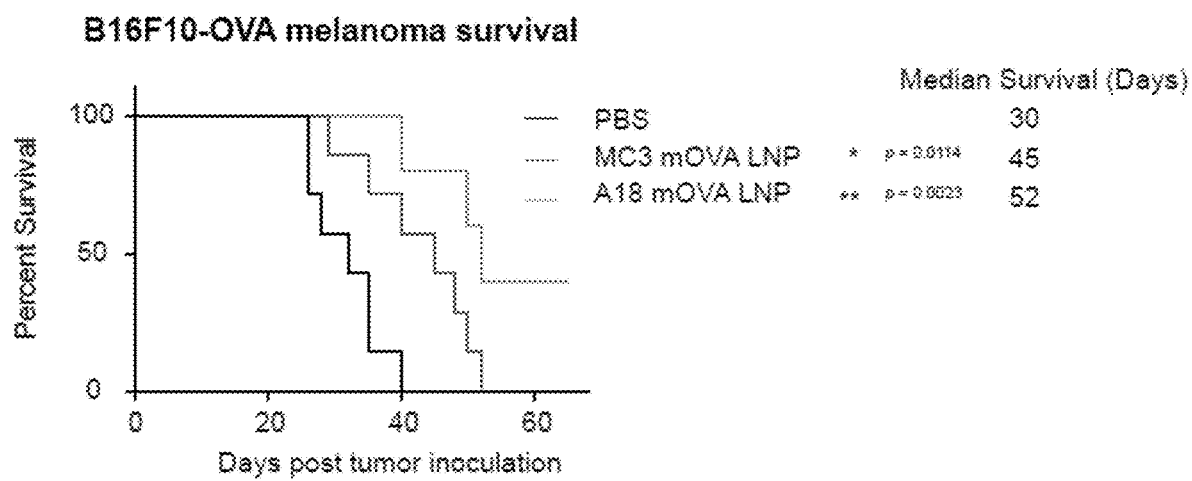
Figure 23:
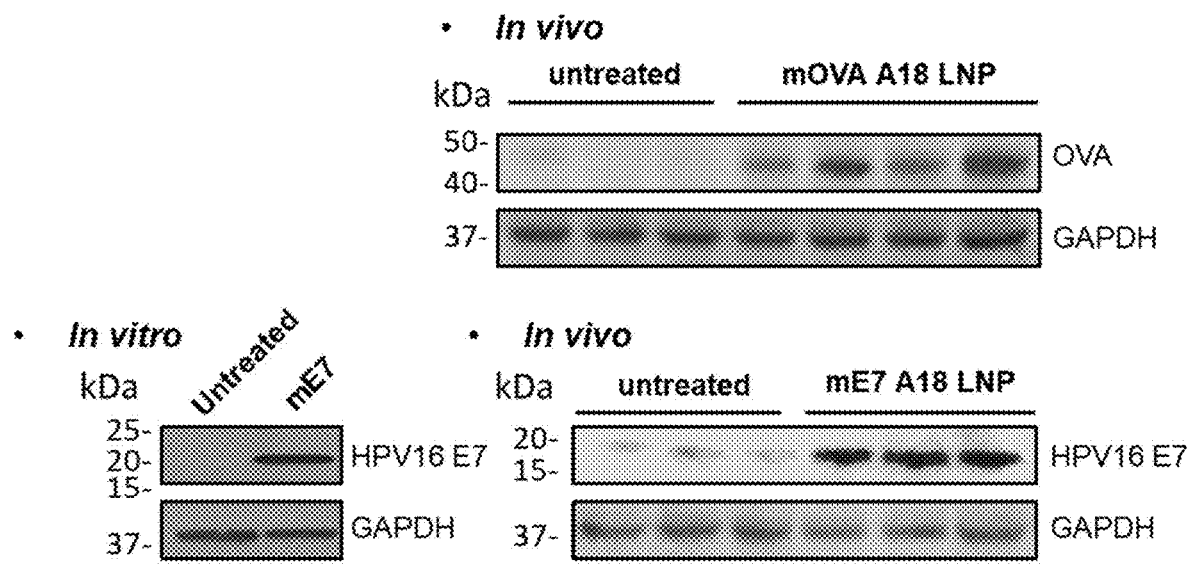
FIG. 23 shows vaccine mRNA expression using A18 LNPs as delivery vector (n=3, 4).

Cyclic Lipidoid-Delivered mRNA Vaccines Induce Robust Antitumor Response in Multiple Tumor Models A18 was identified as a well-performing cyclic lipidoid from the lipidoid library and screening tests. This lipidoid is able to facilitate potent mRNA protein expression (FIG. 23), and induce a strong immune response mediated, in part, through STING activation. mRNA LNP formulations containing this cyclic lipidoid were tested in a variety of tumor models. Using the B16-OVA melanoma model described earlier, it was demonstrated that a single vaccination of A18 mOVA LNPs significantly prolonged survival, compared to either a PBS control group or mOVA vaccinations delivered using commercially available MC3 LNPs. 50% of animals treated with A18 LNPs survived over 40 days, and 3 out of 11 animals were tumor free up to day 60 (FIGS. 6A, 6B, and 24).

Figure 6C:
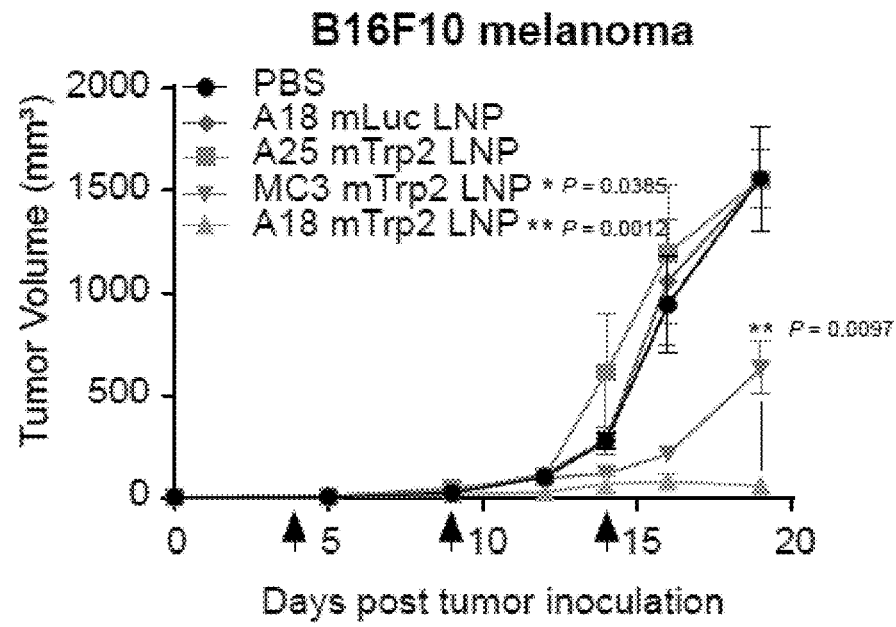
Figure 6D:
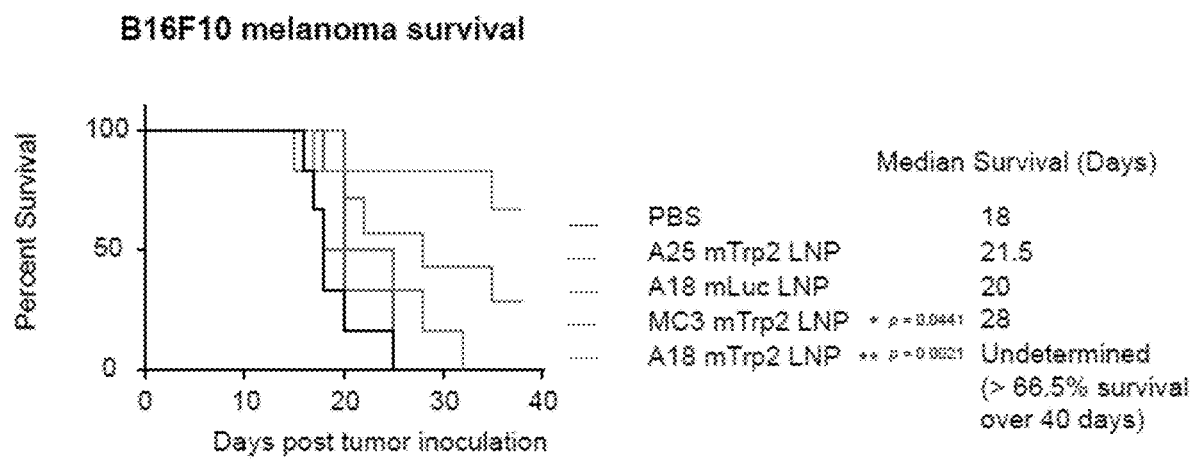

Next, vaccination with tyrosinase-related protein 2 (Trp2) was investigated; a tumor associated antigen (TAA) known to be important in the B16F10 melanoma model. As both humans and mice share the same recognition sequence, this antigen has potential for clinical translation. Here, three doses of 15 µg Trp2 mRNA (mTRP2) were delivered in A18, A25 and MC3 LNPs, alongside a Luciferase mRNA control (FIGS. 6C, 6D, and 24). A18 LNPs were able to significantly slow tumor growth, and were demonstrated to be good delivery systems. Mice treated with the A18 mTRP2 LNPs showed a marked increase in survival, with >60% living beyond 40 days.

Figure 6E:
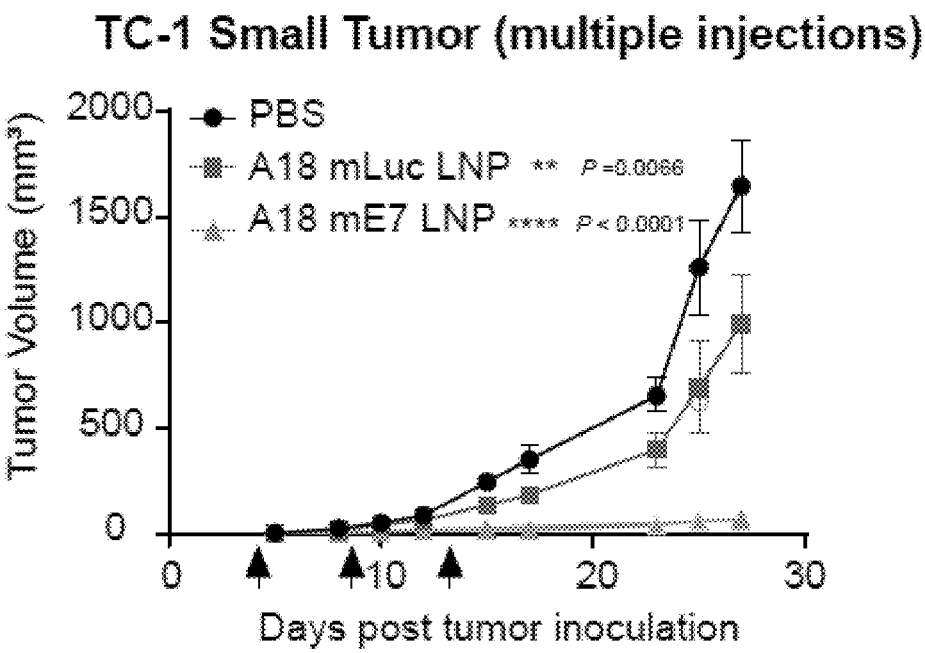
Figure 6F:
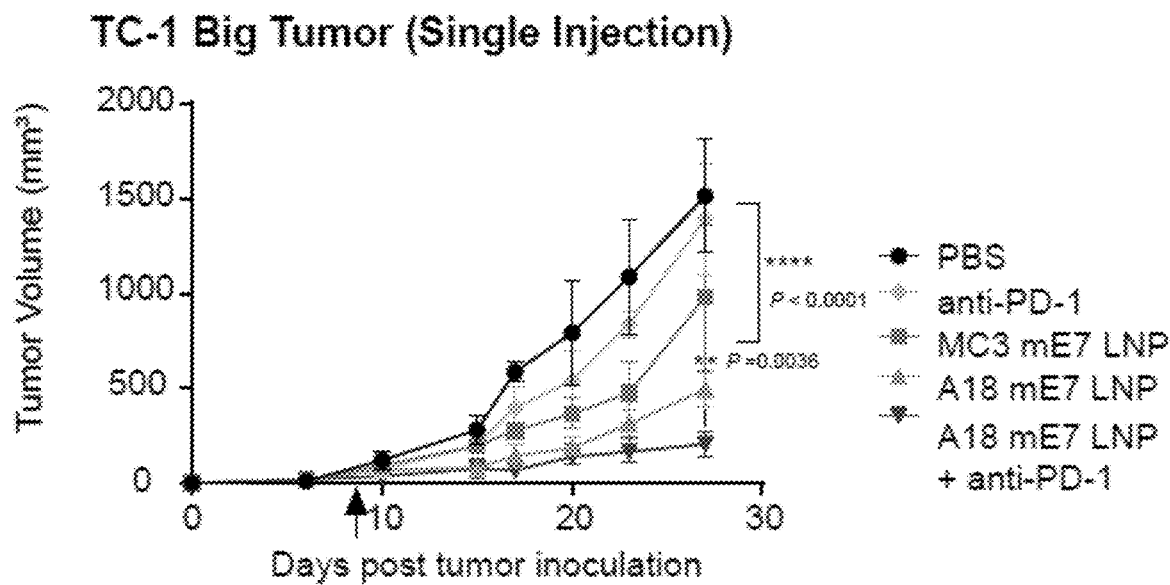
Figure 6G:
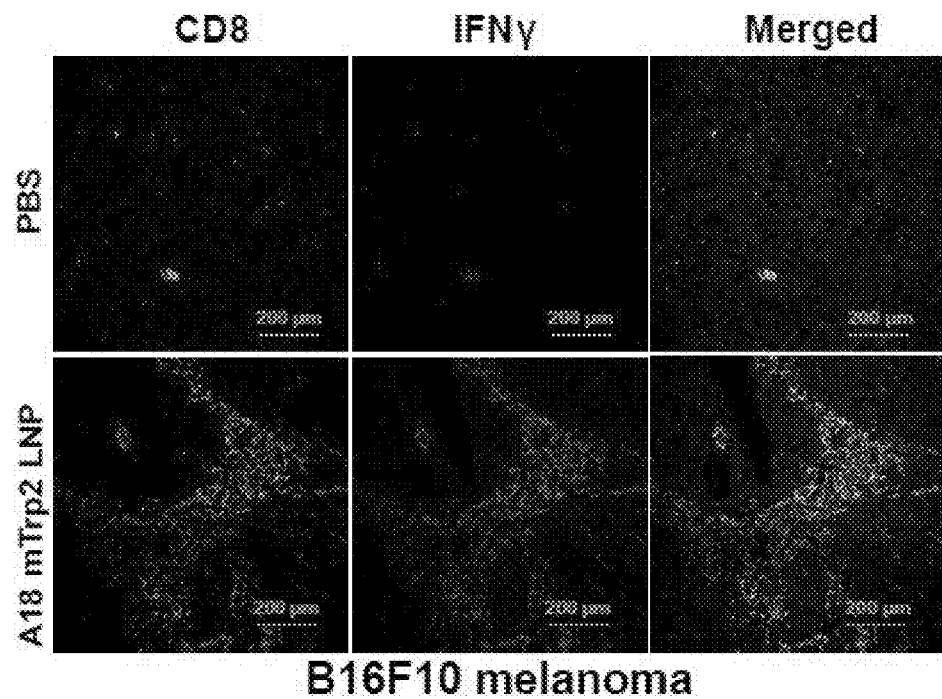
Figure 6H:
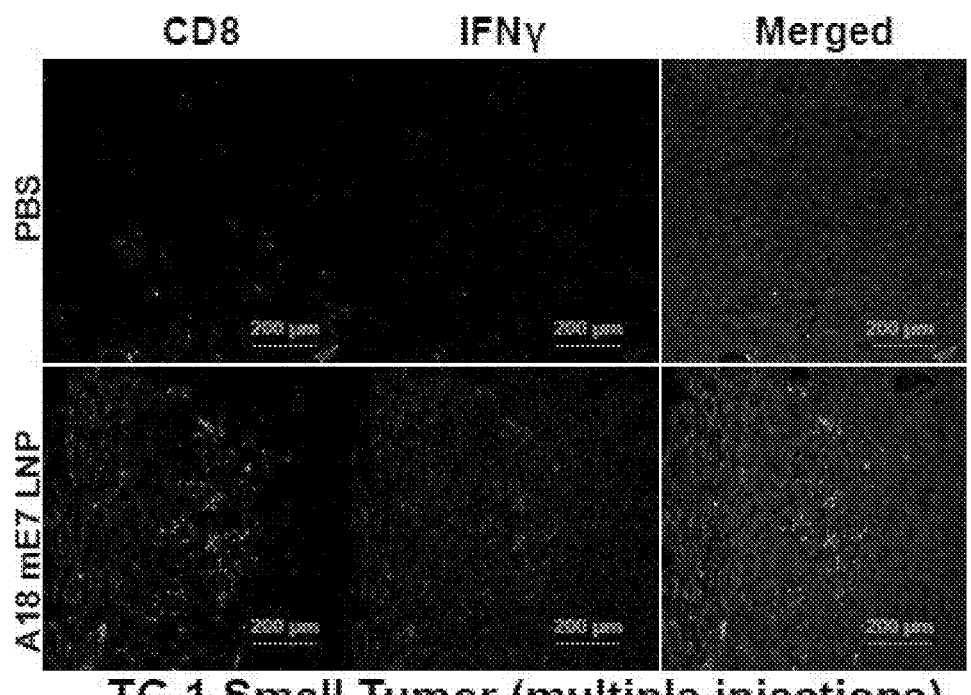
Figure 6I:
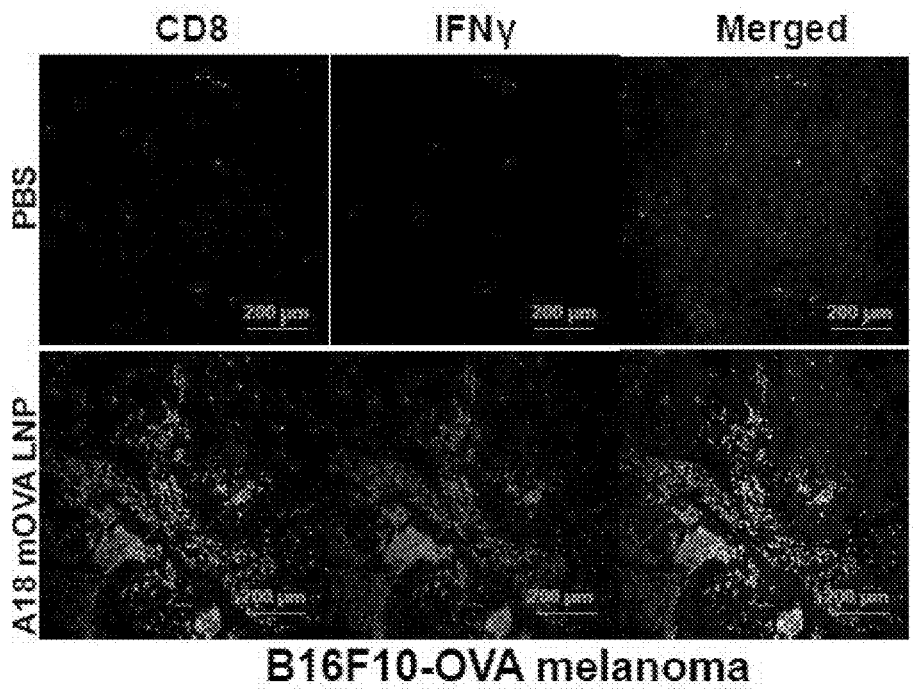
Figure 24:
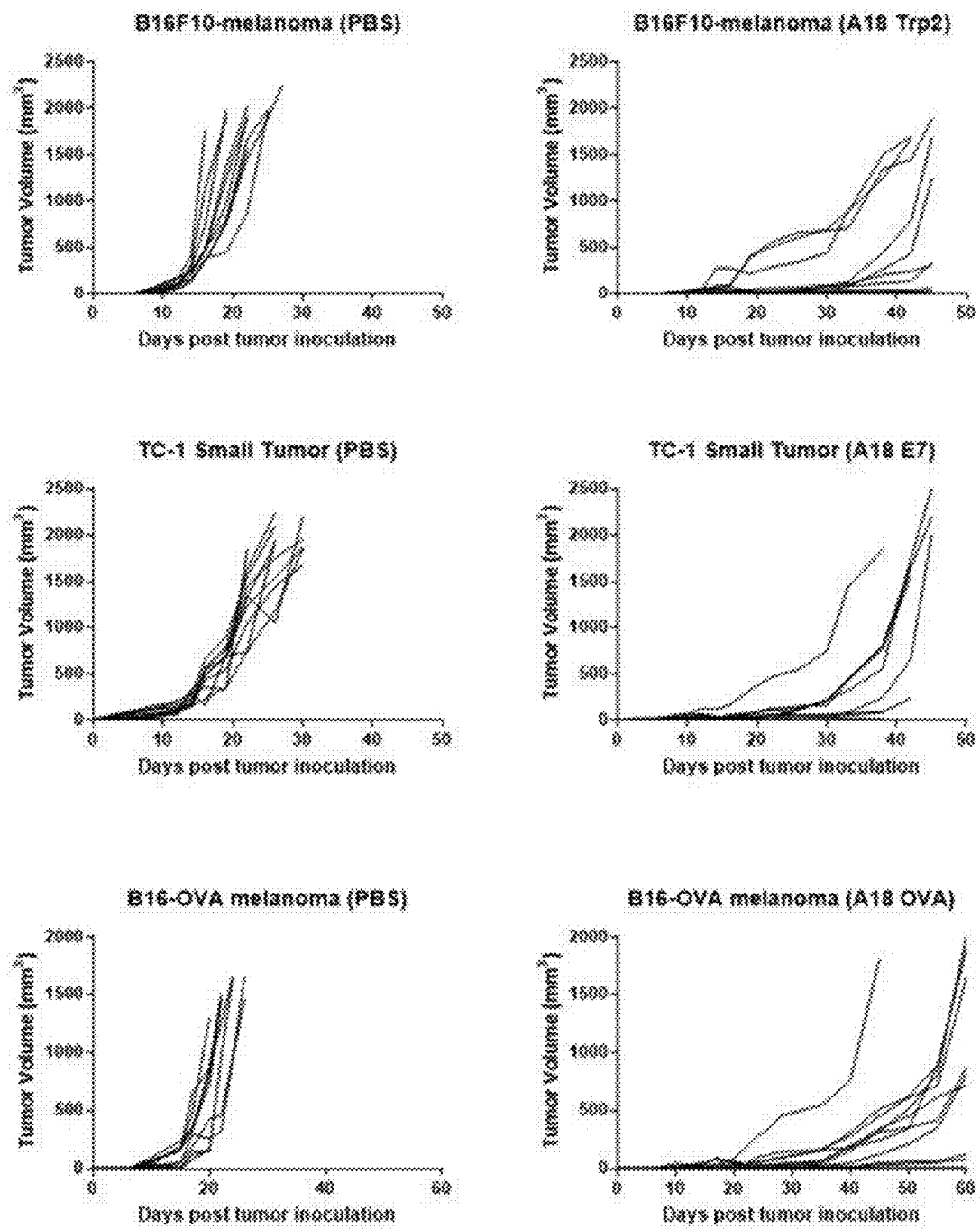
FIG. 24 shows tumor growth curves per mouse in different treatment groups and tumor models (n=8-11).
Figure 25:
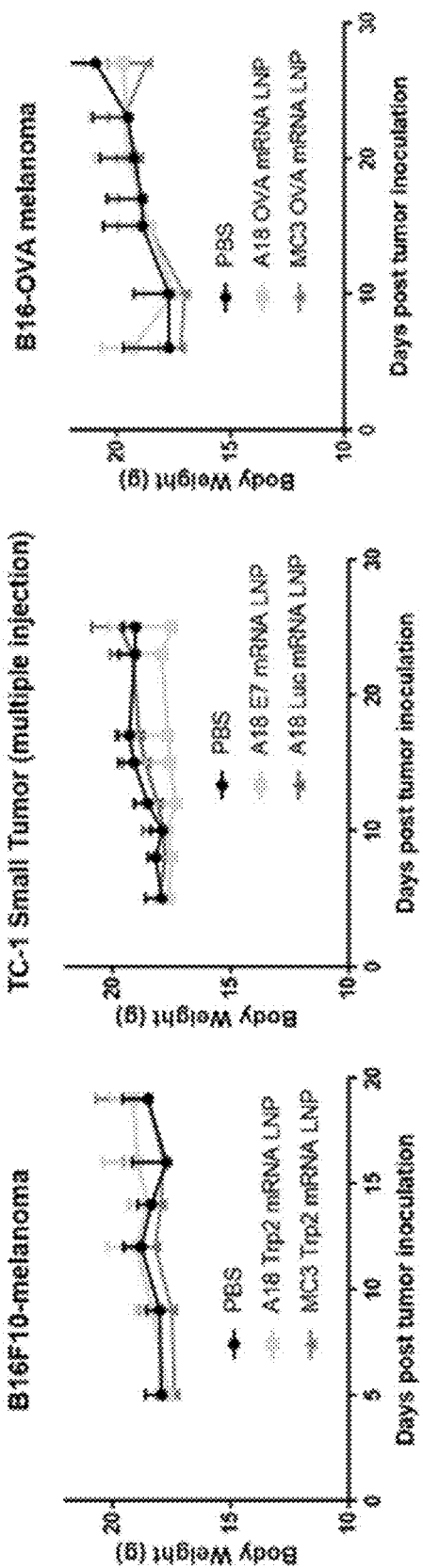
FIG. 25 shows the body weight of tumor bearing mice in different treatment groups (n=5-6).
Figure 26:
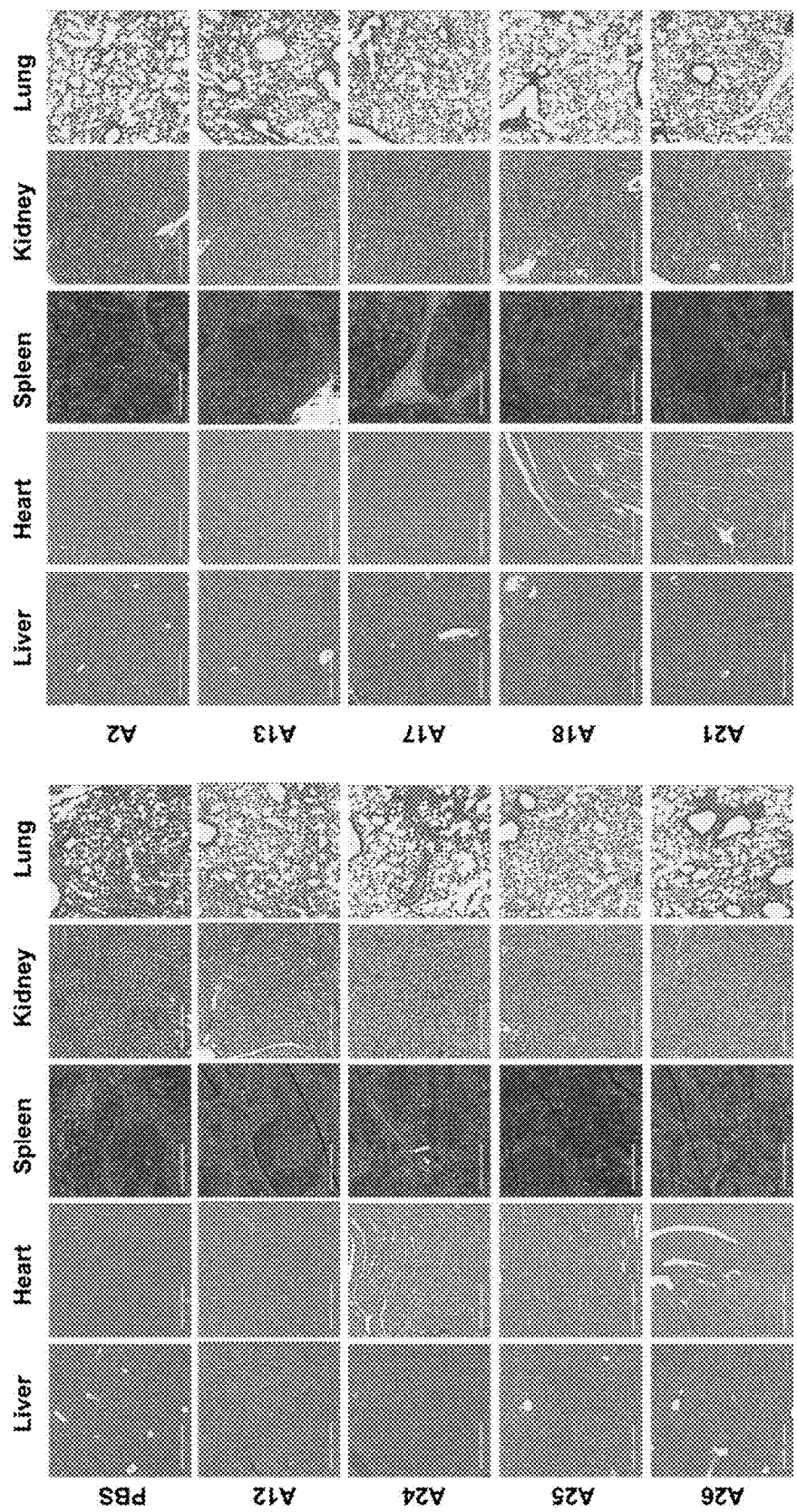
FIG. 26 shows histology toxicity studies of major organs in different OVA mRNA loaded LNP treatment groups. Two doses of 25 μg mRNA/mouse vaccination were given before mice were sacrificed.

Finally, mRNA delivery was tested in TC-1 cells expressing the human papillomavirus (HPV) E7 protein, as a model for viral oncogene/mutant neo-epitope driven cancer with translational vaccination potential.[16] Vaccination using viral oncogene-coding E7 mRNA-A18 LNPs on or before day 5 significantly reduced tumor burden (FIGS. 6E and 24). When the A18 LNPs were co-administered with an anti-PD1 antibody therapy, animals demonstrated robust cures, even in late stage treatment plans (FIG. 6F) (vaccination given from day 9 onwards; 30% mouse survival at 40 days and 10% over 2 months[30,31]). Tumor tissue was collected from all three mouse models, and immunostaining indicated activated CD8+ T cell infiltration in all models treated with A18 LNPs, confirming these LNPs can induce a strong adaptive immune response (FIGS. 6G to 6I). Finally, blood AST, ALT, BUN and creatine levels were evaluated to determine whether repeated lipidoid injection caused systemic toxicity. Major organs were also compared post-vaccination using histology, and no observable toxicity was found (FIGS. 25, 26, and Table 5).

Analysis

A novel class of cyclic lipidoids has been identified that provide robust anti-tumor efficacy through adjuvant-assisted mRNA vaccination in a number of mouse models. A large lipidoid library was rapidly synthesized using a 3-component reaction (3-CR), synthesizing over 1,000 lipidoids in a single day. This reaction scheme expands classical multi-component reactions[25] by using an isocyanide mediated three component system, which allowed the vast increase of the molecular diversity of the combinatorial library. Although MCR techniques have previously been used to generate molecular libraries[25, 48, 49, 50], it is believed that this is early evidence of a 3-CR lipidoid library for gene delivery, and early evidence of an isocyanide mediated system. The addition of the isocyanide moiety allows the formation of a dihydroimidazole linker, and it is believed that the results also show an early example of dihydroimidazole-containing LNPs for optimized mRNA delivery.

From this library, 9 well-performing lipidoids were identified that facilitated robust in vivo protein expression and antigen presentation (FIG. 4A). Interestingly, lipidoids containing cyclic amino head groups (in particular piperidinyl six-member cyclic groups) were able to act as mRNA delivery vehicles but also facilitate APC maturation in an mRNA independent manner (FIG. 5B). These cyclic head groups bind to STING proteins, induce type I IFN stimulation, and thereby facilitate antigen specific T cell responses. This is the first known demonstration of LNPs with MyD88- and mRNA-independent, STING-mediated adjuvant effects. The STING pathway is emerging as an important regulator of innate immune cell behavior[18]. Alongside innate immune targets such as TLRs and RLRs, the STING pathway is reported to be involved in tumor-induced immunosuppression; activation of these pathways has been reported to correlate with reduced disease progression and better clinical outcomes in human cancer patients.[8, 9, 10] A number of small molecule STING agonists are currently in clinical trials,[10, 51] however their success has been limited due to the challenges with cytosolic delivery of these molecules.[23]

In the present system, the STING agonist is a lipidoid component of a lipid nanoparticle delivery system, which facilitates internalization. This combinatorial lipid nanoparticle intrinsically provides targeted adjuvant stimulation via the STING pathway, and facilitates efficient mRNA delivery. These materials have been used to deliver antigen specific mRNA vaccines in a number of in vivo tumor models, demonstrating significant survival advantage in animals treated with a well-performing exemplary LNP A18.

Methods

Lipidoids were synthesized through one-pot mixing of amine, ketone and isocyanide. Amines were purchased from Sigma-Aldrich, TCI America, and Alfa Aesar. All isocyanides were purchased from Sigma-Aldrich. Ketones were mainly purchased from Sigma-Aldrich, Alfa Aesar and TCI America. All chemicals obtained from commercial sources were used as received. The lipidoid was synthesized with a molar ratio of amine:isocyanide:ketone at 1:1:1. All library reactions were carried out in 96 well deep-well plate with glass insert (VWR). The reaction was taken place at room temperature for 24 h. For in vitro high throughput transfection study or in vivo batch analysis assay, the lipid mixtures were used without purification. Otherwise, the lipid was purified by flash column chromatography on a Isco Combiflash systems. Structure was confirmed by nuclear magnetic resonance spectra of $^1H$ and $^{13}C$ (Bruker AVANCE-400 NMR spectrometer with a Magnex Scientific superconducting magnet) and LC-Mass spectra (Waters Acquity LC-MS instrument) (See Examples: Methods 1 and 2).

Lipid Nanoparticle Synthesis.

An organic phase was prepared by solubilizing with ethanol a mixture of the synthesized cationic lipid, 1,2-dioleoyl-sn-glycero-3-phosphoethanolamine (DOPE, Avanti), cholesterol (Avanti), and 1,2-dimyristoyl-sn-glycero-3-phosphoethanolamine-N-[methoxy-(polyethyleneglycol)-2000] (ammonium salt) (C14-PEG 2000, Avanti) at a predetermined molar ratio and an lipidoid:mRNA weight ratio of 10:1. The aqueous phase was prepared in 10 mM citrate buffer (pH 3.0, fisher) with either FLuc mRNA (Firefly luciferase mRNA, Translate), antigen mRNA or non-translating Cy5-labelled FLuc mRNA (TriLink Bio-Technologies). All mRNAs were stored at −80° C., and were allowed to thaw on ice prior to use. The ethanol and aqueous phases were mixed at a 3:1 ratio in a microfluidic chip device using syringe pumps as previously described. Resultant LNPs were dialyzed against 1×PBS in a 20,000 MWCO cassette (Fisher) at 4° C. for 1 hour and were stored at 4° C. prior to injection.

LNP Formulation Optimization.

The molar ratio of lipid component, the weight ratio between mRNA and total lipid would affect the encapsulation, morphology and transfection efficiency of LNPs[34], thus these factors was optimized using 4 factor (DOPE, C14-PEG, cationic lipid, mRNA/lipid ratio) 4 level central composite design. The experiments were designed and analyzed using Design-Expert® software version 11 (Stat-Ease, Inc.).[38, 52, 53]

LNP Characterization. The size, polydispersity index (PDI) and zeta potentials of LNPs were measured using dynamic light scattering (ZetaPALS, Brookhaven Instruments). Diameters are reported as the intensity mean peak average. To calculate the nucleic acid encapsulation efficiency, a modified Quant-iT RiboGreen RNA assay (Invitrogen) was used as previously described.[34, 40]

RNA Synthesis.

RNAs for studies of Firefly-luciferase and cOVA expression in tissue culture and in vivo were obtained from Translate Inc. and Trilink Inc.[34, 36, 40] E7 mRNA were generated from linearized plasmid vectors by in vitro transcription using MEGAscript kits (Life Technologies), 5' capped to produce cap-0 structured 7-methylguanylate 5' ends using ScriptCap m7G Capping System kits (CellScript), and 3' poly(A)-tailed using A-Plus Poly(A) Polymerase Tailing kits (CellScript, Inc.), all according to the manufacturers' protocols. For all other experiments, replicon RNAs were synthesized essentially the same way, except for inclusion of 2'-O-methyltransferase (from Script-Cap 2'-O-methyltransferase kits; CellScript, according to the manufacturer's protocol) in the capping step to methylate the cap-adjacent 5' nucleotide of the RNA, thus producing a cap-1 structure and ensuring more efficient first-round endogenous translation. Conventional mRNA was synthesized from the pcDNA3-derived plasmids carrying the antigen cloned into the HindIII/XbaI sites using T7 RNA polymerase after linearization with SacI.

In vitro high throughput screening and in vivo batch analysis. The unpurified lipid library was directed added to ethanol containing DOPE, cholesterol, C14-PEG at predetermined molar ratio in ethanol, and then mixed with Fluc mRNA aqueous solution. For in vitro transfection, the lipid-mRNA mixture (with 0.1 µg) mRNA were added to 96-well plate pre-seeded with HeLa cells. After overnight incubation, the luciferase mRNA transfection efficiency and the cell viability were simultaneously measured using ONE-Glo™ Luciferase Assay System (Promega) according to manufacturer's instruction. For the in vivo batch analysis assay, lipid mRNA mixtures within one classification group were mixed and dialysis before injecting to mice. 15 µg Fluc mRNA per mice were injected for each lipid group. Six hours after injection, mice were subjected to the bioluminescence assay using IVIS kinetic imaging system (Perkin Elmer).

Animals and Cells.

All animal procedures were performed with ethical compliance and approval by the Massachusetts Institute of Technology Committee on Animal Care (CAC). Female C57BL/6 mice (4-8 weeks) were obtained from Jackson Laboratory Inc. and Charles River Laboratories Inc. INF-α/βR$^{-/-}$ (B6.129S2-Ifnar1$^{tm1.4gt}$/Mmjax 32045) mice, STING$^{gt/gt}$ (C57BL/6J-Tmem173$^{gt}$/J, 017537) mice and Ail4D (C57BL/6J mice and B6.Cg-Gt(ROSA) 26Sor$^{tm14(CAG-tdTomato)Hze}$/J, 007914) mice were purchased from the Jackson Laboratory and housed in an MIT animal facility. All strains were maintained on a C57BL/6J background. For each experiment, mice were randomly allocated by blinded investigators to each group. STING$^{gt/gt}$ and INF-α/βR$^{-/-}$ BMDCs were derived from corresponding knockout mice and then cultured in GM-CSF-containing medium for 6-7 days. THP-1 cells were kindly provided by Tyler Jacks lab (MIT). THP1-Dual™ cells, THP1-Dual™ KO-MyD cells (with stable knockout of the MyD88 gene) and THP1-Dual™ KO-STING cells THP-1 (with stable knockout of the STING gene) were purchased from Invivo-Gen Inc. (CA). B16-OVA cell line was kindly given by Dr. Kenneth Rock, Dana-Farber Cancer Institute, Boston. TC-1 cells were kindly provided by Darrell Irvine lab (MIT). B16-F10 cells and HeLa cells were purchased from ATCC.

All cell lines were routinely tested using a *mycoplasma* contamination kit (R&D). Cells were cultured in complete medium (RPMI 1640, 10% fetal bovine serum, Pen-Strep (100 U/ml-100 jag/ml), 100 μg/ml Normocin™), 2 mM L-glutamine, 25 mM HEPES (all from Invitrogen)) at 37° C. in 5% $CO_2$.

Bioluminescence.

Six, twenty-four and forty-eight hours after the injection of the mRNA LNPs, mice were injected intravenously with 0.2 mL of D-luciferin (10 mg/mL in PBS). The mice were anesthetized in a ventilated anesthesia chamber with 1.5% isofluorane in oxygen and imaged 10 min after the injection with an in vivo imaging system (IVIS, PerkinElmer, Waltham, Mass.). Luminescence was quantified using the Living Image software (PerkinElmer).[34]

Ai14D Reporter Mice Transfection Analysis.

Ai14D mice were immunized with A2 and A12 LNPs containing mRNA coding for either Cre-recombinase or irrelevant mRNA (trilink). Two days after vaccination, the draining lymph nodes, the inguinal lymph nodes, were removed and digested in a medium containing collagenase D (1 mg/mL, sigma) for 40 min at 37° C. The solution was then filtered through a 70 μm cell strainer and centrifuged. The cells were resuspended at 4° C. in staining buffer for 30 min at 4° C. The staining buffer contained antibodies specific for different cell markers and analyzed by flow cytometry.

In vivo cytotoxicity lysis (CTL) assay. Groups of C57BL/6 mice were injected (10 μg free or LNP-loaded OVA mRNA, E7 mRNA or control luciferase mRNA, or OVA (E7) peptide, OVA protein with other adjuvant (LPS or cGAMP (InvivoGen)) with the same dose) subcutaneously at the lower left flank of the mice. Five days later of the second injection, naive C57BL/6 mice were sacrificed and splenocytes were dissociated and collected. Half of the splenocytes were pulsed with $OVA_{257-263}$ or $E7_{4-57}$ peptides in complete medium at 37° C. for 2 h. The unpulsed and peptide-pulsed cells were labelled with 0.05 μM or 0.5 carboxyfluorescein succinimidyl ester (CFSE) (Invitrogen), respectively, in PBS for 20 min. After washing of the CFSE, equal numbers ($1\times10^7$) of $CFSE_{low}$ (unpulsed) and $CFSE_{high}$ (peptide pulsed) cells were mixed together and instantly injected intravenously into the immunized mice. Eighteen hours after injection, splenocytes and lymph nodes from the treated mice were collected, dissociated and subjected to flow cytometry analysis. The numbers of $CFSE_{high}$ and $CFSE_{low}$ cells were confirmed and used to calculate the percentage of peptide-pulsed target cell killing. Specific killing was defined as Percentage of specific lysis=[1−non-transferred control ratio/experimental ratio]×100.[20]

ELISpot Assay.

Multiscreen filter plates (R&D systems), pre-coated with antibodies specific for IFNγ (R&D systems) were washed with PBS and blocked with full medium for 3 h. $2\times10^5$ effector cells (splenocytes, purified CD4+ T cells or purified CD8+ T cells (using untouched CD8α T cells or CD4α T cells isolation kit II (Miltenyi Biotech)) per well were stimulated for 16-20 h with 2 μg/mL OVA or E7 peptide or autologous DCs loaded with RNA or loaded with peptides. All tests were performed in duplicate or triplicate and included assay positive controls as well as cells from a reference donor with known reactivity. Spots were visualized with a biotin-conjugated anti-IFNγ antibody (R&D systems) followed by incubation with ExtrAvidin-Alkaline Phosphatase (R&D systems) and BCIP/NBT substrate (R&D systems). Plates were scanned using CTL Immuno-Spot Series S five Versa ELISpot Analyzer (S5Versa-02-9038) and analyzed by ImmunoCapture V6.3 software.[37, 54]

ELISA Assay.

For antibody detection, groups of C57BL/6 mice were immunized with different vaccines on days 0 and 6. On day 7, 10 and 14, 100 μl blood was drawn from the tail vein, and levels of antigen-specific IgG in the serum were measured by ELISA. For ELISA assay, flat-bottomed 96-well plates (Nunc) were precoated with OVA protein at a concentration of 2 μg protein per well in 100 mM carbonate buffer (pH 9.6) at 4° C. overnight, which were then blocked with 10% FBS in PBST. Antisera obtained from immunized animals were diluted 50 times in PBS-0.05% Tween (PBS-T), pH 7.4, and were added to the wells and incubated at 37° C. for 2 h. Horseradish peroxidase (HRP) conjugated goat anti-mouse IgG (Cell Signaling) were used at a dilution of 1:5,000 in PBS-T-10% FBS for labelling. After adding the HRP substrates, optical densities were determined at a wavelength of 450 nm in an ELISA plate reader (Bio-Rad).[20, 36, 40]

BMDC Activation and Antigen Presentation Assay.

Bone marrow derived dendritic cells (BMDCs) were prepared as described previously.[20, 41] In brief, bone marrow cells flushed from the femurs of C57BL/6J mice were cultured in the DC medium: RPMI 1640 supplemented with 10% FBS, Pen/Strep and 20 ng/mL GM-CSF. The medium was half replaced every 2 days. On day 6, non-adherent and loosely adherence immature DCs were collected and plated at $5\times10^5$ cells per well in a 24-well plate. The phenotype of DCs were pre-determined using CD11c (routinely 60-80% CD11c+). After 24 h, BMDCs were incubated with 0.5~2.5 μg OVA mRNA in various LNP formulations or with blank LNPs at the same dosage in complete media for different lengths of time (10 h, 24 h, 48 h) at 37° C. with 5% $CO_2$, LPS was used as an DC activation positive control. After co-incubation, BMDCs were harvested, washed with FACS buffer (1% BSA, 10% FBS in PBS), incubated with anti-CD16/32 at room temperature and then stained on ice with fluorophore-labelled antibodies against CD45, CD1 c, CD40, CD86, F4/80, MHCII or PE-conjugated anti-mouse SIINFEKL/H-2 Kb monoclonal antibody 24-D1.16 (ebioscience). The activation of DCs and antigen presentation were quantified using the mean fluorescence intensity (MFI) of cells by flow cytometry analysis. In another study, the LNP-treated BMDCs were collected at different time points. Whole RNA was extracted from the BMDCs, and reverse-transcribed into cDNA. Type I interferon pathway activation was determined by analyzing the downstream RNA using primers against CXCL10, IRF7 and IFNβ.

Flow Cytometry and Antibodies.

Antibodies were purchased from Biolegend, ebioscience and BD for flow cytometry, ELISA and western blot, and listed below. For the flow cytometry analysis of surface marker, cells were pre-incubated with anti-CD16/32 antibody and stained on ice with fluorophore conjugated antibody. For the staining of intracellular marker, e.g. IFN-γ, cells were pre-stimulated with the Cell Stimulation Cocktail (eBioscience™) for 6 h, and fixed and permeablized using the fixation/permeabilization solution kit (BD). Then cells were stained with both anti-IFN-γ or other surface antibodies. Flow data were acquired on a BD LSR II flow cytometer and analyzed using FlowJo software.

TABLE 1

Lipid Library synthesis.

| Name | Fluorescence | Dilution F | Company | Catalog |
|---|---|---|---|---|
| CD11b | APC | 1-800 | Ebioscience | 17-0112-82 |
| CD11c | PE-Cy7 | 1-800 | Ebioscience | 25-0114-82 |
| Gr-1 | FITC | 1-200 | Ebioscience | 11-5931-82 |
| Gr-1 | PE | 1-200 | Ebioscience | 12-5931-81 |
| MHCII | APC-Cy7 | 1-200 | Ebioscience | 47-5321-82 |
| CD8a | Alexa 700 | 1-400 | Ebioscience | 56-0081-82 |
| CD4 | PerCP-Cy5.5 | 1-400 | BD | 550954 |
| CD4 | FITC | 1-400 | BD | 553046 |
| B220 | PE-Txred | 1-200 | Invitrogen | 50-113-7696 |
| B220 | APC | 1-800 | BD | 561880 |
| B19 | PE-Cy7 | 1-800 | Biolegend | 50-154-69 |
| CD45.2 | V500 | 1-200 | BD | 562129 |
| F4/80 | FITC | 1-400 | Biolegend | 123107 |
| F4/80 | APC-Cy7 | 1-400 | Biolegend | 50-14-062 |
| NK1.1 | APC-Cy7 | 1-400 | BD | 560618 |
| CD3 | APC | 1-400 | Ebioscience | 50-148-40 |
| CD16/32 | Blocking | 1-50 | Biolegend | 101320 |
| 25-D1.16 | APC | 1-200 | Biolegend | 141605 |
| 25-D1.16 | PE | 1-200 | Biolegend | 141603 |
| CD86 | pacific blue | 1-400 | biolegend | 105022 |
| CD40 | PE-Cy7 | 1-400 | biolegend | 124621 |
| IFN-gamma | PE | 1-200 | BD | 562020 |

Quantitative Reverse Transcription Polymerase Chain Reaction (qRT-PCR).

Local lymph nodes and tumors were taken at indicated time points after injection with LNP loaded mRNA antigen. For the in vitro study, BMDCs were cultured and treated as mentioned above. Total RNAs were extracted by RNeasy Kit (Qiagen, Inc.) from cells or tissues according to manufacturer's instructions. cDNA was generated using SuperScript™ III First-Strand Synthesis System (Invitrogen, Inc.). qRT-PCR was performed according to the TaqMan Gene Expression Assay protocols (Invitrogen, Inc.) using a 384-well LightCycler 480 (Roche).[20, 55] Samples were run in triplicate. The following primers were used for qRT-PCR.

TABLE 2

Primers used for qRT-PCR.

| Gene | Species | Amplicon Lengths | Assay ID | Brand, company |
|---|---|---|---|---|
| Cxcl10 | mouse | 59 | Mm00445235_m1 | Taqman, Invitrogen |
| Ifnb1 | mouse | 69 | Mm00439552_s1 | Taqman, Invitrogen |
| Irf7 | mouse | 64 | Mm00516793_g1 | Taqman, Invitrogen |
| Gapdh | mouse | 109 | Mm99999915_g1 | Taqman, Invitrogen |

STING Pulldown Assay.

To investigate the STING interaction with cyclic lipidoid, His-Sting CTD was prepared and purified according to a previous method.[20] The His-STING was bind to Ni-NTA followed by co-incubation with lipidoids for 1 h at room temperature. The extra lipidoids were washed 4 times with cold PBS. Lipidoid bond to protein was finally extracted using propanol and quantified using LC-MS.

Immunization and Tumor Therapy Experiments.

Four- to six-week-old mice (n=10 for each group) were injected subcutaneously with B16-OVA or B16F10 melanoma cells (1.5×105), TC-1 cells (1.5×105) into the right flank of mice. On day 5 after tumor inoculation, animals were immunized by subcutaneous injection of different LNP formulations containing 15 ag OVA mRNA, luciferase mRNA, E7 mRNA or E7 replicons or the relevant dose of OVA, E7 peptide, OVA protein with adjuvants as described in the main text. In some of the studies, second vaccination boost was given on the seventh day. For the combinatorial immunotherapy, at days 5, 8, 11 and 14 after inoculation, some groups were intraperitoneally injected with 200 μg checkpoint inhibitors (anti-mPD-1, BioXcell, BE0146). Tumor growth was subsequently measured three times a week using a digital caliper and calculated as 0.5×length×width[2, 20, 41] Mice were killed when the tumor volumes reached 2,000 mm$^3$. For the lung metastasis re-challenge model, tumor bearing vaccinated mouse or non-vaccinated mouse were re-challenged by intravenous injection of 5×10$^4$ B16OVA cells per mouse, and lungs were excised on day 21. On day 20, three mice from each group were sacrificed, tumor tissues were processed for flow analysis, western blot, rt-PCR and histology analysis.

H&E Morphology Evaluation and Blood Chemistry Analysis. Three days after second vaccination in tumor free and tumor bearing mice with different treatments were all subjected to a toxicity assay. Creatinine, total Bilirubin, blood urea nitrogen (BUN), serum aspartate aminotransferase (AST), and alanine aminotransferase (ALT) in the serum were assayed as indicators of renal and liver function, respectively. Major organs including the heart, liver, spleen, lungs, and kidneys were collected and fixed for H&E staining by the KI Swanson Biotechnology Center to evaluate the organ-specific toxicity.

Statistical Analysis.

Based on pilot immunization and tumor treatment studies, group sizes of three to six animals per group were used for immunogenicity measurements and ten animals per group for tumor inhibition study. A two-tailed Student's t test or a one-way analysis of variance (ANOVA) was performed when comparing two groups or larger than two groups, respectively. Statistical analysis was performed using Microsoft Excel and Prism 7.0 (GraphPad). Data are expressed as means±SEM. Difference was considered to be significant if $P<0.05$ (*$P<0.05$, $P<0.01$, *$P<0.001$, unless otherwise indicated). The survival rates of the two groups were analyzed using a log-rank test and were considered statistically significant if $P<0.05$.

Synthesis of Exemplary Lipidoids

Method 1: Synthesis and Characterization of Exemplary Lipidoids

Synthesis of A12 ethyl 1-(3-(dimethylamino)propyl)-5,5-di((Z)-heptadec-8-en-1-yl)-2,5-dihydro-1H-imidazole-2-carboxylate A mixture of 3-(Dimethylamino)-1-propylamine (20.4 mg, 0.2 mmol), Ethyl isocyanoacetate (22.6 mg, 0.2 mmol), 9,26-Pentatriacontadien-18-one (100.6 mg, 0.2 mmol) in anhydrous mixed solvent consisting of 80 uL dichloromethane (DCM) and 120 uL ethanol was stirred in capped glass vials at room temperature overnight. The mixture was purified by flash column chromatography to obtain compound A12 as a yellow oil. Yield: 39.8 mg (0.057 mmol, 28.4%). MS: m/z 700.7 (M+H$^+$); $^1$H NMR (400 MHz, CHLOROFORM-d) δ ppm 0.81-0.89 (m, 6H), 1.10-1.17 (m, 3H), 1.20-1.52 (m, 50H), 1.68-1.80 (m, 2H), 1.85-2.08 (m, 8H), 2.12-2.27 (m, 6H), 2.28-2.39 (m, 2H), 2.83-3.15 (m, 2H, NCH$_2$), 4.14-4.25 (q, 2H), 4.51 (s, 1H), 5.27-5.50 (m, 4H), 7.09 (s, 1H). $^{13}$C NMR (400 MHz, CHLOROFORM-d) δ 171.4 (C═O), 156.2 (CH═N), 129.6 (CH═CH), 73.5 (N—CH—N), 70.3 (C—N), 60.5 (O—CH$_2$), 56.3

(N—CH₂), 45.0 (N—CH₃), 39.4 (N—CH₂), 22.3 (CH₂), 23.4 (CH₂), 28.9 (CH₂), 29.0 (CH₂), 29.1 (CH₂), 29.3 (CH₂), 29.6 (CH₂), 31.5 (CH₂), 32.2 (CH₂), 34.7 (CH₂), 13.9 (CH₃), 13.8 (CH₃).

Synthesis of A2 ethyl 5,5-di((Z)-heptadec-8-en-1-yl)-1-(3-(pyrrolidin-1-yl)propyl)-2,5-dihydro-1H-imidazole-2-carboxylate Following the procedure described for A12, the compound was made from 1-(3-Aminopropyl)pyrrolidine (38.5 mg, 0.3 mmol), Ethyl isocyanoacetate (33.9 mg, 0.3 mmol), 9,26-Pentatriacontadien-18-one (150.9 mg, 0.3 mmol) in DCM (120 uL) and ethanol (180 uL) and was obtained as a yellow oil. Yield: 74.1 g (0.1 mmol, 34%). MS: m/z 726.7 (M+H⁺); ¹H NMR (400 MHz, CHLOROFORM-d) δ ppm 0.83-0.94 (m, 6H), 1.10-1.19 (m, 3H), 1.21-1.87 (m, 54H), 1.90-2.12 (m, 8H), 2.43-2.61 (m, 6H), 2.95-3.13 (m, 2H), 4.19-4.30 (q, 2H), 4.55 (s, 1H), 5.26-5.43 (m, 4H), 7.03 (s, 1H).

Synthesis of A13 ethyl 5,5-di((Z)-heptadec-8-en-1-yl)-1-(3-(piperidin-1-yl)propyl)-2,5-dihydro-1H-imidazole-2-carboxylate Following the procedure described for A12, the compound was made from N-(3-Aminopropyl)piperidine (21.1 mg, 0.16 mmol), Ethyl isocyanoacetate (18.6 mg, 0.16 mmol), 9,26-Pentatriacontadien-18-one (82.5 mg, 0.16 mmol) in DCM (60 uL) and ethanol (90 uL) and was obtained as a yellow oil. Yield: 25.2 mg (0.034 mmol, 21.3%). MS: m/z 740.7 (M+H⁺); ¹H NMR (400 MHz, CHLOROFORM-d) δ ppm 0.85-0.94 (m, 6H), 0.97-1.10 (m, 3H), 1.11-1.91 (m, 56H), 1.92-2.12 (m, 8H), 2.38-2.58 (m, 6H), 2.96-3.15 (m, 2H), 4.18-4.32 (q, 2H), 4.54 (s, 1H), 5.30-5.47 (m, 4H), 7.10 (s, 1H).

Synthesis of A17 ethyl 1-(3-(5-ethyl-2-methylpiperidin-1-yl)propyl)-5,5-di((Z)-heptadec-8-en-1-yl)-2,5-dihydro-1H-imidazole-2-carboxylate Following the procedure described for A12, the compound was made from 3-(5-ethyl-2-methyl-1-piperidinyl)-1-propanamine (36.9 mg, 0.2 mmol), Ethyl isocyanoacetate (22.6 mg, 0.2 mmol), 9,26-Pentatriacontadien-18-one (100.6 mg, 0.2 mmol) in DCM (80 uL) and ethanol (120 uL) and was purified as a yellow oil. Yield: 10.4 mg (0.013 mmol, 6.6%). MS: m/z 782.7 (M+H⁺); ¹H NMR (400 MHz, CHLOROFORM-d) δ ppm 0.86-0.97 (m, 12H), 0.98-1.09 (m, 3H), 1.11-1.89 (m, 56H), 1.94-2.09 (m, 8H), 2.35-3.12 (m, 7H), 4.17-4.31 (q, 2H), 4.54 (s, 1H), 5.31-5.46 (m, 4H), 7.08 (s, 1H).

Synthesis of A18 ethyl 1-(3-(2-ethylpiperidin-1-yl)propyl)-5,5-di((Z)-heptadec-8-en-1-yl)-2,5-dihydro-1H-imidazole-2-carboxylate Following the procedure described for A12, the compound was made from 3-(2-ethyl-1-piperidinyl)-1-propanamine (34.1 mg, 0.2 mmol), Ethyl isocyanoacetate (22.6 mg, 0.2 mmol), 9,26-Pentatriacontadien-18-one (100.6 mg, 0.2 mmol) in DCM (80 uL) and ethanol (120 uL) and was obtained as a yellow oil. Yield: 22.4 g (0.029 mmol, 14.6%). MS: m/z 768.7 (M+H⁺); ¹H NMR (400 MHz, CHLOROFORM-d) δ ppm 0.86-0.96 (m, 9H), 0.97-1.13 (m, 3H), 1.14-1.89 (m, 54H), 1.91-2.11 (m, 8H), 2.34-2.51 (m, 2H), 2.68-3.15 (m, 5H), 4.14-4.30 (q, 2H), 4.55 (s, 1H), 5.28-5.47 (m, 4H), 7.05 (s, 1H).

Synthesis of A21 ethyl 1-(3-(azepan-1-yl)propyl)-5,5-di((Z)-heptadec-8-en-1-yl)-2,5-dihydro-1H-imidazole-2-carboxylate Following the procedure described for A12, the compound was made from 3-(1-azepanyl)-1-propanamine (46.9 mg, 0.3 mmol), Ethyl isocyanoacetate (33.9 mg, 0.3 mmol), 9,26-Pentatriacontadien-18-one (152.7 mg, 0.3 mmol) in DCM (120 uL) and ethanol (180 uL) and was obtained as a yellow oil. Yield: 35.9 mg (0.048 mmol, 15.8%). MS: m/z 754.7 (M+H⁺); ¹H NMR (400 MHz, CHLOROFORM-d) δ ppm 0.81-0.99 (m, 6H), 1.00-1.12 (m, 3H), 1.14-1.86 (m, 58H), 1.90-2.12 (m, 8H), 2.51-2.76 (m, 6H), 2.94-3.16 (m, 2H), 4.17-4.32 (q, 2H), 4.54 (s, 1H), 5.28-5.48 (m, 4H), 7.08 (s, 1H).

Synthesis of A24 ethyl 1-(3-(diethylamino)propyl)-5,5-di((Z)-heptadec-8-en-1-yl)-2,5-dihydro-1H-imidazole-2-carboxylate Following the procedure described for A12, the compound was made from 3-(5-ethyl-2-methyl-1-piperidinyl)-1-propanamine (32.6 mg, 0.25 mmol), Ethyl isocyanoacetate (28.3 mg, 0.25 mmol), 9,26-Pentatriacontadien-18-one (125.7 mg, 0.25 mmol) in DCM (100 uL) and ethanol (150 uL) and was obtained as a yellow oil. Yield: 56.4 mg (0.077 mmol, 31.0%). MS: m/z 728.7 (M+H⁺); ¹H NMR (400 MHz, CHLOROFORM-d) δ ppm 0.80-1.12 (m, 15H), 1.13-1.87 (m, 50H), 1.94-2.12 (m, 8H), 2.51-2.64 (m, 6H), 2.94-3.12 (m, 2H), 4.21-4.30 (q, 2H), 4.54 (s, 1H), 5.33-5.47 (m, 4H), 7.10 (s, 1H).

Synthesis of A25 ethyl 1-(3-(dibutylamino)propyl)-5,5-di((Z)-heptadec-8-en-1-yl)-2,5-dihydro-1H-imidazole-2-carboxylate Following the procedure described for A12, the compound was made from 3-(Dibutylamino)propylamine (46.6 mg, 0.25 mmol), Ethyl isocyanoacetate (28.3 mg, 0.25 mmol), 9,26-Pentatriacontadien-18-one (125.7 mg, 0.25 mmol) in DCM (100 uL) and ethanol (150 uL) and was obtained as a yellow oil. Yield: 7.7 mg (0.010 mmol, 3.9%). MS: m/z 784.7 (M+H⁺); ¹H NMR (400 MHz, CHLOROFORM-d) δ ppm 0.81-1.09 (m, 15H), 1.13-1.86 (m, 58H), 1.92-2.10 (m, 8H), 2.59-2.74 (m, 6H), 2.96-3.12 (m, 2H), 4.22-4.30 (q, 2H), 4.55 (s, 1H), 5.30-5.45 (m, 4H), 7.06 (s, 1H).

Synthesis of A26 ethyl 1-(3-(dipropylamino)propyl)-5,5-di((Z)-heptadec-8-en-1-yl)-2,5-dihydro-1H-imidazole-2-carboxylate Following the procedure described for A12, the compound was made from N(1),N(1)-Dipropyl-1,3-propanediamine (47.5 mg, 0.3 mmol), Ethyl isocyanoacetate (33.9 mg, 0.3 mmol), 9,26-Pentatriacontadien-18-one (150.9 mg, 0.3 mmol) in DCM (120 uL) and ethanol (180 uL) and was obtained as a yellow oil. Yield: 25.3 mg (0.033 mmol, 11.2%). MS: m/z 756.7 (M+H⁺); ¹H NMR (400 MHz, CHLOROFORM-d) δ ppm 0.79-1.03 (m, 15H), 1.12-1.85 (m, 54H), 1.91-2.08 (m, 8H), 2.42-2.63 (m, 6H), 2.99-3.15 (m, 2H), 4.21-4.33 (q, 2H), 4.55 (s, 1H), 5.29-5.49 (m, 4H), 7.14 (s, 1H).

Method 2: Formulation Optimization of an Exemplary 3-CR Lipidoid

Figure 10A:
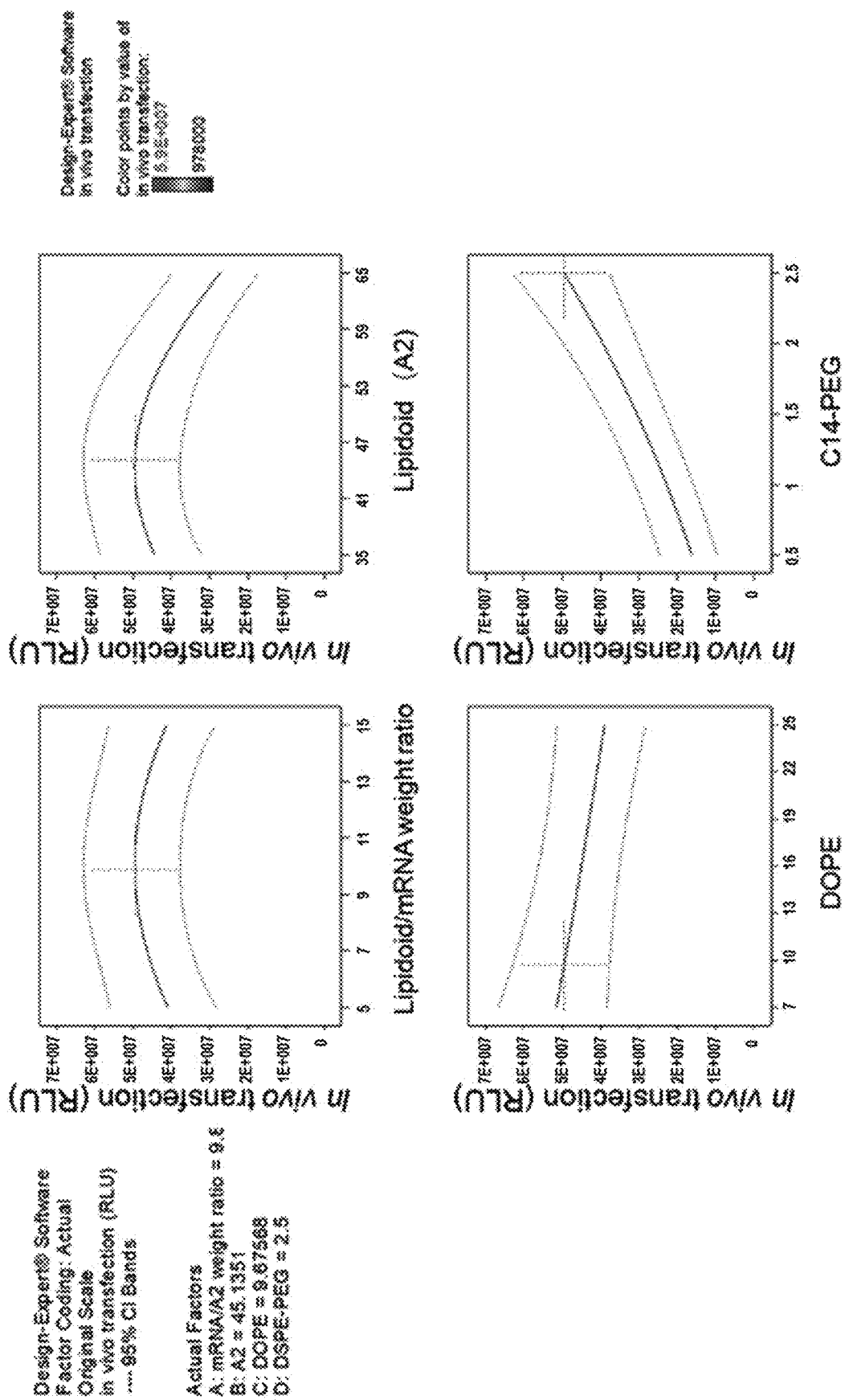
FIGS. 10A and 10B show the model obtained from RSM for prediction of in vivo transfection efficacy of lipidoid formulations.
Figure 10B:
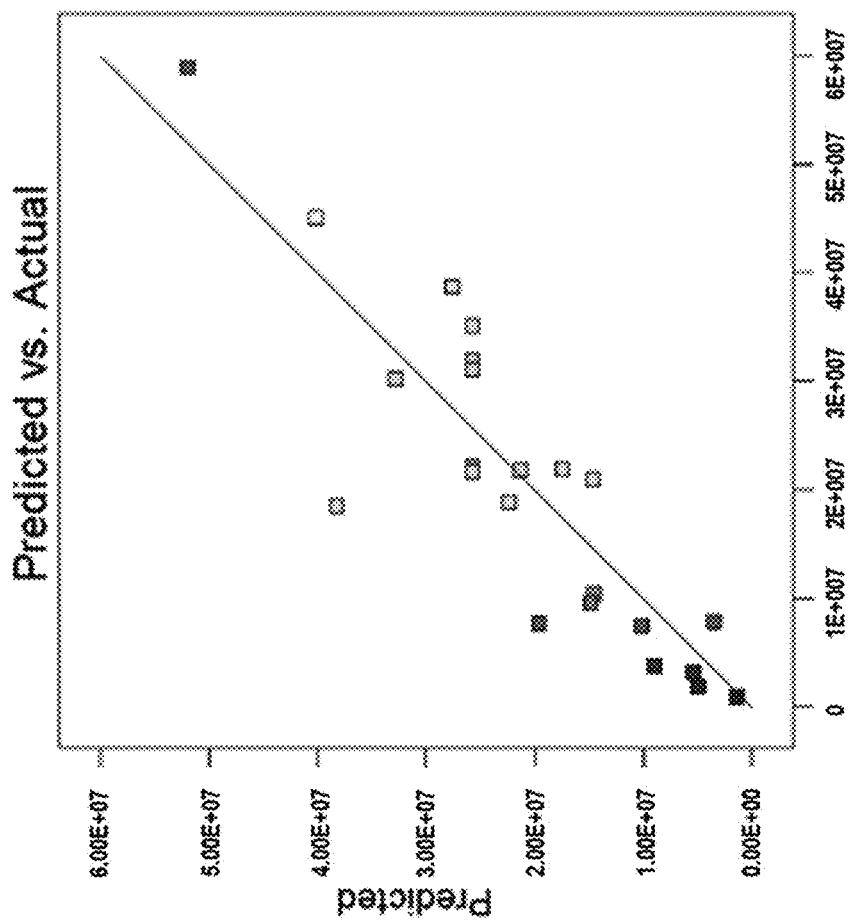

As A2, A12, and subsequent lipids share a similar backbone, lipid formulation was optimized using A2 as a model lipid. Previous experiments suggested that strong-second-order effects between different parameters would affect the efficiency of delivery in various formulations[1], so instead it was chosen to vary all the potential independent parameters simultaneously. The effect of varying the A2:mRNA weight ratio, and the interaction of this parameter with three independent lipid nanoparticle composition parameters (i.e. mol % of A2, DOPE and C14-PEG) was optimized using a 4 factor 3 level Response Surface Methodology (RSM) as shown in Table 3, designed and analyzed by Design Expert® Software Version 11 (Stat-Ease, Inc.).[2] An initial 22 formulations were created based on this method. Particle size, PDI, encapsulation efficiency (EE %), and in vivo & in vitro transfection were examined in different formulations. In vivo mRNA delivery is a crucial parameter in successful mRNA LNP therapy, therefore in vivo transfection efficiency was considered as the crucial response factor. A reduced quadratic model was selected to analyze the formulations, using a significant sum-of-squares p-value and a non-significant Lack of fit p-value (Table 4).[2] The effects of various factors on the in vivo delivery efficiency is shown in (Table 3, FIGS. 10A and 10B). The ANOVA analysis indicates that the mol % of A2, DOPE and PEG has a significant effect on the delivery efficiency. The in vivo delivery efficiency is maximal when the lipid/mRNA weight ratio is approximately 10, the mol % of DOPE is around 10-20%, and the mol % of A2 is around 35-50% (FIGS. 10A and 10B). There is no strong correlation between these independent parameters and the particle size. Almost all the formulations are between 80-150 nm in size with a PDI lower than 0.3, which is qualified as suitable for in vivo injection, except for formulation 4 which has a mRNA/lipid ratio. As a potential explanation, this may be caused by, but is not limited to the incomplete condensation between reduced amounts of cationic lipid and mRNA, which would likely lead to larger but loosely associated particles. It was also observed that EE is not a direct indicator of higher transfection efficiency. EE of between 50%-70% appears optimal for in vitro and in vivo transfection, a phenomenon that has been previously observed in the literature.[1] As the PEG component was increased, encapsulation efficiency was also increased, likely caused by increased stability and shielding of the particles. A secondary library composed of 11 formulations was explored based on the analysis of the first library. Results are shown in Table 3. An exemplary optimized formulation is composed of the following parameters; Lipid:mRNA weight ratio of 10:1, lipid composition of 45:10:42.5:2.5 of A2:DOPE:Cholesterol:C14-PEG. The delivery efficacy of this formulation was 3 times higher than formulations used for other lipidoids reported elsewhere (Formulation 23, Table 3), but similar to the original formulation (A2:DOPE:Cholesterol:C14-PEG: 35:16:37.5:2.5) adopted from the study of Kauffman et al.[1] The (A2:DOPE:Cholesterol:C14-PEG: 35:16:37.5:2.5) formulation was used for the high throughput screening assay and for the remainder of the study.

Method 3: Synthesis of Exemplary Acyclic Lipidoid

Following the procedure described for the preparation of A12, the exemplary acyclic lipidoid compound was made from $N^1,N^1$-dimethylethane-1,2-diamine (1.76 mg, 0.02 mmol), tert-Butyl isocyanide (1.66 mg, 0.02 mmol), 9,26-Pentatriacontadien-18-one (10.06 mg, 0.02 mmol) in 20 μL propanol and was obtained as a yellow oil.

(Z)—N-(tert-butyl)-2-((2-(dimethylamino)ethyl)amino)-2-((Z)-heptadec-8-en-1-yl)nonadec-10-enamide

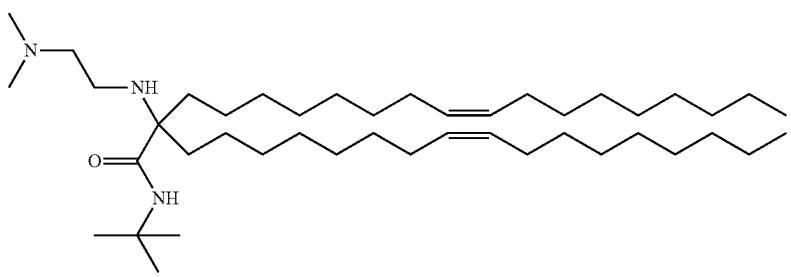 [SMILES: CCCCCCCC/C=C\CCCCCCCC(CCCCCCC/C=C\CCCCCCCC)(NCCN(C)C)C(=O)NC(C)(C)C]

The synthesis of the exemplary acyclic lipidoid compound (Z)—N-(tert-butyl)-2-((2-(dimethylamino)ethyl)amino)-2-((Z)-heptadec-8-en-1-yl)nonadec-10-enamide was conducted using the following steps.

(Z)—N-(tert-butyl)-2-((2-(dimethylamino)ethyl)amino)-2-((Z)-heptadec-8-en-1-yl)nonadec-10-enamide was synthesized; EE 65.6%. Confirmed by ESI-MS. Purified. In vitro transfection in Macrophage: 6.5±0.15 E+03 (see Table 5).

TABLE 3

The independent factors and dependent response used for LNP optimization designed by the Response Surface Methodology.

| | Factor | | | | Response | | | | | |
|---|---|---|---|---|---|---|---|---|---|---|
| # | Lipid/mRNA weight ratio | A2 mol % | DOPE mol % | PEG mol % | Avg. Size (nm) | Avg. PDI | EE % | Avg. RLU In vivo Transfection | In vitro HeLa | In vitro B16F10 |
| 1 | 15.0 | 35.0 | 25.0 | 2.5 | 99.9 | 0.1 | 61.3 | 3.9E+07 | 2.2E+07 | 2.0E+06 |
| 2 | 10.0 | 50.0 | 16.0 | 1.5 | 76.9 | 0.2 | 55.3 | 3.5E+07 | 1.7E+07 | 2.0E+06 |
| 3 | 10.0 | 50.0 | 16.0 | 2.9 | 101.0 | 0.2 | 60.6 | 5.9E+07 | 6.9E+06 | 1.3E+06 |
| 4 | 2.9 | 50.0 | 16.0 | 1.5 | 259.6 | 0.3 | 25.5 | 2.1E+07 | 1.2E+07 | 2.2E+06 |
| 5 | 5.0 | 35.0 | 7.0 | 0.5 | 115.9 | 0.3 | 64.7 | 7.5E+06 | 1.2E+07 | 6.1E+06 |
| 6 | 15.0 | 65.0 | 7.0 | 0.5 | 137.9 | 0.2 | 57.9 | 7.9E+06 | 1.4E+04 | 4.8E+03 |
| 7 | 5.0 | 65.0 | 25.0 | 2.5 | 167.9 | 0.2 | 22.5 | 1.1E+07 | 4.9E+06 | 2.7E+06 |
| 8 | 17.1 | 50.0 | 16.0 | 1.5 | 122.4 | 0.3 | 96.4 | 9.6E+06 | 3.5E+06 | 9.7E+05 |
| 9 | 10.0 | 50.0 | 16.0 | 1.5 | 95.9 | 0.2 | 59.5 | 3.2E+07 | 1.7E+07 | 1.6E+06 |
| 10 | 10.0 | 71.2 | 16.0 | 1.5 | 72.3 | 0.2 | 56.4 | 2.0E+06 | 4.2E+06 | 9.2E+05 |
| 11 | 10.0 | 50.0 | 16.0 | 1.5 | 94.0 | 0.2 | 68.1 | 2.2E+07 | 2.5E+07 | 1.6E+06 |
| 12 | 10.0 | 28.8 | 16.0 | 1.5 | 84.9 | 0.2 | 64.3 | 4.2E+07 | 1.5E+07 | 2.0E+06 |
| 13 | 5.0 | 65.0 | 7.0 | 2.5 | 127.8 | 0.2 | 57.2 | 1.9E+07 | 4.0E+06 | 5.5E+05 |
| 14 | 10.0 | 50.0 | 16.0 | 1.5 | 84.9 | 0.2 | 57.5 | 3.1E+07 | 1.4E+07 | 1.8E+06 |
| 15 | 15.0 | 35.0 | 7.0 | 2.5 | 108.7 | 0.1 | 65.2 | 1.9E+07 | 9.9E+06 | 1.7E+06 |
| 16 | 10.0 | 50.0 | 3.3 | 1.5 | 94.9 | 0.3 | 21.7 | 3.0E+07 | 7.6E+06 | 3.8E+05 |
| 17 | 10.0 | 50.0 | 16.0 | 1.5 | 91.8 | 0.2 | 70.2 | 2.2E+07 | 1.9E+07 | 1.8E+06 |
| 18 | 5.0 | 35.0 | 25.0 | 0.5 | 129.4 | 0.2 | 53.9 | 3.2E+06 | 2.0E+07 | 3.7E+06 |
| 19 | 10.0 | 50.0 | 28.7 | 1.5 | 83.2 | 0.3 | 41.3 | 7.7E+06 | 5.2E+06 | 8.6E+05 |
| 20 | 15.0 | 65.0 | 25.0 | 0.5 | 110.7 | 0.1 | 98.9 | 9.8E+05 | 1.1E+04 | 3.5E+04 |
| 21 | 10.0 | 50.0 | 16.0 | 0.1 | 154.9 | 0.1 | 9.4 | 3.9E+05 | 3.7E+06 | 2.2E+06 |
| 22 | 10.0 | 35.0 | 16.0 | 2.5 | 102.5 | 0.2 | 60.3 | 5.3E+07 | 6.3E+06 | 1.1E+06 |
| 23 | 10.0 | 50.0 | 25.0 | 1.5 | 119.8 | 0.3 | 79.0 | 2.2E+07 | N/A | N/A |
| 24 | 10.0 | 35.0 | 16.0 | 2.5 | 102.5 | 0.2 | 60.3 | 5.5E+07 | N/A | N/A |
| 25 | 15.0 | 35.0 | 16.0 | 2.5 | 110.6 | 0.1 | 50.4 | 3.15E+07 | N/A | N/A |
| 26 | 10.0 | 35.0 | 25.0 | 2.5 | 105.5 | 0.2 | 60.3 | 3.13E+07 | N/A | N/A |
| 27 | 10.0 | 35.0 | 28.0 | 2.5 | 108.6 | 0.2 | 45.5 | 2.58E+07 | N/A | N/A |
| 28 | 10.0 | 35.0 | 20.0 | 2.5 | 112.5 | 0.1 | 54.5 | 2.67E+07 | N/A | N/A |
| 29 | 10.0 | 50.0 | 10.0 | 2.5 | 94.8 | 0.1 | 75.5 | 7.70E+06 | N/A | N/A |
| 30 | 10.0 | 45.0 | 16.0 | 2.5 | 115.6 | 0.2 | 76.5 | 1.96E+07 | N/A | N/A |
| 31 | 10.0 | 45.0 | 10.0 | 2.5 | 87.6 | 0.2 | 45.5 | 6.0E+07 | N/A | N/A |
| 32 | 10.0 | 35.0 | 16.0 | 1.5 | 140.6 | 0.1 | 55.5 | 3.04E+07 | N/A | N/A |
| 33 | 10.0 | 35.0 | 16.0 | 2.8 | 88.6 | 0.2 | 65.6 | 4.91E+07 | N/A | N/A |
| | Four Independent Factors | | | | Five Dependent Responses | | | | | |

Note:
the secondary library is italicized; *31 exemplary optimized formulations

TABLE 4

ANOVA Reduced Quadratic model to predict LNPs in vivo delivery efficiency

| Source | Sum of Squares | df | Mean Square | F Value | p-value Prob > F | |
|---|---|---|---|---|---|---|
| Model | 5.568E+007 | 6 | 9.281E+006 | 10.65 | <0.0001 | Significant |
| A-mRNA/A2 weight ratio | 1059.50 | 1 | 1059.50 | 1.216E−003 | 0.9726 | |
| B-A2 | 6.877E+006 | 1 | 6.877E+006 | 7.89 | 0.0126 | |
| C-DOPE | 2.855E+006 | 1 | 2.855E+006 | 3.28 | 0.0891 | |
| D-DSPE-PEG | 2.995E+007 | 1 | 2.995E+007 | 34.37 | <0.0001 | |
| $A^2$ | 3.848E+006 | 1 | 3.848E+006 | 4.42 | 0.0518 | |
| $B^2$ | 9.033E+006 | 1 | 9.033E+006 | 10.37 | 0.0053 | |
| Residual | 1.394E+007 | 16 | 8.712E+005 | | | |
| Lack of Fit | 1.257E+007 | 12 | 1.048E+006 | 3.07 | 0.1445 | not significant |
| Pure Error | 1.365E+006 | 4 | 3.411E+005 | | | |
| Cor Total | 6.962E+007 | 22 | | | | |

TABLE 5

Characterization of Exemplary Lipidoids

| Category | Label | Chemo-phyiscal Characterization | | | EE (Luc mRNA) % | EE (OVA mRNA) % | Transfection (luc) | |
|---|---|---|---|---|---|---|---|---|
| | | Size (nm) | PDI /— | Zeta (mV) | | | In vitro (Macrophage) RLU (2.5 µg/mL) | In vivo (s.c.) Total flux (p/s) (0.5 mg/kg) |
| Cyclic Head | 2DA2C18 | 99.9 | 0.1 | 4.4 | 77.0 ± 2.6 | 68.4 ± 3.2 | 6.88 ± 0.08E+04 | 1.8 ± 0.4E+07 |
| | 2DA13C18 | 86.9 | 0.2 | 8.4 | 61.2 ± 3.7 | 85.8 ± 6.7 | 1.54 ± 0.12E+05 | 2.0 ± 0.2E+07 |
| | 2DA15C18 | 91.0 | 0.2 | 2.4 | 76.8 ± 2.5 | 74.3 ± 4.6 | 6.52 ± 0.49E+04 | 1.4 ± 0.03E+07 |
| | 2DA17C18 | 89.6 | 0.2 | 4.5 | 63.4 ± 4.6 | 67.3 ± 3.5 | 7.92 ± 1.69E+04 | 2.7 ± 0.4E+07 |
| | 2DA18C18 | 95.9 | 0.2 | 6.4 | 67.6 ± 5.1 | 70.3 ± 4.6 | 4.01 ± 0.60E+05 | 4.4 ± 0.6E+08 |
| | 2DA21C18 | 97.9 | 0.1 | 4.4 | 61.2 ± 4.6 | 70.2 ± 6.3 | 3.08 ± 0.51E+05 | 1.6 ± 0.05E+08 |
| Linear Head | 2DA12C18 | 87.9 | 0.1 | 4.9 | 68.4 ± 2.8 | 76.1 ± 2.5 | 5.01 ± 0.80E+04 | 1.6 ± 0.3E+07 |
| | 2DA24C18 | 92.4 | 0.2 | 5.5 | 67.2 ± 2.9 | 64.3 ± 3.7 | 3.41 ± 0.22E+04 | 1.2 ± 0.1E+07 |
| | 2DA25C18 | 95.9 | 0.2 | 6.4 | 67.5 ± 6.5 | 64.1 ± 4.5 | 9.71 ± 1.45E+04 | 1.5 ± 0.1E+07 |
| | 2DA26C18 | 92.3 | 0.2 | 5.4 | 67.8 ± 2.4 | 68.5 ± 2.7 | 1.43 ± 0.05E+05 | 1.1 ± 0.02E+07 |
| Lipidoid Control | MC3 | 94.0 | 0.2 | 6.6 | 85.4 ± 4.1 | 84.4 ± 3.1 | 2.47 ± 0.34E+04 | 1.1 ± 0.2E+08 |
| | KC3 | 84.9 | 0.2 | 7.7 | 70.4 ± 3.6 | 68.4 ± 2.6 | 1.45 ± 0.25E+04 | 9.4 ± 0.4E+06 |

| Category | CTL Cell Lysis % | Elispot Spots Count | Antibody Titer ELISA RLU | Toxicity (MTT in vitro) | | | Toxicity (In vivo) AST IU/L |
|---|---|---|---|---|---|---|---|
| | | | | 0.5 µg/mL % | 1.5 µg/mL % | 5 µg/mL % | |
| Cyclic Head | 53.3 ± 12.6 | 159.7 ± 56.2 | 200.3 ± 25.7 | 91.1 ± 1.9 | 86.5 ± 1.3 | 84.4 ± 3.4 | 31.7 ± 5.6 |
| | 81.4 ± 3.3 | 357.3 ± 48.7 | 258.3 ± 62.8 | 99.1 ± 10.2 | 87.6 ± 5.9 | 75.4 ± 2.3 | 29.6 ± 8.1 |
| | /— | /— | /— | 99.8 ± 5.2 | 94.1 ± 2.8 | 86.6 ± 4.6 | /— |
| | 96.6 ± 2.1 | 854.3 ± 60.3 | 457.2 ± 22.2 | 95.6 ± 3.8 | 89.2 ± 4.0 | 78.4 ± 2.9 | 31.5 ± 4.0 |
| | 88.7 ± 3.5 | 745.0 ± 13.8 | 379.4 ± 23.2 | 95.6 ± 3.9 | 100.2 ± 3.2 | 99.4 ± 2.1 | 29.5 ± 1.5 |
| | 93.2 ± 2.8 | 478.0 ± 71.2 | 406.2 ± 95.1 | 98.4 ± 7.6 | 89.1 ± 5.7 | 84.5 ± 1.4 | 25.5 ± 0.5 |
| Linear Head | 27.2 ± 1.7 | 14.7 ± 2.5 | 49.5 ± 19.8 | 98.1 ± 2.4 | 91.1 ± 2.3 | 81.1 ± 1.1 | 31.3 ± 2.8 |
| | 20.9 ± 1.3 | 39.3 ± 7.4 | 116.3 ± 73.2 | 88.4 ± 6.1 | 83.7 ± 2.1 | 81.9 ± 2.7 | 31.5 ± 0.5 |
| | 11.5 ± 4.5 | 5.3 ± 0.6 | 30.2 ± 1.9 | 94.1 ± 6.2 | 88.7 ± 3.9 | 85.2 ± 5.8 | 27.5 ± 2.5 |
| | 26.5 ± 2.9 | 36.3 ± 2.5 | 40.3 ± 1.8 | 99.2 ± 5.6 | 96.1 ± 7.7 | 90.8 ± 2.9 | 39.3 ± 5.8 |
| Lipidoid Control | 41.7 ± 2.2 | 85.6 ± 12.6 | 237.4 ± 55.2 | 99.2 ± 5.7 | 91.7 ± 8.4 | 76.5 ± 2.7 | 32.5 ± 1.5 |
| | /— | /— | /— | 88.6 ± 0.7 | 82.9 ± 9.9 | 78.4 ± 4.1 | /— |
| | | | | | | | 17-77 |

| Category | Toxicity (In vivo) | | | | |
|---|---|---|---|---|---|
| | ALT IU/L | Total Bilirubin mg/dL | BUN mg/dL | Creatine mg/dL | Histology |
| Cyclic Head | 132.3 ± 22.4 | 0.13 ± 0.05 | 21.0 ± 4.6 | 0.4 ± 0.1 | OK |
| | 124.3 ± 52.4 | 0.12 ± 0.06 | 21.0 ± 2.4 | 0.4 ± 0.1 | OK |
| | /— | /— | /— | 0.4 ± 0.1 | OK |
| | 128.3 ± 13.3 | 0.2 ± 0.0 | 25.0 ± 3.6 | 0.4 ± 0.1 | OK |
| | 134.3 ± 4.3 | 0.1 ± 0.0 | 20.5 ± 1.5 | 0.4 ± 0.1 | OK |
| | 105.5 ± 5.5 | 0.15 ± 0.05 | 19.5 ± 1.0 | 0.4 ± 0.1 | OK |
| Linear Head | 113.7 ± 8.5 | 0.2 ± 0.05 | 26.0 ± 5.5 | 0.4 ± 0.1 | OK |
| | 117.5 ± 6.5 | 0.2 ± 0.05 | 25.5 ± 0.5 | 0.4 ± 0.1 | OK |
| | 124.5 ± 5.5 | 0.15 ± 0.05 | 32.0 ± 0.5 | 0.4 ± 0.1 | OK |
| | 122.7 ± 10.5 | 0.2 ± 0.05 | 28.0 ± 1.5 | 0.4 ± 0.1 | OK |
| Lipidoid Control | 138.7 ± 2.0 | 0.2 ± 0.05 | 24.0 ± 4.0 | 0.4 ± 0.1 | OK |
| | /— | /— | /— | 0.4 ± 0.1 | OK |
| | 54-298 | 0.1-0.9 | 12.0-28.0 | 0.3-1 | Normal Range |

Figure 27:
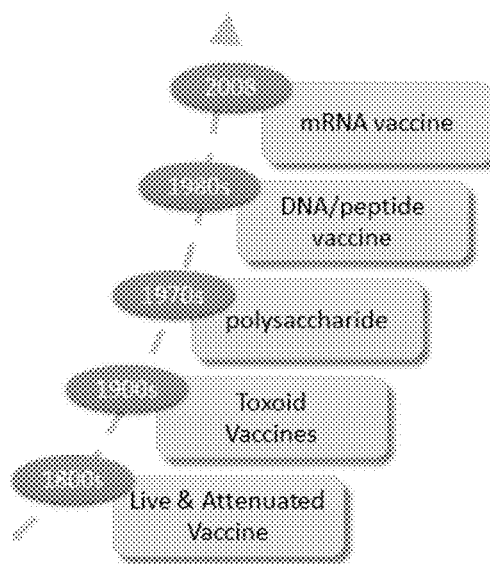
FIG. 27 shows a diagram of the history of vaccines.
Figure 28:
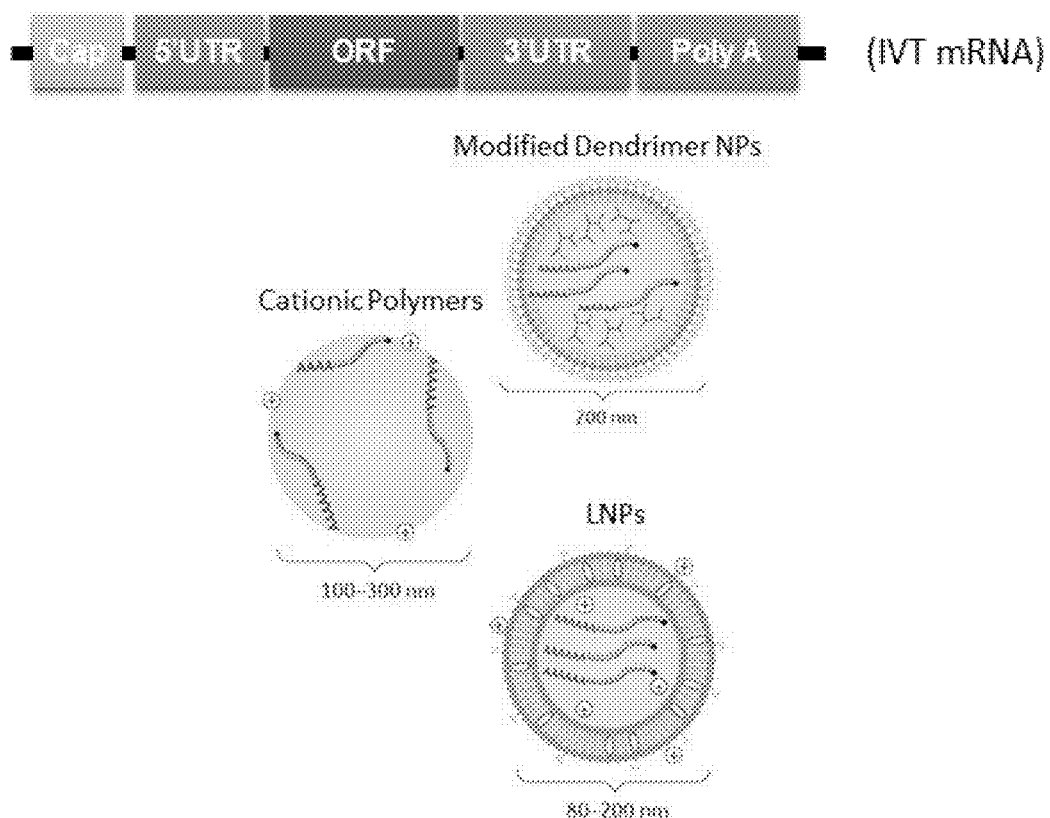
FIG. 28 shows components of the optimization of mRNA.

Example 2. Multi-Component Lipid Library for mRNA Cancer Vaccine Delivery mRNA vaccines provide an alternative to conventional vaccine approaches (FIG. 27). Relevant mRNA vaccine features include high potency (no promoters, active in non-dividing cells), safe administration (no insertional mutagenesis), rapid, inexpensive and scalable manufacturing (~45 days GMP), and inherent innate immunity (PRRs, RNA sensor, TLR or RIGI). Limitations include instability and inefficient in vivo delivery, non-specific immunogenicity (affecting translatability), and unknown tumor-associated/specific antigens.

mRNA is optimized for translation, stability, and immunogenicity. Optimizing mRNA pharmacology involves modified Cap1, regulatory elements in 5'/3'-UTR, modified nucleotides, sequence/codon modification, and purification. The delivery system involves electroporation, protamine, cationic nanoemulsion, dendrimer NPs, lipidoid NPs, and cationic polymers (FIG. 28).

Figure 29:
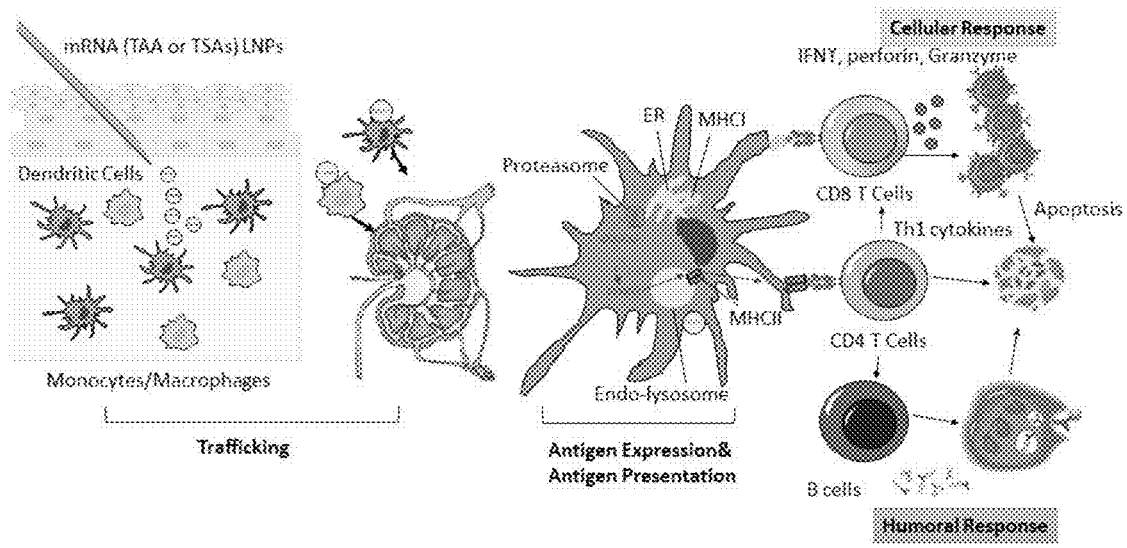
FIG. 29 shows the adaptive immune response and cancer vaccine.

The adaptive immune response and cancer vaccine is illustrated in FIG. 29. Major histocompatibility complex (MHCI) display non-self peptide from within the cell to cytotoxic T cells. An immediate response is triggered from the immune system against a particular non-self antigen. Bind peptides are generated mainly from the degradation of cytosolic proteins by the proteasome. The PNHCI:peptide complex is then inserted via the endoplasmic reticulum into the external plasma membrane of the cells. MHC class I molecules are heterodimers that consist of two polypeptide chains, α and β2-microglobulin (b2m).

Figure 30:
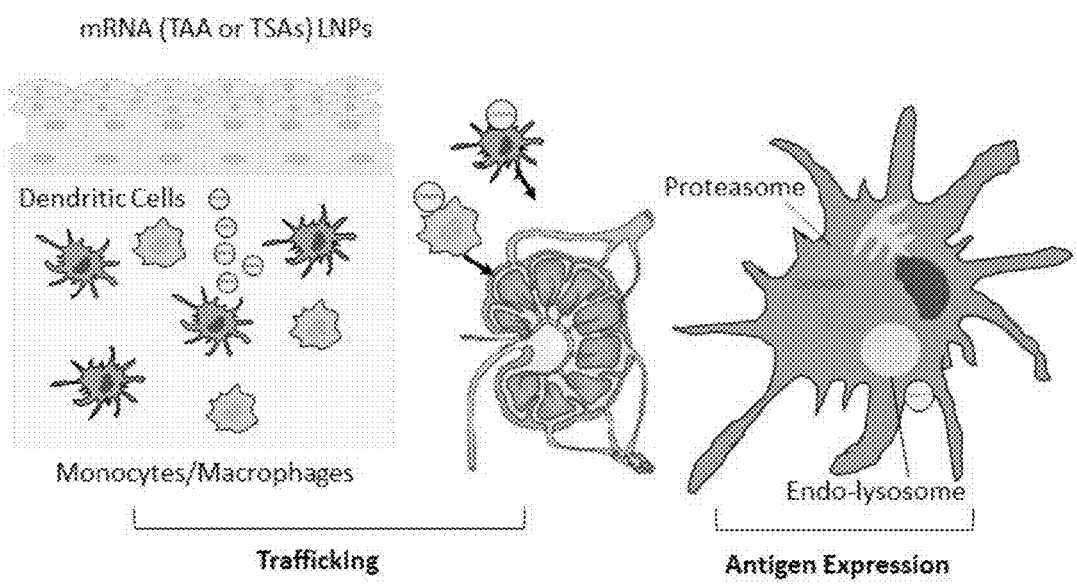
FIG. 30 shows efficient antigen expression, the first step.
Figure 31A:
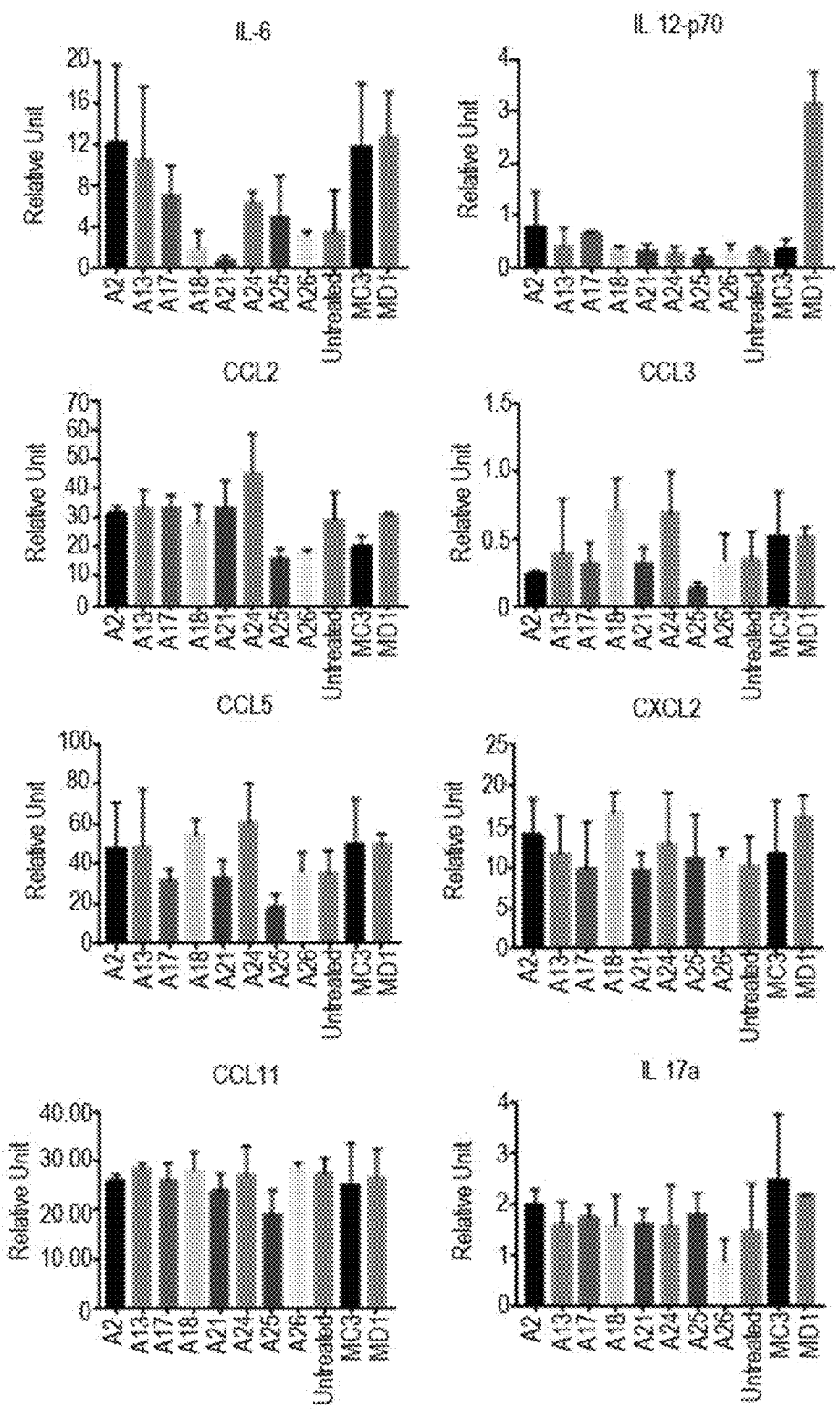
FIGS. 31A-31B show relevant low systemic toxicity.
Figure 31B:
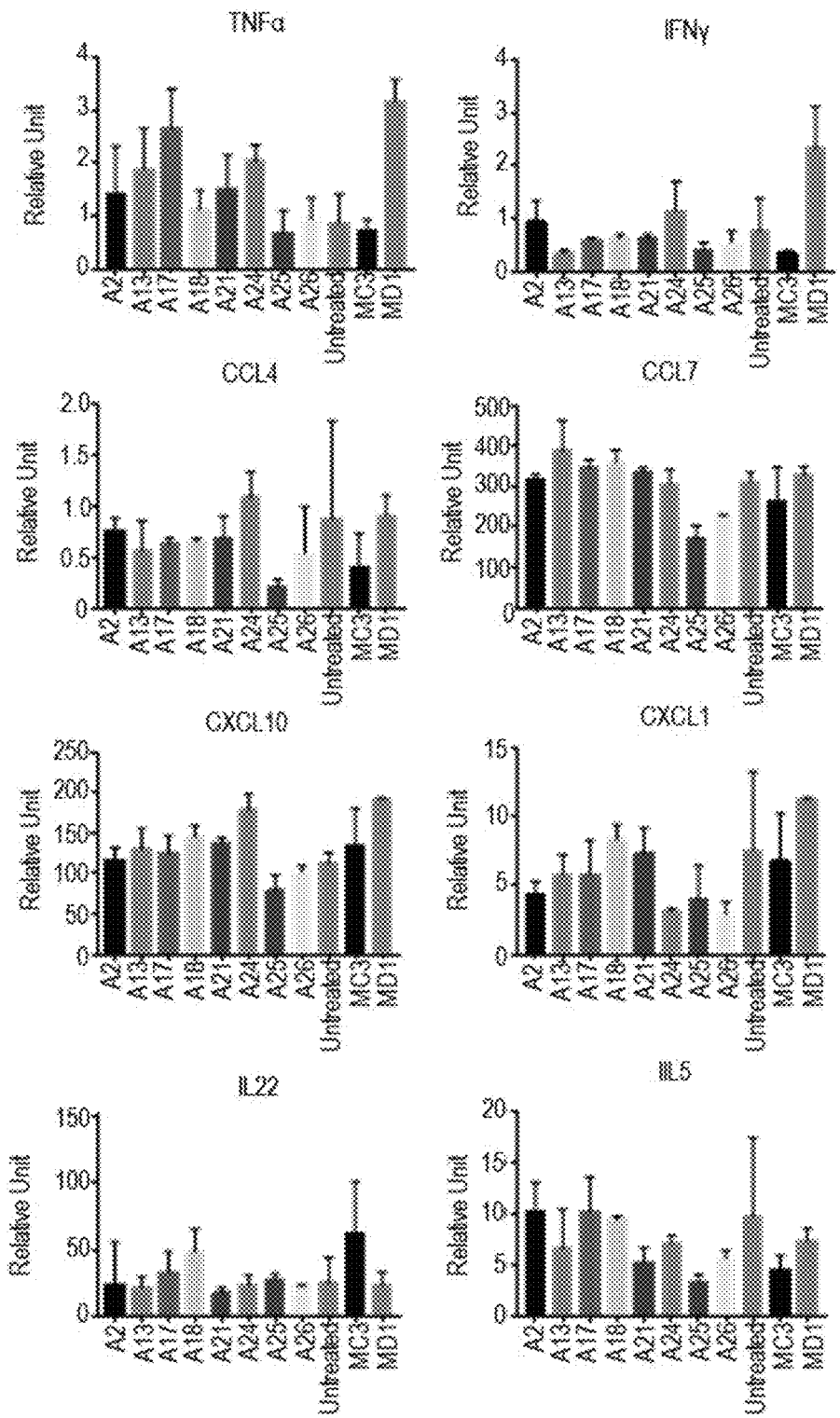
Figure 32:
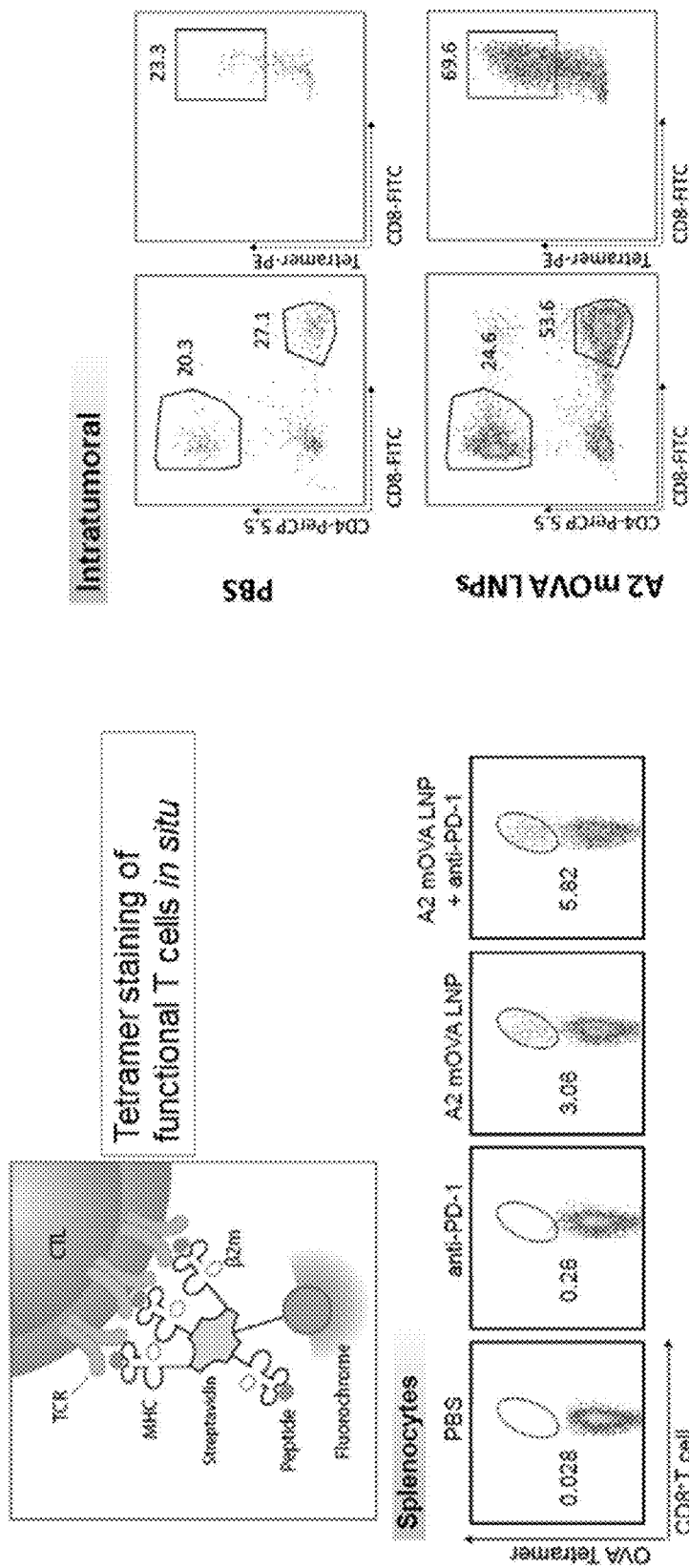
FIG. 32 shows T cell infiltration and activation in OVA-melanoma.

The first step is efficient antigen expression (FIG. 30). Single amino acids were reacted with aldehydes, acrylates, and epoxides to create a multi-dimensional lipid library. The reaction involved three components and one step. Features of 3CR for mRNA delivery are as follows. It is without toxic catalysts, eliminating the need for solvent exchange, purification or concentration. It is an alkyl ketone, with different alkyl chain lengths and saturation. Lastly, a new side chain is introduced from isocyanides in parallel with the ionizable head groups. The in vitro combinatorial transfection assay is modeled in. Antigen expression in major APCs is modeled in FIG. 12. Major antigen presenting cells are bone marrow derived dendritic cells and macrophages. In vivo batch analysis assay in B6 mice is shown in FIG. 4E (Batch 1). These had 0.75 mg/kg luciferase mRNA in total (s.c.), Iso 1-4 (upper) 48 LNP in total; Iso 5-7 (bottom) 36 LNP in total, 6 h after s.c. Batch 2, classified by isocyanide. These had s.c. 0.75 mg/kg Fluc mRNA (non-purified, dialysis, 12 mixed NPs), 5 h; exposure 10 min, 10 mg/mL Luciferin, 200 uL. Exemplary lipids present similar levels of mRNA lymph node delivery (s.c. injection). Major APCs express protein in draining LNs. A2 and A12 LNPs have a tumor inhibition effect in OVA-melanoma. In vivo Cytotoxic Lysis (CTL) suggest that cyclic lipid delivered OVA mRNA can induce strong OVA-specific T cell killing. The cyclic lipidoid mRNA vaccine induces a humoral responseAPC maturation and antigen presentation are shown in FIG. 5A. In vitro APC activation and maturation in bone marrow derived dendritic cells is shown in FIG. 5B. Cyclic lipidoids activate the type I interferon pathway in vivo (FIGS. 5B-5C). STING regulates cyclic lipidoid-mediated type I interferon activation (FIGS. 5E-5G). The STING pathway is confirmed by knock-out mice (FIGS. 5I-5J). Antitumor responses are shown in FIGS. 6A-6F. The human papillomavirus (HPV) E7 protein as TAA is shown in FIGS. 6E-6F, using the murine E7-expressing tumor model (TC1). The early genes E6 and E7 of human papillomavirus type 16 (HPV16) are consistently and exclusively expressed in HPV16-induced cancer lesions and play major roles in the development and maintenance of the malignant phenotype. This protein is a good example of a tumor-associated antigen, we have used E7 as a model antigen to test the potential of an experimental vaccine as an immunotherapeutic approach. In this study, a murine E7-expressing tumor model (TC1 cells) was used to assess effects of an E7-based vaccine on tumor growth. mRNA delivery was tested in TC-1 cells expressing the human papillomavirus (HPV) E7 protein, as a model for viral oncogene/mutant neo-epitope driven cancer with translational vaccination potential. Relevant low systemic toxicity is shown in FIGS. 31A-B. The combinatorial 3-component reaction library is shown in FIG. 1B. High throughput experimentation (HTE) was used and 1080 exemplary lipids were generated. T cell infiltration and activation in OVA-melanoma is shown in FIG. 32.

Example 3. Synthesis and Characterization of Lipidoids

Materials and Instrumentation

All the primary amines were purchased from Millipore-Sigma (St. Louis, Mo., USA) and Thermo Fisher Scientific (Cambridge, Mass., USA). Ethyl isocyanoacetate and tert-butyl isocyanoacetate were purchased from Millipore-Sigma (St. Louis, Mo., USA). Isopropanol isocyanoacetate, propanol isocyanoacetate and 1-butyl isocyanoacetate were synthesized according to the procedure[1,2]. 6Z,9Z,28Z,31Z)-heptatriaconta-6,9,28,31-tetraen-19-one and DLin-MC3-DMA (MC3) were synthesized as previously described[3]. All the solvents were purchased from Millipore-Sigma and Thermo Fisher Scientific (Cambridge, Mass., USA) at ACS grade. All chemical reagents were used as received with no further purification.

Firefly luciferase (FLuc) and human erhthropoietin (hEPO) mRNAs were generously provided by Translate Bio (Lexington, Mass.). Cy-5 labeled luciferase and NLS-Cre recombinase encoding mRNAs were purchased from Tri-Link Biotechnologies (San Diego, Calif.).

Proton nuclear magnetic resonance ($^1$H NMR) spectra were recorded on a Bruker AVANCE-400 400 MHz NMR spectrometer in deuterated chloroform ($CDCl_3$, Millipore-Sigma), using the residual proton resonance of the solvent peak at 7.26 ppm as the internal reference. Chemical shifts are reported in parts per million (ppm) on the δ scale. Data are reported as follows: chemical shift [multiplicity (s=singlet, d=doublet, m=multiplet), integration]. LC-MS was carried out on a Waters UPLC Xevo Q-ToF mass spectrometer with an Acquity UPLC operated by MassLynx software v 4.1. Waters BEH C8 column (2.1 mm×50 mm, 1.7 m particle size) at 40° C., using 0.1% formic acid in water (solvent A) and 0.1% formic acid in isopropanol/acetonitrile (volume ratio 1:4) (solvent B) at 0.6 mL min$^{-1}$. Mass spectra were acquired in positive ion mode with a capillary voltage of 1 kV, a sample cone voltage of 40 V and an extraction cone voltage of 4 V.

Synthesis and Characterization

Synthesis of U4 tert-butyl 1-(3-(dibutylamino)propyl)-5,5-di((9Z,12Z)-octadeca-9,12-dien-1-yl)-2,5-dihydro-1H-imidazole-2-carboxylate. A mixture of 3-(Dibutylamino)propylamine (74.5 mg, 0.4 mmol), tert-butyl isocyanoacetate (56.5 mg, 0.4 mmol), 6Z,9Z,28Z,31Z)-heptatriaconta-6,9,28,31-tetraen-19-one (210.8 mg, 0.4 mmol) in anhydrous mixed solvent consisting of 160 uL dichloromethane (DCM) and 240 uL tert-butanol was stirred in capped glass vials at room temperature overnight. The mixture was purified by flash column chromatography to obtain compound U4 as a yellow oil. Yield: 17.9 mg (0.021 mmol, 28.4%). MS: m/z 836.8 (M+H$^+$); $^1$H NMR (400 MHz, CHLOROFORM-d) δ ppm 0.85-1.04 (m, 12H), 1.14-1.89 (m, 59H), 1.98-2.12 (m, 8H), 2.40-2.60 (m, 6H), 2.72-2.85 (m, 4H), 2.96-3.17 (m, 2H), 4.45 (s, 1H), 5.30-5.48 (m, 8H), 7.09 (s, 1H).

Synthesis of U5 isopropyl 1-(3-(dibutylamino)propyl)-5,5-di((9Z,12Z)-octadeca-9,12-dien-1-yl)-2,5-dihydro-1H-imidazole-2-carboxylate. Following the procedure described for U4, the compound was made from 3-(Dibutylamino)propylamine (74.5 mg, 0.4 mmol), isopropanol isocyanoacetate (50.8 mg, 0.4 mmol), 6Z,9Z,28Z,31Z)-heptatriaconta- 6,9,28,31-tetraen-19-one (210.8 mg, 0.4 mmol) in DCM (160 uL) and isopropanol (240 uL) and was obtained as a yellow oil. Yield: 101.1 g (0.123 mmol, 30.7%). MS: m/z 822.8 (M+H$^+$); $^1$H NMR (400 MHz, CHLOROFORM-d) δ ppm 0.83-1.07 (m, 12H), 1.11-1.79 (m, 56H), 1.91-2.15 (m, 8H), 2.31-2.53 (m, 6H), 2.71-2.85 (m, 4H), 2.89-3.10 (m, 2H), 4.50 (s, 1H), 5.02-5.16 (m, 1H), 5.27-5.47 (m, 8H), 7.03 (s, 1H).

Synthesis of U7 tert-butyl 1-(3-(dipropylamino)propyl)-5,5-di((9Z,12Z)-octadeca-9,12-dien-1-yl)-2,5-dihydro-1H-imidazole-2-carboxylate. Following the procedure described for U4, the compound was made from N(1),N(1)-Dipropyl-1,3-propanediamine (63.3 mg, 0.4 mmol), tert-butyl isocyanoacetate (56.5 mg, 0.4 mmol), 6Z,9Z,28Z,31Z)-heptatriaconta-6,9,28,31-tetraen-19-one (210.8 mg, 0.4 mmol) in DCM (160 uL) and tert-butanol (240 uL) and was obtained as a yellow oil. Yield: 22.4 mg (0.028 mmol, 6.9%). MS: m/z 808.8 (M+H$^+$); $^1$H NMR (400 MHz, CHLOROFORM-d) δ ppm 0.81-1.03 (m, 12H), 1.15-1.77 (m, 42H), 2.00-2.12 (m, 8H), 2.30-2.52 (m, 6H), 2.73-2.85 (m, 4H), 2.91-3.09 (m, 2H), 4.44 (s, 1H), 5.29-5.45 (m, 8H), 7.03 (s, 1H).

Synthesis of U10 tert-butyl 1-(2-methyl-3-(pyrrolidin-1-yl)propyl)-5,5-di((9Z,12Z)-octadeca-9,12-dien-1-yl)-2,5-dihydro-1H-imidazole-2-carboxylate. Following the procedure described for A12, the compound was made from 2-methyl-3-(pyrrolidin-1-yl)propan-1-amine (56.9 mg, 0.4 mmol), tert-butyl isocyanoacetate (56.5 mg, 0.4 mmol), 6Z,9Z,28Z,31Z)-heptatriaconta-6,9,28,31-tetraen-19-one (210.8 mg, 0.4 mmol) in DCM (160 uL) and tert-butanol (120 uL) and was purified as a yellow oil. Yield: 88.9 mg (0.112 mmol, 28.1%). MS: m/z 792.7 (M+H$^+$); $^1$H NMR (400 MHz, CHLOROFORM-d) δ ppm 0.80-1.00 (m, 9H), 1.14-1.89 (m, 54H), 1.92-2.10 (m, 8H), 2.18-2.50 (m, 6H), 2.57-2.83 (m, 4H), 3.02-3.15 (q, 2H), 4.41 (d, 1H), 5.27-5.43 (m, 8H), 6.95 (d, 1H).

Lipid Nanoparticles Synthesis

LNPs were synthesized using a microfluidics chip device as previously described[4]. LNPs were formed by mixing a lipid-containing ethanol phase with a mRNA-containing aqueous phase, and pumped through microfluidic channel in the PDMS (poly-dimethyl-siloxane) chip at a specific rate. To incorporate the synthetic lipids into the ethanol solution, we solubilized mixtures containing ionizable lipids with 1,2-distearoyl-sn-glycero-3-phosphocholine (DSPC, Avanti), cholesterol (Sigma) and 1,2-dimyristoyl-sn-glycero-3-phosphoethanolamine-N-[methoxy(polyethylene glycol)-2000] (ammonium salt) (C14-PEG$_{2000}$, Avanti) at a predetermined molar ratio[3] of 50:10:38.5:1.5 and a lipid: mRNA weight ratio of 10:1 into ethanol. All chemicals obtained from commercial sources were stored following the manufacturer's note and used without further purification. The aqueous phase was prepared in 10 mM citrate buffer (pH 3.0, fisher) with either FLuc mRNA (Firefly luciferase mRNA, Translate Bio), Cre mRNA (Cre recombinase mRNA, TriLink), or non-translating Cy5-labelled Fluc mRNA (TriLink BioTechnologies). All mRNAs were stored at −80° C., and were allowed to thaw on ice prior to use. The ethanol and aqueous phases were mixed at a 3:1 ratio in a microfluidic chip device using syringe pumps as previously described. The remaining LNPs were dialyzed against 1×PBS in a 20,000 MWCO cassette (Invitrogen) at 4° C. for 1 h and were stored at 4° C. prior to injection.

Lipid Nanoparticle Characterization

The nucleic acid encapsulation of LNPs was calculated by using a modified Quanti-iI RiboGreeen RNA assay (Invitrogen). Dynamic light scattering (ZetaPALS, Brookhaven Instruments) was used to measure the diameter, zeta potential and polydispersity (PDI) of the LNPs. LNP diameters are reported as the largest intensity mean peak average, which constituted >95% of the nanoparticles present in the sample. The pKa of each ionizable lipidoid was determined in LNPs using TNS and preformed lipid nanoparticles composed of cationic lipid/DSPC/cholesterol/C14-PEG (50:10:38.5:1.5 mol %) in PBS at a concentration of ~6 mM total lipid. TNS was prepared as a 100 μM stock solution in distilled water. LNPs were diluted to 100 μM lipid in 90 μL of buffered solutions (triplicates) containing 10 mM HEPES, 10 mM 4-morpholineethanesulfonic acid, 10 mM ammonium acetate, 130 mM NaCl, where the pH ranged from 1.92 to 11.22. Ten μL of stock TNS was added to the LNP solutions and mixed well in a black-96 well plate. Fluorescence intensity was monitored in a Tecan Pro200 plate reader using excitation and emission wavelengths of 321 nm and 445 nm. With the resulting fluorescence values, a sigmoidal plot of fluorescence versus buffer pH was created. The log of the inflection point of this curve was the apparent pKa of the LNP formulation.

In Vitro mRNA Transfection Efficiency Assay

HeLa cells were obtained from ATCC (Manassas, Va.). Cells were maintained in Dulbecco's modified Eagle's medium (Invitrogen, Carlsbad, Calif.) supplemented with penicillin, streptomycin, and fetal bovine serum. For transfection experiments, cells were seeded in 96-well plates (Greiner, Kremsmünster, Austria) overnight and then mLuc RNA containing LNPs were incubated with cells overnight. The luciferase expression efficiency and cytotoxicity were measured by One-Glo™+Tox luciferase Reporter and Cell Viability assay kit (promega) following instructions.

Animal Experiments

All animal studies were approved by the MIT Institutional Animal Care and Use Committee (CAC) and were consistent with local, state, and federal regulations as applicable. All experimental procedures were performed with ethical compliance and approval under the guidelines for Division of Comparative Medicine by Massachusetts Institute of Technology. Female C57BL/6 mice (4-8 weeks) were obtained from Charles River Laboratories Inc. Ai14D (C57BL/6J) mice and B6.Cg-Gt(ROSA) 26Sor$^{tm14(CAG\text{-}tdTomato)Hze}$/J, 007914) mice were purchased from the Jackson Laboratory and housed in an MIT animal facility. All strains were maintained on a C57BL/6J background. For each experiment, mice were randomly grouped by blinded investigators to each group.

For analysis of hEPO, blood was collected from mice via the tail vein, allowed to clot at room temperature in 1.5 mL Eppendorf tubes (Fisher Scientific, Boston, Mass.). The tubes were then centrifuged at 8,000 rpm for 15 min and the sera samples aliquoted and stored at −80° C. before analysis. hEPO concentrations were determined using a hEPO ELISA assay (R&D Technologies, Cambridge) according to the manufacturer's instructions.

Toxicity assay data was collected three days after injection of mEPO LNPs at dose of 0.75, 1.5 and 8 mg/kg. Creatinine, total Bilirubin, blood urea nitrogen (BUN), serum aspartate aminotransferase (AST), and alanine aminotransferase (ALT) in the serum were assayed as indicators of renal and liver function, respectively. Major organs including the heart, liver, spleen, lungs, and kidneys were collected and fixed for H&E staining by the KI Swanson Biotechnology Center to evaluate the organ-specific toxicity.

Flow Cytometry

The antibodies used for flow cytometry were listed below in Table C. Using flow cytometry analysis, cells were pre-incubated with anti-CD16/32 antibody and stained on ice with a fluorophore conjugated antibody to analyze surface markers. For the staining of IFN-γ, an intracellular marker, cells were pre-stimulated with the Cell Stimulation Cocktail (eBioscience™) for 6 h, and fixed and permeablized (fixation/permeabilization solution kit, BD). Later, cells were stained with both the anti-IFN-γ or other surface antibodies. Flow data were acquired on a BD LSR II flow cytometer and analyzed using FlowJo software.

TABLE C

List of antibodies used for flow cytometry

| Panel 1 | Panel 2 |
|---|---|
| CD45 BUV 737 | CD45 BUV 737 |
| CD11b BV510 | CD3 PE/Cy7 |
| CD11c BV510 | CD19 PE/Cy7 |
| CD3 APC | CD11b AF700 |
| TCRB BV421 | CD11c BV786 |
| CD19 BV786 | F4/80 BUV395 |
| CD4 BUV395 | Lyle C AF488 |
| CD8 AF488 | Lyle G BV510 |
| NK1.1 BV605 | SiglecF BV605 |
|  | CD200R3 APC |
|  | CD169 BV421 |

Statistical Analysis

Statistical analysis of the results was tested by a two-tailed un-paired Student's t-test, assuming equal variances to compare two replicate means, or One-Way ANOVA followed by Bonferroni post-hoc analysis to compare multiple replicate means. Statistical analysis was performed using Microsoft Excel and Prism 7.0 (GraphPad). Data are expressed as means±SD. Difference was considered to be significant if P<0.05 (*P<0.05, P<0.01, *P<0.001, unless otherwise indicated).

REFERENCES

1. Pardi N, Hogan M J, Porter F W, Weissman D. mRNA vaccines—a new era in vaccinology. *Nat Rev Drug Discov* 2018.
2. Pollard C, Rejman J, De Haes W, Verrier B, Van Gulck E, Naessens T, et al. Type I IFN counteracts the induction of antigen-specific immune responses by lipid-based delivery of mRNA vaccines. *Mol Ther* 2013, 21(1): 251-259.
3. Jayaraman M, Ansell S M, Mui B L, Tam Y K, Chen J, Du X, et al. Maximizing the potency of siRNA lipid nanoparticles for hepatic gene silencing in vivo. *Angew Chem Int Ed Engl* 2012, 51(34): 8529-8533.
4. Kauffman K J, Webber M J, Anderson D G. Materials for non-viral intracellular delivery of messenger RNA therapeutics. *J Control Release* 2016, 240: 227-234.
5. Richner J M, Himansu S, Dowd K A, Butler S L, Salazar V, Fox J M, et al. Modified mRNA Vaccines Protect against Zika Virus Infection. *Cell* 2017, 168(6): 1114-1125 e1110.
6. Kariko K, Muramatsu H, Welsh F A, Ludwig J, Kato H, Akira S, et al. Incorporation of pseudouridine into mRNA yields superior nonimmunogenic vector with increased translational capacity and biological stability. *Mol Ther* 2008, 16(11): 1833-1840.
7. Li K, Qu S, Chen X, Wu Q, Shi M. Promising Targets for Cancer Immunotherapy: TLRs, RLRs, and STING-Mediated Innate Immune Pathways. *Int J Mol Sci* 2017, 18(2).
8. Zevini A, Olagnier D, Hiscottt J. Crosstalk between Cytoplasmic RIG-I and STING Sensing Pathways. *Trends Immunol* 2017, 38(3): 194-205.
9. Barber G N. STING: infection, inflammation and cancer. *Nat Rev Immunol* 2015, 15(12): 760-770.
10. Corrales L, Glickman L H, McWhirter S M, Kanne D B, Sivick K E, Katibah G E, et al. Direct Activation of STING in the Tumor Microenvironment Leads to Potent and Systemic Tumor Regression and Immunity. *Cell Rep* 2015, 11(7): 1018-1030.
11. Iribarren K, Bloy N, Buque A, Cremer I, Eggermont A, Fridman W H, et al. Trial Watch: Immunostimulation with Toll-like receptor agonists in cancer therapy. *Oncoimmunology* 2016, 5(3): e1088631.
12. Nguyen D N, Mahon K P, Chikh G, Kim P, Chung H, Vicari A P, et al. Lipid-derived nanoparticles for immunostimulatory RNA adjuvant delivery. *Proc Natl Acad Sci USA* 2012, 109(14): E797-803.
13. Nguyen D N, Chen S C Y, Lu J, Goldberg M, Kim P, Sprague A, et al. Drug Delivery-mediated Control of RNA Immunostimulation. *Molecular Therapy* 2009, 17(9): 1555-1562.
14. Steinhagen F, Kinjo T, Bode C, Klinman D M. TLR-based immune adjuvants. *Vaccine* 2011, 29(17): 3341-3355.
15. Van Lint S, Goyvaerts C, Maenhout S, Goethals L, Disy A, Benteyn D, et al. Preclinical evaluation of TriMix and antigen mRNA-based antitumor therapy. *Cancer Res* 2012, 72(7): 1661-1671.
16. Kranz L M, Diken M, Haas H, Kreiter S, Loquai C, Reuter K C, et al. Systemic RNA delivery to dendritic cells exploits antiviral defence for cancer immunotherapy. *Nature* 2016, 534(7607): 396-401.
17. Broos K, Van der Jeught K, Puttemans J, Goyvaerts C, Heirman C, Dewitte H, et al. Particle-mediated Intravenous Delivery of Antigen mRNA Results in Strong Antigen-specific T-cell Responses Despite the Induction of Type I Interferon. *Mol Ther Nucleic Acids* 2016, 5(6): e326.
18. Iurescia S, Fioretti D, Rinaldi M. Nucleic Acid Sensing Machinery: Targeting Innate Immune System for Cancer Therapy. *Recent Pat Anticancer Drug Discov* 2018, 13(1): 2-17.
19. Wang J, Li P, Wu M X. Natural STING Agonist as an "Ideal" Adjuvant for Cutaneous Vaccination. *J Invest Dermatol* 2016, 136(11): 2183-2191.
20. Luo M, Wang H, Wang Z, Cai H, Lu Z, Li Y, et al. A STING-activating nanovaccine for cancer immunotherapy. *Nat Nanotechnol* 2017, 12(7): 648-654.
21. Caucheteux S M, Piguet V. New Cutaneous Vaccine Adjuvant that STINGs a Little Less. *J Invest Dermatol* 2016, 136(11): 2127-2128.
22. Fu J, Kanne D B, Leong M, Glickman L H, McWhirter S M, Lemmens E, et al. STING agonist formulated cancer vaccines can cure established tumors resistant to PD-1 blockade. *Sci Transl Med* 2015, 7(283): 283ra252.
23. Wilson D R, Sen R, Sunshine J C, Pardoll D M, Green J J, Kim Y J. Biodegradable STING agonist nanoparticles for enhanced cancer immunotherapy. *Nanomedicine* 2018, 14(2): 237-246.
24. Demaria O, De Gassart A, Coso S, Gestermann N, Di Domizio J, Flatz L, et al. STING activation of tumor endothelial cells initiates spontaneous and therapeutic antitumor immunity. *Proc Natl Acad Sci USA* 2015, 112(50): 15408-15413.
25. Hulme C, Gore V. "Multi-component reactions: emerging chemistry in drug discovery" 'from xylocain to crixivan'. *Curr Med Chem* 2003, 10(1): 51-80.

26. Tanaka Y, Hasui T, Suginome M. Acid-free, aminoborane-mediated Ugi-type reaction leading to general utilization of secondary amines. *Org Lett* 2007, 9(22): 4407-4410.
27. Kazmaier U, Ackermann S. A straightforward approach towards thiazoles and endothiopeptides via Ugi reaction. *Org Biomol Chem* 2005, 3(17): 3184-3187.
28. Pan S C, List B. Catalytic three-component Ugi reaction. *Angew Chem Int Ed Engl* 2008, 47(19): 3622-3625.
29. Fenton O S, Kauffman K J, Mcclellan R L, Appel E A, Dorkin J R, Tibbitt M W, et al. Bioinspired Alkenyl Amino Alcohol Ionizable Lipid Materials for Highly Potent In Vivo mRNA Delivery. *Adv Mater* 2016, 28(15): 2939-2943.
30. Akinc A, Zumbuehl A, Goldberg M, Leshchiner E S, Busini V, Hossain N, et al. A combinatorial library of lipid-like materials for delivery of RNAi therapeutics. *Nat Biotechnol* 2008, 26(5): 561-569.
31. Koopmanschap G, Ruijter E, Orru R V. Isocyanide-based multicomponent reactions towards cyclic constrained peptidomimetics. *Beilstein J Org Chem* 2014, 10: 544-598.
32. Whitehead K A, Dorkin J R, Vegas A J, Chang P H, Veiseh O, Matthews J, et al. Degradable lipid nanoparticles with predictable in vivo siRNA delivery activity. *Nat Commun* 2014, 5: 4277.
33. Semple S C, Akinc A, Chen J, Sandhu A P, Mui B L, Cho C K, et al. Rational design of cationic lipids for siRNA delivery. *Nat Biotechnol* 2010, 28(2): 172-176.
34. Kauffman K J, Dorkin J R, Yang J H, Heartlein M W, DeRosa F, Mir F F, et al. Optimization of Lipid Nanoparticle Formulations for mRNA Delivery in Vivo with Fractional Factorial and Definitive Screening Designs. *Nano Letters* 2015, 15(11): 7300-7306.
35. Whitehead K A, Matthews J, Chang P H, Niroui F, Dorkin J R, Severgnini M, et al. In vitro-in vivo translation of lipid nanoparticles for hepatocellular siRNA delivery. *ACS Nano* 2012, 6(8): 6922-6929.
36. Chahal J S, Khan O F, Cooper C L, McPartlan J S, Tsosie J K, Tilley L D, et al. Dendrimer-RNA nanoparticles generate protective immunity against lethal Ebola, H1N1 influenza, and *Toxoplasma gondii* challenges with a single dose. *Proc Natl Acad Sci USA* 2016, 113(29): E4133-4142.
37. Sahin U, Derhovanessian E, Miller M, Kloke B P, Simon P, Lower M, et al. Personalized RNA mutanome vaccines mobilize poly-specific therapeutic immunity against cancer. *Nature* 2017, 547(7662): 222-226.
38. Gu B, Linehan B, Tseng Y C. Optimization of the Buchi B-90 spray drying process using central composite design for preparation of solid dispersions. *Int J Pharm* 2015, 491(1-2): 208-217.
39. Heyes J, Palmer L, Bremner K, MacLachlan I. Cationic lipid saturation influences intracellular delivery of encapsulated nucleic acids. *J Control Release* 2005, 107(2): 276-287.
40. Oberli M A, Reichmuth A M, Dorkin J R, Mitchell M J, Fenton O S, Jaklenec A, et al. Lipid Nanoparticle Assisted mRNA Delivery for Potent Cancer Immunotherapy. *Nano Lett* 2017, 17(3): 1326-1335.
41. Kuai R, Ochyl L J, Bahjat K S, Schwendeman A, Moon J J. Designer vaccine nanodiscs for personalized cancer immunotherapy. *Nat Mater* 2017, 16(4): 489-496.
42. Ciavarra R P, Taylor L, Greene A R, Yousefieh N, Horeth D, van Rooijen N, et al. Impact of macrophage and dendritic cell subset elimination on antiviral immunity, viral clearance and production of type 1 interferon. *Virology* 2005, 342(2): 177-189.
43. Ma D Y, Clark E A. The role of CD40 and CD154/CD40L in dendritic cells. *Semin Immunol* 2009, 21(5): 265-272.
44. Walseng E, Furuta K, Goldszmid R S, Weih K A, Sher A, Roche P A. Dendritic cell activation prevents MHC class II ubiquitination and promotes MHC class II survival regardless of the activation stimulus. *J Biol Chem* 2010, 285(53): 41749-41754.
45. Mata-Haro V, Cekic C, Martin M, Chilton P M, Casella C R, Mitchell T C. The vaccine adjuvant monophosphoryl lipid A as a TRIF-biased agonist of TLR4. *Science* 2007, 316(5831): 1628-1632.
46. Vandepapeliere P, Horsmans Y, Moris P, Van Mechelen M, Janssens M, Koutsoukos M, et al. Vaccine adjuvant systems containing monophosphoryl lipid A and QS21 induce strong and persistent humoral and T cell responses against hepatitis B surface antigen in healthy adult volunteers. *Vaccine* 2008, 26(10): 1375-1386.
47. Fotin-Mleczek M, Duchardt K M, Lorenz C, Pfeiffer R, Ojkic-Zrna S, Probst J, et al. Messenger RNA-based vaccines with dual activity induce balanced TLR-7 dependent adaptive immune responses and provide antitumor activity. *J Immunother* 2011, 34(1): 1-15.
48. Aviles E, Prudhomme J, Le Roch K G, Franzblau S G, Chandrasena K, Mayer A M, et al. Synthesis and preliminary biological evaluation of a small library of hybrid compounds based on Ugi isocyanide multicomponent reactions with a marine natural product scaffold. *Bioorg Med Chem Lett* 2015, 25(22): 5339-5343.
49. Ugi. I W B, Domling. A. The chemistry of isocyanides, their multicomponent reactions and their libraries. *Molecules* 2003, 8: 4.
50. Wada J, Suzuki T, Iwasaki M, Miyamatsu H, Ueno S, Shimizu M. A new nonsteroidal antiinflammatory agent. 2-Substituted 5- or 6-benzothiazoleacetic acids and their derivatives. *J Med Chem* 1973, 16(8): 930-934.
51. Ohkuri T, Kosaka A, Ishibashi K, Kumai T, Hirata Y, Ohara K, et al. Intratumoral administration of cGAMP transiently accumulates potent macrophages for anti-tumor immunity at a mouse tumor site. *Cancer Immunol Immunother* 2017, 66(6): 705-716.
52. Rao R S, Kumar C G, Prakasham R S, Hobbs P J. The Taguchi methodology as a statistical tool for biotechnological applications: a critical appraisal. *Biotechnol J* 2008, 3(4): 510-523.
53. Belliveau N M, Huft J, Lin P J, Chen S, Leung A K, Leaver T J, et al. Microfluidic Synthesis of Highly Potent Limit-size Lipid Nanoparticles for In Vivo Delivery of siRNA. *Mol Ther Nucleic Acids* 2012, 1: e37.
54. Feig C, Jones J O, Kraman M, Wells R J, Deonarine A, Chan D S, et al. Targeting CXCL12 from FAP-expressing carcinoma-associated fibroblasts synergizes with anti-PD-L1 immunotherapy in pancreatic cancer. *Proc Natl Acad Sci USA* 2013, 110(50): 20212-20217.
55. Maruggi G, Chiarot E, Giovani C, Buccato S, Bonacci S, Frigimelica E, et al. Immunogenicity and protective efficacy induced by self-amplifying mRNA vaccines encoding bacterial antigens. *Vaccine* 2017, 35(2): 361-368.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:
1. A compound of Formula (I-A):

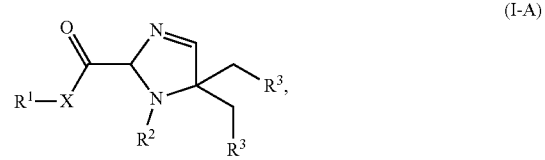

or a pharmaceutically acceptable salt, co-crystal, tautomer, stereoisomer, solvate, hydrate, polymorph, or isotopically enriched derivative thereof, wherein:
X is NH, O, or S;
R$^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
R$^2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group; and
each instance of R$^3$ is independently optionally substituted alkyl, optionally substituted alkenyl, or optionally substituted alkynyl; or wherein two instances of R$^3$ are taken together with their intervening atoms to form a ring.

2. The compound of claim 1, or a pharmaceutically acceptable salt, co-crystal, tautomer, stereoisomer, solvate, hydrate, polymorph, or isotopically enriched derivative thereof, wherein X is O.

3. The compound of claim 1, or a pharmaceutically acceptable salt, co-crystal, tautomer, stereoisomer, solvate, hydrate, polymorph, or isotopically enriched derivative thereof, wherein R$^1$ is optionally substituted C$_{1-6}$ alkyl.

4. The compound of claim 1, or a pharmaceutically acceptable salt, co-crystal, tautomer, stereoisomer, solvate, hydrate, polymorph, or isotopically enriched derivative thereof, wherein R$^2$ is optionally substituted C$_{1-6}$ alkyl.

5. The compound of claim 1, or a pharmaceutically acceptable salt, co-crystal, tautomer, stereoisomer, solvate, hydrate, polymorph, or isotopically enriched derivative thereof, wherein R$^1$ is optionally substituted C$_{1-6}$ alkyl, R$^2$ is optionally substituted C$_{1-6}$ alkyl, and each R$^3$ independently is optionally substituted C$_{1-20}$ alkyl, optionally substituted C$_{2-20}$ alkenyl, or optionally substituted C$_{2-20}$ alkynyl.

6. The compound of claim 1, or a pharmaceutically acceptable salt, co-crystal, tautomer, stereoisomer, solvate, hydrate, polymorph, or isotopically enriched derivative thereof, wherein R$^2$ is of the formula: —(CH$_2$)$_n$N(R$^{D1a}$)$_2$, wherein:
each instance of R$^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or optionally two instances of $R^{D1a}$ are taken together with their intervening atoms to form a substituted or unsubstituted heterocyclic or substituted or unsubstituted heteroaryl ring; and n is 1, 2, 3, 4, 5, or 6.

ally substituted heteroaryl, or an oxygen protecting group when attached to an oxygen atom; and n is 1, 2, 3, 4, 5, or 6.

9. The compound of claim 1, wherein the compound is of the formula:

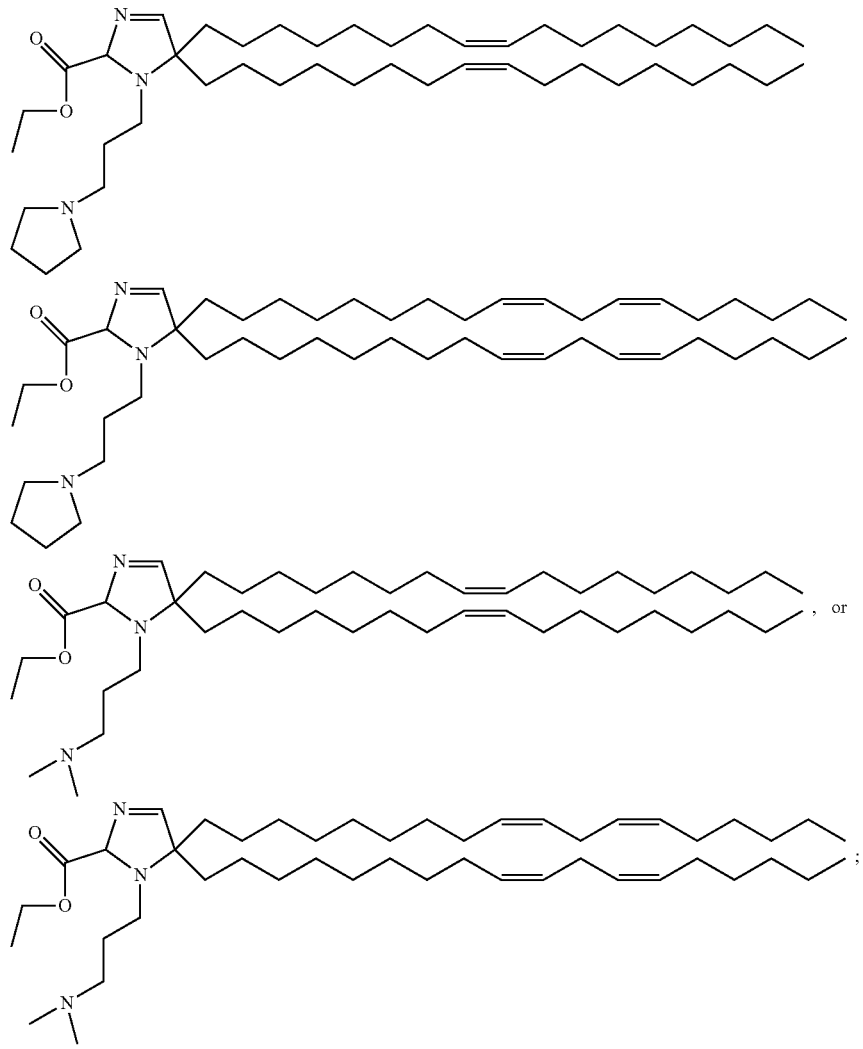

, or

7. The compound of claim 6, or a pharmaceutically acceptable salt, co-crystal, tautomer, stereoisomer, solvate, hydrate, polymorph, or isotopically enriched derivative thereof, wherein at least one instance of $R^{D1a}$ is hydrogen, or wherein at least one instance of $R^{D1a}$ is optionally substituted $C_{1-6}$ alkyl.

8. The compound of claim 1, or a pharmaceutically acceptable salt, co-crystal, tautomer, stereoisomer, solvate, hydrate, polymorph, or isotopically enriched derivative thereof, wherein $R^2$ is of the formula: $-(CH_2)_n OR^{D1}$, and wherein:

$R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionor a pharmaceutically acceptable salt thereof.

10. The compound of claim 1, or a pharmaceutically acceptable salt thereof, wherein the compound is synthesized by a method comprising reacting:

an amine of Formula (A):

(A)

an isocyanide of Formula (B):

(B)

and
a ketone of Formula (C):

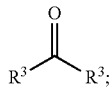

(C)

to form a compound of claim 1; wherein:
X is NH, O, or S;
R¹ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
R² is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group; and
each instance of R³ is independently optionally substituted alkyl, optionally substituted alkenyl, or optionally substituted alkynyl.

11. The compound of claim 10, or a pharmaceutically acceptable salt thereof, wherein X is O.

12. A composition comprising a compound of claim 1, or a pharmaceutically acceptable salt, co-crystal, tautomer, stereoisomer, solvate, hydrate, polymorph, or isotopically enriched derivative thereof, and an agent.

13. The composition of claim 12, wherein the agent is a small organic molecule, inorganic molecule, nucleic acid, protein, peptide, or polynucleotide.

14. The composition of claim 13, wherein the agent is a polynucleotide.

15. The composition of claim 14, wherein the polynucleotide is DNA.

16. The composition of claim 14, wherein the polynucleotide is RNA.

17. The composition of claim 16, wherein the RNA is double-stranded RNA (dsRNA), small interfering RNA (siRNA), short hairpin RNA (shRNA), micro RNA (mi RNA), messenger RNA (mRNA), or antisense RNA.

18. The composition of claim 16, wherein the RNA is mRNA.

19. The composition of claim 18, wherein the mRNA encodes a protein.

20. The composition of claim 19, wherein the protein is an antigen.

21. The composition of claim 18, wherein the mRNA is an mRNA vaccine.

22. The composition of claim 12, wherein the agent is an anti-cancer agent.

* * * * *